United States Patent
Salas et al.

(10) Patent No.: US 10,202,595 B2
(45) Date of Patent: *Feb. 12, 2019

(54) CHIMERIC CLOTTING FACTORS

(71) Applicant: Bioverativ Therapeutics Inc., Waltham, MA (US)

(72) Inventors: Joe Salas, Wayland, MA (US); Elena Kistanova, Brookline, MA (US); Vu Phong Hong, Cambridge, MA (US); Adam R. Meso, Carmel, IN (US); Robert T. Peters, Needham, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 142 days.

This patent is subject to a terminal disclaimer.

(21) Appl. No.: 14/406,160

(22) PCT Filed: Jun. 7, 2013

(86) PCT No.: PCT/US2013/044842
§ 371 (c)(1),
(2) Date: Dec. 5, 2014

(87) PCT Pub. No.: WO2013/185114
PCT Pub. Date: Dec. 12, 2013

(65) Prior Publication Data
US 2015/0353911 A1    Dec. 10, 2015

Related U.S. Application Data

(60) Provisional application No. 61/829,775, filed on May 31, 2013, provisional application No. 61/801,603, filed on Mar. 15, 2013, provisional application No. 61/759,817, filed on Feb. 1, 2013, provisional application No. 61/657,685, filed on Jun. 8, 2012.

(51) Int. Cl.
| *C12N 9/64* | (2006.01) |
| *A61K 47/62* | (2017.01) |
| *A61K 38/36* | (2006.01) |
| *A61K 38/48* | (2006.01) |

(52) U.S. Cl.
CPC ............ *C12N 9/6432* (2013.01); *A61K 38/36* (2013.01); *A61K 38/4846* (2013.01); *A61K 47/62* (2017.08); *C12N 9/6437* (2013.01); *C12Y 304/21006* (2013.01); *C12Y 304/21021* (2013.01)

(58) Field of Classification Search
None
See application file for complete search history.

(56) References Cited

U.S. PATENT DOCUMENTS

| 4,868,112 | A | 9/1989 | Toole, Jr. |
| 5,112,950 | A | 5/1992 | Meulien et al. |
| 5,171,844 | A | 12/1992 | van Ooyen et al. |
| 5,460,950 | A | 10/1995 | Barr et al. |
| 5,543,502 | A | 8/1996 | Nordfang et al. |
| 5,595,886 | A | 1/1997 | Chapman et al. |
| 5,610,278 | A | 3/1997 | Nordfang et al. |
| 5,643,575 | A | 7/1997 | Martinez et al. |
| 5,648,260 | A | 7/1997 | Winter et al. |
| 5,712,122 | A | 1/1998 | Boime et al. |
| 5,739,277 | A | 4/1998 | Presta et al. |
| 5,789,203 | A | 8/1998 | Chapman et al. |
| 5,834,250 | A | 11/1998 | Wells et al. |
| 5,840,529 | A | 11/1998 | Seidah et al. |
| 5,846,951 | A | 12/1998 | Gregoriadis |
| 5,869,046 | A | 2/1999 | Presta et al. |
| 5,935,815 | A | 8/1999 | Van De Ven et al. |
| 5,972,885 | A | 10/1999 | Spira et al. |
| 6,030,613 | A | 2/2000 | Blumberg et al. |
| 6,048,720 | A | 4/2000 | Dalborg et al. |
| 6,060,447 | A | 5/2000 | Chapman et al. |
| 6,086,875 | A | 7/2000 | Blumberg et al. |
| 6,096,871 | A | 8/2000 | Presta et al. |
| 6,121,022 | A | 9/2000 | Presta et al. |
| 6,194,551 | B1 | 2/2001 | Idusogie et al. |
| 6,228,620 | B1 | 5/2001 | Chapman et al. |
| 6,242,195 | B1 | 6/2001 | Idusogie et al. |
| 6,277,375 | B1 | 8/2001 | Ward |
| 6,316,226 | B1 | 11/2001 | van Ooyen et al. |
| 6,346,513 | B1 | 2/2002 | van Ooyen et al. |
| 6,380,171 | B1 | 4/2002 | Day et al. |
| 6,458,563 | B1 | 10/2002 | Lollar |
| 6,485,726 | B1 | 11/2002 | Blumberg et al. |
| 6,528,624 | B1 | 3/2003 | Idusogie et al. |
| 6,538,124 | B1 | 3/2003 | Idusogie et al. |
| 6,696,245 | B2 | 2/2004 | Winter et al. |
| 6,737,056 | B1 | 5/2004 | Presta |
| 6,821,505 | B2 | 11/2004 | Ward |

(Continued)

FOREIGN PATENT DOCUMENTS

| EP | 0120694 A2 | 10/1984 |
| EP | 0125023 A1 | 11/1984 |

(Continued)

OTHER PUBLICATIONS

Wajima, T., et al. 2009 Clinical Pharmacology & Therapeutics 86(3): 290-298.*

(Continued)

*Primary Examiner* — Marsha Tsay
(74) *Attorney, Agent, or Firm* — Sterne, Kessler, Goldstein & Fox P.L.L.C.

(57) ABSTRACT

The invention provides chimeric clotting factors comprising an activatable clotting factor and an enhancer moiety. The activatable clotting factor allows the chimeric clotting factor to be activated at the site of coagulation. The enhancer moiety can additionally improve procoagulation activities of the chimeric clotting factors. The chimeric clotting factors can further be improved by fusion to a half-life extender, which improves a pharmacokinetics property of the chimeric clotting factor. The invention also includes methods of making and methods of using these chimeric clotting factors.

14 Claims, 25 Drawing Sheets
Specification includes a Sequence Listing.

(56) References Cited

U.S. PATENT DOCUMENTS

| | | | |
|---|---|---|---|
| 6,998,253 B1 | 2/2006 | Presta et al. | |
| 7,041,635 B2 | 5/2006 | Kim et al. | |
| 7,083,784 B2 | 8/2006 | Dall'Acqua et al. | |
| 7,091,186 B2 | 8/2006 | Senter et al. | |
| 7,199,223 B2 | 4/2007 | Bossard et al. | |
| 7,317,091 B2 | 1/2008 | Lazar et al. | |
| 7,348,004 B2 | 3/2008 | Peters et al. | |
| 7,375,078 B2 | 5/2008 | Feng | |
| 7,381,408 B2 | 6/2008 | Mezo et al. | |
| 7,404,956 B2 | 7/2008 | Peters et al. | |
| 7,589,178 B2 | 9/2009 | Le Bonniec et al. | |
| 7,659,241 B2 | 2/2010 | Senter et al. | |
| 7,691,962 B2 | 4/2010 | Boyd et al. | |
| 7,709,224 B2 | 5/2010 | Fang et al. | |
| 7,754,681 B2 | 7/2010 | Feng | |
| 7,807,644 B2 | 10/2010 | Lind et al. | |
| 7,846,445 B2 | 12/2010 | Schellenberger et al. | |
| 7,855,279 B2 | 12/2010 | Schellenberger et al. | |
| 7,862,820 B2 | 1/2011 | Peters et al. | |
| 2003/0069395 A1 | 4/2003 | Sato et al. | |
| 2003/0130189 A1 | 7/2003 | Senter et al. | |
| 2003/0235536 A1 | 12/2003 | Blumberg et al. | |
| 2005/0147618 A1* | 7/2005 | Rivera | A61K 47/4843 424/178.1 |
| 2005/0256030 A1 | 11/2005 | Feng | |
| 2006/0269480 A1 | 11/2006 | Amir et al. | |
| 2007/0191597 A1 | 8/2007 | Jain et al. | |
| 2007/0218067 A1 | 9/2007 | Buttner et al. | |
| 2007/0231329 A1 | 10/2007 | Lazar et al. | |
| 2007/0237765 A1 | 10/2007 | Lazar et al. | |
| 2007/0237766 A1 | 10/2007 | Lazar et al. | |
| 2007/0237767 A1 | 10/2007 | Lazar et al. | |
| 2007/0243188 A1 | 10/2007 | Lazar et al. | |
| 2007/0248603 A1 | 10/2007 | Lazar et al. | |
| 2007/0286859 A1 | 12/2007 | Lazar et al. | |
| 2008/0004206 A1 | 1/2008 | Rosen et al. | |
| 2008/0057056 A1 | 3/2008 | Lazar et al. | |
| 2008/0153751 A1 | 6/2008 | Rosen et al. | |
| 2008/0161243 A1 | 7/2008 | Rosen et al. | |
| 2008/0194481 A1 | 8/2008 | Rosen et al. | |
| 2008/0241102 A1 | 10/2008 | Hersel et al. | |
| 2008/0260738 A1 | 10/2008 | Moore et al. | |
| 2008/0261877 A1 | 10/2008 | Ballance et al. | |
| 2009/0087411 A1 | 4/2009 | Fares et al. | |
| 2009/0092582 A1 | 4/2009 | Bogin et al. | |
| 2010/0092496 A1 | 4/2010 | Boyd et al. | |
| 2010/0145036 A1 | 6/2010 | Sufi et al. | |
| 2010/0239554 A1 | 9/2010 | Schellenberger et al. | |
| 2010/0292130 A1 | 11/2010 | Skerra et al. | |
| 2010/0323956 A1 | 12/2010 | Schellenberger et al. | |
| 2010/0330059 A1* | 12/2010 | Stafford | C12Y 304/21021 424/94.3 |
| 2011/0046060 A1 | 2/2011 | Schellenberger et al. | |
| 2011/0046061 A1 | 2/2011 | Schellenberger et al. | |
| 2011/0077199 A1 | 3/2011 | Schellenberger et al. | |
| 2011/0172146 A1 | 7/2011 | Schellenberger et al. | |
| 2011/0189182 A1 | 8/2011 | Metzner et al. | |
| 2012/0121613 A1 | 5/2012 | Tang et al. | |
| 2012/0263701 A1 | 10/2012 | Schellenberger et al. | |
| 2013/0017997 A1 | 1/2013 | Schellenberger et al. | |
| 2013/0202596 A1* | 8/2013 | Salas | C07K 14/745 424/134.1 |
| 2013/0216513 A1* | 8/2013 | Salas | C07K 14/745 424/94.3 |
| 2015/0184142 A1 | 7/2015 | Hong et al. | |

FOREIGN PATENT DOCUMENTS

| | | | |
|---|---|---|---|
| EP | 0295597 A2 | 12/1988 | |
| WO | WO-8101145 A1 | 4/1981 | |
| WO | WO-8704187 A1 | 7/1987 | |
| WO | WO-8800831 A1 | 2/1988 | |
| WO | WO-8807089 A1 | 9/1988 | |
| WO | WO-9109122 A1 | 6/1991 | |
| WO | WO-9207869 A1 | 5/1992 | |
| WO | WO-9614339 A1 | 5/1996 | |
| WO | WO-9805787 A1 | 2/1998 | |
| WO | WO-9823289 A1 | 6/1998 | |
| WO | WO-9951642 A1 | 10/1999 | |
| WO | WO-9958572 A1 | 11/1999 | |
| WO | WO-0009560 A2 | 2/2000 | |
| WO | WO-0032767 A1 | 6/2000 | |
| WO | WO-0042072 A2 | 7/2000 | |
| WO | WO-0187922 A2 | 11/2001 | |
| WO | WO-0244215 A2 | 6/2002 | |
| WO | WO-02060919 A2 | 8/2002 | |
| WO | WO-03074569 A2 | 9/2003 | |
| WO | WO-03077834 A2 | 9/2003 | |
| WO | WO-03100053 A1 | 12/2003 | |
| WO | WO-2004005347 A1 | 1/2004 | |
| WO | WO-2004016750 A2 | 2/2004 | |
| WO | WO-2004029207 A2 | 4/2004 | |
| WO | WO-2004035752 A2 | 4/2004 | |
| WO | WO-2004063351 A2 | 7/2004 | |
| WO | WO-2004074455 A2 | 9/2004 | |
| WO | WO-2004099249 A2 | 11/2004 | |
| WO | WO-2004101740 A2 | 11/2004 | |
| WO | WO-2005040217 A2 | 5/2005 | |
| WO | WO-2005047327 A2 | 5/2005 | |
| WO | WO-2005070963 A1 | 8/2005 | |
| WO | WO-2005077981 A2 | 8/2005 | |
| WO | WO-2005092925 A2 | 10/2005 | |
| WO | WO-2005123780 A2 | 12/2005 | |
| WO | WO-2006019447 A1 | 2/2006 | |
| WO | WO-2006047350 A2 | 5/2006 | |
| WO | WO-2006085967 A2 | 8/2006 | |
| WO | WO-2007021494 A2 | 2/2007 | |
| WO | WO-2007104529 A2 | 9/2007 | |
| WO | WO-2007112005 A2 | 10/2007 | |
| WO | WO-2007115953 A1 | 10/2007 | |
| WO | WO-2008012543 A1 | 1/2008 | |
| WO | WO-2008033413 A2 | 3/2008 | |
| WO | WO-2008143954 A2 | 11/2008 | |
| WO | WO-2008155134 A1 | 12/2008 | |
| WO | WO-2009058322 A1 | 5/2009 | |
| WO | WO-2010091122 A1 | 8/2010 | |
| WO | WO-2010140148 A1 | 8/2010 | |
| WO | WO-2010115866 A1 | 10/2010 | |
| WO | WO-2010144502 A2 | 12/2010 | |
| WO | WO-2010144508 A1 | 12/2010 | |
| WO | WO-2011028228 A1 | 3/2011 | |
| WO | WO-2011028229 A1 | 3/2011 | |
| WO | WO-2011028344 A2 | 3/2011 | |
| WO | WO-2011069164 A2 | 6/2011 | |
| WO | WO-2012006623 A1 | 1/2012 | |
| WO | WO-2012006624 A2 | 1/2012 | |
| WO | WO 2012006633 A1* | 1/2012 | C07K 14/745 |
| WO | WO-2012006633 A1 | 1/2012 | |
| WO | WO-2012006635 A1 | 1/2012 | |
| WO | WO-2012/170969 A2 | 12/2012 | |
| WO | WO-2012170969 A2 | 12/2012 | |
| WO | WO-2013009627 A2 | 1/2013 | |
| WO | WO-2013106787 A1 | 7/2013 | |
| WO | WO-2013123457 A1 | 8/2013 | |
| WO | WO-2013185113 A1 | 12/2013 | |
| WO | WO-2013185113 A2 | 12/2013 | |
| WO | WO-2013185114 A2 | 12/2013 | |

OTHER PUBLICATIONS

Andersen, L.M., et al., "Antibody-Induced Enhancement of Factor VIIa Activity Through Distinct Allosteric Pathways," The Journal of Biological Chemistry 287(12):8994-9001, American Society for Biochemistry and Molecular Biology, United States (2012).

Andrianomenjanahary, S., et al., "Synthesis of Novel Target Pro-Prodrugs of Anthracyclines Potentially Activated by a Monoclonal Antibody Galactosidase Conjugate (Part 1)," Bioorganic & Medicinal Chemistry Letters 2(9):1093-1096, Pergamon Press, England (1992).

(56) References Cited

OTHER PUBLICATIONS

Armour, K.L., et al., "Recombinant Human IgG Molecules Lacking Fcγ Receptor I Binding and Monocyte Triggering Activities," European Journal of Immunology 29(8):2613-2624, Wiley-VCH, Germany (1999).

Bertrand, P. and Gesson; J.P., "Click Chemistry with O-dimethylpropargylcarbamate for preparation of pH-sensitive functional groups. A Case Study," The Journal of Organic Chemistry 72(9):3596-3599, American Chemical Society, United States (2007).

Blencowe, C.A., et al., "Self-Immolative Linkers in Polymeric Delivery Systems," Polymer Chemistry 2(4):773-790, Royal Society of Chemistry, England (2011).

Brunetti-Pierri, N., et al., "Bioengineered Factor IX Molecules with Increased Catalytic Activity Improve the Therapeutic Index of Gene Therapy Vectors for Hemophilia B," Human Gene Therapy 20(5):479-485, Mary Ann Liebert, Inc., United States (2009).

Burmeister, W.P., et al., "Crystal structure of the complex of rat neonatal Fc receptor with Fc," Nature 372(6504):379-383, Nature Publishing Group, England (1994).

Caliceti, P., et al., "Biopharmaceutical Properties of Uricase Conjugated to Neutral and Amphiphilic Polymers," Bioconjugate Chemistry 10(4):638-646, American Chemical Society, United States (1999).

Carl, P.L., et al., "A Novel Connector Linkage Applicable in Prodrug Design," Journal of Medicinal Chemistry 24(5):479-480, American Chemical Society, United States (1981).

Chang, J., et al., "Changing Residue 338 in Human Factor IX from Arginine to Alanine Causes an Increase in Catalytic Activity," The Journal of Biological Chemistry 273(20):12089-12094, The American Society for Biochemistry and Molecular Biology, Inc., United States (1998).

Cho, J.W. and Troy, F.A. II, "Polysialic Acid Engineering: Synthesis of Polysialylated Neoglycosphingolipids by using the Polysialyltransferase from Neuroinvasive *Escherichia coli* K1," Proceedings of the National Academy of Sciences USA 91(24):11427-11431, National Academy of Sciences, United States (1994).

Delgado, C., et al., "The Uses and Properties of PEG-Linked Proteins," Critical Reviews in Therapeutic Drug Carrier Systems 9(3-4):249-304, CRC Press, Inc., United States (1992).

Dennis, M.S., et al., "Albumin Binding as a General Strategy for Improving the Pharmacokinetics of Proteins," The Journal of Biological Chemistry 277(38):35035-35043, The American Society for Biochemistry and Molecular Biology, Inc., United States (2002).

Everett, S.A., et al., "Bioreductively-Activated Prodrugs for Targeting Hypoxic Tissues: Elimination of Aspirin from 2-Nitroimidazole Derivatives," Bioorganic & Medicinal Chemistry Letters 9(9):1267-1272, Elsevier, England (1999).

Friend, P.J., et al., "Phase I Study of an Engineered Aglycosylated Humanized CD3 Antibody in Renal Transplant Rejection," Transplantation 68(11):1632-1637, Lippincott Williams & Wilkins, Inc., United States (1999).

GenBank, "*Homo sapiens* Transferrin (TF), mRNA," Accession No. NM001063.1, accessed at http://www.ncbi.nlm.nih.gov/nuccore/NM_001063, accessed on Sep. 24, 2014, 5 pages.

GenBank, "*Homo sapiens* Transferrin (TF), mRNA," Accession No. XM002793 published on May 13, 2002, accessed at https://www.ncbi.nlm.nih.gov/nuccore/XM_002793.7?report=genbank, accessed on Sep. 24, 2014, 2 pages.

GenBank, "*Homo sapiens* Transferrin (TF), mRNA," Accession No. XM039847 published on Jul. 16, 2001, accessed at https://www.ncbi.nlm.nih.gov/nuccore/XM_039847.1?report=genbank, accessed on Sep. 24, 2014, 2 pages.

GenBank, "*Homo sapiens* Transferrin (TF), mRNA," Accession No. XM039845 published on Jul. 16, 2001, accessed at https://www.ncbi.nlm.nih.gov/nuccore/XM_039845.1?report=genbank, accessed on Sep. 24, 2014, 2 pages.

GenBank, "Human Transferrin: cDNA Characterization and Chromosomal Localization," Accession No. AAA61140.1, published on Jan. 14, 1995, accessed at https://www.ncbi.nlm.nih.gov/protein/AAA61140, accessed on Jan. 15, 2015, 1 page.

GenBank, "Human Transferrin mRNA, Complete cds," Accession No. M12530.1, published on Jan. 14, 1995, accessed at https://www.ncbi.nlm.nih.gov/nuccore/M1253014, accessed on Jan. 15, 2015, 2 pages.

GenBank, "Transferrin [human, liver, mRNA, 2347 nt]," Accession No. S95936.1 published on May 7, 1993, accessed at https://www.ncbi.nlm.nih.gov/nuccore/S95936, accessed on Sep. 24, 2014, 2 pages.

Hay M.P. and Denny W.A., "A New Synthesis of Carmethizole and Related Nitrogen Analogues," Tetrahedron Letters 38(48):8425-8428, Elsevier, England (1997).

Hay, M.P., et al., "Substituent Effects on the Kinetics of Reductively-Initiated Fragmentation of Nitrobenzyl Carbamates Designed as for Bioreductive Prodrugs," Journal of the Chemical Society, Perkins Transactions 1 19:2759-2770, Royal Society of Chemistry, England (1999).

Hay, M.P., et al., "Synthesis and Evaluation of Nitroheterocyclic Carbamate Prodrugs for Use With Nitroreductase-Mediated Gene-Directed Enzyme Prodrug Therapy," Journal of Medicinal Chemistry 46(25):5533-5345, American Chemical Society, United States (2003).

Holt, L.J., et al., "Anti-Serum Albumin Domain Antibodies for Extending the Half-Lives of Short Lived Drugs," Protein Engineering, Design and Selection 21(5):283-288, Oxford University Press, England (2008).

International Preliminary Report on Patentability for International Application No. PCT/US2013/044842, International Bureau of WIPO, Switzerland, dated Dec. 9, 2014, 8 pages.

International Search Report and Written Opinion for International Application No. PCT/US2011/48517, ISA, United States, dated Mar. 14, 2012.

International Search Report for International Application PCT/US2013/044842, ISA, United States, dated Nov. 25, 2013.

Israel, E.J., et al., "Expression of the neonatal Fc receptor, FcRn, on human intestinal epithelial cells," Immunology 92(1):69-74, Blackwell Sciences, England (1997).

Kobayashi, N., et al., "FcRn-Mediated Transcytosis of Immunoglobulin G in Human Renal Proximal Tubular Epithelial Cells," American Journal of Physiology 282(2):F358-F365, American Physiological Society, United States (2002).

Konig, T. and Skerra, A., "Use of an Albumin-Binding Domain for the Selective Immobilisation of Recombinant Capture Antibody Fragments on ELISA Plates," Journal of Immunological Methods 218(1-2):73-83, Elsevier Science B.V., Netherlands (1998).

Kraulis, P.J., et al., "The Serum Albumin-Binding Domain of Streptococcal Protein G is a Three-Helical Bundle: a Heteronuclear NMR study," FEBS Letters 378(2):190-194, Federation of European Biochemical Societies, England (1996).

Linhult, M., et al., "Mutational Analysis of the Interaction Between Albumin-Binding Domain from Streptococcal Protein G and Human Serum Albumin," Protein Science 11(2):206-213, Cold Spring Harbor Laboratory Press, United States (2002).

Lusson, J., et al., "cDNA Structure of the Mouse and Rat Subtilisin/kexin-like PC5: a Candidate Proprotein Convertase Expressed in Endocrine and Nonendocrine Cells," Proceedings of the National Academy of Sciences USA 90(14):6691-6695, National Academy of Sciences, United States (1993).

McKnight, G.S., et al., "Expression of the Chicken Transferrin Gene in Transgenic Mice," Cell 34(2):335-341, Cell Press, United States (1983).

Morpurgo, M., et al., "Covalent modification of mushroom tyrosinase with different amphiphic polymers for pharmaceutical and biocatalysis applications," Applied Biochemistry and Biotechnology 56(1):59-72, Humana Press, Inc., United States (1996).

Mount, J.D., et al., "Sustained Phenotypic Correction of Hemophilia B dogs with a Factor IX Null Mutation by Liver-Directed Gene Therapy," Blood 99(8):2670-2676, The American Society of Hematology, United States (2002).

Muller, D. and Kontermann, R.E., "Recombinant Bispecific Antibodies for Cellular Cancer Immunotherapy," Current Opinion in Molecular Therapeutics 9(4):319-326, Current Drugs Ltd, England (2007).

(56) References Cited

OTHER PUBLICATIONS

Nakagawa, T., et al., "Identification and Functional Expression of a New Member of the Mammalian Kex2-like Processing Endoprotease Family: its Striking Structural Similarity to PACE4," The Journal of Biochemistry 113(2):132-135, Oxford University Press, England (1993).

Nakayama, K., "Furin: A Mammalian Subtilisin/Kex2p-like Endoprotease Involved in Processing of a Wide Variety of Precursor Proteins," Biochemical Journal 327:625-635, Biochemical Society, England (1997).

Narita, M., et al., "The Low-Density Lipoprotein Receptor-Related Protein (LRP) Mediates Clearance of Coagulation Factor Xa In Vivo," Blood 91(2):555-560, The American Society of Hematology, United States (1998).

Noel, M.J., "Nucleotide sequence of the coat protein gene and flanking regions of cucumber virus (CMV) strain 117F," Nucleic Acids Research 18(5):1332, Oxford University Press, England (1990).

Osterlund, M., et al., "Sequential coagulation factor VIIa domain binding to tissue factor," Biochemcial and Biophysical Research Communications 337(4):1276-1282, Elsevier, United States (2005).

Perry-Feigenbaum, R., et al., "The Pyridinone-Methide Elimination," Organic & Biomolecular Chemistry 7(23):4825-4828, Royal Society of Chemistry, England (2009).

Persson, E., et al., "Rational Design of Coagulation Factor VIIa Variants with Substantially Increased Intrinsic Activity," Proceedings of the National Academy of Sciences USA 98(24):13583-13588, The National Academy of Sciences, United States (2001).

Persson, E., et al., "Substitution of Valine for Leucine 305 in Factor VIIa Increases the Intrinsic Enzymatic Activity," The Journal of Biological Chemistry 276(31):29195-29199, The American Society for Biochemistry and Molecular Biology, Inc., United States (2001).

Petrovan, R.J. and Ruf, W., "Residue Met156 Contributes to the Labile Enzyme Conformation of Coagulation Factor VIIa," The Journal of Biological Chemistry 276(9):6616-6620, The American Society for Biochemistry and Molecular Biology, Inc., United States (2001).

Rautio, J., et al., "Prodrugs: Design and Clinical Applications," Nature Reviews. Drug Discovery 7(3):255-270, Nature Publishing Group, England (2008).

Rehemtulla, A., et al., "PACE4 is a Member of the Mammalian Propeptidase Family that has Overlapping but not Identical Substrate Specificity to PACE," Biochemistry 32(43):11586-11590, American Chemical Society, United States (1993).

Ritchie, K.A., et al., "Allelic Exclusion and Control of Endogenous Immunoglobulin Gene Rearrangement in Kappa Transgenic Mice," Nature 312(5994):517-520, Nature Publishing Group, England (1984).

Roovers, R.C., et al., "Efficient Inhibition of EGFR Signaling and of Tumour Growth by Antagonistic Anti-EGFR Nanobodies," Cancer Immunology, Immunotherapy 56(3):303-317, Springer Verlag, Germany (2007).

Roth, J. et al., "From Microbes to Man" in Polysialic Acid, Roth J., Rutishauser U., Troy F.A., eds., pp. 335-348, BirkhauserVerlag, Basel, Switzerland (1993).

Routledge, E.G., et al., "The Effect of Aglycosylation on the Immunogenicity of a Humanized Therapeutic CD3 Monoclonal Antibody," Transplantation 60(8):847-853, Williams & Wilkins, United States (1995).

Senter, P.D., et al., "Development of Drug-Release Strategy Based on the Reductive Fragmentation of Benzyl Carbamate Disulfides," The Journal of Organic Chemistry 55(9):2975-2978, American Chemical Society, United States (1990).

Shields, R.L., et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry 276(9):6591-6604, The American Society for Biochemistry and Molecular Biology, Inc., United States (2001).

Sichler, K., et al., "Physiological fIXa Activation Involves a Cooperative Conformational Rearrangement of the 99-Loop," The Journal of Biological Chemistry 278(6):4121-4126, The American Society for Biochemistry and Molecular Biology, Inc., United States (2003).

Simioni, P., et al., "X-Linked Thrombophilia with a Mutant Factor IX (factor IX Padua)," The New England Journal of Medicine 361(17):1671-1675, Massachusetts Medical Society, United States (2009).

Simplicio, A.L., et al., "Prodrugs for Amines," Molecules 13(3):519-547, MDPI, Switzerland (2008).

Singh, Y., et al., "Recent Trends in Targeted Anticancer Prodrug and Conjugate Design," Current Medicinal Chemistry 15(18):1802-1826, Bentham Science Publishers, Netherlands (2008).

Soejima, K., et al., "Factor VIIa Modified in the 170 Loop Shows Enhanced Catalytic Activity but Does Not Change the Zymogen-like Property," The Journal of Biological Chemistry 276(20):17229-17235, The American Society for Biochemistry and Molecular Biology, Inc., United States (2001).

Soejima, K., et al., "The 99 and 170 Loop-Modified Factor VIIa Mutants Show Enhanced Catalytic Activity Without Tissue Factor," The Journal of Biological Chemistry 277(50):49027-49035, The American Society for Biochemistry and Molecular Biology, Inc., United States (2002).

Sommermeyer, V.K., et al., "Klinisch Verwendte Hydroxyethylstarke: Physikalisch-Chemische Charakterisierung," Krankenhauspharmazie 8(8):271-278, Deutscher Apotheker Verlag, Birkenwaldstr, Germany (1987).

Spicer, E.K., et al., "Isolation of CDNA Clones Coding for Human Tissue Factor: Primary Structure of the Protein and CDNA," Proceedings of the National Academy of Sciences USA 84(15):5148-5152, National Academy of Sciences, United States (1987).

Story, C.M., et al., "A Major Histocompatibility Complex Class I-like Fc Receptor Cloned from Human Placenta: Possible Role in Transfer of Immunoglobin G from Mother to Fetus," The Journal of Experimental Medicine 180(6):2377-2381, The Rockefeller University Press, United States (1994).

Sturzebecher, J., et al., "Dramatic Enhancement of the Catalytic Activity of Coagulation Factor IXa by Alcohols," FEBS Letters 412(2):295-300, Federation of European Biochemical Societies, Netherlands (1997).

Sykes, B.M., et al., "Leaving Group Effects in Reductively Triggered Fragmentation of 4-Nitrobenzyl Carbamates ," Journal of the Chemical Society, Perkin Transactions 1 10:1601-1608, Royal Society of Chemistry, England (2000).

Taylor, L.D., et al., "Use of O- and P-Hydroxybenzyl Functions as Blocking Groups Which are Removable with Base," Journal of Organic Chemistry 43(6):1197-1200, American Chemical Society, United States (1978).

Trussel, S., et al., "New Strategy for the Extension of the Serum Half-Life of Antibody Fragments," Bioconjugate Chemistry 20(12):2286-2292, American Chemical Society, United States (2009).

Uniprot KB, accession No. P12259, Coagulation factor V, *Homo sapiens* (Human), accessed at http://www.uniprot.org/uniprot/P12259, accessed on May 15, 2015, 26 pages.

UniprotKB, accession No. P13726-1, Tissue factor, *Homo sapiens* (Human), accessed at http://www.uniprot.org.uniprot/P13726, accessed on May 15, 2015, 18 pages.

Van Den Ouweland, A.M., et al., "Structural Homology between the Human Fur Gene Product and the Subtilisin-like Protease Encoded by Yeast KEX2," Nucleic Acids Research 18(3):664, Oxford University Press, England (1990).

Vorobjev, P.E., et al., "Oligonucleotide Conjugated to Linear and Branched High Molecular Weight Polyethylene Glycol as Substrates for RNase H," Nucleosides & Nucleotides 18(11-12):2745-2750, Marcel Dekker, Inc., United States (1999).

Ward, E.S. and Ghetie V., "The Effector Functions of Immunoglobins: Implications for Therapy," Therapeutic Immunology 2(2):77-94, Blackwell Science Ltd., England (1995).

(56) References Cited

OTHER PUBLICATIONS

Wasley, L.C., et al., "PACE/Furin Can Process the Vitamin K-Dependent Pro-Factor IX Precursor with the Secretory Pathway," The Journal of Biological Chemistry 268(12):8458-8465, The American Society for Biochemistry and Molecular Biology, Inc., United States (1993).

Weidler, B., et al., "Pharmakokinetische Merkmale als Kriterien fur den klinischen Einsatz von Hydroxyethylstarke," Arzneimittel-Forschung 41(5):494-498, Editio Cantor, Germany (1991).

Weinstain, R., et al., "Real-Time Monitoring of Drug Release," Chemical Communications 46(4):553-555, Royal Society of Chemistry, England (2010).

Zogg, T. and Branstetter, H., "Structural Basis of the Cofactor- and Substrate-Assisted Activation of Human Coagulation Factor IXa," Structure 17(12):1669-1678, Cell Press, United States (2009).

Supplementary Partial European Search Report for EP Application No. 13799824.1, European Patent Office, Germany, dated Mar. 10, 2016, 11 pages.

Biogen Idec, "Hemophilia R&D Roundtable," phx.corporate-ir.net, accessed at http://www.google.de/url?sa=t&rct=j&q=&esrc=s&source=web&cd=9&ved=0ahUKEwi9rODXvpDLAhZkbZoKHbeJDXIQFghfMAg&url=http%3A%2F%2Fphx.corporate-ir.net%2FExternal.File%3Fitem%3DUGFyZW50SUQ9NDOwMDk1fENoaWxkSUQ9NDYxNzcxfFR5cGU9MQ%3D%3D%26t%3D1&usg=AFQjCNHEQPyuN7AIPzPikX2uAUL5fv5JoQ&sig2=8Ur9s6EFYDdNUXKKaqwzQ, accessed on Feb. 24, 2016, 52 pages (2011).

Dumont, J.A., et al., "Prolonged activity of a recombinant factor VIII-Fc fusion protein in hemophilia A mice and dogs," *Blood* 119(13):3024-3030, The American Society of Hematology, United States (2012).

Persson, E., "Novel molecules for the correction of factor Xa generation and phenotype in hemophilia," *Thrombosis Research* 129(Suppl 2):S51-S53, Elsevier Ltd., England (2012).

Peters, R.T., et al., "Prolonged activity of factor IX as a monomeric Fc fusion protein," *Blood* 115(10):2057-2064, American Society of Hematology, United States (2010).

Salas, J., et al., "Enhanced pharmacokinetics of factor VIIa as a monomeric Fc fusion," *Journal of Thrombosis and Haemostasis* 9(Suppl 2):268, Abstract O-TU-026, International Society on Thrombosis and Haemostasis, United States (2011).

Salas, J., et al., "Targeting factor VIIa to platelet receptors results in enhanced activity," *Journal of Thrombosis and Haemostasis* 9(Suppl 2):285, Abstract O-TU-078, International Society on Thrombosis and Haemostasis, United States (2011).

Salas, J., et al., "Enhanced pharmacokinetics of factor VIIa as a monomeric Fc fusion," *Thrombosis Research* 135:970-976, Elsevier Ltd., England (Jan. 2015).

Tan, S., et al., "Enhancing the Acute Hemostatic Efficacy in Cynomolgus Monkeys by Targeting Activated Coagulation Factor VII to Platelets," Abstract 1488, 56th ASH Annual Meeting and Exposition, San Francisco, CA, Dec. 6-9, 2014, American Society of Hematology, United States, 1 page (Dec. 2014).

Wolberg, A.S. and Mast, A.E., "Tissue factor and factor VIIa—Hemostasis and Beyond," *Thrombosis Research* 129(Suppl 2):S1-S4, Elsevier Ltd., England (2012).

Extended European Search Report for EP Application No. 13799824.1, European Patent Office, Germany, dated Jul. 7, 2016, 14 pages.

Bajaj, S.P., et al., "Redetermination of the Rate-Limiting Step in the Activation of Factor IX by Factor XIa and by Factor VIIa/tissue Factor. Explanation for Different Electrophoretic Radioactivity Profiles Obtained on Activation of 3H- and 125I-labeled Factor IX," Biochemistry 22(17):4047-4053, American Chemical Society, United States (1983).

Bovenschen N., et al., "LDL Receptor Cooperates with LDL Receptor-Related Protein in Regulating Plasma Levels of Coagulation Factor VIII in Vivo," Blood 106(3):906-912, The American Society of Hematology, United States (2005).

Bovenschen, N., "LDL Receptor Polymorphisms Revisited," Blood 116(25):5439-5440, The American Society of Hematology, United States (2010).

Brady, S.F., et al., "Design and Synthesis of a Pro-Drug of Vinblastine Targeted at Treatment of Prostate Cancer with Enhanced Efficacy and Reduced Systemic Toxicity," Journal of Medicinal Chemistry 45(21):4706-4715, American Chemical Society, United States (2002).

Brandstetter, H., et al., "X-Ray Structure of Clotting Factor IXa: Active Site and Module Structure Related to Xase Activity and Hemophilia B," Proceedings of the National Academy of Sciences of the United States of America 92(21):9796-9800, The National Academy of Sciences, United States (1995).

Bunce, M.W., et al., "Zymogen-like: Factor Xa Variants Restore Thrombin Generation and Effectively Bypass the Intrinsic Pathway in vitro," Blood 117(1): 290-298, The American Society of Hematology, United States (2011).

Capon, D.J., et al., "Designing CD4 Immunoadhesins for AIDS Therapy," Nature 37(6207):525-531, Nature Publishing Group, England (1989).

Cripe, L.D., et al., "Structure of the gene for human coagulation factor V," Biochemistry 31(15):3777-3785, American Chemical Society, United States (1992).

De Groot, F.M., et al., "Elongated Multiple Electronic Cascade and Cyclization Spacer Systems in Activatible Anticancer Prodrugs for Enhanced Drug Release," The Journal of Organic Chemistry 66(26):8815-8830, American Chemical Society, United States (2001).

Doronina, S.O., et al., "Development of Potent Monoclonal Antibody Auristatin Conjugates for Cancer Therapy," Nature Biotechnology 21(7):778-784, Nature America Publishing, United States (2003).

Eaton, D., et al., "Proteolytic Processing of Human Factor VIII. Correlation of Specific Cleavages by Thrombin, Factor Xa, and Activated Protein C with Activation and Inactivation of Factor VIII Coagulant Activity," Biochemistry 25(2):505-512, American Chemical Society, United States (1986).

Eaton, D.L., et al., "Construction and Characterization of an Active Factor VIII Variant Lacking the central One-Third of the Molecule," Biochemistry 25(26):8343-8347, American Chemical Society, United States (1986).

English language Abstract of European Patent Publication No. EP0295597A2, European Patent office, Espacenet database—Worldwide (1988).

Extended European Search Report for EP Application No. 13799785.4, European Patent Office, Germany, dated Aug. 25, 2016, 15 pages. (Outstanding EESR in 4159.389EP02).

Fay, P.J., et al., "Human Factor VIIIa Subunit Structure. Reconstruction of Factor VIIIa from the Isolated A1/A3-C1-C2 Dimer and A2 Subunit," The Journal of Biological Chemistry 266(14):8957-8962, The American Society for Biochemistry and Molecular Biology, Inc., United States (1991).

Gallwitz, M., et al., "The Extended Cleavage Specificity of Human Thrombin," PLoS One 7(2):e31756, Public Library of Science, United States (2012).

Geys, J., et al., "Acute Toxicity and Prothrombotic Effects of Quantum Dots: Impact of Surface Charge," Environonrnental Health Perspectives 116(12):1607-1613, National Institute of Environmental Health Sciences, United States (2008).

Gitschier, J., et al., "Characterization of the Human Factor VIII Gene," Nature 312(5992):326-330, Nature Publishing Group, England (1984).

Greenwald, R.B., et al., "Drug Delivery Systems Based on Trimethyl Lock Lactonization: Poly(Ethylene Glycol) Prodrugs of Amino-Containing Compounds," Journal of Medicinal Chemistry 43(3):475-487, American Chemical Society, United States (2000).

Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (1990).

International Preliminary Report on Patentability for International Application No. PCT/US2013/044841, International Bureau of WIPO, Switzerland, dated Dec. 9, 2014, 14 pages.

(56) References Cited

OTHER PUBLICATIONS

International Search Report and Written Opinion for International Application No. PCT/US2013/044841, International Searching Authority, Alexandria, Virginia, USA, dated Nov. 20, 2013, 18 pages.
Izquierdo, C. and Burguillo, F.J., "Synthetic Substrates for Thrombin," International Journal of Biochemistry 21(6):579-592 Pergamon Press, England (1989).
Jaffer, F.A., et al., "In Vivo Imaging of Thrombin Activity in Experimental Thrombi With Thrombin-Sensitive Near-Infrared Molecular Probe," Arteriosclerosis, Thrombosis and Vascular Biology 22(11):1929-1935, Lippincott Williams & Wilkins, United States (2002).
Jenny, R.J., et al., "Complete cDNA and Derived Amino acid Sequence of Human Factor V," Proceedings of the National Academy of Sciences USA 84(14):4846-4850, National Academy of Sciences, United States (1987).
Kane, W.H. and Davie, E.W., "Cloning of a cDNA Coding for Human Factor V, a Blood Coagulation Factor Homologous to Factor VIII and Ceruloplasmin," Proceedings of the National Academy of Sciences USA 83(18):6800-6804, National Academy of Sciences, United States (1986).
Kohchi, Y., et al., "Design and Synthesis of Novel Prodrugs of 2'-Deoxy-2'-Methylidenecytidine Activated by Membrane Dipeptidase Overexpressed in Tumor Tissues," Bioorganic & Medicinal Chemistry Letters 17(8):2241-2245, Elsevier Science Ltd, England (2007).
Langner, K-D., et al., "Synthesis of Biologically Active Deletion Mutants of Human Factor VIII:C," Behring Institute Mitteilungen 82: 16-25, Behringwerke AG, Germany (1988).
Lenting, P.J., et al., "Biochemistry of FVIII and Inhibitors: The Disappearing Act of Factor VIII," Haemophilia 16(102):6-15, Blackwell Publishing Ltd, England (2010).
Lin, C.N., et al., "Generation of a Novel Factor IX with Augmented Clotting Activities in Vitro and in Vivo," Journal of Thrombosis and Haemostasis 8(8):1773-1783, International Society on Thrombosis and Haemostasis, England (2010).
Lollar, P. and Parker, E.T., "Structural Basis for the Decreased Procoagulant Activity of Human Factor VIII Compared to the Porcine Homolog," Journal of Biological Chemistry 266(19):12481-12486, The American Society for Biochemistry and Molecular Biology, Inc., United States (1991).
Louvain-Quintard, V.B., et al., "Thrombin-activable Factor X Reestablishes an Intrinsic Amplification in Tenase-deficient Plasmas," The Journal of Biological Chemistry 280(50):41352-41359, The American Society for Biochemistry and Molecular Biology, Inc., United States (2005).
Martinelli, N., et al., "Polymorphisms at LDLR Locus may be Associated with Coronary Artery Disease through Modulation of Coagulation Factor VIII Activity and Independently from Lipid Profile," Blood 116(25):5688-5697, The American Society of Hematology, United States (2010).
Mei, B., et al., "Rational Design of a Fully active, Long-Acting PEGylated Factor VIII for Hemophilia A Treatment," Blood 116(2):270-279, The American Society of Hematology, United States (2010).
Meulien, P., et al., "A New Recombinant Procoagulant Protein Derived from the cDNA Encoding Human Factor VIII," Protein Engineering 2(4):301-306, IRL Press Ltd., England (1988).
Meyer, Y., et al., "A Comparative Study of the Self-Immolation of para-Aminobenzylalcohol and Hemithioaminal-Based Linkers in the Context of Protease-Sensitive Fluorogeinc Probes," Organic & Biomolecular Chemistry 8(8):1777-1780, Royal Society of Chemistry, England (2010).
Pan, J., et al., "Enhanced Efficacy of Recombinant FVIII in Noncovalent Complex with PEGylated Liposome in Hemophilia A Mice," Blood 114(13):2802-2811, The American Society of Hematology, United States (2009).
Partial Supplementary European Search Report for EP Application No. 13799785.4, European Patent Office, Germany, dated May 3, 2016, 7 pages.

Peterson, J.A., et al., "A site Involving the "hybrid" and PSI Homology Domains of GPIIIa (beta 3-integrin subunit) is a Common Target for Antibodies Associated with Quinine-Induced Immune Thrombocytopenia," Blood 101(3):937-942, The American Society of Hematology, United States (2003).
Peyvandi, F., et al., "Genetic Diagnosis of Gaemophilia and Other Inherited Bleeding Disorders," Haemophilia 12(Suppl 3):82-89, Blackwell Publishing Ltd., England (2006).
Rijkers, D.T., et al., "Design and Synthesis of Thrombin Substrates With Modified Kinetic Parameters," Thrombosis Research 79(5-6):491-499, Pergamon Press., United States (1995).
Rostin, J., et al., "B-Domain Deleted Recombinant Coagulation Factor VIII Modified with Monomethoxy Polyethylene Glycol," Bioconjugate Chemistry 11(3):387-396, American Chemical Society, United States (2000).
Sarver, N., et al., "Stable Expression of Recombinant Factor VIII Molecules Using a Bovine Papillomavirus Vector," DNA 6(6):553-564, Mary Ann Liebert, Inc., United States (1987).
Schulte, S., "Use of Albumin: Fusion. Technology to Prolong the Half-Life of Recombinant Factor VIIa," Thrombosis Research 122(Suppl 4):S14-S19, Pergamon Press, United States (2008).
Schwarz, M., et al., "Conformation-Specific Blockade of the Integrin GPIIb/IIIa: a Novel Antiplatelet Strategy that Selectively Targets Activated Platelets," Circulation Research 99(1):25-33, American Heart Association, Inc., United States (2006).
Spira, J., et al., "Prolonged Bleeding-Free Period Following Prophylactic Infusion of Recombinant Factor VIII Reconstituted With Pegylated Liposomes," Blood 108(12):3668-3673, The American Society of Hematology, United States (2006).
Spitzer, S.G., et al., "Replacement of Isoleucine-397 by Threonine in the Clotting Proteinase Factor IXa (Los Angeles and Long Beach variants) Affects Macromolecular Catalysis but not L-Tosylarginine Methyl Ester Hydrolysis. Lack of Correlation between the ox Brain Prothrombin Time and the Mutation Site in the Variant Proteins," The Journal of Biological Chemistry 265(1):219-225, The American Society of Biochemistry and Molecular Biology, Inc., United States (1990).
Stennicke, H.R., et al., "Generation and Biochemical Characterization of GlycoPEGylated Factor VIIa Derivatives," Thrombosis and Haemostasis 100(5):920-928, Schattauer GmbH, Germany (2008).
Strickland, D.K. and Medved, L., "Low-Density Lipoprotein Receptor-Related Protein (LRP)-Mediated Clearance of Activated Blood Coagulation Co-Factors and Proteases: Clearance Mechanism or Regulation?," Journal of Thrombosis and Haemostasis 4(7):1484-1486, International Society on Thrombosis and Haemostasis, England (2006).
Stubbs, J.D., et al., "cDNA Cloning of a Mouse Mammary Epithelial Cell Surface Protein Reveals the Existence of Epidermal Growth Factor-like Domains Linked to Factor VIII-Like Sequences," Proceedings of the National Academy of Sciences 87(21):8417-8421, The National Academy of Sciences of the United States (1990).
Takahashi, N., et al., "Single-Chain Structure of Human Ceruplasmin: the Complete Amino Acid Sequence of the Whole Molecule," Proceedings of the National Academy of Sciences 81(2):390-394, National Academy of Sciences, United States (1984).
Tanihara, M., et al., "Thrombin-Sensitive Peptide Linkers for Biological Signal-Responsive Drug Release Systems," Peptides 19(3):421-425, Elsevier Science Inc., United States (1998).
Toole, J.J., et al., "A Large Region (≈95 kDa) of Human Factor VIII is Dispensable for in vitro Procoagulant Activity," Proceedings of the National Academy of Sciences USA 83(16):5939-5942, National Academy of Sciences, United States (1986).
Toole, J.J., et al., "Molecular Cloning of a cDNA Encoding Human Antihaemophilic Factor," Nature 312(5992):342-347, Nature Publishing Group, England (1984).
Tung, C.H., et al., "A Novel Near-Infrared Fluorescence Sensor for Detection of Thrombin Activation in Blood," European Journal of Chemical Biology 3(2-3):207-211, Wiley-VCH Verlag, Germany (2002).
Vehar, G.A., et al., "Structure of Human Factor VIII," Nature 312(5992):337-342, Nature Publishing Group, England (1984).

(56) References Cited

OTHER PUBLICATIONS

Vysotchin, A., et al., "Domain structure and domain-domain interactions in human coagulation factor IX," The Journal of Biological Chemistry 268(12):8436-8446, The American Society for Biochemistry and Molecular Biology, Inc., United States (1993).
Wolf, D.L. et al. "Procoagulant Activity of Reversibly Acylated Human Factor Xa," Blood 86(11):4153-4157, The American Society of Hematology, United States (1995).
Non-Final Office Action dated Dec. 8, 2016, in U.S. Appl. No. 14/406,163, inventors Hong V., et al., filed Dec. 5, 2014.
Non-Final Office Action dated Jul. 20, 2015, in U.S. Appl. No. 13/809,287, inventors Salas J., et al., filed Apr. 29, 2013.
Final Office Action dated Jan. 21, 2016, in U.S. Appl. No. 13/809,287, inventors Salas J., et al., filed Apr. 29, 2013.
Non-Final Office Action dated Sep. 28, 2016, in U.S. Appl. No. 13/809,287, inventors Salas J., et al., filed Apr. 29, 2013.
Non-Final Office Action dated Nov. 13, 2015, in U.S. Appl. No. 14/125,040, inventors Thorn K., et al., filed May 13, 2014.
Non-Final Office Action dated Dec. 27, 2011, in U.S. Appl. No. 12/949,564, inventors Rivera D., et al., filed Nov. 18, 2010.
Final Office Action dated May 16, 2012, in U.S. Appl. No. 12/949,564, inventors Rivera D., et al., filed Nov. 18, 2010.
Final Office Action dated Apr. 5, 2017, in U.S. Appl. No. 14/406,163, inventors Hong V., et al., filed Dec. 5, 2014.
Non-Final Office Action dated Dec. 22, 2017, in U.S. Appl. No. 14/406,163, inventors Hong V., et al., filed Dec. 5, 2014.
Final Office Action dated Jun. 26, 2018, in U.S. Appl. No. 14/406,163, inventors Hong V., et al., filed Jun. 7, 2013.

\* cited by examiner

FIG. 8 FVII-133 activity in human hemophilia A blood by ROTEM assays

CHIMERIC CLOTTING FACTORS

REFERENCE TO A SEQUENCE LISTING SUBMITTED ELECTRONICALLY VIA EFS-WEB

The content of the electronically submitted sequence listing (Name: 4159.3920004_SeqListing_ST25.txt; Size: 136,761 bytes; and Date of Creation: Aug. 29, 2018) is herein incorporated by reference in its entirety.

BACKGROUND OF THE INVENTION

Initiation of the extrinsic clotting pathway is mediated by the formation of a complex between tissue factor, which is exposed as a result of injury to a vessel wall, and Factor VIIa. This complex then converts Factors IX and X to their active forms (Factor IXa and Xa). Factor Xa converts limited amounts of prothrombin to thrombin on the tissue factor-bearing cell. This resulting thrombin is then able to diffuse away from the tissue-factor bearing cell and activate platelets, and Factors V and VIII, making Factors Va and VIIIa. During the propagation phase of coagulation, Factor Xa is generated by Factor IXa (in complex with factor VIIIa) on the surface of activated platelets. Factor Xa, in complex with the cofactor Factor Va, activates prothrombin into thrombin, generating a thrombin burst. The cascade culminates in the conversion of fibrinogen to fibrin by thrombin, which results in the formation of a fibrin clot. Factor VII and tissue factor are key players in the initiation of blood coagulation.

Factor VII is a plasma glycoprotein that circulates in blood as a single-chain zymogen, which is catalytically inactive. Although single-chain Factor VII may be converted to two-chain Factor VIIa by a variety of factors in vitro, Factor Xa is an important physiological activator of Factor VII. The conversion of zymogen Factor VII into the activated two-chain molecule occurs by cleavage of the peptide bond linking the Arginine residue at amino acid position 152 and the Ile residue at amino acid position 153. In the presence of tissue factor, phospholipids and calcium ions, the two-chain Factor VIIa activates Factor X or Factor IX. Factor VIIa is thought to be the physiologic initiator of the clotting cascade by acting at the surface of a TF-bearing cell and generating the initial amount of thrombin that then diffuses to platelets to activate and prime them for the propagation phase of thrombin generation. Therapeutically, recombinant FVIIa acts by activating Factor X on the surface of activated platelets, bypassing the need for FIXa or FVIIIa to generate a thrombin burst during the propagation phase of coagulation. Since FVIIa has relatively low affinity for platelets, recombinant FVIIa is dosed at supra-physiological levels. This process is thought to be tissue factor-independent.

Factor X is also synthesized as a single-chain polypeptide containing the light and heavy chains connected by an Arg-Lys-Arg tripeptide. The single-chain molecule is then converted to the light and heavy chains by cleavage of two (or more) internal peptide bonds. In plasma, these two chains are linked together by a disulfide bond, forming Factor X. Activated Factor X, Factor Xa, participates in the final common pathway whereby prothrombin is converted to thrombin, which in turn converts fibrinogen to fibrin.

Clotting factors have been administered to patients to improve hemostasis for some time. The advent of recombinant DNA technology has significantly improved treatment for patients with clotting disorders, allowing for the development of safe and consistent protein therapeutics. For example, recombinant activated factor VII has become widely used for the treatment of major bleeding, such as that which occurs in patients having haemophilia A or B, deficiency of coagulation Factors XI or VII, defective platelet function, thrombocytopenia, or von Willebrand's disease.

Although such recombinant molecules are effective, there is a need for improved versions which localize the therapeutic to sites of coagulation, have improved pharmacokinetic properties, have reduced clearance rates, have improved manufacturability, have reduced thrombogenicity, or have enhanced activity, or more than one of these characteristics.

SUMMARY OF THE INVENTION

The present invention provides a chimeric protein comprising (i) an activatable clotting factor (Ac), (ii) an enhancer moiety (Em), and (iii) an optionally linker moiety (L or L1) between the activatable clotting factor and the enhancer moiety. The activatable clotting factor and the enhancer moiety can be linked or associated with each other, but may not be chemically crosslinked. The chimeric protein can be represented by formula Ac-L-Em or Em-L-Ac, wherein Ac comprises the activatable clotting factor; L comprises the optional linker moiety; and Em comprises the enhancer moiety.

In one embodiment, the activatable clotting factor comprises a clotting factor zymogen comprising a heavy chain (HC) and a light chain (LC) and a protease-cleavage site inserted between the HC and the LC. The clotting factor zymogen can be a FVII protein (e.g., FVII, functional fragments, derivatives, or variants thereof) or a FX protein (FX, functional fragments, derivatives, or variants thereof). Embodiments of the present invention include a chimeric protein further comprising a self-immolative moiety (e.g., PABC) inserted between the protease-cleavage site and the HC. The protease-cleavage site inserted between the HC and the LC can be cleaved by a protease selected from thrombin (factor IIa), factor XIa, factor XIIa, kallikrein, factor VIIa, factor IXa, factor Xa, or any combinations thereof, wherein the protease-cleavage site is not naturally occurring in the clotting factor zymogen.

In another embodiment, the enhancer moiety comprises a clotting cofactor, a procoagulant peptide, or an antigen-binding moiety. Examples of the clotting cofactors include, but are not limited to, Tissue Factor, a fragment (e.g., soluble tissue factor), a variant, or a derivative thereof or FVa, a fragment, a variant, or derivative thereof. Non-limiting examples of the antigen binding moiety include an antibody or an antigen-binding fragment thereof which is capable of binding to the FVII protein or the FX protein and enhances the activity of FVII or FX, respectively.

In some embodiments, the chimeric protein further comprises a heterologous moiety (Het) (e.g., a half-life extender) linked to the activatable clotting factor, the linker moiety, or the enhancer moiety. Non-limiting examples of the half-life extender include an immunoglobulin constant region or a portion thereof (e.g., an Fc moiety or an FcRn binding partner), albumin, transferrin, an albumin binding moiety, a PAS sequence, an XTEN sequence, a HES sequence, the β subunit of the C-terminal peptide (CTP) of human chorionic gonadotropin, polyethylene glycol (PEG), hydroxyethyl starch (HES), albumin-binding small molecules, or any combinations thereof. The immunoglobulin constant region or a portion thereof can comprise an Fc moiety or an FcRn binding partner.

In other embodiments, the chimeric protein comprises a first heterologous moiety (Het1) and a second heterologous moiety (Het2). Either or both of Het1 and Het2 can comprise a half-life extender, e.g., an immunoglobulin constant region or a portion thereof (e.g., an Fc moiety or an FcRn binding partner), albumin, transferrin, an albumin binding moiety, a PAS sequence, an XTEN sequence, a HES sequence, the β subunit of the C-terminal peptide (CTP) of human chorionic gonadotropin, polyethylene glycol (PEG), hydroxyethyl starch (HES), albumin-binding small molecules, or any combinations thereof. Optionally, in certain embodiments, the first heterologous moiety is linked to the activatable clotting factor via a first linker (L1), and the second heterologous moiety is linked to an enhancer moiety via a second linker (L2). The chimeric protein may comprise only one linker (either L1 or L2) or both linkers.

In yet other embodiments, the chimeric protein comprises a first polypeptide chain and a second polypeptide chain, wherein the first polypeptide chain comprises the activatable clotting factor (Ac) and the second polypeptide chain comprises the enhancer moiety (Em), wherein the first polypeptide chain and the second polypeptide chain are associated with each other. For example, the first polypeptide chain can comprise the activatable clotting factor (Ac), the first heterologous moiety (Het1), and the first optional linker moiety (L1), and the second polypeptide chain can comprise the enhancer moiety (Em), the second heterologous moiety (Het2), and the second optional linker moiety (L2), wherein the first polypeptide chain and the second polypeptide chain are associated with each other.

In still other embodiments, the chimeric protein has a structure selected from:
(a) Ac linked to Het1 via the linker moiety, and Em linked to Het2;
(b) Ac linked to Het1 via the first linker moiety, and Em linked to Het2 via the second linker moiety;
(c) Ac linked to Het1, and Em linked to Het2 via the linker moiety;
(d) Ac linked to Het1, and Em linked to Het2;
(e) Em linked to Het1 via the linker moiety, and Ac linked to Het2;
(f) Em linked to Het1 via the first linker moiety, and Ac linked to Het2 via the second linker moiety;
(g) Em linked to Het1, and Ac is linked to Het2 via the linker moiety; or,
(h) Em linked to Het1, and Ac linked to Het2.

In yet other embodiments, the chimeric protein comprising two polypeptide chains can comprise:
(a) the first polypeptide comprises a structure represented by the formula Ac-L1-Het1, and the second polypeptide comprises a structure represented by the formula Em-Het2;
(b) the first polypeptide comprises a structure represented by the formula Ac-L1-Het1, and the second polypeptide comprises a structure represented by the formula Em-L2-Het2;
(c) the first polypeptide comprises a structure represented by the formula Ac-Het1, and the second polypeptide comprises a structure represented by the formula Em-Het2;
(d) the first polypeptide comprises a structure represented by the formula Ac-Het1, and the second polypeptide comprises a structure represented by the formula Em-L1-Het2;
(e) the first polypeptide comprises a structure represented by the formula Em-L2-Het1, and the second polypeptide comprises a structure represented by the formula Ac-L1-Het2;
(f) the first polypeptide comprises a structure represented by the formula Em-L1-Het1, and the second polypeptide comprises a structure represented by the formula Ac-Het2;
(g) the first polypeptide comprises a structure represented by the formula Em-Het1, and the second polypeptide comprises a structure represented by the formula Ac-Het2; and,
(h) the first polypeptide comprises a structure represented by the formula Em-Het1, and the second polypeptide comprises a structure represented by the formula Ac-L1-Het2; wherein Het1 and Het2 of the two polypeptide chains form a disulfide bond.

In some embodiments, the chimeric protein is a single polypeptide chain. For example, the chimeric protein can further comprise a scFc linker (X) linked to the enhancer moiety and the first heterologous moiety linked to the activatable clotting factor or the activatable clotting factor and the second heterologous moiety linked to the enhancer moiety. Examples of the single chain chimeric protein can comprise a formula selected from:
(1) Ac-Het1-X-Em-Het2;
(2) Ac-Het1-X-Em-L2-Het2;
(3) Ac-L1-Het1-X-Em-Het2;
(4) Ac-L1-Het1-X-Em-L2-Het2;
(5) Het2-Em-X-Het1-Ac;
(6) Het2-L2-Em-X-Het1-Ac;
(7) Het2-Em-X-Het1-L1-Ac; or
(8) Het2-L2-Em-X-Het1-L1-Ac,
wherein (a) Ac is the activatable clotting factor, (b) L1 is the first optional linker moiety; (c) Het1 is the first heterologous moiety; (d) X is the scFc linker; (e) Em is the enhancer moiety; (f) L2 is the optional second linker moiety; (g) Het2 is the second heterologous moiety, and (h) (–) is a peptide bond or one or more amino acids. In one embodiment, the scFc linker is a processable linker (cscFc), which comprises at least one intracellular processing site. The processable linker may be processed into two or more polypeptide chains by one or more intracellular processing enzymes selected from a yeast Kex2, PCSK1, PCSK2, PCSK3, PCSK4, PCSK5, PCSK6, PCSK7, or any combinations thereof. In one embodiment, the intracellular processing site is processed by PCSK5.

In some embodiments, the chimeric protein is polysialylated, pegylated, glycosylated, hesylated, gamma-carboxylated, or any combinations thereof.

Also included is a nucleic acid molecule encoding the chimeric protein or a complement thereof, a set of nucleic acid molecules comprising a first nucleotide sequence (NA1) and a second nucleotide sequence (NA2), wherein NA1 encodes the first polypeptide of the two chain chimeric protein or a complement thereof, and NA2 encodes the second polypeptide of the two chain chimeric protein or a complement thereof, the vectors comprising the nucleic acid molecule or the set of nucleic acid molecules, or the host cell comprising the vector or the set of vectors.

The invention is also directed to a pharmaceutical composition comprising the chimeric protein, the nucleic acid molecule, the vector, and the host cell and to methods for treating, ameliorating, or preventing a bleeding disease or disorder in a subject in need thereof comprising administering to the subject an effective amount of the chimeric protein, the nucleic acid molecule or the set of nucleic acid molecules, the vector or the set of vectors, the host cell, or a pharmaceutical composition. The bleeding disease or disorder treatable or preventable by the composition is selected from hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath. The composition of the present invention can also be used to treat, ameliorate, or prevent a coagulation factor deficiency in a mammalian subject comprising administering to the subject an effective amount of the chimeric protein, the nucleic acid molecule or the set of nucleic acid molecules, the vector or the set of vectors, the host cell, or the pharmaceutical composition, wherein the coagulation factor is selected from FVII, FVIIa, FVIII, FIX, or FXI.

In a specific embodiment, the chimeric protein or the composition is used to treat, ameliorate, or prevent a bleeding disease or disorder in a bypass therapy. In the bypass therapy, the subject may have developed or may be subject to develop an inhibitor against Factor VIII.

The invention also includes methods of producing a chimeric protein comprising expressing a nucleotide sequence encoding the single chain chimeric protein, which comprises a scFc linker, wherein the scFc linker is cleaved intracellularly by an intracellular processing enzyme. The chimeric protein produced by the nucleotide sequence would comprise two polypeptide chains due to the processing of the intracellular processing site.

BRIEF DESCRIPTION OF THE DRAWINGS

FIG. 1A shows a FVII or FX light chain with optional activation peptide for FX linked to a coagulation cascade protease cleavage site (e.g., thrombin cleavage site or FXIa cleavage site), which is further linked to a FVII or FX heavy chain. The FVII or FX heavy chain is then linked to an enhancer moiety via a linker. When the construct in FIG. 1A is dosed as a zymogen (non-active form), the construct is resistant to protease inhibitors upon administration (prior to activation). When the clotting factors are activated at the site of an injury as shown in FIG. 1B, the clotting factors can display high activity stimulated by the enhancer moiety.

FIG. 2A shows a FVII light chain linked to a thrombin cleavage site, which is further linked to a FVII heavy chain. The FVII heavy chain is then linked to an enhancer moiety via a linker, resulting in a non-active and zymogen form. When dosed in animals, this zymogen is resistant to protease inhibitors in the circulation and can be converted to the activated form (FIG. 2B) at the site of an injury. Activity of the clotting factors can be stimulated by an enhancer moiety. Examples for the enhancer moieties include soluble tissue factor (sTF), procoagulant peptides and antibody fragments.

FIG. 4A (left construct) shows a single polypeptide sequence encoding a FVII light chain, a thrombin cleavage site (ALRPR (SEQ ID NO: 1)), a FVII heavy chain, a first linker, a first Fc moiety (Het1), a first intracellular processing site (e.g., RRRR (SEQ ID NO: 2)), a second linker, a second intracellular processing site (e.g., RKRRKR (SEQ ID NO: 3)), sTF, a third linker, and a second Fc moiety (Het2) in the N-terminus to C-terminus order. A nucleotide sequence (FVIII-133) encoding the single polypeptide sequence can be expressed in a host cell, and the single polypeptide sequence undergoes intracellular processing such that the first intracellular processing site and the second intracellular processing site are cleaved by a propeptide endopeptidase, e.g., PCSK5. The second linker interposed between the first intracellular processing site and the second intracellular processing site can thus be removed by PCSK5. FIG. 4B shows the final construct, after the linker is removed by processing, which may contain a portion of the intracellular processing site which remains after cleavage. This remaining linker portion may comprise a series of amino acids from about 1 to about 10, 1 to about 4. FIG. 4C shows an SDS-PAGE of the thrombin-activatable FVII-Fc/sTF-Fc chimeric protein under either non-reducing condition or reducing condition as indicated.

FIGS. 7A and 7B show clotting time and alpha angle for FVII-133. FIGS. 7C and 7D show clotting time and alpha angle of FVIIaFc and vehicle respectively.

FIGS. 8A, 8B, and 8C show a graph of the results of the clotting time, clotting formation time, and alpha angle, respectively. FVIIa was used as a control for FVIIa activity.

FIG. 22A shows a cleavable polypeptide comprising FVIILC (FVII light chain)-Proprotein Convertase Processing Site by a proprotein convertase (e.g., PACE processing site, e.g., 2×(RKR) (SEQ ID NO: 3))-Linker1-SUMO-Truncated FVIIHC (FVII heavy chain without IVGGKV (SEQ ID NO: 60) at the N-terminus)-Linker2-Fc Region2-Linker3-Fc Region2. FIG. 22B shows a schematic diagram of a cleavable polypeptide that has been processed by PACE. The processed cleavable polypeptide comprises two polypeptide chains, the first chain comprising FVIILC linked to the Proprotein Convertase processing site and the second chain comprising Linker1-SUMO-Truncated FVIIHC (FVII heavy chain without IVGGKV (SEQ ID NO: 60) at the N-terminus)-Linker2-Fc Region1-Linker3-Fc Region2.

FIG. 23A is identical to the construct in FIG. 22B. FIG. 23B shows that, after FVII-186 is cleaved by a SUMO protease, the resulting cleaved polypeptide construct comprises two chains, the first chain comprising FVIILC and Proprotein Convertase Site and the second chain comprising Truncated FVIIHC (FVII heavy chain without IVGGKV (SEQ ID NO: 60) at the N-terminus)-Linker2-Fc Region1-Linker3-Fc Region2. The first chain and the second chain are bound by a disulfide bond. FIG. 23C shows that after the cleaved polypeptide construct in FIG. 23B is ligated with a thioester peptide (D-Phe-Pip-Arg-PABC-IVGGKV-COSBn), the resulting construct comprises two polypeptide chains, the first chain comprising FVIILC and Proprotein Convertase Processing Site and the second chain comprising Thrombin cleavage site—FVIIHC (FVII heavy chain)-Linker2-Fc Region1-Linker3-Fc Region2 (TA-FVII-186).

DETAILED DESCRIPTION OF THE INVENTION

Figure 1:
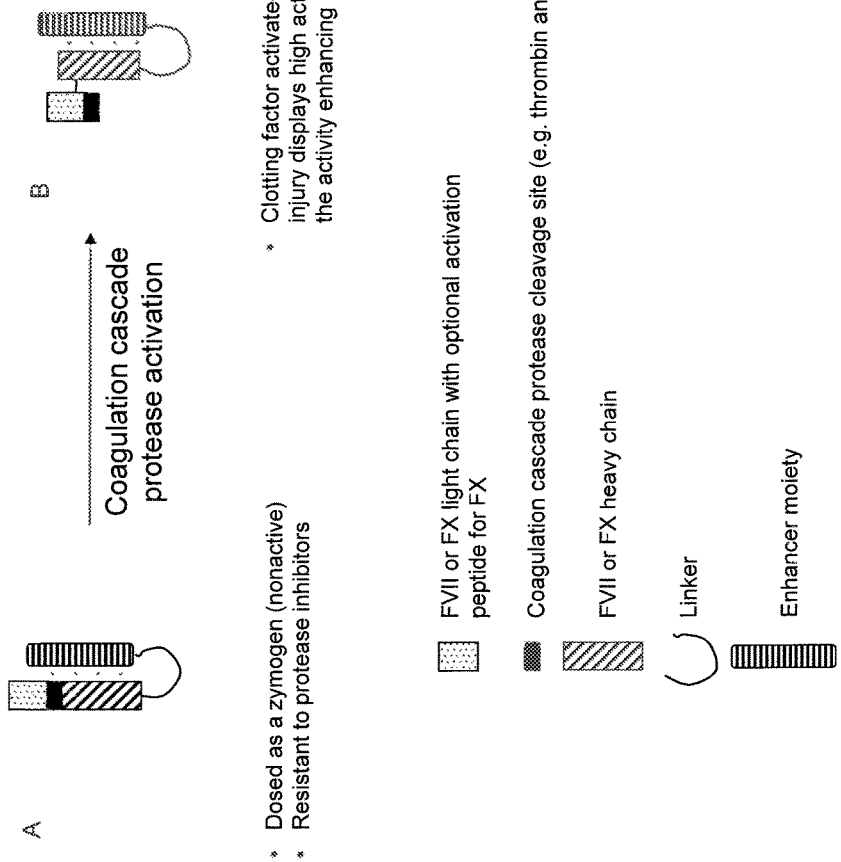
FIG. 1 illustrates a schematic diagram of an exemplary chimeric protein (e.g., a chimeric clotting factor) comprising a thrombin-activatable or FXIa-activatable clotting factor and an enhancer moiety (sometimes referred to as "an activity enhancing moiety").

The present invention relates to chimeric proteins comprising an activatable clotting factor and an enhancer moiety. The present invention is based, at least in part, on the development of novel ways to enhance the efficacy, pharmacokinetic properties, and/or manufacturability of clotting factors. The activatable clotting factor is in a form that is activatable at the site of coagulation. For use in bypass therapy, exogenous clotting factors are only efficacious when given in the activated form. However, such activated clotting factors are rapidly inactivated by endogenous pathways (e.g. antithrombin III, TFPI), leading to their fast clearance and a short effective half-life in circulation. Giving higher doses does not solve this problem as it can result in thrombogenic effects. Thus, in one embodiment, the invention pertains to an activity-enhanced chimeric protein constructs which comprise an activatable clotting factor fused to or associated with an enhancer moiety. The "activatable" clotting factor comprises a heavy chain and a light chain of a clotting factor zymogen and a heterologous protease cleavage site (i.e., not naturally occurring in the clotting factor zymogen) inserted between the heavy chain and the light chain. These molecules circulate as enhanced zymogen fusion proteins and have a longer half-life than their activated counterparts due to the lack of inactivation, but can readily be activated at the site of clotting due to the cleavage of the heavy chain and the light chain by a protease that is activated or localized at the site of clotting. Incorporating an enhancer moiety can also improve their procoagulant activities.

Exemplary constructs of the invention are illustrated in the accompanying Figures and sequence listing. In one embodiment, the invention pertains to a polypeptide having the structure as set forth in the Figures. In another embodiment, the invention pertains to a polypeptide having the sequence set forth in the accompanying sequence listing or the nucleic acid molecule encoding such polypeptides. In one embodiment, the invention pertains to a mature form of a polypeptide having the sequence set forth in the accompanying sequence listing. It will be understood that these constructs and nucleic acid molecules encoding them can be used to improve hemostasis in a subject.

In order to provide a clear understanding of the specification and claims, the following definitions are provided below.

I. Definitions

As used herein, the term "protein" or "polypeptide" refers to a polymer of two or more of the natural amino acids or non-natural amino acids.

The term "amino acid" includes alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (Ile or I): leucine (Leu or L); lysine (Lys or K); methionine (Met or M); phenylalanine (Phe or F); proline (Pro or P); serine (Ser or S); threonine (Thr or T); tryptophan (Trp or W); tyrosine (Tyr or Y); and valine (Val or V). Non-traditional amino acids are also within the scope of the invention and include norleucine, omithine, norvaline, homoserine, and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. Introduction of the non-traditional amino acid can also be achieved using peptide chemistries known in the art. As used herein, the term "polar amino acid" includes amino acids that have net zero charge, but have non-zero partial charges in different portions of their side chains (e.g. M, F, W, S, Y, N, Q, C). These amino acids can participate in hydrophobic interactions and electrostatic interactions. As used herein, the term "charged amino acid" includes amino acids that can have non-zero net charge on their side chains (e.g. R, K, H, E, D). These amino acids can participate in hydrophobic interactions and electrostatic interactions.

An "amino acid substitution" refers to the replacement of at least one existing amino acid residue in a predetermined amino acid sequence (an amino acid sequence of a starting polypeptide) with a second, different "replacement" amino acid residue. An "amino acid insertion" refers to the incorporation of at least one additional amino acid into a predetermined amino acid sequence. While the insertion will usually consist of the insertion of one or two amino acid residues, the present larger "peptide insertions", can be made, e.g. insertion of about three to about five or even up to about ten, fifteen, or twenty amino acid residues. The inserted residue(s) may be naturally occurring or non-naturally occurring as disclosed above. An "amino acid deletion" refers to the removal of at least one amino acid residue from a predetermined amino acid sequence.

Polypeptides may be either monomers or multimers. For example, in one embodiment, a protein of the invention is a dimer. A dimeric polypeptide of the invention may comprise two polypeptide chains or may consist of one polypeptide chain (e.g., in the case of a scFc molecule). In one embodiment, the dimers of the invention are homodimers, comprising two identical monomeric subunits or polypeptides (e.g., two identical Fc moieties or two identical biologically active moieties). In another embodiment, the dimers of the invention are heterodimers, comprising two non-identical monomeric subunits or polypeptides (e.g., comprising two different clotting factors or portions thereof or one clotting factor only). See, e.g., U.S. Pat. No. 7,404,956, incorporated herein by reference.

As used herein, the term "peptide linker(s)," "linker(s)," or "linker moiety" refers to a peptide or polypeptide sequence (e.g., a synthetic peptide or polypeptide sequence) which connects two domains in a linear amino acid sequence of a polypeptide chain. In one embodiment, the polypeptides of invention are encoded by nucleic acid molecules that encode peptide linkers which either directly or indirectly connect the two Fc moieties which make up the construct. These linkers are referred to herein as "scFc linkers" and the scFc linker is interposed between the two Fc moieties of a polypeptide which comprises it. If the scFc linker connects two Fc moieties contiguously in the linear polypeptide sequence, it is a "direct" linkage. In contrast, the scFc linkers may link the first Fc moiety to a binding moiety which is, in turn, linked to the second Fc moiety, thereby forming an indirect linkage. These scFc linkers permit the formation of a single chain genetic construct. In one embodiment, the polypeptides also comprise intracellular processing sites which result in the scFc linker being processed (a cscFc linker) and, in one embodiment, substantially excised (e.g., during processing by a cell). Thus, the resulting processed polypeptide is a dimeric molecule comprising at least two amino acid chains and substantially lacking extraneous linker amino acid sequences. In some embodiments, all or substantially all of the linker is excised, while in some embodiments, a portion of the cleavage site may remain, e.g., four arginines of the RRRR cleavage site. In another embodiment, the linker or peptide linker may not typically cleaved; however in certain embodiments, such cleavage may be desirable. Exemplary positions of the linkers are shown in the accompanying drawings. Linkers can be located between the activatable clotting factors, enhancing moieties, and/or heterologous moieties, e.g., at the N or C terminus of these moieties. In one embodiment, these linkers are not removed during processing.

A third type of linker which may be present in an activatable clotting factor is herein referred to as a "cleavable linker" which comprises a heterologous protease-cleavage site (e.g., a factor XIa or thrombin cleavage site) that are not naturally occurring in the clotting factor and which may include additional linkers on either the N terminal of C terminal or both sides of the cleavage site. Exemplary locations for such sites are shown in the accompanying drawings and include, e.g., placement between a heavy chain of a clotting factor zymogen and a light chain of a clotting factor zymogen. In another embodiment, such linkers can further comprises a self-immolative moiety. For example, in one embodiment, a self-immolative moiety linked to a cleavable linker may be fused to the N terminus of the heavy chain of a clotting factor. In such cases, the cleavable linker may include additional linkers at the N terminus of the cleavage site, but requires direct fusion at the C-terminus of the cleavage site to the amino terminus of the heavy chain of the clotting factor.

As used herein, the term "gly-ser peptide linker" refers to a peptide that consists of glycine and serine residues. An exemplary gly/ser peptide linker comprises the amino acid sequence $(Gly_4 Ser)_n$ (SEQ ID NO: 4) Another exemplary gly/ser peptide linker comprises the amino acid sequence $S(Gly_4 Ser)_n$ (SEQ ID NO: 5) wherein n is an integer that is the same or higher than 1, 2, 3, 4, 5, 6, 7, 8, 9, 10, 15, 20, 25, 30, 35, 40, 46, 50, 55, 60, 70, 80, 90, or 100.

In one embodiment, n=1. In one embodiment, n=2. In another embodiment, n=3. In another embodiment, n=4. In another embodiment, n=5. In yet another embodiment, n=6. In another embodiment, n=7. In yet another embodiment, n=8. In another embodiment, n=9. In yet another embodiment, n=10. Another exemplary gly/ser peptide linker comprises the amino acid sequence $Ser(Gly_4 Ser)_n$ (SEQ ID NO: 5). In one embodiment, n=1. In one embodiment, n=2. In a preferred embodiment, n=3. In another embodiment, n=4. In another embodiment, n=5. In yet another embodiment, n=6.

"Derivatives" of polypeptides or proteins of the invention are polypeptides or proteins which have been altered so as to exhibit additional features not found on the native polypeptide or protein. Also included as "derivatives" are those peptides that contain one or more naturally occurring amino acid derivatives of the twenty standard amino acids. A polypeptide or amino acid sequence "derived from" a designated polypeptide or protein refers to the origin of the polypeptide. In one embodiment, the polypeptide or amino acid sequence which is derived from a particular sequence has an amino acid sequence that is essentially identical to that sequence or a portion thereof, wherein the portion consists of at least about 10 to about 20 amino acids, at least about 20 to about 30 amino acids, or at least about 30 to about 50 amino acids, or which is otherwise identifiable to one of ordinary skill in the art as having its origin in the sequence.

Polypeptides that are "variants" of another peptide may have one or more mutations relative to the starting polypeptide, e.g., one or more amino acid residues which have been substituted with another amino acid residue or which has one or more amino acid residue insertions or deletions. In one embodiment, the polypeptide comprises an amino acid sequence which is not naturally occurring. Such variants necessarily have less than 100% sequence identity or similarity with the starting polypeptide. In another embodiment, the variant will have an amino acid sequence from about 75% to less than 100% amino acid sequence identity or similarity with the amino acid sequence of the starting polypeptide, for example, from about 80% to less than 100%, from about 85% to less than 100%, from about 90% to less than 100% (e.g., 91%, 92%, 93%, 94%, 95%, 96%, 97%, 98%, 99%) and from about 95% to less than 100%, e.g., over the length of the variant molecule. In one embodiment, there is one amino acid difference between a starting polypeptide sequence and the sequence derived therefrom. Identity or similarity with respect to this sequence is defined herein as the percentage of amino acid residues in the candidate sequence that are identical (i.e. same residue) with the starting amino acid residues, after aligning the sequences and introducing gaps, if necessary, to achieve the maximum percent sequence identity.

The term "fragment" when referring to polypeptides and proteins of the present invention include any polypeptides or proteins which retain at least some of the properties of the reference polypeptide or protein. Fragments of polypeptides include proteolytic fragments, as well as deletion fragments.

In one embodiments, polypeptides of the invention comprise an amino acid sequence (e.g., at least one clotting factor or Fc moiety or domain) derived from a human protein sequence. However, polypeptides may comprise one or more amino acids from another mammalian species. For example, a clotting factor, Fc domain, or enhancing moiety may be derived from a non-human species and included in the subject polypeptides. Alternatively, one or more amino acids may be present in a polypeptide which are derived from a non-human species. In a particular embodiment, the polypeptides of the invention are not immunogenic.

It will also be understood by one of ordinary skill in the art that the polypeptides of the invention may be altered such that they vary in amino acid sequence from the naturally occurring or native polypeptides from which they were derived, while retaining the desirable activity of the native polypeptides. For example, nucleotide or amino acid substitutions leading to conservative substitutions or changes at "non-essential" amino acid residues may be made. An isolated nucleic acid molecule encoding a non-natural variant of a polypeptide derived from an immunoglobulin (e.g., an Fc domain, moiety, or antigen binding site) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis.

The polypeptides of the invention may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a polypeptide may be replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into polypeptides of the invention and screened for their ability to bind to the desired target.

In the context of polypeptides, a "linear sequence" or a "sequence" is the order of amino acids in a polypeptide in an amino to carboxyl terminal direction in which residues that neighbor each other in the sequence are contiguous in the primary structure of the polypeptide.

As used herein, the terms "linked," "fused", or "fusion" refer to linkage via a peptide bonds (e.g., genetic fusion), chemical conjugation or other means. For example, one way in which molecules or moieties can be linked employs peptide linkers which link the molecules or moieties via peptide bonds. The terms "genetically fused," "genetically linked" or "genetic fusion" are used interchangeably and refer to the co-linear, covalent linkage or attachment of two or more proteins, polypeptides, or fragments thereof via their individual peptide backbones, through genetic expression of a single polynucleotide molecule encoding those proteins, polypeptides, or fragments. Such genetic fusion results in the expression of a single contiguous genetic sequence. Preferred genetic fusions are in frame, i.e., two or more open reading frames (ORFs) are fused to form a continuous longer ORF, in a manner that maintains the correct reading frame of the original ORFs. Thus, the resulting recombinant fusion protein is a single polypeptide containing two or more protein segments that correspond to polypeptides encoded by the original ORFs (which segments are not normally so joined in nature). In this case, the single polypeptide is cleaved during processing to yield dimeric molecules comprising two polypeptide chains.

As used herein the term "associated with" refers to a covalent or non-covalent bond formed between a first amino acid chain and a second amino acid chain. In one embodiment, the term "associated with" means a covalent, non-peptide bond or a non-covalent bond. In another embodiment, the term "associated with" refers to a covalent, non-peptide bond or a non-covalent bond that is not chemically crosslinked. In some embodiments this association is indicated by a colon, i.e., (:). In another embodiment, it means a covalent bond except a peptide bond. For example, the amino acid cysteine comprises a thiol group that can form a disulfide bond or bridge with a thiol group on a second cysteine residue. In most naturally occurring IgG molecules, the CH1 and CL regions are associated by a disulfide bond and the two heavy chains are associated by two disulfide bonds at positions corresponding to 239 and 242 using the Kabat numbering system (position 226 or 229, EU numbering system). Examples of covalent bonds include, but are not limited to, a peptide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. Non-limiting examples of non-covalent bond include an ionic bond (e.g., cation-pi bond or salt bond), a metal bond, an hydrogen bond (e.g., dihydrogen bond, dihydrogen complex, low-barrier hydrogen bond, or symmetric hydrogen bond), van der Walls force, London dispersion force, a mechanical bond, a halogen bond, aurophilicity, intercalation, stacking, entropic force, or chemical polarity.

As used herein, the term "chemically crosslinked" refers to linking by covalent bonds between acid side chains of amino acids, either directly or via a linker, e.g., a peptide linker. Chemical crosslinking does not include intramolecular or intermolecular disulfide bonds between Fc moieties of a dimeric Fc region, or non-engineered disulfide bonds between an amino acid of the activatable clotting factor and an amino acid of the enhancer moiety. Chemical crosslinking generally takes place by addition of a crosslinking agent, e.g., a heterobifunctional crosslinking agent. Examples of chemical crosslinking includes one or more photo-reactive bonds by chemically connecting photo-Ile, photo-Met, and photo-Leu. See Suchanek et al., (2005) Nature methods, 2: 261-267.

As used herein, the term "Fc region" is defined as the portion of a polypeptide which corresponds to the Fc region of native immunoglobulin, i.e., as formed by the dimeric association of the respective Fc domains of its two heavy chains. A native Fc region is homodimeric and comprises two polypeptide chains. In contrast, the term "genetically-fused Fc region" or "single-chain Fc region" (scFc region), as used herein, refers to a synthetic dimeric Fc region comprised of Fc domains genetically linked within a single polypeptide chain (i.e., encoded in a single contiguous genetic sequence).

As used herein, the term "Fc domain" refers to the portion of a single immunoglobulin heavy chain beginning in the hinge region just upstream of the papain cleavage site (i.e.

residue 216 in IgG, taking the first residue of heavy chain constant region to be 114) and ending at the C-terminus of the antibody. Accordingly, a complete Fc domain comprises at least a hinge domain, a CH2 domain, and a CH3 domain.

As used herein, the term "Fc domain portion" or "Fc moiety" includes an amino acid sequence of an Fc domain or derived from an Fc domain. In certain embodiments, an Fc moiety comprises at least one of: a hinge (e.g., upper, middle, and/or lower hinge region) domain, a CH2 domain, a CH3 domain, a CH4 domain, or a variant, portion, or fragment thereof. In other embodiments, an Fc moiety comprises a complete Fc domain (i.e., a hinge domain, a CH2 domain, and a CH3 domain). In one embodiment, a Fc moiety comprises a hinge domain (or portion thereof) fused to a CH3 domain (or portion thereof). In another embodiment, an Fc moiety comprises a CH2 domain (or portion thereof) fused to a CH3 domain (or portion thereof). In another embodiment, an Fc moiety consists of a CH3 domain or portion thereof. In another embodiment, an Fc moiety consists of a hinge domain (or portion thereof) and a CH3 domain (or portion thereof). In another embodiment, a Fc moiety consists of a CH2 domain (or portion thereof) and a CH3 domain. In another embodiment, a Fc moiety consists of a hinge domain (or portion thereof) and a CH2 domain (or portion thereof). In one embodiment, an Fc moiety lacks at least a portion of a CH2 domain (e.g., all or part of a CH2 domain).

As used herein, the term "half-life" refers to a biological half-life of a particular polypeptide in vivo. Half-life may be represented by the time required for half the quantity administered to a subject to be cleared from the circulation and/or other tissues in the animal. When a clearance curve of a given polypeptide is constructed as a function of time, the curve is usually biphasic with a rapid α-phase and longer β-phase. The α-phase typically represents an equilibration of the administered chimeric polypeptide between the intra- and extra-vascular space and is, in part, determined by the size of the polypeptide. The β-phase typically represents the catabolism of the polypeptide in the intravascular space. Therefore, in a particular embodiment, the term half-life as used herein refers to the half-life of the polypeptide in the β-phase. The typical β-phase half-life of a human antibody in humans is 21 days.

As used herein, the term "half-life extender" refers to a heterologous moiety which increases the in vivo half-life of a protein. In vivo half-life of a chimeric clotting factor of the invention can be determined by any method known to those of skill in the art, e.g., FVII activity level assays. In certain embodiments, the half-life extender can comprise an attachment site for a non-polypeptide moiety such as polyethylene glycol (PEG), hydroxyethyl starch (HES), polysialic acid, or any derivatives, variants, or combinations of these elements.

As used herein the term "moiety" refers to a component part or constituent of a chimeric polypeptide.

As used herein, the term "enhancer moiety" refers to a molecule, fragment, derivative, or variant thereof or a component of a polypeptide which is capable of enhancing the procoagulant activity of a clotting factor. In one embodiment, a chimeric clotting factor of the invention comprises an "enhancer moiety" which enhances the activity of the polypeptide, e.g., by acting as a cofactor. Such a moiety may be, e.g., a clotting cofactor, such as a soluble tissue factor (sTF), or a Factor Va protein, but does not include a targeting moiety, e.g., a platelet targeting moiety. In another embodiment, the enhancer moiety interacts with the activatable clotting factor, thereby increasing procoagulant activity of the clotting factor. The enhancer moiety may be genetically fused to the construct, chemically conjugated to the construct, or linked to the construct via a linker. For example, enhancer moieties may be attached to a construct of the invention by formation of a bond between the enhancer moiety and an activatable clotting factor of a construct, where the enhancer moiety comprises a first functional group and the activatable clotting factor comprises a second functional group, and where the first and second functional groups are capable of reacting with each other to form a chemical bond. Exemplary enhancer moieties are described in more detail below.

As used herein, the term "self-immolative moiety" refers to a molecule that can be included in a cleavable linker to enhance its function. In one embodiment, a self-immolative moiety is interposed between a heavy chain of a clotting factor zymogen and a protease cleavage site. Such self-immolating moieties have the advantage that the cleavability of the protease cleavage site is not negatively impacted by the terminal amino acid residue of the first moiety. Exemplary self-immolative moieties are disclosed, e.g., in U.S. Pat. No. 7,375,078 and U.S. Pat. No. 7,754,681, which are incorporated herein by reference in their entirety.

As used herein, the term "heterologous moiety" refers to a moiety that does not naturally occur with the components of the chimeric protein, e.g., an activatable clotting factor, a linker moiety, or an enhancer moiety and/or is linked to or associated with the components of the chimeric protein. In one embodiment, the heterologous moiety is capable of extending the half-life of the activatable clotting factor. In another embodiment, the heterologous moiety increases the hydrodynamic radius of the activatable or activated clotting factor. In other embodiments, a heterologous moiety improves one or more pharmacokinetic properties of the clotting factor without significantly affecting its biological activity or function (e.g., its procoagulant activity). In still other embodiments, the heterologous moiety is a non-polypeptide moiety, e.g., chemical modification or a combination of a peptide or polypeptide and a non-polypeptide moiety. In yet other embodiments, the heterologous moiety is a polypeptide. In some embodiments, the chimeric clotting factor is linked or connected to the heterologous moiety by a linker. Non-limiting examples of heterologous polypeptide moieties comprise an immunoglobulin constant region or a portion thereof, albumin or a fragment thereof, an albumin binding moiety, a PAS sequence, a HAP sequence, transferrin or a fragment thereof, the β subunit of the C-terminal peptide (CTP) of human chorionic gonadotropin, albumin binding small molecule, an XTEN sequence, or two or more combinations thereof. Non-limiting examples of the heterologous non-polypeptide moiety include polyethylene glycol (PEG), polysialic acid, hydroxyethyl starch (HES), a derivative thereof, or any combinations thereof. Exemplary heterologous moieties include, e.g., FcRn binding moieties (e.g., complete Fc regions or portions thereof which bind to FcRn), single chain Fc regions (ScFc regions, e.g., as described in US 2008/0260738, WO 2008/012543, or WO 2008/1439545), processable scFc regions (comprising a cscFc regions as described herein).

In one embodiment an enhancer moiety for use in a construct of the invention comprises an antibody variant. The term "antibody variant" or "modified antibody" includes an antibody which does not occur in nature and which has an amino acid sequence or amino acid side chain chemistry which differs from that of a naturally-derived antibody by at least one amino acid or amino acid modification as described herein. As used herein, the term "antibody variant" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules; single-chain antibodies; diabodies; triabodies; and antibodies with altered effector function and the like.

As used herein, the term "Gla domain" refers to the conserved membrane binding motif which is present in vitamin K-dependent proteins, such as prothrombin, coagulation factors VII, IX and X, proteins C, S, and Z. These proteins require vitamin K for the posttranslational synthesis of g-carboxyglutamic acid, an amino acid clustered in the N-terminal Gla domain of these proteins. All glutamic residues present in the domain are potential carboxylation sites and many of them are therefore modified by carboxylation. In the presence of calcium ions, the Gla domain interacts with phospholipid membranes that include phosphatidylserine. The Gla domain also plays a role in binding to the FVIIa cofactor, tissue factor (TF). Complexed with TF, the Gla domain of FVIIa is loaded with seven Ca2+ ions, projects three hydrophobic side chains in the direction of the cell membrane for interaction with phospholipids on the cell surface, and has significant contact with the C-terminal domain of TF.

As used herein the term "scFv molecule" includes binding molecules which consist of one light chain variable domain (VL) or portion thereof, and one heavy chain variable domain (VH) or portion thereof, wherein each variable domain (or portion thereof) is derived from the same or different antibodies. scFv molecules preferably comprise an scFv linker interposed between the VH domain and the VL domain. ScFv molecules are known in the art and are described, e.g., in U.S. Pat. No. 5,892,019, Ho et al. 1989. Gene 77:51; Bird et al. 1988 Science 242:423; Pantoliano et al. 1991. Biochemistry 30:10117; Milenic et al. 1991. Cancer Research 51:6363; Takkinen et al. 1991. Protein Engineering 4:837.

A "scFv linker" as used herein refers to a moiety interposed between the VL and VH domains of the scFv. scFv linkers preferably maintain the scFv molecule in an antigen binding conformation. In one embodiment, a scFv linker comprises or consists of an scFv linker peptide. In certain embodiments, an scFv linker peptide comprises or consists of a gly-ser peptide linker. In other embodiments, an scFv linker comprises a disulfide bond.

The term "glycosylation" refers to the covalent linking of one or more carbohydrates to a polypeptide. Typically, glycosylation is a posttranslational event which can occur within the intracellular milieu of a cell or extract therefrom. The term glycosylation includes, for example, N-linked glycosylation (where one or more sugars are linked to an asparagine residue) and/or O-linked glycosylation (where one or more sugars are linked to an amino acid residue having a hydroxyl group (e.g., serine or threonine). In one embodiment, a molecule of the invention is glycosylated. In another embodiment, a molecule of the invention is aglycosylated. In yet another embodiment, a molecule of the invention has reduced glycosylation as compared to that in a wild type Fc region.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by native disulfide bonds and the two heavy chains are linked by two native disulfide bonds at positions corresponding to 239 and 242 using the Kabat numbering system (position 226 or 229, EU numbering system).

The term "vector" or "expression vector" is used herein to mean vectors used in accordance with the present invention as a vehicle for introducing into and expressing a desired polynucleotide in a cell. As known to those skilled in the art, such vectors may easily be selected from plasmids, phages, viruses or retroviruses. In general, vectors compatible with the instant invention will comprise a selection marker, appropriate restriction sites to facilitate cloning of the desired gene and the ability to enter and/or replicate in eukaryotic or prokaryotic cells.

Numerous expression vector systems may be employed to produce the chimeric clotting factors of the invention. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. In one embodiment, an inducible expression system can be employed. Additional elements may also be needed for optimal synthesis of mRNA. These elements may include signal sequences, splice signals, as well as transcriptional promoters, enhancers, and termination signals. In one embodiment, a secretion signal, e.g., any one of several well characterized bacterial leader peptides (e.g., pelB, phoA, or ompA), can be fused in-frame to the N terminus of a polypeptide of the invention to obtain optimal secretion of the polypeptide. (Lei et al. (1988), Nature, 331:543; Better et al. (1988) Science, 240:1041; Mullinax et al., (1990). PNAS, 87:8095).

The term "host cell" refers to a cell that has been transformed with a vector constructed using recombinant DNA techniques and encoding at least one heterologous gene. In descriptions of processes for isolation of proteins from recombinant hosts, the terms "cell" and "cell culture" are used interchangeably to denote the source of protein unless it is clearly specified otherwise. In other words, recovery of protein from the "cells" may mean either from spun down whole cells, or from the cell culture containing both the medium and the suspended cells. The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), PerC6 cells), HAK (hamster kidney line), SP2/O (mouse myeloma), P3x63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature. The polypeptides of the invention can also be expressed in non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the polypeptides typically become part of inclusion bodies. The polypeptides must be isolated, purified and then assembled into functional molecules.

In addition to prokaryotes, eukaryotic microbes may also be used. *Saccharomyces cerevisiae*, or common baker's yeast, is the most commonly used among eukaryotic microorganisms although a number of other strains are commonly available including *Pichia pastoris*. For expression in *Saccharomyces*, the plasmid YRp7, for example, (Stinchcomb et al., (1979), *Nature,* 282:39; Kingsman et al., (1979), *Gene,* 7:141; Tschemper et al., (1980), *Gene,* 10:157) is commonly used. This plasmid already contains the TRP1 gene which provides a selection marker for a mutant strain of yeast lacking the ability to grow in tryptophan, for example ATCC No. 44076 or PEP4-1 (Jones, (1977), *Genetics,* 85:12). The presence of the trp1 lesion as a characteristic of the yeast host cell genome then provides an effective environment for detecting transformation by growth in the absence of tryptophan.

As used herein the term "endogenous" refers to molecules (e.g. nucleic acid and/or protein molecules) that are naturally present in a cell. In contrast, the term "exogenous" or "heterologous" refers to such molecules that are not normally found in a given context, e.g., in a cell or in a polypeptide. For example, an exogenous or heterologous molecule may be introduced into a cell and are only present after manipulation of the cell, e.g., by transfection or other forms of genetic engineering or a heterologous amino acid sequence may be present in a protein in which it is not naturally found.

As used herein, the term "cleavage site" or "protease-cleavage site" refers to a site recognized by a protease. In one embodiment, a polypeptide has a protease-cleavage site cleaved by a protease that is activated during the clotting cascade, such that cleavage of such sites occurs at the site of clot formation. Exemplary such sites include e.g., those recognized by thrombin, Factor XIa or Factor Xa. Exemplary FXIa cleavage sites include, e.g., TQSFNDFTR (SEQ ID NO: 6) and SVSQTSKLTR (SEQ ID NO: 7). Exemplary thrombin cleavage sites include, e.g., DFLAEGGGVR (SEQ ID NO: 8), TTKIKPR (SEQ ID NO: 9), LVPRG (SEQ ID NO: 10) and ALRPR (SEQ ID NO: 1). Other protease-cleavage sites are described in detail below.

As used herein, the term "processing site" or "intracellular processing site" refers to a type of enzymatic cleavage site in a polypeptide which is the target for enzymes that function after translation of the polypeptide. In one embodiment, such enzymes function during transport from the Golgi lumen to the trans-Golgi compartment. Intracellular processing enzymes cleave polypeptides prior to secretion of the protein from the cell. Examples of such processing sites include, e.g., those targeted by the PACE/furin (where PACE is an acronym for Paired basic Amino acid Cleaving Enzyme) family of endopeptidases. These enzymes are localized to the Golgi membrane and cleave proteins on the carboxyterminal side of the sequence motif Arg-[any residue]-(Lys or Arg)-Arg. As used herein the "furin" family of enzymes includes, e.g., furin, a yeast Kex2, PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art.

In constructs that include more than one processing or cleavage site, it will be understood that such sites may be the same or different.

In vitro production allows scale-up to give large amounts of the desired altered polypeptides of the invention. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, hydrophobic interaction chromatography (HIC, chromatography over DEAE-cellulose or affinity chromatography.

As used herein, the phrase "subject that would benefit from administration of a polypeptide" or "subject in need thereof" includes subjects, such as mammalian subjects, that would benefit from administration of polypeptides of the invention, e.g., to improve hemostasis. In one embodiment, the subjects include, but are not limited to, the individuals who have developed a FVIII inhibitor and thus are in need of a bypass therapy. In another embodiment, the subjects also include the individuals who have not yet developed a FVIII inhibitor, but have a tendency to develop a FVIII inhibitor. The subject can be an adult or a minor (e.g., under 12 years old).

A "chimeric protein" or "fusion protein", as used herein, refers to any protein comprised of a first amino acid sequence derived from a first source, bonded, covalently or non-covalently, to a second amino acid sequence derived from a second source, wherein the first and second source are not the same. A first source and a second source that are not the same can include two different biological entities, or two different proteins from the same biological entity, or a biological entity and a non-biological entity. A chimeric protein can include for example, a protein derived from at least 2 different biological sources. A biological source can include any non-synthetically produced nucleic acid or amino acid sequence (e.g. a genomic or cDNA sequence, a plasmid or viral vector, a native virion or a mutant or analog, as further described herein, of any of the above). A synthetic source can include a protein or nucleic acid sequence produced chemically and not by a biological system (e.g. solid phase synthesis of amino acid sequences). A chimeric protein can also include a protein derived from at least 2 different synthetic sources or a protein derived from at least one biological source and at least one synthetic source. A chimeric protein may also comprise a first amino acid sequence derived from a first source, covalently or non-covalently linked to a nucleic acid, derived from any source or a small organic or inorganic molecule derived from any source. The chimeric protein may comprise a linker molecule between the first and second amino acid sequence or between the first amino acid sequence and the nucleic acid, or between the first amino acid sequence and the small organic or inorganic molecule.

As used herein, the term "clotting factor," refers to molecules, or analogs thereof, naturally occurring or recombinantly produced which prevent or decrease the duration of a bleeding episode in a subject. In other words, it means molecules having pro-clotting activity, i.e., are responsible for the conversion of fibrinogen into a mesh of insoluble fibrin causing the blood to coagulate or clot. An "activatable clotting factor" is a clotting factor in an inactive form (e.g., in its zymogen form) that is capable of being converted to an active form.

Clotting activity, as used herein, means the ability to participate in a cascade of biochemical reactions that culminates in the formation of a fibrin clot and/or reduces the severity, duration or frequency of hemorrhage or bleeding episode.

Hemostasis, as used herein, means the stopping or slowing of bleeding or hemorrhage; or the stopping or slowing of blood flow through a blood vessel or body part.

Hemostatic disorder, as used herein, means a genetically inherited or acquired condition characterized by a tendency to hemorrhage, either spontaneously or as a result of trauma, due to an impaired ability or inability to form a fibrin clot. Examples of such disorders include the hemophilias. The three main forms are hemophilia A (factor VIII deficiency), hemophilia B (factor IX deficiency or "Christmas disease") and hemophilia C (factor XI deficiency, mild bleeding tendency), Von Willebrand disease, factor Xi deficiency (PTA deficiency), Factor XII deficiency, deficiencies or structural abnormalities in fibrinogen, prothrombin, Factor V, Factor VII, Factor X or factor XIII, Bernard-Soulier syndrome is a defect or deficiency in GPIb. GPIb, the receptor for vWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this may increase bleeding risk.

The chimeric molecules of the invention can be used prophylactically. As used herein the term "prophylactic treatment" refers to the administration of a molecule prior to a bleeding episode. In one embodiment, the subject in need of a general hemostatic agent is undergoing, or is about to undergo, surgery. The chimeric protein of the invention can be administered prior to or after surgery as a prophylactic. The chimeric protein of the invention can be administered during or after surgery to control an acute bleeding episode. The surgery can include, but is not limited to, liver transplantation, liver resection, or stem cell transplantation On-demand treatment includes treatment for a bleeding episode, hemarthrosis, muscle bleed, oral bleed, hemorrhage, hemorrhage into muscles, oral hemorrhage, trauma, trauma capitis (head trauma), gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. The subject may be in need of surgical prophylaxis, peri-operative management, or treatment for surgery. Such surgeries include, e.g., minor surgery, major surgery, tooth extraction, tonsillectomy, inguinal herniotomy, synovectomy, total knee replacement, craniotomy, osteosynthesis, trauma surgery, intracranial surgery, intra-abdominal surgery, intrathoracic surgery, or joint replacement surgery.

As used herein the term "acute bleeding" refers to a bleeding episode regardless of the underlying cause. For example, a subject may have trauma, uremia, a hereditary bleeding disorder (e.g., factor VII deficiency) a platelet disorder, or resistance owing to the development of antibodies to clotting factors.

Treat, treatment, treating, as used herein refers to, e.g., the reduction in severity of a disease or condition; the reduction in the duration of a disease course; the amelioration of one or more symptoms associated with a disease or condition; the provision of beneficial effects to a subject with a disease or condition, without necessarily curing the disease or condition, the prophylaxis of one or more symptoms associated with a disease or condition.

As used herein, the term "solid phase peptide synthesis" refers to the in vitro synthesis of polypeptide molecules immobilized on a solid surface. The general principle of SPPS is one of repeated cycles of coupling-wash-deprotection-wash. The free N-terminal amine of a solid-phase attached peptide is coupled to a single N-protected amino acid unit. This unit is then deprotected, revealing a new N-terminal amine to which a further amino acid may be attached. Solid phase peptide synthesis was originally described in Merrifield et al., "Solid Phase Peptide Synthesis. I. The Synthesis of a Tetrapeptide". J. Am. Chem. Soc. 85 (14): 2149-2154 (1963). For example, the compounds of the present disclosure can be synthesised using solid-phase peptide synthesis as described in "Fmoc Solid Phase Peptide Synthesis—A Practical Approach", edited by W. C. Chan, P. D. White, Oxford University Press, New York 2000 and references therein. Solid phase peptide synthesis includes the synthesis of polypeptides comprising natural amino acids, unnatural amino acids including D-amino acids, peptide/protein backbone modification, and conjugation of peptidic and non-peptidic moieties.

II. Chimeric Proteins

The present invention is directed to a chimeric protein comprising an activatable clotting factor and an enhancer moiety. The activatable clotting factor in the chimeric protein is administered as an inactive form (i.e., zymogen) and is activated by a protease after administration in vivo, for example, at the site of an injury. Once the activatable clotting factor is activated, the enhancer moiety associated with or linked to the activated clotting factor can enhance the activity of the clotting factor by acting as a partner in the coagulation pathway. Therefore, the chimeric protein of the invention can also be described as an enhanced or improved zymogen or an enhanced or improved zymogen fusion protein (e.g., FVII enhanced zymogen fusion protein or FX enhanced zymogen fusion protein). Examples of the activatable clotting factors useful for the chimeric protein include, but are not limited to, Factor VII or Factor X as described in section (A) below.

The activatable clotting factor is further improved by bringing an enhancer moiety (e.g., a clotting cofactor, e.g., Tissue Factor) in close proximity to the activatable clotting factor. Thus, when the clotting factor is cleaved into a heterodimer, the enhancer moiety can interact with the clotting factor heterodimer and can induce conformational changes to enhance the procoagulant activities. Examples of the enhancer moiety useful for the invention include, but are not limited to, a clotting cofactor, a procoagulant peptide, or an antigen binding moiety as described in section (B) below. In some embodiments, the enhancer moiety interacts with the clotting factor without cleavage of the clotting factor into a heterodimer.

While cleavage of a light chain from a heavy chain of a clotting factor makes two-chain activated form of the clotting factor, the clotting factor may still be present as a zymogen-like protein when the N-terminus of the heavy chain is not completely cleaved. One embodiment of the invention includes a chimeric protein comprising a heterodimeric zymogen-like protein comprising a light chain and a heavy chain, wherein the N-terminus of the heavy chain is linked to a protease-cleavage site. The cleavage of the protease-cleavage site at the site of injury can activate the clotting factor in vivo.

In one embodiment, an activatable clotting factor in a chimeric protein is linked to an enhancer moiety by a covalent bond, e.g., a peptide bond, a disulfide bond, a metal bond, a hydrogen bond, a disulfide bond, a sigma bond, a pi bond, a delta bond, a glycosidic bond, an agnostic bond, a bent bond, a dipolar bond, a Pi backbond, a double bond, a triple bond, a quadruple bond, a quintuple bond, a sextuple bond, conjugation, hyperconjugation, aromaticity, hapticity, or antibonding. In another embodiment, the linkage between the activatable clotting factor and the enhancer moiety is a non-covalent interaction, e.g., an ionic interaction, a hydrophobic interaction, a hydrophilic interaction, a Van der Waals interaction, or a hydrogen bond. In some embodiments, the linkage between the activatable clotting factor and the enhancer moiety is a covalent bond or a non-covalent bond, but is not a chemical crosslinking, e.g., a photo reactive bond. In a particular embodiment, the linkage between the activatable clotting factor and the enhancer moiety is a disulfide bond.

In one aspect, a chimeric protein comprising an activatable clotting factor and an enhancer moiety further comprises one or more linker moieties. For example, a chimeric protein can comprise a formula of Ac-L-Em or Em-L-Ac, wherein Ac is an activatable clotting factor, L is a linker moiety, and Em is an enhancer moiety. In one embodiment, the linker moiety can be a peptide linker. Non-limiting examples of the peptide linkers are described in section (D) below. In another embodiment, the linker moiety is a low complex polypeptide, e.g., an XTEN sequence. A linker moiety useful for the chimeric protein comprises at least about five, at least about 10, at least about 20, at least about 30, at least about 40, at least about 50, at least about 60, at least about 70, at least about 80, at least about 90, at least about 100, at least about 110, at least about 120 amino acids, at least 150 amino acids, at least 200 amino acids, at least 500 amino acids, at least 1000 amino acids, or at least 2000 amino acids.

In another aspect, the chimeric protein of the invention comprises an activatable clotting factor, an enhancer moiety, and one or more heterologous moieties (sometimes indicated herein as Het, Het1, or Het2). Heterologous moieties can comprise a heterologous polypeptide moiety, a non-polypeptide moiety, or both. The heterologous polypeptide moiety can be selected from an immunoglobulin constant region or portion thereof, albumin or a fragment, derivative, or variant thereof, an albumin binding moiety, an albumin biding small molecule, a PAS sequence, an XTEN sequence, a HAP sequence, transferrin or a fragment, derivative, or variant thereof, or any combination thereof. In other embodiments, the heterologous moiety is an immunoglobulin constant region or portion thereof, e.g., an Fc moiety. In still other embodiments, the non-polypeptide moiety is selected from polyethylene glycol (PEG), polysialic acid, hydroxyethyl starch (HES), a derivative thereof, or any combinations thereof. The heterologous moiety can be linked to the N-terminus or C-terminus of the activating clotting factor (either the light chain, the heavy chain, or both) or inserted between two amino acids within the activating clotting factor (either the light chain, the heavy chain, or both) or to the N-terminus or C-terminus of the enhancing moiety or inserted between two amino acids within the enhancing moiety. Examples of the heterologous moiety are described in section (C) below.

In some embodiments, a chimeric protein comprises two or more heterologous moieties. The chimeric protein comprising two or more heterologous moieties can have a single polypeptide chain, two polypeptide chains, three polypeptide chains, or more. For example, a chimeric protein can comprise a single chain represented by a formula of Ac-Het1-Em-Het2, Het2-Em-Het1-Ac, Ac-Em-Het1-Het2, Het2-Het1-Em-Ac, Het1-Het2-Ac-Em, Em-Ac-Het2-Het1, Het1-Em-Het2-Ac, Ac-Het1-Em-Het2, Em-Het2-Ac-Het1, Het1-Ac-Het2-Em, Het2-Ac-Het1-Em, and Em-Het1-Ac-Het2, wherein Ac is an activatable clotting factor, Het1 is a first heterologous moiety, Em is an enhancer moiety, Het2 is a second heterologous moiety, and (-) is a peptide bond or one or more amino acids.

The chimeric protein comprising two polypeptide chain can be represented by a formula of Ac-Het1:Em-Het2, Het1-Ac:Het2-Em, Ac-Het1:Het2-Em, or Het1-Ac:Em-Het2, wherein Ac is an activatable clotting factor, Em is an enhancer moiety, Het1 is a first heterologous moiety (e.g., a first Fc moiety), Het2 is a second heterologous moiety (e.g., a second Fc moiety), (-) is a peptide bond or one or more amino acids, and (:) is an association between the two polypeptide chains (e.g., Ac-Het1 and Em-Het2). The association (:) as set forth herein represents a covalent bond or a non-covalent bond, e.g., at least one non-peptide bond. In one embodiment, the association, i.e., (:), is a covalent bond. In another embodiment, the association, i.e., (:), is a non-covalent interaction, e.g., an ionic interaction, a hydrophobic interaction, a hydrophilic interaction, a Van der Waals interaction, a hydrogen bond. In other embodiments, (:) is a non-peptide covalent bond. In still other embodiments, (:) is a peptide bond. In yet other embodiments, (:) in formulas set forth herein represents a physical or chemical association between two sequences, but not a chemical crosslinking, wherein a portion of the first sequence is in close proximity to the second sequence such that the first sequence and the second sequence interacts with each other upon activation of either or both the first sequence and the second sequence.

Formulas set forth herein are merely non-limiting examples of constructs of the present invention. The orientation of the polypeptide formulas is shown from N-terminus (left) to C-terminus (right). For example, formula Ac-Het1 means formula NH2-Ac-Het1-COOH. In addition, (:) can be an association or interaction between two polypeptide chains by a covalent bond or a non-covalent bond between any part of the first chain and any part of the second chain unless otherwise noted. For example, formula Ac-Het1:Em-Het2 has two polypeptide chains, the first chain being Ac-Het1 and the second chain being Em-Het2, wherein Ac in the first chain interacts or associates with Em in the second chain and/or Het1 in the first chain interacts or associates with Het2 in the second chain. In some embodiments, (:) means a covalent, non-peptide bond or non-covalent bond.

In a further aspect, a chimeric protein of the invention comprises an activatable clotting factor, an enhancer moiety, one or more linker moieties, and one or more heterologous moieties. In one embodiment, the chimeric protein comprises an activatable clotting factor (Ac), an enhancer moiety (Em), one linker moiety (L), and one heterologous moiety (Het), wherein the components are linked to or associated with each other. The chimeric protein can be represented by a formula of Ac-L-Het: Em, Het-L-Ac:Em, Em-L-Het:Ac, Het-L-Em:Ac, Ac-L-Het-Em, or Em-Het-L-Ac. In another embodiment, the chimeric protein comprises an activatable clotting factor (Ac), an enhancer moiety (Em), two linker moieties (L1 and L2), and one heterologous moiety (Het). The chimeric protein can be represented by a formula of Ac-L1-Het-L2-Em and Em-L2-Het-L1-Ac. In other embodiments, the chimeric protein comprises an activatable clotting factor (Ac), an enhancer moiety (Em), two linker moieties (L1 and L2), and two heterologous moieties (Het1 and Het2), wherein the components are linked to or associated with each other. The chimeric protein can be represented by a formula Ac-L1-Het1:Em-L2-Het2, Het1-L2-Ac: Em-L2-Het2, or Het1-L2-Ac:Het2-L2-Em, wherein Ac comprises, consisting essentially of, or consisting of an activatable clotting factor, L1 comprises, consisting essentially of, or consisting of an first optional linker moiety, e.g., a first linker, Het1 comprises, consisting essentially of, or consisting of a first heterologous moiety (e.g., a first Fc moiety), Em comprises, consisting essentially of, or consisting of an enhancer moiety, L2 comprises, consisting essentially of, or consisting of a second optional linker moiety, e.g., a second linker, Het2 comprises, consisting essentially of, or consisting of a second optional heterologous moiety (e.g., a second Fc moiety), (–) comprises, consisting essentially of, or consisting of a peptide bond or one or more amino acids, and (:) is an association between Ac-L1-Het1 and Em-L2-Het2. The association (:) as set forth herein represents a covalent bond or a non-covalent bond, e.g., at least one non-peptide bond. In one embodiment, the association, i.e., (:), is a covalent bond. In a particular embodiment, the association (:) is a disulfide bond between Het1 and Het2. In another embodiment, the association, i.e., (:), is a non-covalent interaction, e.g., an ionic interaction, a hydrophobic interaction, a hydrophilic interaction, a Van der Waals interaction, a hydrogen bond. In other embodiments, (:) is a non-peptide covalent bond. In still other embodiments, (:) is a peptide bond. In yet other embodiments, (:) in formulas set forth herein represents a physical or chemical association between two sequences, but not a chemical crosslinking, wherein a portion of a first sequence is in close proximity to a second sequence such that the first sequence and the second sequence interacts with each other upon activation of either or both the first sequence and the second sequence.

In certain aspects, a chimeric protein of the invention comprises a first polypeptide chain and a second polypeptide chain, wherein the first polypeptide chain comprises an activatable clotting factor and the second polypeptide chain comprises an enhancer moiety, wherein the first polypeptide chain and the second polypeptide chain are linked to or associated with each other. The chimeric protein can further comprise a dimeric heterologous moiety region comprising a first heterologous moiety, Het1 (e.g., a first Fc moiety, e.g., F1) and a second heterologous moiety, Het2 (e.g., a second Fc moiety, e.g., F2), wherein the first heterologous moiety is in the first polypeptide chain and the second heterologous moiety is in the second polypeptide chain. For example, a chimeric protein can comprise a structure selected from:
 (a) Ac linked to Het1 via the linker moiety, and Em linked to Het2;
 (b) Ac linked to Het1 via the first linker moiety, and Em linked to Het2 via the second linker moiety;
 (c) Ac linked to Het1, and Em is linked to Het2 via the linker moiety;
 (d) Ac linked to Het1, and Em linked to Het2;
 (e) Em linked to Het1 via the linker moiety, and Ac linked to Het2;
 (f) Em linked to Het1 via the first linker moiety, and Ac linked to Het2 via the second linker moiety;
 (g) Em linked to Het1, and Ac is linked to Het2 via the linker moiety; or,
 (h) Em linked to Het1, and Ac linked to Het2, wherein Het1 and Het2 form a disulfide bond.

The chimeric protein comprising two polypeptides can also be represented as set forth below:
 (a) the first polypeptide comprises a structure represented by the formula Ac-L1-Het1, and the second polypeptide comprises a structure represented by the formula Em-Het2;
 (b) the first polypeptide comprises a structure represented by the formula Ac-L1-Het1, and the second polypeptide comprises a structure represented by the formula Em-L2-Het2;
 (c) the first polypeptide comprises a structure represented by the formula Ac-Het1, and the second polypeptide comprises a structure represented by the formula Em-L2-Het2;
 (d) the first polypeptide comprises a structure represented by the formula Ac-Het1, and the second polypeptide comprises a structure represented by the formula Em-L1-Het2;
 (e) the first polypeptide comprises a structure represented by the formula Em-L2-Het1, and the second polypeptide comprises a structure represented by the formula Ac-L1-Het2;
 (f) the first polypeptide comprises a structure represented by the formula Em-L1-Het1, and the second polypeptide comprises a structure represented by the formula Ac-Het2;
 (g) the first polypeptide comprises a structure represented by the formula Em-Het1, and the second polypeptide comprises a structure represented by the formula Ac-L1-Het2; and,
 (h) the first polypeptide comprises a structure represented by the formula Em-Het1, and the second polypeptide comprises a structure represented by the formula Ac-Het2;
 wherein Het1 and Het2 of the two polypeptide chains form a disulfide bond.

In yet other aspects, the chimeric protein comprises an activatable clotting factor (Ac), an enhancer moiety (Em), three linker moieties (L1, L2, and X), and two heterologous moieties (Het1 and Het2), wherein the components are linked to each other. The chimeric protein can comprise by a formula selected from Ac-Het1-X-Em-Het2 or Het2-Em-X-Het1-Ac, wherein Ac is an activatable clotting factor, Het1 is a first heterologous moiety, X is a scFc linker, Em is an enhancer moiety, and Het2 is a second heterologous moiety. The chimeric protein can also comprise one or more linker moieties. For example, a chimeric protein can comprise a formula selected from Ac-L1-Het1-X-Em-Het2, Ac-Het1-X-Em-L2-Het2, Ac-L1-Het1-X-Em-L2-Het2, Het2-Em-X-Het1-L1-Ac, Het2-L2-Em-X-Het1-Ac, or Het2-L2-Em-X-Het1-L1-Ac, wherein Ac is an activatable clotting factor, L1 is a first optional linker moiety, Het1 is a first heterologous moiety, X is a scFc linker, Em is an enhancer moiety, L2 is a second optional linker moiety, and Het2 is a second heterologous moiety.

In one embodiment, either or both of the heterologous moieties (Het1 and Het2) are a heterologous polypeptide moiety, which are the same or different. In another embodiment, either or both of Het1 and Het2 are a non-polypeptide moiety. In other embodiments, either or both of the heterologous moieties (Het1 and Het2) can be a half-life extender. Examples of the half-life extender include, but are not limited to, an immunoglobulin constant region or a portion thereof, albumin, transferrin, an albumin binding moiety, a PAS sequence, a HES sequence, the β subunit of the C-terminal peptide (CTP) of human chorionic gonadotropin, polyethylene glycol (PEG), an XTEN sequence, hydroxyethyl starch (HES), albumin-binding small molecules, von Willebrand Factor or a fragment, derivative, or variant thereof, or any combinations thereof. Examples of the heterologous moiety are shown in section (C) below.

In another embodiment, the first and second heterologous moieties (Het1 and Het2) are linked to each other by a peptide bond or a linker (e.g., scFc linker (sometimes also indicated as "X")) or associated by a covalent or non-covalent bond, e.g., a disulfide bond. For example, a scFc linker can link a first Fc moiety and a second Fc moiety, thereby forming a dimeric Fc region. The scFc linker can further comprise an intracellular processing site, which enables processing of the chimeric protein when expressed in a host cell. Examples of the scFc linker are shown in section (C.3) below.

Each component of the chimeric proteins is described below.

A. Activatable Clotting Factors
1. Clotting Factors

In particular, the invention pertains to improved versions of factors VII and X. These factors are all structurally related in that in each the amino terminal end of the light chain is not amenable to the incorporation of additional moieties. Similarly, the amino terminal end of the heavy chain of these three clotting factors is not amenable to the incorporation of additional moieties, with the exception of cleavable moieties, i.e., moieties linked via a cleavage site or moieties which consist of a cleavage site. The chimeric clotting factor constructs of the invention were designed based on these shared properties and it will be understood that although factor VII is often shown to illustrate exemplary embodiments of the invention, the subject constructs may be made using factor VII or X. For example, one of skill in the art would understand that the FVII portion of a construct of the invention could be substituted with a FX portion to make an enhanced version of one of these clotting factors.

Clotting factors given for bypass therapy are efficacious when given in the activated form, since exogenous clotting factors are often not activated with sufficient kinetics to be effective. However, they are also rapidly inactivated by endogenous pathways (e.g., by antithrombin III or TFPI), leading to clearance of the active form and a short effective half-life. In order to prevent rapid inactivation by endogenous enzymes and clearance, the chimeric clotting factor of the invention is constructed as an "activatable" form. Such activatable constructs circulate as an enhanced zymogen with a longer half-life, but can be readily cleaved at the site of clotting when necessary.

Exemplary chimeric clotting factor constructs of the invention are set forth in the accompanying Figures. The chimeric clotting factor useful for the invention is expressed in inactive form, is subsequently administered as inactive form, and then is activated upon administration in vivo. Inactive forms of Factors VII and X are single chain zymogens. Active forms of Factors VII and X are comprised of dimeric molecules in which the heavy chain and the light chain are linked by a covalent bond, e.g., a disulfide bond.

An activatable clotting factor comprises a light chain of the clotting factor zymogen linked to a protease-cleavage site, which is further linked to a heavy chain of the clotting factor zymogen. The light chain or the heavy chain of the clotting factor zymogen can include a fragment, a variant, a derivative, or an analog thereof that retains the function of the light chain or the heavy chain of the clotting factor zymogen, respectively.

In one embodiment, a clotting factor of the invention is a mature form of Factor VII or a variant thereof. Factor VII (FVII, F7; also referred to as Factor 7, coagulation factor VII, serum factor VII, serum prothrombin conversion accelerator, SPCA, proconvertin and eptacog alpha) is a serine protease that is part of the coagulation cascade. FVII includes a Gla domain, two EGF domains (EGF-1 and EGF-2), and a serine protease domain (or peptidase Si domain) that is highly conserved among all members of the peptidase Si family of serine proteases, such as for example with chymotrypsin. FVII occurs as a single chain zymogen (i.e., activatable FVII) and a fully activated two-chain form.

As used herein, the term "a FVII protein" includes wild-type FVII, mature FVII, full-length FVII, a functional fragment of FVII, a variant, or a derivative thereof. Exemplary FVII variants include those with increased specific activity, e.g., mutations that increase the activity of FVII by increasing its enzymatic activity (Kcat or Km). Such variants have been described in the art and include, e.g., mutant forms of the molecule as described for example in Persson et al. 2001. PNAS 98:13583; Petrovan and Ruf 2001. J. Biol. Chem. 276:6616; Persson et al. 2001 J. Biol. Chem. 276:29195; Soejima et al. 2001. J. Biol. Chem. 276:17229; Soejima et al. 2002. J. Biol. Chem. 247:49027. In one embodiment, a variant form of FVII includes the mutations. Exemplary mutations include V158D-E296V-M298Q. In another embodiment, a variant form of FVII includes a replacement of amino acids 608-619 (LQQSRKVGDSPN (SEQ ID NO: 65), corresponding to the 170-loop) from the FVII mature sequence with amino acids EASYPGK (SEQ ID NO: 66) from the 170-loop of trypsin. High specific activity variants of FIX are also known in the art. For example, Simioni et al. (2009 N. E. Journal of Medicine 361:1671) describe an R338L mutation. Chang et al. (1988 JBC 273:12089) and Pierri et al. (2009 Human Gene Therapy 20:479) describe an R338A mutation. Other mutations are known in the art and include those described, e.g., in Zogg and Brandstetter. 2009 Structure 17:1669; Sichler et al. 2003. J. Biol. Chem. 278:4121; and Sturzebecher et al. 1997. FEBS Lett 412:295. The contents of these references are incorporated herein by reference. Exemplary FVII amino acid and nucleotide sequences are disclosed in the Sequence Listing as a portion of SEQ ID NOs: 44 and 45, respectively.

Factor VII or Factor X activation occurs when the immediate upstream of a heavy chain of a FVII zymogen or a FX zymogen is cleaved. For example, FVII is activated when the immediate upstream of the first residue of the FVII heavy chain, I.e., Ile-153, is cleaved.

In one embodiment, a clotting factor of the invention is a mature form of Factor X. Factor X is a vitamin-K dependent glycoprotein of a molecular weight of 58.5 kDa, which is secreted from liver cells into the plasma as a zymogen. Initially factor X is produced as a prepropeptide with a signal peptide consisting in total of 488 amino acids. The signal peptide is cleaved off by signal peptidase during export into the endoplasmatic reticulum, the propeptide sequence is cleaved off after gamma carboxylation took place at the first 11 glutamic acid residues at the N-terminus of the mature N-terminal chain. A further processing step occurs by cleavage between Arg182 and Ser183. This processing step also leads concomitantly to the deletion of the tripeptide Arg180-Lys181-Arg182. The resulting secreted factor X zymogen consists of an N-terminal light chain of 139 amino acids (M, 16,200) and a C-terminal heavy chain of 306 amino acids (M, 42,000) which are covalently linked via a disulfide bridge between Cys172 and Cys342. Further posttranslational processing steps include the .beta.-hydroxylation of Asp103 as well as N- and O-type glycosylation.

TABLE 1

Amino acid Sequence of Factor X zymogen (SEQ ID NO: 11)
MGTPLHLVLL SASLAGLLL GESLFIRREQ ANNILARVTR ANSFLEEMKK GHLERECMEE TCSYEEAREV FEDSDKTNEF WNKYKDGDQC ETSPCQNQGK CKDGLGEYTC TCLEGFEGKN
CELFTRKLCS LDNGDCDQFC HEEQNSVVCS CARGYTLADN GKACIPTGPY PCGKQTLERR
KRSVAQATSS SGEAPDSITW KPYDAADLDP TENPFDLLDF NQTQPERGDN NLTRIVGGQE
CKDGECPWQA LLINEENEGF CGGTILSEFY ILTAAHCLYQ AKRFKVRVGD RNTEQEEGGE
AVHEVEVVIK HNRFTKETYD FDIAVLRLKT PITFRMNVAP ACLPERDWAE STLMTQKTGI
VSGFGRTHEK GRQSTRLKML EVPYVDRNSC KLSSSFIITQ NMFCAGYDTK QEDACQGDSG
GPHVTRFKDT YFVTGIVSWG EGCARKGKYG IYTKVTAFLK WIDRSMKTRG LPKAKSHAPE
VITSSPLK Nucleotide Sequence Encoding Factor X Zymogen (SEQ NO: 12)
atggggcgcc cactgcacct cgtcctgctc agtgcctccc tggctggcct cctgctgctc
ggggaaagtc tgttcatccg cagggagcag gccaacaaca tcctggcgag ggtcacgagg
gccaattcct ttcttgaaga gatgaagaaa ggacacctcg aaagagagtg catggaagag
acctgctcat acgaagaggc ccgcgaggtc tttgaggaca gcgacaagac gaatgaattc
tggaataaat acaaagatgg cgaccagtgt gagaccagtc cttgccagaa ccagggcaaa
tgtaaagacg gcctcgggga atacacctgc acctgtttag aaggattcga aggcaaaaac
tgtgaattat tcacacggaa gctctgcagc ctggacaacg gggactgtga ccagttctgc
cacgaggaac agaactctgt ggtgtgctcc tgcgcccgcg ggtacaccct ggctgacaac
ggcaaggcct gcattccac agggccctac ccctgtggga aacagaccct ggaacgcagg
aagaggtcag tggcccaggc caccagcagc agcggggagg ccctgacag catcacatgg
aagccatatg atgcagccga cctggacccc accgagaacc ccttcgacct gcttgacttc
aaccagacgc agcctgagag gggcgacaac aacctcacca ggatcgtggg aggccaggaa
tgcaaggacg gggagtgtcc ctggcaggcc ctgctcatca atgaggaaaa cgagggtttc
tgtggtggaa ccattctgag cgagttctac atcctaacgg cagcccactg tctctaccaa
gccaagagat tcaaggtgag ggtagggac cggaacacgg agcaggagga gggcggtgag
gcggtgcacg aggtggaggt ggtcatcaag cacaaccggt tcacaaagga gacctatgac
ttcgacatcg ccgtgctccg gctcaagacc cccatcacct tccgcatgaa cgtggcgcct
gcctgcctcc ccgagcgtga ctgggccgag tccacgctga tgacgcagaa gacggggatt
gtgagcggct tcgggcgcac ccacgagaag ggccggcagt ccaccaggct caagatgctg
gaggtgccct acgtggaccg caacagctgc aagctgtcca gcagcttcat catcacccag
aacatgttct gtgccggcta cgacaccaag caggaggatg cctgccaggg ggacacgggg
ggcccgcacg tcacccgctt caaggacacc tacttcgtga caggcatcgt cagctgggga
gagggctgtg cccgtaaggg gaagtacggg atctacacca aggtcaccgc cttcctcaag
tggatcgaca ggtccatgaa aaccaggggc ttgcccaagg ccaagagcca tgccccggag
gtcataacgt cctctccatt aaagtga It will be understood that in addition to wild type (WT) versions of these clotting factors or biologically active portions thereof, the present invention may also employ precursor truncated forms thereof that have activity, allelic variants and species variants, variants encoded by splice variants, and other variants, including polypeptides that have at least 40%, 45%, 50%, 55%, 65%, 70%, 75%, 80%, 85%, 90%, 95%, 96%, 97%, 98%, 99% or more sequence identity to the mature form of the clotting factor and which retain the ability to promote clot formation. For example, modified FVII polypeptides and variants thereof which retain at least one activity of a FVII, such as TF binding, factor X binding, phospholipid binding, and/or coagulant activity of a FVII may be employed. By retaining activity, the activity can be altered, such as reduced or increased, as compared to a wild-type clotting factor so long as the level of activity retained is sufficient to yield a detectable effect. Exemplary sequences of clotting factors that can be used in the constructs of the invention are found in the accompanying sequence listing.

Exemplary modified polypeptides include, but are not limited to, tissue-specific isoforms and allelic variants thereof, synthetic molecules prepared by translation of nucleic acids, proteins generated by chemical synthesis, such as syntheses that include ligation of shorter polypeptides, through recombinant methods, proteins isolated from human and non-human tissue and cells, chimeric polypeptides and modified forms thereof. The instant clotting factors may also consist of fragments or portions of WT molecules that are of sufficient length or include appropriate regions to retain at least one activity (upon activation if needed) of a full-length mature polypeptide. Exemplary clotting factor variants are known in the art.

In one embodiment, activatable clotting factors are modified to lack a Gla domain. In the case of Factor VII, the Gla domain is present at the amino terminus of the light chain and consists of amino acids 1-35. The GLA domain is responsible for the high-affinity binding of calcium ions. It starts at the N-terminal extremity of the mature form of proteins and ends with a conserved aromatic residue. A conserved Gla-x(3)-Gla-x-Cys motif is found in the middle of the domain which seems to be important for substrate recognition by the carboxylase.

Using stopped-flow fluorescence kinetic measurements in combination with surface plasmon resonance analysis, the Gla domain has been found to be important in the sequence of events whereby the protease domain of FVIIa initiates contact with sTF (Biochemical and Biophysical Research Communications. 2005. 337:1276). In addition, clearance of clotting factors may be significantly mediated through Gla interactions, e.g., on liver cells and clearance receptors, e.g., EPCR.

Therefore, the Gla domain is responsible for mediating clearance of clotting factors via multiple pathways, such as binding to liver cells, clearance receptors such as EPCR, etc. Thus, eliminating the Gla domain has beneficial effects on half-life of the clotting factors. The Gla domain of factor VII comprises the uncommon amino acid-carboxyglutamic acid (Gla), which plays a vital role in the binding of clotting factors to negatively charged phospholipid surfaces.

Exemplary clotting factors are those of mammalian, e.g., human, origin. The sequences of exemplary clotting factors are presented in the accompanying sequence listing, e.g., alone or in the context of a chimeric clotting factor construct.

2. Protease-Cleavage Site

A protease-cleavage site linking a light chain of a clotting factor zymogen and a heavy chain of the clotting factor zymogen can be selected from any protease-cleavage site known in the art. In one embodiment, the protease-cleavage site is cleaved by a protease selected from factor XIa, factor XIIa, kallikrein, factor VIIa, factor IXa, factor Xa, factor IIa (thrombin), or any combinations thereof. The protease-cleavage sites allow the light chain and the heavy chain of the clotting factor to be cleaved and dissociated from each other at the site of injury. Exemplary FXIa cleavage sites include, e.g., KLTR (SEQ ID NO: 13), DFTR (SEQ ID NO: 14), TQSFNDFTR (SEQ ID NO: 6) and SVSQTSKLTR (SEQ ID NO: 7). Exemplary thrombin cleavage sites include, e.g, DFLAEGGGVR (SEQ ID NO: 8), TTKIKPR (SEQ ID NO: 9), LVPRG (SEQ ID NO: 10) and ALRPR (SEQ ID NO: 1).

In some embodiments, the protease-cleavage site can be combined with an intracellular processing site for efficient cleavage and activation. For example, an activatable clotting factor in the chimeric protein may comprise a heterodimer, which comprises a light chain of a clotting factor associated with a heavy chain of the clotting factor by a covalent bond, wherein the N-terminus of the heavy chain of the clotting factor is linked to a protease-cleavage site. The protease-cleavage site can be cleaved off at the site of coagulation, thus activating the clotting factor. Such constructs can be designed by inserting an intracellular processing site between the light chain of the clotting factor zymogen and the protease-cleavage site, which is linked to the heavy chain of the clotting factor zymogen. The intracellular processing site inserted therein can be processed (cleaved) by an intracellular processing enzyme upon expression in a host cell, thereby allowing formation of a zymogen-like heterodimer. Examples of the intracellular processing enzymes include furin, a yeast Kex2, PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). Other processing sites are known in the art.

3. Self-Immolative Moiety

In certain embodiments, the protease-cleavage site is linked to a heavy chain of a clotting factor zymogen via a self-immolative moiety. The term "self-immolative moiety" as used herein refers to a bifunctional chemical moiety which is capable of covalently linking together two spaced moieties (e.g., a heavy chain of a clotting factor and a protein-cleavage site) into a normally stable tripartate molecule. The self-immolative moiety will spontaneously separate from the second moiety (e.g., a heavy chain of a clotting factor) if it is bound to the first moiety (e.g., a protein-cleavage site) is cleaved.

In some aspects, the self-immolative moiety comprises an aminobenzyl carbamate group, an aminobenzyl ether group, or an aminobenzyl carbonate group. In one aspect, the self-immolative moiety is p-amino benzyl carbamate (PABC).

P-amino benzyl carbamate (PABC) is the most efficient and most widespread connector linkage for self-immolative site-specific prodrug activation (see, e.g., Carl et al. J. Med. Chem. 24:479-480 (1981); WO 1981/001145; Rautio et la, Nature Reviews Drug Discovery 7:255-270 (2008); Simplicio et al., Molecules 13:519-547 (2008);). PABC allows the release of any amine drugs, peptides, and proteins upon cleavage by a protease and 1,6 spontaneous fragmentation.

The aromatic ring of the aminobenzyl group may optionally be substituted with one or more (e.g., $R_1$ and/or $R_2$) substituents on the aromatic ring, which replace a hydrogen that is otherwise attached to one of the four non-substituted carbons that form the ring. As used herein, the symbol "$R_x$" (e.g., $R_1$, $R_2$, $R_3$, $R_4$) is a general abbreviation that represents a substituent group as described herein.

Substituent groups can improve the self-immolative ability of the p-aminobenzyl group (Hay et al., J. Chem Soc., Perkin Trans. 1:2759-2770 (1999); see also, Sykes et al. J. Chem. Soc., Perkin Trans. 1:1601-1608 (2000)).

The following formula shows the general topology of a p-amino benzyl immolative linker and the relative locations of an exemplary protease-cleavage site ($Aa_1Aa_2Aa_3Aa_4$) and a heavy chain of a clotting factor (POI). The formula indicates possible locations of R substituent groups ($R_1$, $R_2$, $R_3$).

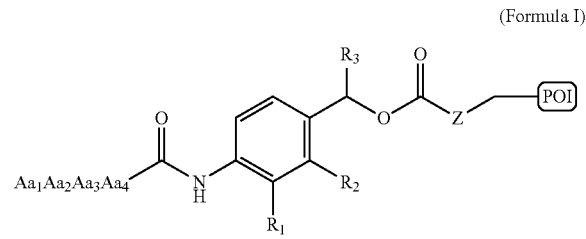

(Formula I)

The substituents, which may be a single atom, e.g., a halogen, or a multi-atom group, e.g., methyl, are selected in order to impact the stability of the aminobenzyl or the decomposition product thereof. Electron withdrawal from the ring may be used to facilitate the spontaneous decomposition of the aminobenzyl group from the drug after cleavage of the bond between the amino group of the aminobenzyl group and the adjacent peptide linkage. Exemplary aromatic group $R_1$, $R_2$, or $R_3$ substituents include, for example, F, Cl, I, Br, OH, methyl, methoxy, $NO_2$, $NH_2$, $NO^{3+}$, $NHCOCH_3$, $N(CH_3)_2$, $NHCOCF_3$, alkyl, haloalkyl, $C_1$-$C_8$ alkylhalide, carboxylate, sulfate, sulfamate, sulfonate, etc. (see, e.g., U.S. Pat. Nos. 7,091,186 and 7,659,241). The p-aminobenzyl linker can comprise a heteroatom Z connected to the amino terminus of the peptide or protein of interest protein. The term heteroatom, as used herein, includes oxygen (O), nitrogen (N), sulfur (S), silicon (Si), boron (B) and phosphorus (P). In one embodiment, the heteroatoms in Z are 0, S or N.

In some embodiments, only one of the four non-substituted carbons in the p-aminobenzyl ring is substituted. In some other embodiments, two of the four non-substituted carbons in the p-aminobenzyl ring are substituted. In other embodiments, three of the four non-substituted carbons in the p-aminobenzyl ring are substituted. In some embodiments, the four non-substituted carbons in the p-aminobenzyl ring are substituted.

Self-immolative elimination can take place, e.g., via 1,4 elimination, 1,6 elimination (e.g., PABC), 1,8 elimination (e.g., p-amino-cinnamyl alcohol), cyclisation-elimination (e.g., 4-aminobutanol ester and ethylenediamines), etc. In some aspects, the self-immolative moiety can comprise, e.g., an cinnamyl, naphthyl, or biphenyl groups (see, e.g., Blencowe et al. Polym. Chem. 2:773-790 (2011)). In some aspects, the self-immolative moiety comprises a heterocyclic ring (see, e.g., U.S. Pat. Nos. 7,375,078; 7,754,681). Numerous homoaromatic (see, e.g., Carl et al. J. Med. Chem. 24:479 (1981); Senter et al. J. Org. Chem. 55:2975 (1990); Taylor et al. J. Org. Chem. 43:1197 (1978); Andrianomenjanahary et al. Bioorg. Med. Chem. Lett. 2:1903 (1992)), and coumarin (see, e.g., Weinstein et al. Chem. Commun. 46:553 (2010)), furan, thiophene, thiazole, oxazole, isoxazole, pyrrole, pyrazole (see, e.g., Hay et al. J. Med. Chem. 46:5533 (2003)), pyridine (see, e.g., Perry-Feigenbaum et al. Org. Biomol. Chem. 7:4825 (2009)), imidazone (see, e.g., Nailor et al. Bioorg. Med. Chem. Lett. Z:1267 (1999); Hay and Denny, Tetrahedron Lett. 38:8425 (1997)), and triazole (see, e.g., Bertrand and Gesson, J. Org. Chem. 72:3596 (2007)) based heteroaromatic groups that are self-immolative under both aqueous and physiological conditions are known in the art. See also, U.S. Pat. Nos. 7,691,962; 7,091,186; U.S. Pat. Publ. Nos. US2006/0269480; 052010/0092496; 052010/0145036; US2003/0130189; US2005/0256030)

Where substituent groups in the self-immolative linkers are specified by their conventional chemical formulae, written from left to right, they equally encompass the chemically identical substituents, which would result from writing the structure from right to left. For example, "—CH$_2$O—" is intended to also recite "—OCH$_2$—". Substituent groups in self-immolative, for example, R$_1$ and/or R$_2$ substituents in a p-aminobenzyl self-immolative linker as discuss above can include, e.g., alkyl, alkylene, alkenyl, alkynyl, alkoxy, alkylamino, alkylthio, heteroalkyl, cycloalkyl, heterocycloalkyl, aryl, arylalkyl, aryloxy, heteroaryl, etc. When a compound of the present disclosure includes more than one substituent, then each of the substituents is independently chosen.

B. Enhancer Moieties (Em)

The present invention provides an improved or enhanced activatable clotting factor such that by fusing the activatable clotting factor to an "enhancer moiety," the properties of an activatable clotting factor of the invention are improved compared to the activatable clotting factor which is not fused to the enhancer moiety. The improved properties include a procoagulant activity of the clotting factor. The increase in the procoagulant activity is relative to the free, or un-fused, activatable clotting factor. An enhancer moiety can be any molecule which has the ability to enhance the procoagulant activity of a clotting factor. The enhancer moiety useful for the invention can have a physical interaction with the activatable clotting factor, and the physical interaction can induce increase in procoagulant activity.

The chimeric protein of the invention can comprise one or more than one enhancer moieties. Additionally, two or more enhancer moieties may be linked to each other (e.g., via a linker) in series, and the tandem array operably linked to a construct of the invention. When two or more enhancer moieties are present in a chimeric clotting factor of the invention, the moieties may be the same or different.

In one embodiment, the enhancer moiety is located on the C-terminus of the heavy chain of factor VII or factor X. In another embodiment, the enhancer moiety is located on the N-terminus of the light chain of factor VII or factor X. In other embodiments, the enhancer moiety is located on the C-terminus of the light chain of factor VII or factor X. In embodiments in which an Fc domain or portion thereof is employed, the enhancer moiety may be positioned at the N or C terminus of the second Fc moiety, or the C-terminus of either or both Fc moieties.

In one embodiment, an enhancer moiety is not genetically fused directly to a construct, but rather is linked via a linker or a chemical bond to the construct. For example, enhancer moieties may be attached to a construct of the invention by formation of a bond between the enhancer moiety and an Fc moiety of a construct, where the enhancer moiety comprises a first functional group and the Fc moiety comprises a second functional group, and where the first and second functional groups are capable of reacting with each other to form a chemical bond (see, e.g., U.S. Pat. No. 7,381,408).

In certain embodiments, the enhancer moieties of the invention can be blood coagulation pathway proteins (e.g., cofactors), procoagulant peptides, or antigen binding molecules. Examples of enhancer moieties are found in the instant examples and Figures. Other molecules useful as enhancer moieties can readily be selected by one of skill in the art based upon the teaching herein.

1. Clotting Cofactors

An enhancer moiety useful for the chimeric protein can be a clotting cofactor. The "clotting cofactor" as used herein means a clotting factor that forms a complex with another clotting factor, e.g., Factor VII or Factor X, and becomes an activated complex having procoagulant activity. For example, a clotting cofactor for FVII is Tissue Factor, which forms the TF-FVIIa complex. A clotting cofactor for FX is FVa, which forms the prothrombinase complex and thereby activates prothrombin to thrombin.

In one embodiment, the clotting factor zymogen is a FVII protein, and the clotting cofactor is a Tissue Factor (TF) polypeptide. Tissue Factor initiates blood coagulation by forming a complex with circulating factor VII or VIIa. The [TF:VIIa] complex activates factors IX or X by specific limited proteolysis. TF plays a role in normal hemostasis by initiating the cell-surface assembly and propagation of the coagulation protease cascade. TF is also known as coagulation factor III, thromboplastin, CD142, and F3. The full-length tissue factor polypeptide has Accession Number P13726-1 in UniProtKB entry and consists of the signal peptide (amino acids 1 to 32), the extracellular domain (amino acids 33 to 251), the transmembrane domain (amino acids 252 to 274) and the cytoplasmic domain (amino acids 275 to 295), total of 295 amino acids. The nucleotide and amino acid sequences of Tissue Factor are represented herein as SEQ ID NO: 16 and SEQ ID NO: 15, respectively. An isoform of Accession Number P13726-1 (No. P13726-2) (SEQ ID NO: 15) contains a substitution of amino acids 199-238:TAKTNTNEFL . . . TVNRKSTDSP→YSTSLELWYL . . . WGRAGRRTPH and a deletion of amino acids 239 to 295. Variants of human Tissue Factor include, but are not limited to, the polypeptides with the following mutations: T36A, I145V, R163W, or G281E. Also included is PCSK1 from a different species, e.g., mouse, rat, monkey, dog, *drosophila*, or porcine. As used herein, a tissue factor polypeptide refers to a polypeptide comprising the soluble ectodomain of Tissue Factor (sTF) (approximately amino acids 33-251), or functional variants, fragments, analogues, or derivatives thereof. sTF lacks the transmembrane and cytoplasmic domains. The full length sequence of mature human Tissue Factor is disclosed in Spicer et al. Proc. Natl. Acad. Sci, USA, 84, 5148-5152 (1987).

TABLE 2

Tissue Factor Sequences

Tissue Factor Amino Acid Sequence- isoform 1
(SEQ ID NO: 15)

METPAWPRVP RPETAVARTL LLGWVFAQVA GASGTTNTVA

AYNLTWKSTN FKTILEWEPK PVNQVYTVQI STKSGDWKSK

CFYTTDTECD LTDEIVKDVK QTYLARVFSY PAGNVESTGS

AGEPLYENSP EFTPYLETNL GQPTIQSFEQ VGTKVNVTVE

DERTLVRRNN TFLSLRDVFG KDLIYTLYYW KSSSSGKKTA

TABLE 2-continued

Tissue Factor Sequences

KTNTNEFLID VDKGENYCFS VQAVIPSRTV NRKSTDSPVE

CMGQEKGEFR EIFYIIGAVV FVVIILVIIL AISLHKCRKA

GVGQSWKENS PLNVS

Tissue Factor Nucleic Acid Sequence
(SEQ ID NO: 16)
ATGGAGACCCCTGCCTGGCCCCGGGTCCCGCGCCCCGAGACCG

CCGTCGCTCGGACGCTCCTGCTCGGCTGGGTCTTCGCCCAGGT

GGCCGGCGCTTCAGGCACTACAAATACTGTGGCAGCATATAAT

TTAACTTGGAAATCAACTAATTTCAAGACAATTTTGGAGTGGG

AACCCAAACCCGTCAATCAAGTCTACACTGTTCAAATAAGCAC

TAAGTCAGGAGATTGGAAAAGCAAATGCTTTTACACAACAGAC

ACAGAGTGTGACCTCACCGACGAGATTGTGAAGGATGTGAAGC

AGACGTACTTGGCACGGGTCTTCTCCTACCCGGCAGGGAATGT

GGAGAGCACCGGTTCTGCTGGGGAGCCTCTGTATGAGAACTCC

CCAGAGTTCACACCTTACCTGGAGACAAACCTCGGACAGCCAA

CAATTCAGAGTTTTGAACAGGTGGGAACAAAAGTGAATGTGAC

CGTAGAAGATGAACGGACTTTAGTCAGAAGGAACAACACTTTC

CTAAGCCTCCGGGATGTTTTTGGCAAGGACTTAATTTATACAC

TTTATTATTGGAAATCTTCAAGTTCAGGAAAGAAAACAGCCAA

AACAAACACTAATGAGTTTTTGATTGATGTGGATAAAGGAGAA

AACTACTGTTTCAGTGTTCAAGCAGTGATTCCCTCCCGAACAG

TTAACCGGAAGAGTACAGACAGCCCGGTAGAGTGTATGGGCCA

GGAGAAGGGGAATTCAGAGAAATATTCTACATCATTGGAGCT

GTGGTATTTGTGGTCATCATCCTTGTCATCATCCTGGCTATAT

CTCTACACAAGTGTAGAAAGGCAGGAGTGGGGCAGAGCTGGAA

GGAGAACTCCCCACTGAATGTTTCATAA

The tissue factor polypeptide used for the present invention comprises an amino acid sequence, which is at least 60%, 70%, 75%, 80%, 85%, 90%, 95%, 96%, 97%, 98%, 99%, or 100% identical to amino acids 33-251 of SEQ ID NO: 15, (sTF), wherein the amino acid sequence is capable of forming a complex with FVII or FVIIa. The term "TF protein" as used herein includes full-length TF, functional fragments (e.g., an extracellular domain), variants, analogues, or derivatives thereof. The term "soluble TF" as used herein includes any functional fragments, variants, analogues, or derivatives thereof that retain one or more activities of the complete extracellular domain of TF. In one embodiment, soluble TF (and its functional fragments, variants, analogues, or derivatives thereof) is capable of binding to FVII. In another embodiment, soluble TF can act as a clotting cofactor for FVII.

In another embodiment, the clotting factor zymogen is a FX protein, and the clotting cofactor is a FVa protein. A FVa protein serves as a critical cofactor for the prothrombinase activity of factor Xa that results in the activation of prothrombin to thrombin. Factor Va, the activated form of factor V, is composed of a heavy chain and a light chain, non-covalently bound. The interaction between the two chains is calcium-dependent. Factor V is also known as coagulation factor V, activated protein C cofactor, proaccelerin, and labile factor and can be cleaved into two chains, a heavy chain and a light chain. The full-length Factor V polypeptide has Accession No. P12259 in UniProtKB entry and consists of the signal peptide (amino acids 1 to 28), the heavy chain (amino acids 29 to 737), the activation peptide (also called as connecting region, amino acids 734 to 1573), and the light chain (amino acids 1574 to 2224). The nucleotide and amino acid sequences of FV are represented herein as SEQ ID NO: 18 and SEQ ID NO: 17, respectively. Variants of human Factor V include, but are not limited to, the polypeptides with the following mutations: G15S, D107H, R334G, R334T, I387T, M413T, R513K, R534Q, C613R, S775A, S781R, P809S, N817T, K858R, H865R, T915S, K925E, N969S, R980L, H1146Q, L1285I, H1327R, L1397F, P1404S, E1530A, T1685S, Y1730C, L1749V, M1764V, M1820I, R2102C, R2102H, M2148T, K2185R, or D2222G. Also included is a Factor V protein from a different species, e.g., mouse, rat, monkey, dog, drosophila, or porcine.

TABLE 3

Factor V Sequences

Factor V Amino Acid Sequence
(SEQ ID NO: 17)
MFPGCPRLWV LVVLGTSWVG WGSQGTEAAQ LRQFYVAAQG ISWSYRPEPT NSSLNLSVTS

FKKIVYREYE PYFKKEKPQS TISGLLGPTL YAEVGDIIKV HFKNKADKPL SIHPQGIRYS

KLSEGASYLD HTFPAEKMDD AVAPGREYTY EWSISEDSGP THDDPPCLTH IYYSHENLIE

DFNSGLIGPL LICKKGTLTE GGTQKTFDKQ IVLLFAVFDE SKSWSQSSSL MYTVNGYVNG

TMPDITVCAH DHISWHLLGM SSGPELFSIH FNGQVLEQNH HKVSAITLVS ATSTTANMTV

GPEGKWIiSS LTPKHLQAGM QAYIDIKNCP KKTRNLKKIT REQRRHMKRW EYFIAAEEVI

WDYAPVIPAN MDKKYRSQHL DNFSNQIGKH YKKVMYTQYE DESFTKHTVN PNMKEDGILG

PIIRAQVRDT LKIVFKNMAS RPYSIYPHGV TFSPYEDEVN SSFTSGRNNT MIRAVQPGET

YTYKWNILEF DEPTENDAQC LTRPYYSDVD IMRDIASGLI GLLLICKSRS LDRRGIQRAA

DIEQQAVFAV FDENKSWYLE DNINKFCENP DEVKRDDPKF YESNIMSTIN GYVPESITTL

TABLE 3-continued

Factor V Sequences

GFCFDDTVQW HFCSVGTQNE ILTIHFTGHS FIYGKRHEDT LTLFPMRGES VTVTMDNVGT
WMLTSMNSSP RSKKLRLKFR DVKCIPDDDE DSYEIFEPPE STVMATRKMH DRLEPEDEES
DADYDYQNRL AAALGIRSFR NSSLNQEEEE FNLTALALEN GTEFVSSNTD IIVGSNYSSP
SNISKFTVNN LAEPQKAPSH QQATTAGSPL RHLIGKNSVL NSSTAEHSSP YSEDPIEDPL
QPDVTGIRLL SLGAGEFKSQ EHAKHKGPKV ERDQAAKHRF SWMKLLAHKV GRHLSQDTGS
PSGMRPWEDL PSQDTGSPSR MRPWKDPPSD LLLLKQSNSS KILVGRWHLA SEKGSYEIIQ
DTDEDTAVNN WLISPQNASR AWGESTPLAN KPGKQSGHPK FPRVRHKSLQ VRQDGGKSRL
KKSQFLIKTR KKKKEKHTHH APLSPRTFHP LRSEAYNTFS ERRLKHSLVL HKSNETSLPT
DLNQTLPSMD FGWIASLPDH NQNSSNDTGQ ASCPPGLYQT VPPEEHYQTF PIQDPDQMHS
TSDPSHRSSS PELSEMLEYD RSHKSFPTDI SQMSPSSEHE VWQTVISPDL SQVTLSPELS
QTNLSPDLSH TTLSPELIQR NLSPALGQMP ISPDLSHTTL SPDLSHTTLS LDLSQTNLSP
ELSQTNLSPA LGQMPLSPDL SHTTLSLDFS QTNLSPELSH MTLSPELSQT NLSPALGQMP
ISPDLSHTTL SLDFSQTNLS PELSQTNLSP ALGQMPLSPD PSHTTLSLDL SQTNLSPELS
QTNLSPDLSE MPLFADLSQI PLTPDLDQMT LSPDLGETDL SPNFGQMSLS PDLSQVTLSP
DISDTTLLPD LSQISPPPDL DQIFYPSESS QSLLLQEFNE SFPYPDLGQM PSPSSPTLND
TFLSKSFKPL VIVGLSKDGT DYIEIIPKEE VQSSEDDYAE IDYVPYDDPY KTDVRTNINS
SRDPDNIAAW YLRSNNGNRR KYYIAAEEIS WDYGEFVQRE TDIEDSDDIP EDTTYKKVVF
RKYLDSTFTK RDPRGEYSEH LGILGPIIRA EVDDVXQVRF KNLASRPYSL HAHGLSYEKS
SEGKTYSDDS FEWFKEDNAV QPNSSYTYVW HATERSGPES PGSACRAWAY YSAVNPEKDI
HSGLIGPLLI CQKGILHKDS NMPMDMREFV LLFMTFDEKK SWYYEKKSRS SWRLTSSSMK
KSHEFHAING MIYSLPGEKM YEQEWVRLHL LNIGGSQDIH VVHFHGQTLL ENGMKQHQLG
VWPLLPGSFK TLEMKASKPG WWLLHTEVGE KQFAGHQTPF LIMDRDCRMP MGLSTGIISD
SQIKASEFLG YWEPRLARLN NGGSYNAWSV EKLAAEFASK PWIQVDHQKE VIITGIQTQG
AKHYLKSCYT TEFYVAYSSN QINWQIFKGK STRNVMYFNG NSDASTIKEN QFDPPIVARY
IRISPTRAYN RPTLRLELQG CSVNGCSTPL GMSNGKIENK QITASSFKHS WKGDYWEPFR
ARLNAQGRVN AWQAKANNNK QWLEIDLLKI KKITAIITQG CKSLSSEMYV KSYTIHYSEQ
GVEWKPYRLK SSMVDKIFEG STNTKGBVKN FFNPPIISRF IRVIPKTWNQ SIALRLELFG
CDIY

Factor V Nucleic Acid Sequence (SEQ ID NO: 18)
ATGTT CCCAGGCTGC CCACGCCTCT GGGTCCTGGT
GGTCTTGGGC ACCAGCTGGG TAGGCTGGGG GAGCCAAGGG ACAGAAGCGG CACAGCTAAG
GCAGTTCTAC GTGGCTGCTC AGGGCATCAG TTGGAGCTAC CGACCTGAGC CCACAAACTC
AAGTTTGAAT CTTTCTGTAA CTTCCTTTAA GAAAATTGTC TACAGAGAGT ATGAACCATA
TTTTAAGAAA GAAAAACCAC AATCTACCAT TTCAGGACTT CTTGGGCCTA CTTTATATGC
TGAAGTCGGA GACATCATAA AAGTTCACTT TAAAAATPAG GCAGATAAGC CCTTGAGCAT
CCATCCTCAA GGAATTAGGT ACAGTAAATT ATCAGAAGGT GCTTCTTACC TTGACCACAC
ATTCCCTGCG GAGAAGATGG ACGACGCTGT GGCTCCAGGC CGAGAATACA CCTATGAATG
GAGTATCAGT GAGGACAGTG GACCCACCCA TGATGACCCT CCATGCCTCA CACACATCTA
TTACTCCCAT GAAAATCTGA TCGAGGATTT CAACTCGGGG CTGATTGGGC CCCTGCTTAT TABLE 3-continued Factor V Sequences

CTGTAAAAAA GGGACCCTAA CTGAGGGTGG GACACAGAAG ACGTTTGACA AGCAAATCGT

GCTACTATTT GCTGTGTTTG ATGAAAGCAA GAGCTGGAGC CAGTCATCAT CCCTAATGTA

CACAGTCAAT GGATATGTGA ATGGGACAAT GCCAGATATA ACAGTTTGTG CCCATGACCA

CATCAGCTGG CATCTGCTGG GAATGAGCTC GGGGCCAGAA TTATTCTCCA TTCATTTCAA

CGGCCAGGTC CTGGAGCAGA ACCATCATAA GGTCTCAGCC ATCACCCTTG TCAGTGCTAC

ATCCACTACC GCAAATATGA CTGTGGGCCC AGAGGGAAAG TGGATCATAT CTTCTCTCAC

CCCAAAACAT TTGCAAGCTG GGATGCAGGC TTACATTGAC ATTAAAAACT GCCCAAAGAA

AACCAGGAAT CTTAAGAAAA TAACTCGTGA GCAGAGGCGG CACATGAAGA GGTGGGAATA

CTTCATTGCT GCAGAGGAAG TCATTTGGGA CTATGCACCT GTAATACCAG CGAATATGGA

CAAAAAATAC AGGTCTCAGC ATTTGGATAA TTTCTCAAAC CAAATTGGAA AACATTATAA

GAAAGTTATG TACACACAGT ACGAAGATGA GTCCTTCACC AAACATACAG TGAATCCCAA

TATGAAAGAA GATGGGATTT TGGGTCCTAT TATCAGAGCC CAGGTCAGAG ACACACTC1A

AATCGTGTTC AAAAATATGG CCAGCCGCCC CTATAGCATT TACCCTCATG GAGTGACCTT

CTCGCCTTAT GAAGATGAAG TCAACTCTTC TTTCACCTCA GGCAGGAACA ACACCATGAT

CAGAGCAGTT CAACCAGGGG AAACCTATAC TTATAAGTGG AACATCTTAG AGTTTGATGA

ACCCACAGAA AATGATGCCC AGTGCTTAAC AAGACCATAC TACAGTGACG TGGACATCAT

GAGAGACATC GCCTCTGGGC TAATAGGACT ACTTCTAATC TGTAAGAGCA GATCCCTGGA

CAGGCGAGGA ATACAGAGGG CAGCAGACAT CGAACAGCAG GCTGTGTTTG CTGTGTTTGA

TGAGAACAAA AGCTGGTACC TTGAGGACAA CATCAACAAG TTTTGTGAAA ATCCTGATGA

GGTGAAACGT GATGACCCCA GTTTTATGA ATCAAACATC ATGAGCACTA TCAATGGCTA

TGTGCCTGAG AGCATAACTA CTCTTGGATT CTGCTTTGAT GACACTGTCC AGTGGCACTT

CTGTAGTGTG GGGACCCAGA ATGAAATTTT GACCATCCAC TTCACTGGGC ACTCATTCAT

CTATGGAAAG AGGCATGAGG ACACCTTGAC CCTCTTCCCC ATGCGTGGAG AATCTGTGAC

GGTCACAATG GATAATGTTG GAACTTGGAT GTTAACTTCC ATGAATTCTA GTCCAAGAAG

CAAAAAGCTG AGGCTGAAAT TCAGGGATGT TAAATGTATC CCAGATGATG ATGAAGACTC

ATATGAGATT TTTGAACCTC CAGAATCTAC AGTCATGGCT ACACGAAAA TGCATGATCG

TTTAGAACCT GAAGATGAAG AGAGTGATGC TGACTATGAT TACCAAAGAC TGGCTGCGAC

AGCATTAGGA ATCAGGTCAT TCCGAAACTC ATCATTGAAT CAGGAAGAAG AAGAGTTCAA

TCTTACTGCC CTAGCTCTGG AGAATGGCAC TGAATTCGTT TCTTCAAACA CAGATATAAT

TGTTGGTTCA AATTATTCTT CCCCAAGTAA TATTAGTAAG TTCACTGTCA ATAACCTTGC

AGAACCTCAG AAAGCCCCTT CTCACCAACA AGCCACCACA GCTGGTTCCC CACTGAGACA

CCTCATTGGC AAGAACTCAG TTCTCAATTC TTCCACAGCA GAGCATTCCA GCCCATATTC

TGAAGACCCT ATAGAGGATC CTCTACAGCC AGATGTCACA GGCATACGTC TACTTTCACT

TGGTGCTGGA GAATTCAAAA GTCAAGAACA TGCTAAGCAT AAGGGACCCA AGGTAGAAAG

AGATCAAGCA GCAAAGCACA GGTTCTCCTG GATGAAATTA CTAGCACATA AGTTGGGGAG

ACACCTAAGC CAAGACACTG GTTCTCCTTC CGGAATGAGG CCCTGGGAGG ACCTTCCTAG

CCAAGACACT GGTTCTCCTT CCAGAATGAG GCCCTGGAAG GACCCTCCTA GTGATCTGTT

ACTCTTAAAA CAAAGTAACT CATCTAAGAT TTTGGTTGGG AGATGGCATT TGGCTTCTGA

GAAAGGTAGC TATGAAATAA TCCAAGATAC TGATGAAGAC ACAGCTGTTA ACAATTGGCT

TABLE 3-continued

Factor V Sequences

```
GATCAGCCCC CAGAATGCCT CACGTGCTTG GGGAGAAAGC ACCCTCTTG CCAACAAGCC

TGGAAAGCAG AGTGGCCACC CAAAGTTTCC TAGAGTTAGA CATAAATCTC TACAAGTAAG

ACAGGATGGA GGAAAGAGTA GACTGAAGAA AGCCAGTTT CTCATTAAGA CACGAAAAAA

GAAAAAGAG AAGCACACAC ACCATGCTCC TTTATCTCCC AGGACCTTTC ACCCTCTAAG

AAGTGAAGCC TACAACACAT TTTCAGAAAG AAGACTTAAG CATTCGTTGG TGCTTCATAA

ATCCAATGAA ACATCTCTTC CCACAGACCT CAATCAGACA TTGCCCTCTA TGGATTTTGG

CTGGATAGCC TCACTTCCTG ACCATAATCA GAATTCCTCA ATGACACTG GTCAGGCAAG

CTGTCCTCCA GGTCTTTATC AGACAGTGCC CCCAGAGGAA CACTATCAAA CATTCCCCAT

TCAAGACCCT GATCAAATGC ACTCTACTTC AGACCCAGT CACAGATCCT CTTCTCCAGA

GCTCAGTGAA ATGCTTGAGT ATGACCGAAG TCACAAGTCC TTCCCCACAG ATATAAGTCA

AATGTCCCCT TCCTCAGAAC ATGAAGTCTG GCAGACAGTC ATCTCTCCAG ACCTCAGCCA

GGTGACCCTC TCTCCAGAAC TCACCCAGAC AAACCTCTCT CCAGACCTCA GCCACACGAC

TCTCTCTCCA GAACTCATTC AGAGAAACCT TTCCCCAGCC CTCGGTCAGA TGCCCATTTC

TCCAGACCTC AGCCATACAA CCCTTTCTCC AGACCTCAGC CATACAACCC TTTCTTTAGA

CCTCAGCCAG ACAAACCTCT CTCCAGAACT CAGTCAGACA AACCTTTCTC CAGCCCTCGG

TCAGATGCCC CTTTCTCCAG ACCTCAGCCA TACAACCCTT TCTCTAGACT TCAGCCAGAC

AAACCTCTCT CCAGAACTCA GCCATATGAC TCTCTCTCCA GAACTCAGTC AGACAAACCT

TTCCCCAGCC CTCGGTCAGA TGCCCATTTC TCCAGACCTC ACCCATACAA CCCTTTCTCT

AGACTTCAGC CAGACAAACC TCTCTCCAGA ACTCAGTCAA ACAAACCTTT CCCCAGCCCT

CGGTCAGATG CCCCTTTCTC CAGACCCCAG CCATACAACC CTTTCTCTAG ACCTCAGCCA

GACAAACCTC TCTCCAGAAC TCAGTCAGAC AAACCTTTCC CCAGACCTCA GTGAGATGCC

CCTCTTTGCA GATCTCAGTC AAATTCCCCT TACCCCAGAC CTCGACCAGA TGACACTTTC

TCCAGACCTT GGTGAGACAG ATCTTTCCCC AAACTTTGGT CAGATGTCCC TTTCCCCAGA

CCTCAGCCAG GTGACTCTCT CTCCAGACAT CAGTGACACC ACCCTTCTCC GGATCTCAG

CCAGATATCA CCTCCTCCAG ACCTTGATCA GATATTCTAC CCTTCTGAAT CTAGTCAGTC

ATTGCTTCTT CAAGAATTTA ATGAGTCTTT TCCTTATCCA GACCTTGGTC AGATGCCATC

TCCTTCATCT CCTACTCTCA ATGATACTTT TCTATCAAAG GAATTTAATC CACTGGTTAT

AGTGGGCCTC AGTAAAGATG GTACAGATTA CATTGAGATC ATTCCAAAGG AAGAGGTCCA

GAGCAGTGAA GATGACTATG CTGAAATTGA TTATGTGCCC TATGATGACC CTACAAAAC

TGATGTTAGG ACAAACATCA ACTCCTCCAG AGATCCTGAC AACATTGCAG CATGGTACCT

CCGCAGCAAC AATGGAAACA GAAGAAATTA TTACATTGCT GCTGAAGAAA TATCCTGGGA

TTATTCAGAA TTTGTACAAA GGGAAACAGA TATTGAAGAC TCTGATGATA TTCCAGAAGA

TACCACATAT AAGAAAGTAG TTTTTCGAAA GTACCTCGAC AGCACTTTTA CCAAACGTGA

TCCTCGAGGG GAGTATGAAG AGCATCTCGG AATTCTTGGT CCTATTATCA GAGCTGAAGT

GGATGATGTT ATCCAAGTTC GTTTTAAAAA TTTAGCATCC AGACCGTATT CTCTACATGC

CCATGGACTT TCCTATGAAA AATCATCAGA GGGAAAGACT TATGAAGATG ACTCTCCTGA

ATGGTTTAAG GAAGATAATG CTGTTCAGCC AAATAGCAGT TATACCTACG TATGGCATGC

CACTGAGCGA TCAGGGCCAG PAAGTCCTGG CTCTGCCTGT CGGGCTTGGG CCTACTACTC

AGCTGTGAAC CCAGAAAAAG ATATTCACTC AGGCTTGATA GGTCCCCTCC TAATCTGCCA
```

TABLE 3-continued

Factor V Sequences

```
AAAAGGAATA CTACATAAGG ACAGCAACAT GCCTATGGAC ATGAGAGAAT TTGTCTTACT

ATTTATGACC TTTGATGAAA AGAAGAGCTG GTACTATGAA AAGAAGTCCC GAAGTTCTTG

GAGACTCACA TCCTCAGAAA TGAAAAAATC CCATGAGTTT CACGCCATTA ATGGGATGAT

CTACAGCTTG CCTGGCCTGA AAATGTATGA GCAAGAGTGG CTCAGGTTAC ACCTGCTGAA

CATAGGCGGC TCCCAAGACA TTCACGTGGT TCACTTTCAC GGCCAGACCT TGCTGGAAAA

TGGCAATAAA CAGCACCAGT TAGGGGTCTG GCCCCTTCTG CCTGGTTCAT TTAAAACTCT

TGAAATGAAG CCATCAAAAC CTGGCTGGTG GCTCCTAAAC ACAGAGGTTG GAGAAAACCA

GAGAGCAGGG ATGCAAACGC CATTTCTTAT CATGGACAGA GACTGTAGGA TGCCAATGGG

ACTAAGCACT GGTATCATAT CTGATTCACA GATCAAGGCT TCAGAGTTTC TGGGTTACTG

GGAGCCCAGA TTAGCAAGAT TAAACAATGG TGGATCTTAT AATGCTTGGA GTGTAGAAAA

ACTTGCAGCA GAATTTGCCT CTAAACCTTG GATCCAGGTG GACATGCAAA AGGAAGTCAT

AATCACAGGG ATCCAGACCC AAGGTGCCAA ACACTACCTG AAGTCCTGCT ATACCACAGA

GTTCTATGTA GCTTACAGTT CCAACCAGAT CAACTGGCAG ATCTTCAAAG GGAACAGCAC

AAGGAATGTG ATGTATTTTA ATGGCAATTC AGATGCCTCT ACAATAAAAG AGAATCAGTT

TGACCCACCT ATTGTGGCTA GATATATTAG GATCTCTCCA ACTCGAGCCT ATAACAGACC

TACCCTTCGA TTGGAACTGC AAGGTTGTGA GGTAAATGGA TGTTCCACAC CCTGGGTAT

GGAAAATGGA AAGATAGAAA ACAAGCAAAT CACAGCTTCT TCGTTTAAGA AATCTTGGTG

GGGAGATTAC TGGGAACCCT TCCGTGCCCG TCTGAATGCC CAGGGACGTG TGAATGCCTG

GCAAGCCAAG GCAAACAACA ATAAGCAGTG GCTAGAAATT GATCTACTCA AGATCAAGAA

GATAACGGCA ATTATAACAC AGGGCTGCAA GTCTCTGTCC TCTGAAATGT ATGTAAAGAG

CTATACCATC CACTACAGTG AGCAGGGAGT GGAATGGAAA CCATACAGGC TGAAATCCTC

CATGGTGGAC AAGATTTTTG AAGGAAATAC TAATACCAAA GGACATGTGA AGAACTTTTT

CAACCCCCCA ATCATTTCCA GGTTTATCCG TGTCATTCCT AAAACATGGA ATCAAAGTAT

TGCACTTCGC CTGGAACTCT TTGGCTGTGA TATTTACTAG
```

The FVa protein used for the present invention comprises a heterodimer comprising a heavy chain and a light chain, wherein the heavy chain comprises a first amino acid sequence, which is at least 60%, 70%, 75%, 80%, 85%, 90%, 95%, 96%, 97%, 98%, 99%, or 100% identical to amino acids 29 to 737 of SEQ ID NO: 17 and the light chain comprises a second amino acid sequence, which is at least 60%, 70%, 75%, 80%, 85%, 90%, 95%, 96%, 97%, 98%, 99%, or 100% identical to amino acids 1574 to 2224 of SEQ ID NO: 18, wherein the first amino acid sequence and the second amino acid sequence when formed the heterodimer is capable of forming a complex with FX or FXa. The FVa protein as used herein includes full-length FVa, mature FVa, functional fragments, variants, analogues, or derivatives thereof.

2. Procoagulant Peptides

In other embodiments, the enhancer moiety is a procoagulant peptide. A "procoagulant peptide" is a low molecular weight compound (e.g., peptides or peptide derivatives) with pro-coagulant activity that can be used for the treatment of bleeding diathesis (e.g., blood coagulation disorders/coagulopathies, such as hemophilia A) or for the treatment of deficiencies in at least one of FV, FVII, FVIII, FIX, FX, FXI, and vWF. In some embodiments, when a procoagulant peptide is used as an enhancer moiety, it is capable of increasing the catalytic activity of the clotting factor to which it is fused.

In one embodiment, the procoagulant peptide comprises a compound that includes:

(a) an amino acid sequence including Formula II:

$$C^1LASYC^2 \qquad \text{(Formula II)}$$

or (b) a retro-, an inverso- or a retro-inverso variant of the amino acid sequence of (a). The present disclosure further provides pharmaceutically acceptable salts of the above compound.

In Formula II, $C^1$ and $C^2$ are amino acids having a side chain, wherein the side chains of $C^1$ and $C^2$ are linked to form a loop. In one example, the side chains of $C^1$ and $C^2$ are covalently linked (e.g., via a disulfide bond or an amide bond).

In Formula II, one, two or three additional amino acids can be inserted anywhere between $C^1$ and $C^2$. In one example according to any of the above embodiments, one or two additional amino acids are optionally inserted into Formula (I) anywhere between $C^1$ and $C^2$. In another example, one amino acid is optionally inserted into Formula II anywhere between $C^1$ and $C^2$. In another example, no amino acid is inserted between $C^1$ and C2.

In Formula II, L is L-leucine, A is L-alanine, S is L-serine, and Y is L-tyrosine. In Formula II, one, two or three of L, A, S, and Y are optionally replaced with an independently selected replacement amino acid. In one example, one or two of L, A, S, and Y are optionally replaced with an independently selected replacement amino acid. In another example, exactly one of L, A, S, and Y is optionally replaced with an independently selected replacement amino acid.

In another embodiment, the enhancer moiety in a chimeric protein comprises a compound that contains a peptide of Formula III:

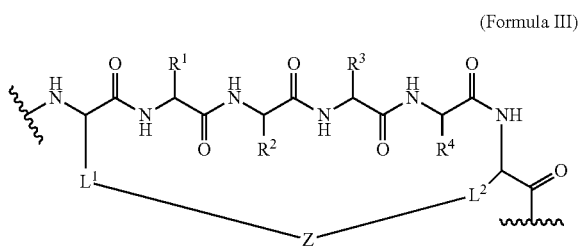

(Formula III)

or a retro-, an inverso- or a retro-inverso variant thereof.

In Formula III, $R^1$, $R^2$, $R^3$ and $R^4$ are members independently selected from amino acid side chains. In Formula III, $L^1$ and $L^2$ are linker groups independently selected from straight or branched alkylene, and straight or branched heteroalkylene.

In Formula III, Z is a linking moiety. In one example, Z is selected from an amino group, an amide group, a disulfide group, a diselenide group, a —S—Se— group, alkylene, e.g., $(C_2-C_4)$alkylene, alkenyl, e.g., $(C_2-C_4)$alkenyl, alkynyl, e.g., $(C_2-C_4)$alkynyl, cycloalkyl (e.g., $(C_3-C_8)$cycloalkyl containing from 1 to 4 double bonds), heterocycloalkyl (e.g., 3- to 8-membered heterocyclic ring comprising from 1 to 6 heteroatoms selected from O, S and N), aryl (e.g., $(C_3-C_7)$ aryl), and heteroaryl (e.g., 3- to 8-membered heteroaryl comprising from 1 to 6 heteroatoms selected from O, S and N).

Exemplary synthetic procoagulant peptides include, for example:

KLTCLASYCWLF; (SEQ ID NO: 19)

RRAPGKLTCLASYCWLFWTGIA; (SEQ ID NO: 20)

RRAPGKLQCLASYCWLFWTGIA; (SEQ ID NO: 21)

PRIRTVGPGSRSASGKLTCLASYCWLFWTGIA; (SEQ ID NO: 22)

SKQGRPISPDRRAAGKLTCLASYCWLFWTGIA; (SEQ ID NO: 23)

PRIRTVGPGSRSASGKSTCLASYCWLFWTGIA; (SEQ ID NO: 24)

SRIRTVSPGSRSASGKSTCLASYCWLFWTGIA; (SEQ ID NO: 25)
or

PRSRTVGPGSRSASGKSTCLASYCWLFWTGIA. (SEQ ID NO: 26)

Exemplary procoagulant peptides are additionally disclosed in U.S. 61/495,818, U.S. 61/600,237, U.S. 61/605,540, U.S. 61/496,540, U.S. 61/496,543, U.S. 61/496,544, U.S. 61/496,541, and U.S. 61/496,542, each of which is incorporated herein by reference in its entirety.

3. Antibodies or Antigen Binding Sites

In other embodiments, the enhancer moiety comprises at least one antigen binding moiety (e.g., an antigen binding site of an antibody, antibody variant, or antibody fragment), a receptor binding portion of ligand, or a ligand binding portion of a receptor. Exemplary antigen binding molecules that can be used as enhancer moieties are disclosed in Andersen L M et al., J Biol Chem. 287: 8994-9001 (January 2012), incorporated herein by reference in its entirety, which discloses FVII activating antibodies and antibody derivatives used for increasing the procoagulant activity of FVIIa and for treating blood coagulation disorders such as hemophilia A and hemorrhagic diathesis.

The term "antigen-binding moiety" refers to a polypeptide fragment of an immunoglobulin, antibody, or antibody variant which binds antigen or competes with intact antibody (i.e., with the intact antibody from which they were derived) for antigen binding (i.e., specific binding). Antigen binding portions can be produced by recombinant or biochemical methods that are well known in the art. Exemplary antigen-binding portions include Fv, Fab, Fab', and (Fab')2 as well as scFv molecules.

In other embodiments, a chimeric clotting factor of the invention may comprise an enhancer moiety comprising a binding site from single chain binding molecule (e.g., a single chain variable region or scFv). Techniques described for the production of single chain antibodies (U.S. Pat. No. 4,694,778; Bird, Science 242:423-442 (1988); Huston et al., Proc. Natl. Acad. Sci. USA 85:5879-5883 (1988); and Ward et al., Nature 334:544-554 (1989)) can be adapted to produce single chain binding molecules. Single chain antibodies are formed by linking the heavy and light chain fragments of the Fv region via an amino acid bridge, resulting in a single chain antibody. Techniques for the assembly of functional Fv fragments in E coli may also be used (Skerra et al., Science 242:1038-1041 (1988)).

In certain embodiments, a chimeric clotting factor of the invention may comprise an enhancer moiety comprising one or more binding sites or regions comprising or consisting of a single chain variable region sequence (scFv). Single chain variable region sequences comprise a single polypeptide having one or more antigen binding sites, e.g., a VL domain linked by a flexible linker to a VH domain. ScFv molecules can be constructed in a VH-linker-VL orientation or VL-linker-VH orientation. The flexible linker that links the VL and VH domains that make up the antigen binding site preferably comprises from about 10 to about 50 amino acid residues. In one embodiment, the peptide linker is a gly-ser peptide linker. An exemplary gly/ser peptide linker is of the formula (Gly4Ser)n, wherein n is a positive integer (e.g., 1, 2, 3, 4, 5, or 6). Other peptide linkers are known in the art. Antibodies having single chain variable region sequences (e.g. single chain Fv antibodies) and methods of making said single chain antibodies are well-known in the art (see e.g., Ho et al. 1989. Gene 77:51; Bird et al. 1988 Science 242:423; Pantoliano et al. 1991. Biochemistry 30:10117; Milenic et al. 1991. Cancer Research 51:6363; Takkinen et al. 1991. Protein Engineering 4:837).

In certain embodiments, a scFv molecule employed in a chimeric clotting factor of the invention is a stabilized scFv molecule. In one embodiment, the stabilized cFv molecule may comprise a scFv linker interposed between a VH domain and a VL domain, wherein the VH and VL domains are linked by a disulfide bond between an amino acid in the VH and an amino acid in the VL domain. In other embodiments, the stabilized scFv molecule may comprise a scFv linker having an optimized length or composition. In yet other embodiments, the stabilized scFv molecule may comprise a VH or VL domain having at least one stabilizing amino acid substitution(s). In yet another embodiment, a stabilized scFv molecule may have at least two of the above listed stabilizing features.

Stabilized scFv molecules have improved protein stability or impart improved protein stability to the polypeptide to which it is operably linked. Preferred scFv linkers of the invention improve the thermal stability of a chimeric clotting factor of the invention by at least about 2° C. or 3° C. as compared to a conventional polypeptide. Comparisons can be made, for example, between the scFv molecules of the invention. In certain embodiments, the stabilized scFv molecule comprises a (Gly4Ser)4 scFv linker and a disulfide bond which links VH amino acid 44 and VL amino acid 100. Other exemplary stabilized scFv molecules which may be employed in the chimeric clotting factor of the invention are described in U.S. Provisional Patent Application No. 60/873,996, filed on Dec. 8, 2006 or U.S. patent application Ser. No. 11/725,970, filed on Mar. 19, 2007, each of which is incorporated herein by reference in its entirety.

Chimeric clotting factor of the invention may comprise a variable region or portion thereof (e.g. a VL and/or VH domain) derived from an antibody using art recognized protocols. For example, the variable domain may be derived from antibody produced in a non-human mammal, e.g., murine, guinea pig, primate, rabbit or rat, by immunizing the mammal with the antigen or a fragment thereof. See Harlow & Lane, supra, incorporated by reference for all purposes. The immunoglobulin may be generated by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes.

While the variable region may be derived from polyclonal antibodies harvested from the serum of an immunized mammal, it is often desirable to isolate individual lymphocytes from the spleen, lymph nodes or peripheral blood to provide homogenous preparations of monoclonal antibodies (MAbs) from which the desired variable region is derived. Rabbits or guinea pigs are typically used for making polyclonal antibodies. Mice are typically used for making monoclonal antibodies. Monoclonal antibodies can be prepared against a fragment by injecting an antigen fragment into a mouse, preparing "hybridomas" and screening the hybridomas for an antibody that specifically binds to the antigen. In this well-known process (Kohler et al., (1975), Nature, 256:495) the relatively short-lived, or mortal, lymphocytes from the mouse which has been injected with the antigen are fused with an immortal tumor cell line (e.g. a myeloma cell line), thus, producing hybrid cells or "hybridomas" which are both immortal and capable of producing the antibody genetically encoded by the B cell. The resulting hybrids are segregated into single genetic strains by selection, dilution, and regrowth with each individual strain comprising specific genes for the formation of a single antibody. They produce antibodies which are homogenous against a desired antigen and, in reference to their pure genetic parentage, are termed "monoclonal".

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunosorbent assay (ELISA). After hybridoma cells are identified that produce antibodies of the desired specificity, affinity and/or activity, the clones may be subcloned by limiting dilution procedures and grown by standard methods (Goding, Monoclonal Antibodies: Principles and Practice, pp 59-103 (Academic Press, 1986)). It will further be appreciated that the monoclonal antibodies secreted by the subclones may be separated from culture medium, ascites fluid or serum by conventional purification procedures such as, for example, affinity chromatography (e.g., protein-A, protein-G, or protein-L affinity chromatography), hydroxylapatite chromatography, gel electrophoresis, or dialysis.

DNA encoding the desired monoclonal antibody or binding site thereof may be readily isolated and sequenced using any of the conventional procedures described supra for the isolation of constant region domain sequences (e.g., by using oligonucleotide probes that are capable of binding specifically to genes encoding the heavy and light chains of murine antibodies). The isolated and subcloned hybridoma cells serve as a preferred source of such DNA. More particularly, the isolated DNA (which may be synthetic as described herein) may be used to clone the desired variable region sequences for incorporation in the chimeric clotting factor of the invention.

In other embodiments, the binding site is derived from a fully human antibody. Human or substantially human antibodies may be generated in transgenic animals (e.g., mice) that are incapable of endogenous immunoglobulin production (see e.g., U.S. Pat. Nos. 6,075,181, 5,939,598, 5,591,669 and 5,589,369, each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

In other aspects, the polypeptides of the invention may comprise antigen binding sites, or portions thereof, derived from modified forms of antibodies. Exemplary such forms include, e.g., minibodies, diabodies, triabodies, nanobodies, camelids, Dabs, tetravalent antibodies, intradiabodies (e.g., Jendreyko et al. 2003. J. Biol. Chem. 278:47813), fusion proteins (e.g., antibody cytokine fusion proteins, proteins fused to at least a portion of an Fc receptor), and bispecific antibodies. Other modified antibodies are described, for example in U.S. Pat. No. 4,745,055; EP 256,654; Faulkner et al., Nature 298:286 (1982); EP 120,694; EP 125,023; Morrison, J. Immun. 123:793 (1979); Kohler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Natl. Acad. Sci. USA 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

In another embodiment, a chimeric clotting factor of the invention comprises an antigen binding site or region which is a diabody or an antigen binding site derived therefrom. Diabodies are dimeric, tetravalent molecules each having a polypeptide similar to scFv molecules, but usually having a short (e.g., less than 10 and preferably 1-5) amino acid residue linker connecting both variable domains, such that the VL and VH domains on the same polypeptide chain cannot interact. Instead, the VL and VH domain of one polypeptide chain interact with the VH and VL domain (respectively) on a second polypeptide chain (see, for example, WO 02/02781). In one embodiment, a chimeric clotting factor of the invention comprises a diabody which is operably linked to the N-terminus and/or C-terminus of at least one genetically-fused Fc region (i.e., scFc region).

In certain embodiments, a chimeric clotting factor of the invention comprises a single domain binding molecule (e.g. a single domain antibody) as an enhancer moiety. Exemplary single domain molecules include an isolated heavy chain variable domain (VH) of an antibody, i.e., a heavy chain variable domain, without a light chain variable domain, and an isolated light chain variable domain (VL) of an antibody, i.e., a light chain variable domain, without a heavy chain variable domain. Exemplary single-domain antibodies employed in the binding molecules of the invention include, for example, the Camelid heavy chain variable domain (about 118 to 136 amino acid residues) as described in Hamers-Casterman, et al., Nature 363:446-448 (1993), and Dumoulin, et al., Protein Science 11:500-515 (2002). Other exemplary single domain antibodies include single VH or VL domains, also known as Dabs® (Domantis Ltd., Cambridge, UK). Yet other single domain antibodies include shark antibodies (e.g., shark Ig-NARs). Shark Ig-NARs comprise a homodimer of one variable domain (V-NAR) and five C-like constant domains (C-NAR), wherein diversity is concentrated in an elongated CDR3 region varying from 5 to 23 residues in length. In camelid species (e.g., llamas), the heavy chain variable region, referred to as VHH, forms the entire antigen-binding domain. The main differences between camelid VHH variable regions and those derived from conventional antibodies (VH) include (a) more hydrophobic amino acids in the light chain contact surface of VH as compared to the corresponding region in VHH, (b) a longer CDR3 in VHH, and (c) the frequent occurrence of a disulfide bond between CDR1 and CDR3 in VHH. Methods for making single domain binding molecules are described in U.S. Pat. Nos. 6,005,079 and 6,765,087, both of which are incorporated herein by reference. Exemplary single domain antibodies comprising VHH domains include Nanobodies® (Ablynx NV, Ghent, Belgium).

C. Heterologous Moieties (e.g., Het1, Het2, ..., $Het_n$)

Some embodiments of the invention comprise one or more heterologous moieties (indicated herein as "Het1" or "Het2"). In other embodiments, the chimeric protein of the invention can comprise two heterologous moieties ("Het1" and "Het2"). In yet other embodiments, the chimeric protein of the invention can comprise more than two heterologous moieties, e.g., three, four, five, or more than five heterologous moieties. In some embodiments, all the heterologous moieties are identical. In some embodiments, at least one heterologous moiety is different from the other heterologous moieties. In some embodiments, the chimeric protein of the invention can comprise two, three or more than three heterologous moieties in tandem. In other embodiments, the chimeric protein of the invention can comprise two, three, or more than heterologous moieties wherein at least an additional moiety (e.g., an activatable clotting factor, a linker moiety, a protease-cleavage site, a self-immolative moiety, an enhancer moiety, or combinations thereof) is interposed between two heterologous moieties.

A heterologous moiety can comprise a heterologous polypeptide moiety, or a heterologous non-polypeptide moiety, or both. In one specific embodiment, Het1 is a first heterologous moiety, e.g., a half-life extending molecule which is known in the art. In some embodiments, Het2 is a second heterologous moiety that can also be a half-life extending molecule which is known in the art. In some aspects, the heterologous moiety comprises a combination of a heterologous polypeptide and a non-polypeptide moiety.

In certain embodiments, the first heterologous moiety (e.g., a first Fc moiety) and the second heterologous moiety (e.g., a second Fc moiety) are associated with each other to form a dimer. In one embodiment, the second heterologous moiety is a second Fc moiety, wherein the second Fc moiety is linked to or associated with the first heterologous moiety, e.g., the first Fc moiety. For example, the second heterologous moiety (e.g., the second Fc moiety) can be linked to the first heterologous moiety (e.g., the first Fc moiety) by a linker or associated with the first heterologous moiety by a covalent or non-covalent bond In some embodiments, the Het1 and Het2 heterologous moieties are peptides and polypeptides with either unstructured or structured characteristics that are associated with the prolongation of in vivo half-life when incorporated in a chimeric protein of the invention. Non-limiting examples include albumin, albumin fragments, Fc fragments of immunoglobulins, the β subunit of the C-terminal peptide (CTP) of human chorionic gonadotropin, a HAP sequence, an XTEN sequence, a transferrin or a fragment thereof, a PAS polypeptide, polyglycine linkers, polyserine linkers, albumin-binding moieties, or any fragments, derivatives, variants, or combinations of these polypeptides. In other related aspects a heterologous moiety can include an attachment site (e.g., a cysteine amino acid) for a non-polypeptide moiety such as polyethylene glycol (PEG), hydroxyethyl starch (HES), polysialic acid, or any derivatives, variants, or combinations of these elements. In some aspects, a heterologous moiety consisting of a cysteine amino acid that function as an attachment site for a non-polypeptide moiety such as polyethylene glycol (PEG), hydroxyethyl starch (HES), polysialic acid, or any derivatives, variants, or combinations of these elements.

In some embodiments, the heterologous moiety is a polypeptide comprising, consisting essentially of, or consisting of at least about 10, 100, 200, 300, 400, 500, 600, 700, 800, 900, 1000, 1100, 1200, 1300, 1400, 1500, 1600, 1700, 1800, 1900, 2000, 2500, 3000, or 4000 amino acids. In other embodiments, the heterologous moiety is a polypeptide comprising, consisting essentially of, or consisting of about 100 to about 200 amino acids, about 200 to about 300 amino acids, about 300 to about 400 amino acids, about 400 to about 500 amino acids, about 500 to about 600 amino acids, about 600 to about 700 amino acids, about 700 to about 800 amino acids, about 800 to about 900 amino acids, or about 900 to about 1000 amino acids.

In certain embodiments, a heterologous moiety improves one or more pharmacokinetic properties of the chimeric protein without significantly affecting the biological activity or function of the activatable clotting factor and/or the enhancer moiety (e.g., procoagulant activity of a clotting factor or a fragment thereof, or of activity enhancing property of an enhancer moiety).

In certain embodiments, a heterologous moiety increases the in vivo and/or in vitro half-life of the clotting factor of the invention. In other embodiments, a heterologous moiety facilitates visualization or localization of the clotting factor of the invention or a fragment thereof (e.g., a fragment comprising a heterologous moiety after proteolytic cleavage of the activatable clotting factor). Visualization and/or location of the chimeric protein of the invention or a fragment thereof can be in vivo, in vitro, ex vivo, or combinations thereof.

In other embodiments, a heterologous moiety increases stability of the chimeric protein of the invention or a fragment thereof (e.g., a fragment comprising a heterologous moiety after proteolytic cleavage of the activatable clotting factor). As used herein, the term "stability" refers to an art-recognized measure of the maintenance of one or more physical properties of the activatable clotting factor in response to an environmental condition (e.g., an elevated or lowered temperature). In certain aspects, the physical property can be the maintenance of the covalent structure of the chimeric protein (e.g., the absence of proteolytic cleavage, unwanted oxidation or deamidation). In other aspects, the physical property can also be the presence of the chimeric protein in a properly folded state (e.g., the absence of soluble or insoluble aggregates or precipitates). In one aspect, the stability of the chimeric protein is measured by assaying a biophysical property of the chimeric protein, for example thermal stability, pH unfolding profile, stable removal of glycosylation, solubility, biochemical function (e.g., ability to bind to a protein, receptor or ligand), etc., and/or combinations thereof. In another aspect, biochemical function is demonstrated by the binding affinity of the interaction. In one aspect, a measure of protein stability is thermal stability, i.e., resistance to thermal challenge. Stability can be measured using methods known in the art, such as, HPLC (high performance liquid chromatography), SEC (size exclusion chromatography), DLS (dynamic light scattering), etc. Methods to measure thermal stability include, but are not limited to differential scanning calorimetry (DSC), differential scanning fluorimetry (DSF), circular dichroism (CD), and thermal challenge assay.

In certain aspects, a chimeric protein of the invention comprises at least one half-like extender, i.e., a heterologous moiety which increases the in vivo half-life of the chimeric protein with respect to the in vivo half-life of the corresponding chimeric protein lacking such heterologous moiety. In vivo half-life of a chimeric protein can be determined by any method known to those of skill in the art, e.g., activity assays (chromogenic assay or one stage clotting aPTT assay), ELISA, etc.

In some embodiments, the presence of one or more half-life extenders results in the half-life of the chimeric protein to be increased compared to the half-life of the corresponding protein lacking such one or more half-life extenders. The half-life of the chimeric protein comprising a half-life extender is at least about 1.5 times, at least about 2 times, at least about 2.5 times, at least about 3 times, at least about 4 times, at least about 5 times, at least about 6 times, at least about 7 times, at least about 8 times, at least about 9 times, at least about 10 times, at least about 11 times, or at least about 12 times longer than the in vivo half-life of the corresponding chimeric protein lacking such half-life extender.

In one embodiment, the half-life of the chimeric protein comprising a half-life extender is about 1.5-fold to about 20-fold, about 1.5 fold to about 15 fold, or about 1.5 fold to about 10 fold longer than the in vivo half-life of the corresponding protein lacking such half-life extender. In another embodiment, the half-life of chimeric protein comprising a half-life extender is extended about 2-fold to about 10-fold, about 2-fold to about 9-fold, about 2-fold to about 8-fold, about 2-fold to about 7-fold, about 2-fold to about 6-fold, about 2-fold to about 5-fold, about 2-fold to about 4-fold, about 2-fold to about 3-fold, about 2.5-fold to about 10-fold, about 2.5-fold to about 9-fold, about 2.5-fold to about 8-fold, about 2.5-fold to about 7-fold, about 2.5-fold to about 6-fold, about 2.5-fold to about 5-fold, about 2.5-fold to about 4-fold, about 2.5-fold to about 3-fold, about 3-fold to about 10-fold, about 3-fold to about 9-fold, about 3-fold to about 8-fold, about 3-fold to about 7-fold, about 3-fold to about 6-fold, about 3-fold to about 5-fold, about 3-fold to about 4-fold, about 4-fold to about 6 fold, about 5-fold to about 7-fold, or about 6-fold to about 8 fold as compared to the in vivo half-life of the corresponding protein lacking such half-life extender.

In other embodiments, the half-life of the chimeric protein comprising a half-life extender is at least about 17 hours, at least about 18 hours, at least about 19 hours, at least about 20 hours, at least about 21 hours, at least about 22 hours, at least about 23 hours, at least about 24 hours, at least about 25 hours, at least about 26 hours, at least about 27 hours, at least about 28 hours, at least about 29 hours, at least about 30 hours, at least about 31 hours, at least about 32 hours, at least about 33 hours, at least about 34 hours, at least about 35 hours, at least about 36 hours, at least about 48 hours, at least about 60 hours, at least about 72 hours, at least about 84 hours, at least about 96 hours, or at least about 108 hours.

In still other embodiments, the half-life of the chimeric protein comprising a half-life extender is about 15 hours to about two weeks, about 16 hours to about one week, about 17 hours to about one week, about 18 hours to about one week, about 19 hours to about one week, about 20 hours to about one week, about 21 hours to about one week, about 22 hours to about one week, about 23 hours to about one week, about 24 hours to about one week, about 36 hours to about one week, about 48 hours to about one week, about 60 hours to about one week, about 24 hours to about six days, about 24 hours to about five days, about 24 hours to about four days, about 24 hours to about three days, or about 24 hours to about two days.

In some embodiments, the average half-life per subject of the chimeric protein comprising a half-life extender is about 15 hours, about 16 hours, about 17 hours, about 18 hours, about 19 hours, about 20 hours, about 21 hours, about 22 hours, about 23 hours, about 24 hours (1 day), about 25 hours, about 26 hours, about 27 hours, about 28 hours, about 29 hours, about 30 hours, about 31 hours, about 32 hours, about 33 hours, about 34 hours, about 35 hours, about 36 hours, about 40 hours, about 44 hours, about 48 hours (2 days), about 54 hours, about 60 hours, about 72 hours (3 days), about 84 hours, about 96 hours (4 days), about 108 hours, about 120 hours (5 days), about six days, about seven days (one week), about eight days, about nine days, about 10 days, about 11 days, about 12 days, about 13 days, or about 14 days.

1. An Immunoglobulin Constant Region or a Portion Thereof

In another aspect, a heterologous moiety comprises one or more immunoglobulin constant region or a portion thereof (e.g., an Fc moiety). In one embodiment, a chimeric protein comprises an activatable clotting factor, an enhancer moiety, and at least two heterologous moieties, a first heterologous moiety comprises a first immunoglobulin constant region or a portion thereof (e.g., a first Fc moiety), which is linked to the activatable clotting factor and a second heterologous moiety comprises a second immunoglobulin constant region or a portion thereof (e.g., a second Fc moiety), which is linked to the enhancer moiety. The first immunoglobulin constant region or a portion thereof and the second immunoglobulin constant region or a portion thereof can form a covalent bond (e.g., a disulfide bond), thereby placing the activatable clotting factor and the enhancer moiety close in proximity to allow interaction between the activated clotting factor and the enhancer moiety at the site of injury.

An immunoglobulin constant region is comprised of domains denoted CH (constant heavy) domains (CH1, CH2, etc.). Depending on the isotype, (i.e. IgG, IgM, IgA IgD, or IgE), the constant region can be comprised of three or four CH domains. Some isotypes (e.g. IgG) constant regions also contain a hinge region. See Janeway et al. 2001, *Immunobiology*, Garland Publishing, N.Y., N.Y.

An immunoglobulin constant region or a portion thereof for producing the chimeric protein of the present invention may be obtained from a number of different sources. In one embodiment, an immunoglobulin constant region or a portion thereof is derived from a human immunoglobulin. It is understood, however, that the immunoglobulin constant region or a portion thereof may be derived from an immunoglobulin of another mammalian species, including for example, a rodent (e.g. a mouse, rat, rabbit, guinea pig) or non-human primate (e.g. chimpanzee, macaque) species. Moreover, the immunoglobulin constant region or a portion thereof may be derived from any immunoglobulin class, including IgM, IgG, IgD, IgA and IgE, and any immunoglobulin isotype, including IgG1, IgG2, IgG3 and IgG4. In one embodiment, the human isotype IgG1 is used.

A variety of the immunoglobulin constant region gene sequences (e.g. human constant region gene sequences) are available in the form of publicly accessible deposits. Constant region domains sequence can be selected having a particular effector function (or lacking a particular effector function) or with a particular modification to reduce immunogenicity. Many sequences of antibodies and antibody-encoding genes have been published and suitable Ig constant region sequences (e.g. hinge, CH2, and/or CH3 sequences, or portions thereof) can be derived from these sequences using art recognized techniques. The genetic material obtained using any of the foregoing methods may then be altered or synthesized to obtain polypeptides of the present invention. It will further be appreciated that the scope of this invention encompasses alleles, variants and mutations of constant region DNA sequences.

The sequences of the immunoglobulin constant region or a portion thereof can be cloned, e.g., using the polymerase chain reaction and primers which are selected to amplify the domain of interest. To clone a sequence of the immunoglobulin constant region or a portion thereof from an antibody, mRNA can be isolated from hybridoma, spleen, or lymph cells, reverse transcribed into DNA, and antibody genes amplified by PCR. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270). PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250). The cloning of antibody sequences is further described in Newman et al., U.S. Pat. No. 5,658,570, filed Jan. 25, 1995, which is incorporated by reference herein.

An immunoglobulin constant region used herein can include all domains and the hinge region or portions thereof. In one embodiment, the immunoglobulin constant region or a portion thereof comprises CH2 domain, CH3 domain, and a hinge region, i.e., an Fc domain or an FcRn binding partner.

An immunoglobulin constant region or a portion thereof can be an FcRn binding partner. FcRn is active in adult epithelial tissues and expressed in the lumen of the intestines, pulmonary airways, nasal surfaces, vaginal surfaces, colon and rectal surfaces (U.S. Pat. No. 6,485,726). An FcRn binding partner is a portion of an immunoglobulin that binds to FcRn.

The FcRn receptor has been isolated from several mammalian species including humans. The sequences of the human FcRn, monkey FcRn, rat FcRn, and mouse FcRn are known (Story et al. 1994, J. Exp. Med. 180:2377). The FcRn receptor binds IgG (but not other immunoglobulin classes such as IgA, IgM, IgD, and IgE) at relatively low pH, actively transports the IgG transcellularly in a luminal to serosal direction, and then releases the IgG at relatively higher pH found in the interstitial fluids. It is expressed in adult epithelial tissue (U.S. Pat. Nos. 6,485,726, 6,030,613, 6,086,875; WO 03/077834; US2003-0235536A1) including lung and intestinal epithelium (Israel et al. 1997, Immunology 92:69) renal proximal tubular epithelium (Kobayashi et al. 2002, Am. J. Physiol. Renal Physiol. 282:F358) as well as nasal epithelium, vaginal surfaces, and biliary tree surfaces.

FcRn binding partners useful in the present invention encompass molecules that can be specifically bound by the FcRn receptor including whole IgG, the Fc fragment of IgG, and other fragments that include the complete binding region of the FcRn receptor. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The FcRn binding partners include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U.S. Department of Public Health, Bethesda, Md.

Fc regions or FcRn binding partners bound to FcRn can be effectively shuttled across epithelial barriers by FcRn, thus providing a non-invasive means to systemically administer a desired therapeutic molecule. Additionally, fusion proteins comprising an Fc region or an FcRn binding partner are endocytosed by cells expressing the FcRn. But instead of being marked for degradation, these fusion proteins are recycled out into circulation again, thus increasing the in vivo half-life of these proteins. In certain embodiments, the portions of immunoglobulin constant regions are an Fc region or an FcRn binding partner that typically associates, via disulfide bonds and other non-specific interactions, with another Fc region or another FcRn binding partner to form dimers and higher order multimers.

Two FcRn receptors can bind a single Fc molecule. Crystallographic data suggest that each FcRn molecule binds a single polypeptide of the Fc homodimer. In one embodiment, linking the FcRn binding partner, e.g., an Fc fragment of an IgG, to a biologically active molecule provides a means of delivering the biologically active molecule orally, buccally, sublingually, rectally, vaginally, as an aerosol administered nasally or via a pulmonary route, or via an ocular route. In another embodiment, the chimeric protein can be administered invasively, e.g., subcutaneously, intravenously.

An FcRn binding partner region is a molecule or portion thereof that can be specifically bound by the FcRn receptor with consequent active transport by the FcRn receptor of the Fc region. Specifically bound refers to two molecules forming a complex that is relatively stable under physiologic conditions. Specific binding is characterized by a high affinity and a low to moderate capacity as distinguished from nonspecific binding which usually has a low affinity with a moderate to high capacity. Typically, binding is considered specific when the affinity constant KA is higher than $10^6$ $M^{-1}$, or higher than $10^8$ $M^{-1}$. If necessary, non-specific binding can be reduced without substantially affecting specific binding by varying the binding conditions. The appropriate binding conditions such as concentration of the molecules, ionic strength of the solution, temperature, time allowed for binding, concentration of a blocking agent (e.g. serum albumin, milk casein), etc., may be optimized by a skilled artisan using routine techniques.

In certain embodiments, a chimeric protein of the invention comprises one or more truncated Fc regions that are nonetheless sufficient to confer Fc receptor (FcR) binding properties to the Fc region. For example, the portion of an Fc region that binds to FcRn (i.e., the FcRn binding portion) comprises from about amino acids 282-438 of IgG1, EU numbering (with the primary contact sites being amino acids 248, 250-257, 272, 285, 288, 290-291, 308-311, and 314 of the CH2 domain and amino acid residues 385-387, 428, and 433-436 of the CH3 domain. Thus, an Fc region of the invention may comprise or consist of an FcRn binding portion. FcRn binding portions may be derived from heavy chains of any isotype, including IgG1, IgG2, IgG3 and IgG4. In one embodiment, an FcRn binding portion from an antibody of the human isotype IgG1 is used. In another embodiment, an FcRn binding portion from an antibody of the human isotype IgG4 is used.

The Fc moieties denoted as F, F1, or F2 herein may be obtained from a number of different sources. In one embodiment, an Fc moiety of the polypeptide is derived from a human immunoglobulin. It is understood, however, that an Fc moiety may be derived from an immunoglobulin of another mammalian species, including for example, a rodent (e.g. a mouse, rat, rabbit, guinea pig) or non-human primate (e.g. chimpanzee, macaque) species. Moreover, the polypeptide of the Fc domains or portions thereof may be derived from any immunoglobulin class, including IgM, IgG, IgD, IgA and IgE, and any immunoglobulin isotype, including IgG1, IgG2, IgG3 and IgG4. In another embodiment, the human isotype IgG1 is used.

In certain embodiments, the Fc variant confers a change in at least one effector function imparted by an Fc moiety comprising said wild-type Fc domain (e.g., an improvement or reduction in the ability of the Fc region to bind to Fc receptors (e.g. FcγRI, FcγRII, or FcγRIII) or complement proteins (e.g. C1q), or to trigger antibody-dependent cytotoxicity (ADCC), phagocytosis, or complement-dependent cytotoxicity (CDCC)). In other embodiments, the Fc variant provides an engineered cysteine residue.

The Fc moiety of the invention may employ art-recognized Fc variants which are known to impart a change (e.g., an enhancement or reduction) in effector function and/or FcR or FcRn binding. Specifically, a binding molecule of the invention may include, for example, a change (e.g., a substitution) at one or more of the amino acid positions disclosed in International PCT Publications WO88/07089A1, WO96/14339A1, WO98/05787A1, WO98/23289A1, WO99/51642A1, WO99/58572A1, WO00/09560A2, WO00/32767A1, WO00/42072A2, WO02/44215A2, WO02/060919A2, WO03/074569A2, WO04/016750A2, WO04/029207A2, WO04/035752A2, WO04/063351A2, WO04/074455A2, WO04/099249A2, WO05/040217A2, WO04/044859, WO05/070963A1, WO05/077981A2, WO05/092925A2, WO05/123780A2, WO06/019447A1, WO06/047350A2, and WO06/085967A2; US Patent Publication Nos. US2007/0231329, US2007/0231329, US2007/0237765, US2007/0237766, US2007/0237767, US2007/0243188, US20070248603, US20070286859, US20080057056; or U.S. Pat. Nos. 5,648,260; 5,739,277; 5,834,250; 5,869,046; 6,096,871; 6,121,022; 6,194,551; 6,242,195; 6,277,375; 6,528,624; 6,538,124; 6,737,056; 6,821,505; 6,998,253; 7,083,784; 7,404,956, and 7,317,091, each of which is incorporated by reference herein. In one embodiment, the specific change (e.g., the specific substitution of one or more amino acids disclosed in the art) may be made at one or more of the disclosed amino acid positions. In another embodiment, a different change at one or more of the disclosed amino acid positions (e.g., the different substitution of one or more amino acid position disclosed in the art) may be made.

The Fc moiety or FcRn binding partner of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example, the following single amino acid residues in human IgG1 Fc (Fc γ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, P331A, E333A, K334A, T335A, S337A, K338A, K340A, Q342A, R344A, E345A, Q347A, R355A, E356A, M358A, T359A, K360A, N361A, Q362A, Y373A, S375A, D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. As an example, a specific embodiment incorporates the N297A mutation, removing a highly conserved N-glycosylation site. In addition to alanine other amino acids may be substituted for the wild type amino acids at the positions specified above. Mutations may be introduced singly into Fc giving rise to more than one hundred Fc regions distinct from the native Fc. Additionally, combinations of two, three, or more of these individual mutations may be introduced together, giving rise to hundreds more Fc moieties. Moreover, one of the Fc moiety of a construct of the invention may be mutated and the other Fc moiety of the construct not mutated at all, or they both may be mutated but with different mutations.

Certain of the above mutations may confer new functionality upon the Fc moiety or FcRn binding partner. For example, one embodiment incorporates N297A, removing a highly conserved N-glycosylation site. The effect of this mutation is to reduce immunogenicity, thereby enhancing circulating half-life of the Fc region, and to render the Fc region incapable of binding to FcγRI, FcγRIIA, FcγRIIB, and FcγRIIIA, without compromising affinity for FcRn (Routledge et al. 1995, Transplantation 60:847; Friend et al. 1999, Transplantation 68:1632; Shields et al. 1995, J. Biol. Chem. 276:6591). As a further example of new functionality arising from mutations described above affinity for FcRn may be increased beyond that of wild type in some instances. This increased affinity may reflect an increased "on" rate, a decreased "off" rate or both an increased "on" rate and a decreased "off" rate. Examples of mutations believed to impart an increased affinity for FcRn include, but not limited to, T256A, T307A, E380A, and N434A (Shields et al. 2001, J. Biol. Chem. 276:6591).

Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII, which mediate various effector functions will not bind to IgG1 when such mutations have been introduced. Ward and Ghetie 1995, Therapeutic Immunology 2:77 and Armour et al. 1999, Eur. J. Immunol. 29:2613.

In one embodiment, the immunoglobulin constant region or a portion thereof, e.g, an Fc moiety, is a polypeptide including the sequence PKNSSMISNTP (SEQ ID NO: 27) and optionally further including a sequence selected from HQSLGTQ (SEQ ID NO: 28), HQNLSDGK (SEQ ID NO: 29), HQNISDGK (SEQ ID NO: 30), or VISSHLGQ (SEQ ID NO: 31) (U.S. Pat. No. 5,739,277).

In another embodiment, the immunoglobulin constant region or a portion thereof comprises an amino acid sequence in the hinge region or a portion thereof that forms one or more disulfide bonds with another immunoglobulin constant region or a portion thereof. The disulfide bond by the immunoglobulin constant region or a portion thereof places the first polypeptide comprising an activatable clotting factor and the second polypeptide comprising the enhancer moiety together so that upon activation of the clotting factor, the enhancer moiety is available to enhance activity of the clotting factor. The hinge region or a portion thereof can further be linked to one or more domains of CH1, CH2, CH3, a fragment thereof, or any combinations thereof.

In certain embodiments, the immunoglobulin constant region or a portion thereof is hemi-glycosylated. For example, the chimeric protein comprising two Fc moieties or FcRn binding partners may contain a first, glycosylated, Fc moiety (e.g., a glycosylated CH2 region) or FcRn binding partner and a second, aglycosylated, Fc moiety (e.g., an aglycosylated CH2 region) or FcRn binding partner. In one embodiment, a linker may be interposed between the glycosylated and aglycosylated Fc moieties. In another embodiment, the Fc moiety or FcRn binding partner is fully glycosylated, i.e., all of the Fc moieties are glycosylated. In other embodiments, the Fc moiety may be aglycosylated, i.e., none of the Fc moieties are glycosylated.

In certain embodiments, a chimeric protein of the invention comprises an amino acid substitution to an immunoglobulin constant region or a portion thereof (e.g., Fc variants), which alters the antigen-independent effector functions of the Ig constant region, in particular the circulating half-life of the protein.

Such proteins exhibit either increased or decreased binding to FcRn when compared to proteins lacking these substitutions and, therefore, have an increased or decreased half-life in serum, respectively. Fc variants with improved affinity for FcRn are anticipated to have longer serum half-lives, and such molecules have useful applications in methods of treating mammals where long half-life of the administered polypeptide is desired, e.g., to treat a chronic disease or disorder (see, e.g, U.S. Pat. Nos. 7,348,004, 7,404,956, and 7,862,820). In contrast, Fc variants with decreased FcRn binding affinity are expected to have shorter half-lives, and such molecules are also useful, for example, for administration to a mammal where a shortened circulation time may be advantageous, e.g. for in vivo diagnostic imaging or in situations where the starting polypeptide has toxic side effects when present in the circulation for prolonged periods. Fc variants with decreased FcRn binding affinity are also less likely to cross the placenta and, thus, are also useful in the treatment of diseases or disorders in pregnant women. In addition, other applications in which reduced FcRn binding affinity may be desired include those applications in which localization the brain, kidney, and/or liver is desired. In one exemplary embodiment, the chimeric protein of the invention exhibits reduced transport across the epithelium of kidney glomeruli from the vasculature. In another embodiment, the chimeric protein of the invention exhibits reduced transport across the blood brain barrier (BBB) from the brain, into the vascular space. In one embodiment, a protein with altered FcRn binding comprises at least one Fc moiety or FcRn binding partner (e.g, one or two Fc regions or FcRn binding partners) having one or more amino acid substitutions within the "FcRn binding loop" of an Ig constant region. The FcRn binding loop is comprised of amino acid residues 280-299 (according to EU numbering) of a wild-type, full-length, Fc region. In other embodiments, an Ig constant region or a portion thereof in a chimeric protein of the invention having altered FcRn binding affinity comprises at least one Fc region or FcRn binding partner having one or more amino acid substitutions within the 15 Å FcRn "contact zone." As used herein, the term 15 Å FcRn "contact zone" includes residues at the following positions of a wild-type, full-length Fc moiety: 243-261, 275-280, 282-293, 302-319, 336-348, 367, 369, 372-389, 391, 393, 408, 424, 425-440 (EU numbering). In other embodiments, a Ig constant region or a portion thereof of the invention having altered FcRn binding affinity comprises at least one Fc moiety or FcRn binding partner having one or more amino acid substitutions at an amino acid position corresponding to any one of the following EU positions: 256, 277-281, 283-288, 303-309, 313, 338, 342, 376, 381, 384, 385, 387, 434 (e.g., N434A or N434K), and 438. Exemplary amino acid substitutions which altered FcRn binding activity are disclosed in International PCT Publication No. WO05/047327 which is incorporated by reference herein.

An Fc moiety or FcRn binding partner used in the invention may also comprise an art recognized amino acid substitution which alters the glycosylation of the chimeric protein. For example, the Fc moiety or FcRn binding partner of the chimeric protein linked to an activatable clotting factor or an enhancer moiety may comprise an Fc moiety having a mutation leading to reduced glycosylation (e.g., N- or O-linked glycosylation) or may comprise an altered glycoform of the wild-type Fc moiety (e.g., a low fucose or fucose-free glycan).

In one embodiment, a chimeric protein of the invention may comprise a genetically fused Fc region (i.e., scFc region) having two or more of its constituent Ig constant region or portion thereof independently selected from the Ig constant region or portion thereof described herein. In one embodiment, the Fc domains of a dimeric Fc region are the same. In another embodiment, at least two of the Fc domains are different. For example, the Fc moieties or FcRn binding partners of the proteins of the invention comprise the same number of amino acid residues or they may differ in length by one or more amino acid residues (e.g., by about 5 amino acid residues (e.g., 1, 2, 3, 4, or 5 amino acid residues), about 10 residues, about 15 residues, about 20 residues, about 30 residues, about 40 residues, or about 50 residues). In yet other embodiments, the Fc moieties or FcRn binding partners of the protein of the invention may differ in sequence at one or more amino acid positions. For example, at least two of the Fc moieties or FcRn binding partners may differ at about 5 amino acid positions (e.g., 1, 2, 3, 4, or 5 amino acid positions), about 10 positions, about 15 positions, about 20 positions, about 30 positions, about 40 positions, or about 50 positions).

2. scFc Regions

In one embodiment, the invention provides for unprocessed chimeric polypeptides comprising an activatable clotting factor, an enhancer moiety, and at least one genetically fused Fc region or portion thereof within a single polypeptide chain (i.e., polypeptides comprising a single-chain Fc (scFc) region). The unprocessed polypeptides comprise at least two immunoglobulin constant regions or portions thereof (e.g., Fc moieties or domains (e.g., 2, 3, 4, 5, 6, or more Fc moieties or domains)) within the same linear polypeptide chain that are capable of folding (e.g., intramolecularly or intermolecularly folding) to form one functional scFc region which is linked by an Fc peptide linker. For example, in one embodiment, a polypeptide of the invention is capable of binding, via its scFc region, to at least one Fc receptor (e.g. an FcRn, an FcγR receptor (e.g., FcγRIII), or a complement protein (e.g. C1q)) in order to improve half-life or trigger an immune effector function (e.g., antibody-dependent cytotoxicity (ADCC), phagocytosis, or complement-dependent cytotoxicity (CDCC) and/or to improve manufacturability).

A variety of polypeptides of alternative designs are within the scope of the invention. For example, in one embodiment, a polypeptide comprises the moieties:

A-F1-P1-L-P2-B-F2 (_)

in linear sequence from the amino to carboxy terminus wherein A, if present, is an activatable clotting factor or portion thereof, F1 is a first immunoglobulin constant region or a portion thereof, P1 is a first intracellular processing site, L is a scFc linker, P2 is a second intracellular processing site; B is an enhancer moiety, F2 is a second immunoglobulin constant region or a portion thereof; and "—" represents a peptide bond. Formula (_) comprises at least a P1 or a P2 and optionally both. P1 and P2, if both present, can be the same or different. Formula (_) comprises at least a F1, a F2, or both. F1 and F2, if both present, can be the same or different.

3. CTP

In certain aspects, a chimeric protein of the invention comprises at least one heterologous moiety comprising one β subunit of the C-terminal peptide (CTP) of human chorionic gonadotropin or fragment, variant, or derivative thereof. One or more CTP peptides inserted into a recombinant protein is known to increase the in vivo half-life of that protein. See, e.g., U.S. Pat. No. 5,712,122, incorporated by reference herein in its entirety.

Exemplary CTP peptides include DPRFQDSSSSKAP-PPSLPSPSRLPGPSDTPIL (SEQ ID NO: 32) or SSSSKAP-PPSLPSPSRLPGPSDTPILPQ. (SEQ ID NO: 33). See, e.g., U.S. Patent Application Publication No. US 2009/0087411 A1, incorporated by reference.

4. XTEN Sequence

In some embodiments, a heterologous moiety in the chimeric protein comprises one or more XTEN sequences, fragments, variants, or derivatives thereof. As used here "XTEN sequence" refers to extended length polypeptides with non-naturally occurring, substantially non-repetitive sequences that are composed mainly of small hydrophilic amino acids, with the sequence having a low degree or no secondary or tertiary structure under physiologic conditions. As a heterologous moiety, XTENs can serve as a half-life extension moiety. In addition, XTEN can provide desirable properties including but are not limited to enhanced pharmacokinetic parameters and solubility characteristics.

The incorporation of a heterologous moiety comprising an XTEN sequence into a chimeric protein of the invention can confer to the chimeric protein one or more of the following advantageous properties: conformational flexibility, enhanced aqueous solubility, high degree of protease resistance, low immunogenicity, low binding to mammalian receptors, or increased hydrodynamic (or Stokes) radii.

In certain aspects, an XTEN sequence can improve pharmacokinetic properties such as extending in vivo half-life or increasing total exposure (area under the curve (AUC)), so that a chimeric protein of the invention displays prolonged efficacy for controlling bleeds compared to a chimeric protein with the same but without the XTEN heterologous moiety.

Examples of XTEN sequences that can be used as heterologous moieties in chimeric proteins of the invention are disclosed, e.g., in U.S. Pat. Nos. 7,855,279 and 7,846,445, U.S. Patent Publication Nos. 2009/0092582 A1, 2010/0239554 A1, 2010/0323956 A1, 2011/0046060 A1, 2011/0046061 A1, 2011/0077199 A1, 2013/0017997 A1, or 2012/0263701 A1, or 2011/0172146 A1, or International Patent Publication Nos. WO 2010091122 A1, WO 2010144502 A2, WO 2010144508 A1, WO 2011028228 A1, WO 2011028229 A1, or WO 2011028344 A2, or International Application No. PCT/US2011/48517, filed Aug. 19, 2011, each of which is incorporated by reference herein in its entirety.

5. Albumin or Fragment, Derivative, or Variant Thereof

In certain embodiments, the chimeric protein of the invention comprises a heterologous moiety comprising albumin or a functional fragment thereof. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are incorporated herein by reference in their entireties.

In one embodiment, the chimeric protein of the invention comprises albumin, a fragment, or a variant thereof which is further linked to a heterologous moiety selected from an immunoglobulin constant region or portion thereof (e.g., an Fc region), a PAS sequence, HES, PEG, or any combinations thereof.

6. Albumin Binding Moiety

In certain embodiments, the heterologous moiety is an albumin binding moiety, which comprises an albumin binding peptide, a bacterial albumin binding domain, an albumin-binding antibody fragment, or any combinations thereof.

For example, the albumin binding protein can be a bacterial albumin binding protein, an antibody or an antibody fragment including domain antibodies (see U.S. Pat. No. 6,696,245). An albumin binding protein, for example, can be a bacterial albumin binding domain, such as the one of streptococcal protein G (Konig, T. and Skerra, A. (1998) *J. Immunol. Methods* 218, 73-83). Other examples of albumin binding peptides that can be used as conjugation partner are, for instance, those having a Cys-Xaa$_1$-Xaa$_2$-Xaa$_3$-Xaa$_4$-Cys consensus sequence, wherein Xaa$_1$ is Asp, Asn, Ser, Thr, or Trp; Xaa$_2$ is Asn, Gln, H is, Ile, Leu, or Lys; Xaa$_3$ is Ala, Asp, Phe, Trp, or Tyr; and Xaa$_4$ is Asp, Gly, Leu, Phe, Ser, or Thr (SEQ ID NO: 34) as described in US patent application 2003/0069395 or Dennis et al. (Dennis et al. (2002) *J. Biol. Chem.* 277, 35035-35043).

Domain 3 from streptococcal protein G, as disclosed by Kraulis et al., FEBS Lett. 378:190-194 (1996) and Linhult et al., Protein Sci. 11:206-213 (2002) is an example of a bacterial albumin-binding domain. Examples of albumin-binding peptides include a series of peptides having the core sequence DICLPRWGCLW (SEQ ID NO: 35). See, e,g., Dennis et al., J. Biol. Chem. 2002, 277: 35035-35043 (2002). Examples of albumin-binding antibody fragments are disclosed in Muller and Kontermann, Curr. Opin. Mol. Ther. 9:319-326 (2007); Roovers et al., Cancer Immunol. Immunother. 56:303-317 (2007), and Holt et al., Prot. Eng. Design Sci., 21:283-288 (2008), which are incorporated herein by reference in their entireties. An example of such albumin binding moiety is 2-(3-maleimidopropanamido)-6-(4-(4-iodophenyl)butanamido) hexanoate ("Albu" tag) as disclosed by Trussel et al., Bioconjugate Chem. 20:2286-2292 (2009).

Fatty acids, in particular long chain fatty acids (LCFA) and long chain fatty acid-like albumin-binding compounds can be used to extend the in vivo half-life of chimeric proteins of the invention. An example of a LCFA-like albumin-binding compound is 16-(1-(3-(9-(((2,5-dioxopyrrolidin-1-yloxy) carbonyloxy)-methyl)-7-sulfo-9H-fluoren-2-ylamino)-3-oxopropyl)-2,5-dioxopyrrolidin-3-ylthio) hexadecanoic acid (see, e.g., WO 2010/140148).

7. PAS Sequence

In other embodiments, at least one heterologous moiety is a PAS sequence. A PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. Yet, the skilled person is aware that an amino acid polymer also may form random coil conformation when residues other than alanine, serine, and proline are added as a minor constituent in the PAS sequence. The term "minor constituent" as used herein means that amino acids other than alanine, serine, and proline may be added in the PAS sequence to a certain degree, e.g., up to about 12%, i.e., about 12 of 100 amino acids of the PAS sequence, up to about 10%, i.e. about 10 of 100 amino acids of the PAS sequence, up to about 9%, i.e., about 9 of 100 amino acids, up to about 8%, i.e., about 8 of 100 amino acids, about 6%, i.e., about 6 of 100 amino acids, about 5%, i.e., about 5 of 100 amino acids, about 4%, i.e., about 4 of 100 amino acids, about 3%, i.e., about 3 of 100 amino acids, about 2%, i.e., about 2 of 100 amino acids, about 1%, i.e., about 1 of 100 of the amino acids. The amino acids different from alanine, serine and proline may be selected from Arg, Asn, Asp, Cys, Gln, Glu, Gly, His, Ile, Leu, Lys, Met, Phe, Thr, Trp, Tyr, or Val.

Under physiological conditions, the PAS sequence stretch forms a random coil conformation and thereby can mediate an increased in vivo and/or in vitro stability to the chimeric protein. Since the random coil domain does not adopt a stable structure or function by itself, the biological activity mediated by the activatable clotting factor in the chimeric protein is essentially preserved. In other embodiments, the PAS sequences that form random coil domain are biologically inert, especially with respect to proteolysis in blood plasma, immunogenicity, isoelectric point/electrostatic behaviour, binding to cell surface receptors or internalisation, but are still biodegradable, which provides clear advantages over synthetic polymers such as PEG.

Non-limiting examples of the PAS sequences forming random coil conformation comprise an amino acid sequence selected from ASPAAPAPASPAAPAPSAPA (SEQ ID NO: 36), AAPASPAPAAPSAPAPAAPS (SEQ ID NO: 37), APSSPSPSAPSSPSPASPSS (SEQ ID NO: 38), APSSPSPSAPSSPSPASPS (SEQ ID NO: 39), SSPSAPSPSSPASPSPSSPA (SEQ ID NO: 40), AASPAAPSAPPAAASPAAPSAPPA (SEQ ID NO: 41), ASAAAPAAASAAASAPSAAA (SEQ ID NO: 42) or any combinations thereof. Additional examples of PAS sequences are known from, e.g., US Pat. Publ. No. 2010/0292130 A1 and PCT Appl. Publ. No. WO 2008/155134 A1.

8. HAP Sequence

In certain embodiments, at least one heterologous moiety is a glycine-rich homo-amino-acid polymer (HAP). The HAP sequence can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. In one embodiment, the HAP sequence is capable of extending half-life of a moiety fused to or linked to the HAP sequence. Non-limiting examples of the HAP sequence includes, but are not limited to (Gly)$_n$, (Gly$_4$Ser)$_n$ or S(Gly$_4$Ser)$_n$, wherein n is 1, 2, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200.

9. Transferrin or Fragment Thereof

In certain embodiments, at least one heterologous moiety is transferrin or a fragment thereof. Any transferrin may be used to make the chimeric proteins of the invention. As an example, wild-type human TF (TF) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov/), all of which are herein incorporated by reference in their entirety. Transferrin comprises two domains, N domain and C domain. N domain comprises two subdomains, N1 domain and N2 domain, and C domain comprises two subdomains, C1 domain and C2 domain.

In one embodiment, the transferrin heterologous moiety includes a transferrin splice variant. In one example, a transferrin splice variant can be a splice variant of human transferrin, e.g., Genbank Accession AAA61140. In another embodiment, the transferrin portion of the chimeric protein includes one or more domains of the transferrin sequence, e.g., N domain, C domain, N1 domain, N2 domain, C1 domain, C2 domain or any combinations thereof.

10. Polymer, e.g., Polyethylene Glycol (PEG)

In other embodiments, at least one heterologous moiety is a soluble polymer known in the art, including, but not limited to, polyethylene glycol, ethylene glycol/propylene glycol copolymers, carboxymethylcellulose, dextran, or polyvinyl alcohol. In some embodiments, the chimeric protein comprising a PEG heterologous moiety further comprises a heterologous moiety selected from an immunoglobulin constant region or portion thereof (e.g., an Fc region), a PAS sequence, HES, albumin, fragment, or variant thereof, or any combinations thereof. In still other embodiments, the chimeric protein comprises an activatable clotting factor or fragment thereof and a PEG heterologous moiety, wherein the chimeric protein further comprises a heterologous moiety selected from an immunoglobulin constant region or portion thereof (e.g., an Fc moiety), a PAS sequence, HES, albumin, fragment, or variant thereof, or any combinations thereof. In yet other embodiments, the chimeric protein comprises a clotting factor or fragment thereof, a second clotting factor or fragment thereof, and a PEG heterologous moiety, wherein the chimeric protein further comprises a heterologous moiety selected from an immunoglobulin constant region or portion thereof (e.g., an Fc moiety), a PAS sequence, HES, albumin, fragment, or variant thereof, or any combinations thereof. In other embodiments, the chimeric protein comprises a clotting factor or fragment thereof, a synthetic procoagulant polypeptide, and a PEG heterologous moiety, wherein the chimeric protein further comprises a heterologous moiety selected from an immunoglobulin constant region or portion thereof (e.g., an Fc region), a PAS sequence, HES, albumin, fragment, or variant thereof, or any combinations thereof. In other embodiments, the chimeric protein comprises two synthetic procoagulant peptides and a PEG heterologous moiety, wherein the chimeric protein further comprises a heterologous moiety selected from an immunoglobulin constant region or portion thereof (e.g., an Fc region), a PAS sequence, HES, albumin, fragment, or variant thereof, or any combinations thereof. In yet another embodiment, the chimeric protein comprises a clotting factor or fragment thereof, a clotting factor cofactor (e.g., Factor Va if the clotting factor in Factor X; or Tissue Factor if the clotting factor is Factor VII), and a PEG heterologous moiety, wherein the chimeric protein further comprises a heterologous moiety selected from an immunoglobulin constant region or portion thereof (e.g., an Fc region), a PAS sequence, HES, albumin, fragment, or variant thereof, or any combinations thereof.

Also provided by the invention are chimeric proteins of the invention comprising heterologous moieties which may provide additional advantages such as increased solubility, stability and circulating time of the polypeptide, or decreased immunogenicity (see U.S. Pat. No. 4,179,337). Such heterologous moieties for modification can be selected from water soluble polymers including, but not limited to, polyethylene glycol, ethylene glycol/propylene glycol copolymers, carboxymethylcellulose, dextran, polyvinyl alcohol, or any combinations thereof.

The polymer can be of any molecular weight, and can be branched or unbranched. For polyethylene glycol, in one embodiment, the molecular weight is between about 1 kDa and about 100 kDa for ease in handling and manufacturing. Other sizes may be used, depending on the desired profile (e.g., the duration of sustained release desired, the effects, if any on biological activity, the ease in handling, the degree or lack of antigenicity and other known effects of the polyethylene glycol to a protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

In some embodiments, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), each of which is incorporated herein by reference in its entirety.

The number of polyethylene glycol moieties attached to each chimeric protein of the invention (i.e., the degree of substitution) may also vary. For example, the PEGylated chimeric protein may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

In some embodiments, the chimeric protein can be PEGylated. A PEGylated chimeric protein comprises at least one polyethylene glycol (PEG) molecule. In other embodiments, the polymer can be water-soluble. Non-limiting examples of the polymer can be poly(alkylene oxide), poly(vinyl pyrrolidone), poly(vinyl alcohol), polyoxazoline, or poly(acryloylmorpholine). Additional types of polymer-conjugation to clotting factors are disclosed in U.S. Pat. No. 7,199,223. See also, Singh et al. Curr. Med. Chem. 15:1802-1826 (2008).

11. Hydroxyethyl Starch (HES)

In certain embodiments, at least one heterologous moiety is a polymer, e.g., hydroxyethyl starch (HES) or a derivative thereof. Hydroxyethyl starch (HES) is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., *Krankenhauspharmazie*, 8(8), 271-278 (1987); and Weidler et al., *Arzneim.-Forschung/Drug Res.*, 41, 494-498 (1991)).

Amylopectin contains glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physico-chemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HES is mainly characterized by the molecular weight distribution and the degree of substitution. The degree of substitution, denoted as DS, relates to the molar substitution, is known to the skilled people. See Sommermeyer et al., *Krankenhauspharmazie*, 8(8), 271-278 (1987), as cited above, in particular p. 273.

In one embodiment, hydroxyethyl starch has a mean molecular weight (weight mean) of from 1 to 300 kD, from 2 to 200 kD, from 3 to 100 kD, or from 4 to 70 kD. hydroxyethyl starch can further exhibit a molar degree of substitution of from 0.1 to 3, preferably 0.1 to 2, more preferred, 0.1 to 0.9, preferably 0.1 to 0.8, and a ratio between C2:C6 substitution in the range of from 2 to 20 with respect to the hydroxyethyl groups. A non-limiting example of HES having a mean molecular weight of about 130 kD is a HES with a degree of substitution of 0.2 to 0.8 such as 0.2, 0.3, 0.4, 0.5, 0.6, 0.7, or 0.8, preferably of 0.4 to 0.7 such as 0.4, 0.5, 0.6, or 0.7. In a specific embodiment, HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolemia. The characteristics of VOLUVEN® are a mean molecular weight of 130,000+/−20,000 D, a molar substitution of 0.4 and a C2:C6 ratio of about 9:1. In other embodiments, ranges of the mean molecular weight of hydroxyethyl starch are, e.g., 4 to 70 kD or 10 to 70 kD or 12 to 70 kD or 18 to 70 kD or 50 to 70 kD or 4 to 50 kD or 10 to 50 kD or 12 to 50 kD or 18 to 50 kD or 4 to 18 kD or 10 to 18 kD or 12 to 18 kD or 4 to 12 kD or 10 to 12 kD or 4 to 10 kD. In still other embodiments, the mean molecular weight of hydroxyethyl starch employed is in the range of from more than 4 kD and below 70 kD, such as about 10 kD, or in the range of from 9 to 10 kD or from 10 to 11 kD or from 9 to 11 kD, or about 12 kD, or in the range of from 11 to 12 kD) or from 12 to 13 kD or from 11 to 13 kD, or about 18 kD, or in the range of from 17 to 18 kD or from 18 to 19 kD or from 17 to 19 kD, or about 30 kD, or in the range of from 29 to 30, or from 30 to 31 kD, or about 50 kD, or in the range of from 49 to 50 kD or from 50 to 51 kD or from 49 to 51 kD.

In certain embodiments, the heterologous moiety can be a mixture of hydroxyethyl starches having different mean molecular weights and/or different degrees of substitution and/or different ratios of C2:C6 substitution. Therefore, mixtures of hydroxyethyl starches may be employed having different mean molecular weights and different degrees of substitution and different ratios of C2:C6 substitution, or having different mean molecular weights and different degrees of substitution and the same or about the same ratio of C2:C6 substitution, or having different mean molecular weights and the same or about the same degree of substitution and different ratios of C2:C6 substitution, or having the same or about the same mean molecular weight and different degrees of substitution and different ratios of C2:C6 substitution, or having different mean molecular weights and the same or about the same degree of substitution and the same or about the same ratio of C2:C6 substitution, or having the same or about the same mean molecular weights and different degrees of substitution and the same or about the same ratio of C2:C6 substitution, or having the same or about the same mean molecular weight and the same or about the same degree of substitution and different ratios of C2:C6 substitution, or having about the same mean molecular weight and about the same degree of substitution and about the same ratio of C2:C6 substitution.

12. Polysialic Acids (PSA)

In certain embodiments, at least one heterologous moiety is a polymer, e.g., polysialic acids (PSAs) or a derivative thereof. Polysialic acids (PSAs) are naturally occurring unbranched polymers of sialic acid produced by certain bacterial strains and in mammals in certain cells Roth J., et al. (1993) in *Polysialic Acid: From Microbes to Man*, eds Roth J., Rutishauser U., Troy F. A. (Birkhauser Verlag, Basel, Switzerland), pp 335-348. They can be produced in various degrees of polymerisation from n=about 80 or more sialic acid residues down to n=2 by limited acid hydrolysis or by digestion with neuraminidases, or by fractionation of the natural, bacterially derived forms of the polymer. The composition of different polysialic acids also varies such that there are homopolymeric forms i.e. the alpha-2,8-linked polysialic acid comprising the capsular polysaccharide of *E. coli* strain K1 and the group-B meningococci, which is also found on the embryonic form of the neuronal cell adhesion molecule (N-CAM). Heteropolymeric forms also exist—such as the alternating alpha-2,8 alpha-2,9 polysialic acid of *E. coli* strain K92 and group C polysaccharides of *N. meningitidis*. Sialic acid may also be found in alternating copolymers with monomers other than sialic acid such as group W135 or group Y of *N. meningitidis*. Polysialic acids have important biological functions including the evasion of the immune and complement systems by pathogenic bacteria and the regulation of glial adhesiveness of immature neurons during foetal development (wherein the polymer has an anti-adhesive function) Cho and Troy, *P.N.A.S., USA*, 91 (1994) 11427-11431, although there are no known receptors for polysialic acids in mammals. The alpha-2,8-linked polysialic acid of *E. coli* strain K1 is also known as 'colominic acid' and is used (in various lengths) to exemplify the present invention. Various methods of attaching or conjugating polysialic acids to a polypeptide have been described (for example, see U.S. Pat. No. 5,846,951; WO-A-0187922, and US 2007/0191597 A1, which are incorporated herein by reference in their entireties.

13. Clearance Receptors

In certain aspects, the in vivo half-life of an activatable clotting factor in a chimeric protein of the invention can be extended where the chimeric protein comprises at least one heterologous molecule comprising a clearance receptor, fragment, variant, or derivative thereof. In specific aspects wherein the therapeutic peptide is Factor X, soluble forms of clearance receptors, such as the low density lipoprotein-related protein receptor LRP1, or fragments thereof, can block binding of Factor X to clearance receptors and thereby extend its in vivo half-life.

LRP1 is a 600 kDa integral membrane protein that is implicated in the receptor-mediate clearance of a variety of proteins, such as Factor X. See, e.g., Narita et al., Blood 91:555-560 (1998).

D. Linker Moieties (L, L1, or L2)

Linker moieties useful for the present invention can be either a peptide linker or a non-peptide linker. In one embodiment, the peptide linker can be synthetic.

As used herein, the term "peptide linkers" refers to a peptide or polypeptide sequence (e.g., a synthetic peptide or polypeptide sequence) which connects two domains in a linear amino acid sequence of a polypeptide chain. The polypeptides of invention are encoded by nucleic acid molecules that encode peptide linkers which either directly or indirectly connect the two immunoglobulin constant regions or portions thereof (e.g., Fc moieties) which make up the construct. These linkers are referred to herein as "scFc linkers". If the scFc linker connects two Fc moieties contiguously in the linear polypeptide sequence, it is a "direct" linkage. In contract, the scFc linkers may link the first Fc moiety to a binding moiety which is, in turn, linked to the second Fc moiety, thereby forming an indirect linkage. These scFc linkers (X) result in the formation of a single chain genetic construct. However, in one embodiment, the scFc polypeptides also comprise intracellular processing sites which result in the scFc linker being cleavable (an cscFc linker) and, in one embodiment, substantially excised (e.g., during processing by a cell). Thus, the processed molecule is a dimeric molecule comprising at least two amino acid chains and substantially lacking extraneous linker amino acid sequences. In some embodiments, all or substantially all of the linker is excised, while in some embodiments, a portion of the intracellular processing site may remain, e.g., four arginines of the RRRR cleavage site.

In another embodiment, another type of peptide linker, herein referred to as a "linker moiety" may be used to connect different moieties, e.g., an activatable clotting factor to an enhancer moiety, an activatable clotting factor to a heterologous moiety, and/or an enhancer moiety to a heterologous moiety. This type of peptide linkers may provide flexibility to the polypeptide molecule. Linkers are not typically cleaved, however such cleavage may be desirable. Exemplary positions of linkers are shown in the accompanying drawings. Linkers can be located between the activatable clotting factor and the enhancer moiety, the activatable clotting factor and the heterologous moiety linked thereto, or the enhancer moiety and the heterologous moiety linked thereto, e.g., at the N or C terminus of these moieties. In one embodiment, these linkers are not removed during processing.

A third type of linker which may be present in a chimeric protein of the invention is a protease cleavable linker which comprises a cleavage site (i.e., a protease cleavage site substrate, e.g., a factor XIa, Xa, or thrombin cleavage site) and which may include additional linkers on either the N-terminal of C-terminal or both sides of the cleavage site. These cleavable linkers when incorporated into a clotting factor zymogen result in a chimeric molecule having a heterologous cleavage site. Exemplary locations for such sites are shown in the accompanying drawings and include, e.g., between the light chain and heavy chain of the clotting factor zymogen, between the heavy chain of the clotting factor zymogen and a first heterologous moiety, between the enhancer moiety and a second heterologous moiety.

In one embodiment, an unprocessed polypeptide of the instant invention comprises two or more Fc domains or moieties linked via a cscFc linker to form an Fc region comprised in a single polypeptide chain. The cscFc linker is flanked by at least one intracellular processing site, i.e., a site cleaved by an intracellular enzyme. Cleavage of the polypeptide at the at least one intracellular processing site results in a polypeptide which comprises at least two polypeptide chains. In one embodiment, an cscFc linker links F1 or F2 to, e.g., an activatable clotting factor, optionally via an intracellular processing site or an enhancer moiety via an intracellular processing site.

As is set forth above, other peptide linkers may optionally be used in a construct of the invention, e.g., to connect an activatable clotting factor or an enhancer moiety to an Fc moiety. Some exemplary locations of linkers that can be used in connection with the invention include, e.g., polypeptides comprising GlySer amino acids such as those set forth in the accompanying figures and described in more detail below. In one embodiment, a linker may be adjacent to one or more moieties each independently selected from activatable clotting factor, heterologous moiety, e.g., Fc, cleavage site, and an enhancer moiety.

In one embodiment, the peptide linker is synthetic, i.e., non-naturally occurring. In one embodiment, a peptide linker includes peptides (or polypeptides) (which may or may not be naturally occurring) which comprise an amino acid sequence that links or genetically fuses a first linear sequence of amino acids to a second linear sequence of amino acids to which it is not naturally linked or genetically fused in nature. For example, in one embodiment the peptide linker may comprise non-naturally occurring polypeptides which are modified forms of naturally occurring polypeptides (e.g., comprising a mutation such as an addition, substitution or deletion). In another embodiment, the peptide linker may comprise non-naturally occurring amino acids. In another embodiment, the peptide linker may comprise naturally occurring amino acids occurring in a linear sequence that does not occur in nature. In still another embodiment, the peptide linker may comprise a naturally occurring polypeptide sequence.

For example, in certain embodiments, a peptide linker can be used to fuse identical Fc moieties, thereby forming a homodimeric scFc region. In other embodiments, a peptide linker can be used to fuse different Fc moieties (e.g. a wild-type Fc moiety and an Fc moiety variant), thereby forming a heterodimeric scFc region.

In another embodiment, a peptide linker comprises or consists of a gly-ser linker. In one embodiment, a scFc or cscFc linker comprises at least a portion of an immunoglobulin hinge and a gly-ser linker. As used herein, the term "gly-ser linker" refers to a peptide that consists of glycine and serine residues. An exemplary gly/ser linker comprises an amino acid sequence of the formula $(Gly_4Ser)n$ (SEQ ID NO: 4), wherein is a positive integer (e.g., 1, 2, 3, 4, 5, 6, 7, 8, 9, or 10). An example of gly/ser linker is $(Gly_4Ser)_2$ (SEQ ID NO: 4), (Gly$_4$Ser)$_4$ (SEQ ID NO: 4), or (Gly$_4$Ser)$_6$. (SEQ ID NO: 4) Another exemplary gly-ser linker is GGGSSGGGSG (SEQ ID NO: 43). In certain embodiments, said gly-ser linker may be inserted between two other sequences of the peptide linker (e.g., any of the peptide linker sequences described herein). In other embodiments, a gly-ser linker is attached at one or both ends of another sequence of the peptide linker (e.g., any of the peptide linker sequences described herein). In yet other embodiments, two or more gly-ser linker are incorporated in series in a peptide linker. In one embodiment, a peptide linker of the invention comprises at least a portion of an upper hinge region (e.g., derived from an IgG1, IgG2, IgG3, or IgG4 molecule), at least a portion of a middle hinge region (e.g., derived from an IgG1, IgG2, IgG3, or IgG4 molecule) and a series of gly/ser amino acid residues (e.g., a gly/ser linker such as (Gly$_4$Ser)n) (SEQ ID NO: 4)).

Peptide linkers of the invention are at least one amino acid in length and can be of varying lengths. In one embodiment, a peptide linker of the invention is from about 1 to about 50 amino acids in length. As used in this context, the term "about" indicates +/−two amino acid residues. Since linker length must be a positive integer, the length of from about 1 to about 50 amino acids in length, means a length of from 1-3 to 48-52 amino acids in length. In another embodiment, a peptide linker of the invention is from about 10 to about 20 amino acids in length. In another embodiment, a peptide linker of the invention is from about 15 to about 50 amino acids in length. In another embodiment, a peptide linker of the invention is from about 20 to about 45 amino acids in length. In another embodiment, a peptide linker of the invention is from about 15 to about 35 or about 20 to about 30 amino acids in length. In another embodiment, a peptide linker of the invention is from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 500, 1000, or 2000 amino acids in length. In one embodiment, a peptide linker of the invention is 20 or 30 amino acids in length.

In some embodiments, the peptide linker can comprise at least two amino, at least three, at least four, at least five, at least 10, at least 20, at least 30, at least 40, at least 50, at least 60, at least 70, at least 80, at least 90, or at least 100 amino acids. In other embodiments, the peptide linker can comprise at least 200, at least 300, at least 400, at least 500, at least 600, at least 700, at least 800, at least 900, or at least 1,000 amino acids. In some embodiments, the peptide linker can comprise at least about 10, 20, 30, 40, 50, 60, 70, 80, 90, 100, 150, 200, 300, 400, 500, 600, 700, 800, 900, 1000, 1100, 1200, 1300, 1400, 1500, 1600, 1700, 1800, 1900, or 2000 amino acids. The peptide linker can comprise 1-5 amino acids, 1-10 amino acids, 1-20 amino acids, 10-50 amino acids, 50-100 amino acids, 100-200 amino acids, 200-300 amino acids, 300-400 amino acids, 400-500 amino acids, 500-600 amino acids, 600-700 amino acids, 700-800 amino acids, 800-900 amino acids, or 900-1000 amino acids.

Peptide linkers can be introduced into polypeptide sequences using techniques known in the art. Modifications can be confirmed by DNA sequence analysis. Plasmid DNA can be used to transform host cells for stable production of the polypeptides produced.

III. Preparation of Polypeptides

A variety of methods are available for recombinantly producing a chimeric protein of the invention. In one embodiment, the invention relates to a nucleic acid construct comprising a nucleic acid sequence encoding the chimeric proteins of the invention. It will be understood that because of the degeneracy of the code, a variety of nucleic acid sequences will encode the amino acid sequence of the polypeptide. The desired polynucleotide can be produced by de novo solid-phase DNA synthesis or by PCR mutagenesis of an earlier prepared polynucleotide.

Oligonucleotide-mediated mutagenesis is one method for preparing a substitution, in-frame insertion, or alteration (e.g., altered codon) to introduce a codon encoding an amino acid substitution (e.g., into an Fc variant moiety). For example, the starting polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer. In one embodiment, genetic engineering, e.g., primer-based PCR mutagenesis, is sufficient to incorporate an alteration, as defined herein, for producing a polynucleotide encoding a polypeptide of the invention.

For recombinant production, a polynucleotide sequence encoding the chimeric protein is inserted into an appropriate expression vehicle, i. e., a vector which contains the necessary elements for the transcription and translation of the inserted coding sequence, or in the case of an RNA viral vector, the necessary elements for replication and translation.

The nucleic acid encoding the chimeric protein is inserted into the vector in proper reading frame. The expression vector is then transfected into a suitable target cell which will express the polypeptide. Transfection techniques known in the art include, but are not limited to, calcium phosphate precipitation (Wigler et al. 1978, Cell 14: 725) and electroporation (Neumann et al. 1982, EMBO, J. 1: 841). A variety of host-expression vector systems may be utilized to express the chimeric proteins described herein in eukaryotic cells. In one embodiment, the eukaryotic cell is an animal cell, including mammalian cells (e. g. 293 cells, PerC6, CHO, BHK, Cos, HeLa cells). When the chimeric protein is expressed in a eukaryotic cell the DNA encoding the chimeric protein may also code for a signal sequence that will permit the chimeric protein to be secreted. One skilled in the art will understand that while the protein is translated the signal sequence is cleaved by the cell to form the mature chimeric protein. Various signal sequences are known in the art e. g., native factor V11 signal sequence, native factor IX signal sequence and the mouse IgK light chain signal sequence. Alternatively, where a signal sequence is not included the chimeric protein can be recovered by lysing the cells.

The chimeric protein of the invention can be synthesized in a transgenic animal, such as a rodent, goat, sheep, pig, or cow. The term "transgenic animals" refers to non-human animals that have incorporated a foreign gene into their genome. Because this gene is present in germline tissues, it is passed from parent to offspring. Exogenous genes are introduced into single-celled embryos (Brinster et al. 1985, Proc. Natl. Acad. Sci. USA 82: 4438). Methods of producing transgenic animals are known in the art including transgenics that produce immunoglobulin molecules (Wagner et al. 1981, Proc. Natl. Acad. Sci. USA 78: 6376; McKnight et al. 1983, Cell 34: 335; Brinster et al. 1983, Nature 306: 332; Ritchie et al. 1984, Nature 312: 517; Baldassarre et al. 2003, Theriogenology 59: 831; Robl et al. 2003, Theriogenology 59: 107; Malassagne et al. 2003, Xenotransplantation 10 (3): 267).

The expression vectors can encode for tags that permit for easy purification or identification of the recombinantly produced protein. Examples include, but are not limited to, vector pUR278 (Ruther et al. 1983, EMBO J. 2: 1791) in which the chimeric protein described herein coding sequence may be ligated into the vector in frame with the lac z coding region so that a hybrid protein is produced; pGEX vectors may be used to express proteins with a glutathione S-transferase (GST) tag. These proteins are usually soluble and can easily be purified from cells by adsorption to glutathione-agarose beads followed by elution in the presence of free glutathione. The vectors include cleavage sites (e. g. PreCission Protease (Pharmacia, Peapack, N.J.)) for easy removal of the tag after purification.

For the purposes of this invention, numerous expression vector systems may be employed. These expression vectors are typically replicable in the host organisms either as episomes or as an integral part of the host chromosomal DNA. Expression vectors may include expression control sequences including, but not limited to, promoters (e.g., naturally-associated or heterologous promoters), enhancers, signal sequences, splice signals, enhancer elements, and transcription termination sequences. Preferably, the expression control sequences are eukaryotic promoter systems in vectors capable of transforming or transfecting eukaryotic host cells. Expression vectors may also utilize DNA elements which are derived from animal viruses such as bovine papilloma virus, polyoma virus, adenovirus, vaccinia virus, baculovirus, retroviruses (RSV, MMTV or MOMLV), cytomegalovirus (CMV), or SV40 virus. Others involve the use of polycistronic systems with internal ribosome binding sites.

Commonly, expression vectors contain selection markers (e.g., ampicillin-resistance, hygromycin-resistance, tetracycline resistance or neomycin resistance) to permit detection of those cells transformed with the desired DNA sequences (see, e.g., Itakura et al., U.S. Pat. No. 4,704,362). Cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

A preferred expression vector is NEOSPLA (U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression of antibodies upon incorporation of variable and constant region genes, transfection in cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other embodiments the polypeptides of the invention of the instant invention may be expressed using polycistronic constructs. In these expression systems, multiple gene products of interest such as multiple polypeptides of multimer binding protein may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is also incorporated herein. Those skilled in the art will appreciate that such expression systems may be used to effectively produce the full range of polypeptides disclosed in the instant application.

More generally, once the vector or DNA sequence encoding a polypeptide has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (MA), or flourescence-activated cell sorter analysis (FACS), immunohistochemistry and the like.

As used herein, the term "transformation" shall be used in a broad sense to refer to the introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of polypeptides from recombinant hosts, the terms "cell" and "cell culture" are used interchangeably to denote the source of polypeptide unless it is clearly specified otherwise. In other words, recovery of polypeptide from the "cells" may mean either from spun down whole cells, or from the cell culture containing both the medium and the suspended cells.

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte), PerC6, and 293 (human kidney). Host cell lines are typically available from commercial services, the American Tissue Culture Collection or from published literature.

In one embodiment, a host cell endogenously expresses an enzyme (or the enzymes) necessary to cleave a scFc linker (e.g., if such a linker is present and contains intracellular processing site(s)) during processing to form the mature polypeptide. During this processing, the scFc linker may be substantially removed to reduce the presence of extraneous amino acids. In another embodiment of the invention, a host cell is transformed to express one or more enzymes which are exogenous to the cell such that processing of a scFc linker occurs or is improved.

In one embodiment an enzyme which may be endogenously or exogenously expressed by a cell is a member of the furin family of enzymes. Complete cDNA and amino acid sequences of human furin (i.e., PACE) were published in 1990. Van den Ouweland A M et al. (1990) Nucleic Acids Res. 18:664; Erratum in: Nucleic Acids Res. 18:1332 (1990).

U.S. Pat. No. 5,460,950, issued to Barr et al., describes recombinant PACE and the coexpression of PACE with a substrate precursor polypeptide of a heterologous protein to improve expression of active, mature heterologous protein.

U.S. Pat. No. 5,935,815, issued to van de Ven et al., likewise describes recombinant human furin (i.e., PACE) and the coexpression of furin with a substrate precursor polypeptide of a heterologous protein to improve expression of active, mature heterologous protein. Possible substrate precursors disclosed in this patent include a precursor of Factor IX. Other family members in the mammalian furin/subtilisin/Kex2p-like proprotein convertase (PC) family in addition to PACE are reported to include PCSK1 (also known as PC1/Pc3), PCSK2 (also known as PC2), PCSK3 (also known as furin or PACE), PCSK4 (also known as PC4), PCSK5 (also known as PC5 or PC6), PCSK6 (also known as PACE4), or PCSK7 (also known as PC7/LPC, PC8, or SPC7). While these various members share certain conserved overall structural features, they differ in their tissue distribution, subcellular localization, cleavage specificities, and preferred substrates. For a review, see Nakayama K (1997) Biochem J. 327:625-35. Similar to PACE, these proprotein convertases generally include, beginning from the amino terminus, a signal peptide, a propeptide (that may be autocatalytically cleaved), a subtilisin-like catalytic domain characterized by Asp, His, Ser, and Asn/Asp residues, and a Homo B domain that is also essential for catalytic activity and characterized by an Arg-Gly-Asp (RGD) sequence. PACE, PACE4, and PC5 also include a Cys-rich domain, the function of which is unknown. In addition, PC5 has isoforms with and without a transmembrane domain; these different isoforms are known as PCSB and PCSA, respectively. Comparison between the amino acid sequence of the catalytic domain of PACE and the amino acid sequences of the catalytic domains of other members of this family of proprotein convertases reveals the following degrees of identity: 70 percent for PC4; 65 percent for PACE4 and PC5; 61 percent for PC1/PC3; 54 percent for PC2; and 51 percent for LPC/PC7/PC8/SPC7. Nakayama K (1997) Biochem J. 327:625-35.

PACE and PACE4 have been reported to have partially overlapping but distinct substrates. In particular, PACE4, in striking contrast to PACE, has been reported to be incapable of processing the precursor polypeptide of FIX. Wasley L C et al. (1993) J Biol Chem. 268:8458-65; Rehemtulla A et al. (1993) Biochemistry. 32:11586-90.

U.S. Pat. No. 5,840,529, issued to Seidah et al., discloses nucleotide and amino acid sequences for human PC7 and the notable ability of PC7, as compared to other PC family members, to cleave HIV gp160 to gp120 and gp41.

Nucleotide and amino acid sequences of rodent PC5 were first described as PC5 by Lusson J et al. (1993) Proc Natl Acad Sci USA 90:6691-5 and as PC6 by Nakagawa T et al. (1993) J Biochem (Tokyo) 113:132-5. U.S. Pat. No. 6,380,171, issued to Day et al., discloses nucleotide and amino acid sequences for human PCSA, the isoform without the transmembrane domain. The sequences of these enzymes and method of cloning them are known in the art.

Genes encoding the polypeptides of the invention can also be expressed in non-mammalian cells such as bacteria or yeast or plant cells. In this regard it will be appreciated that various unicellular non-mammalian microorganisms such as bacteria can also be transformed; i.e., those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis*; Pneumococcus; *Streptococcus*, and *Haemophilus influenzae*. It will further be appreciated that, when expressed in bacteria, the polypeptides typically become part of inclusion bodies. The polypeptides must be isolated, purified and then assembled into functional molecules.

In addition to prokaryates, eukaryotic microbes may also be used. *Saccharomyces cerevisiae*, or common baker's yeast, is the most commonly used among eukaryotic microorganisms although a number of other strains are commonly available.

For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trpl lesion as a characteristic of the yeast host cell genome then provides an effective environment for detecting transformation by growth in the absence of tryptophan.

Other yeast hosts such *Pichia* may also be employed. Yeast expression vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Alternatively, polypeptide-coding nucleotide sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for polypeptides in operable linkage with a promoter and enhancer from a mammary gland specific gene, such as casein or beta lactoglobulin.

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein. An affinity tag sequence (e.g. a His(6) tag) may optionally be attached or included within the polypeptide sequence to facilitate downstream purification.

In one embodiment, a host cell of the invention comprises a genetic construct encoding a polypeptide comprising a scFc linker and one or more enzymes that can process a cscFc linker. The construct and the enzyme(s) can be expressed using a single vector or two vectors. The chimeric protein produced by the genetic construct encoding a scFc linker can thus have an additional polypeptide chain due to the intracellular processing. In some embodiments, the chimeric protein may contain the cleaved protease cleavage site (e.g., RRRR (SEQ ID NO: 2)).

In one embodiment, the invention pertains to nucleic acid molecules which encode a polypeptide of the invention. In one embodiment, the nucleic acid molecule encodes a chimeric protein comprising an enhancer moiety and an activatable clotting factor selected from activatable FVII or activatable FX, wherein the enhancer moiety enhances activities of FVII and FX. In another embodiment, the nucleic acid molecule encodes a chimeric protein comprising an enhancer moiety, an activatable clotting factor, and optionally a linker moiety between the activatable clotting factor and the enhancer moiety.

In another embodiment, the invention pertains to a nucleic acid molecule encoding a polypeptide comprising FVII, which FVII which comprises a heterologous enzymatic cleavage site activatable by a component of the clotting cascade.

Once expressed, the chimeric clotting factor can be purified according to standard procedures of the art, including ammonium sulfate precipitation, affinity column chromatography, HPLC purification, gel electrophoresis and the like (see generally Scopes, Protein Purification (Springer-Verlag, N.Y., (1982)) and see specifically the methods used in the instant Examples. Substantially pure proteins of at least about 90 to 95% homogeneity are preferred, and 98 to 99% or more homogeneity most preferred, for pharmaceutical uses.

In other embodiments, the chimeric clotting factor can be produced by combining recombinant DNA technology with chemical synthesis. For example, the present invention includes a method of transfecting a host cell with a polynucleotide encoding a chimeric clotting factor comprising a light chain of a clotting factor, a protease cleavable site (e.g., SUMO), a truncated heavy chain of the clotting factor, an optional linker, and an enhancer moiety. Small Ubiquitin-like Modifier (or SUMO) is a member of the ubiquitin (Ub) and ubiquitin-like (Ubl) family. Post-translational attachment of SUMO to target proteins occurs through an enzymatic cascade analogous to the ubiquitin conjugation cascade (E1-E2-E3 enzymes), ultimately resulting in formation of an isopeptide bond between the Ub/Ubl C-terminal residue and substrate lysine residue.

SUMO Protease, a highly active cysteinyl protease also known as Ulp, is a recombinant fragment of Ulp1 (Ubl-specific protease 1) from *Saccharomyces cerevisiae*. SUMO Protease cleaves in a highly specific manner, recognizing the tertiary structure of the ubiquitin-like (UBL) protein, SUMO, rather than an amino acid sequence. The protease can be used to cleave SUMO from recombinant fusion proteins. The sequence of the SUMO protein comprises:

```
                                        (SEQ ID NO: 70)
SLQDSEVNQEAKPEVKPEVKPETHINLKVSDGSSEIFFKIKKTTPLRRLM

EAFAKRQGKEMDSLRFLYDGIRIQADQAPEDLDMEDNDIIEAHREQIGG
```

In some embodiments, the present invention includes a method of transfecting a host cell with a polynucleotide encoding a chimeric clotting factor comprising a light chain of a clotting factor, an optional intracellular processing site, a protease cleavable site (e.g., SUMO), a truncated heavy chain of the clotting factor, an optional linker, and an enhancer moiety, wherein the chimeric clotting factor is expressed. In certain embodiments, the truncated heavy chain does not comprise one or more amino acids from the N-terminus corresponding to the wild type heavy chain. The heavy chain is missing one or more amino acids to expose a naturally occurring cysteine residue on FVII or FX for chemical ligation to a thioester peptide. In one embodiment, the amino acids missing from the truncated heavy chain are six amino acids, e.g., IVGGKV (SEQ ID NO: 60) for FVII or IVGGQE (SEQ ID NO: 61) for FX. In another embodiment, the amino acids missing from the truncated heavy cahin are 11 amino acids, e.g., IVGGKVCPKGE (SEQ ID NO: 62) for FVII or IVGGQECKDGE (SEQ ID NO: 63) for FX). In other embodiments, the host cell further comprises a polynucleotide sequence encoding an intracellular processing enzyme, thereby processing the light chain of the clotting factor from the chimeric clotting factor. The light chain of the clotting factor can form a disulphide bond with the heavy chain of the clotting factor.

In certain embodiments, the method further comprises combining (or adding) a SUMO protease to the recombinantly expressed chimeric clotting factor, wherein the SUMO protease cleaves SUMO from the chimeric clotting factor. The cleavage of SUMO can expose the N-terminus of the truncated heavy chain of the clotting factor (e.g., Cys) for further reaction.

In other embodiments, the method further comprises adding a thioester peptide to be linked to the N-terminus of the truncated heavy chain of the clotting factor, e.g., at Cys. In one embodiment, the thioester peptide can comprise a thrombin cleavage site (e.g., D-Phe-Pip-Arg). In another embodiment, the thioester peptide comprises a thrombin cleavage site (e.g., D-Phe-Pip-Arg) and a self-immolative linker (e.g., PABC). In other embodiments, the thioester peptide comprises a thrombin cleavage site (e.g., D-Phe-Pip-Arg), a self-immolative linker (e.g., PABC), and the one or more amino acids identical to the amino acids missing from the N-terminus of the truncated heavy chain of the clotting factor. In one embodiment, the one or more amino acids in the thioester peptide comprises six amino acids missing from the truncated heavy chain (e.g., IVGGKV (SEQ ID NO: 60) for FVII or IVGGQE (SEQ ID NO: 61) for FX). In another embodiment, the one or more amino acids in the thioester peptide comprises 11 amino acids missing from the truncated heavy chain (e.g., IVGGKVCPKGE (SEQ ID NO: 62) for FVII or IVGGQECKDGE (SEQ ID NO: 63) for FX). Therefore, when the thioester peptide is fused to the truncated heavy chain of the clotting factor, the chimeric clotting factor can comprise an activatable clotting factor, an optional linker, and an enhancing moiety, wherein the activatable clotting factor comprises the thrombin cleavage site (e.g., D-Phe-Pip-Arg), the self-immolative linker (e.g., PABC), and the full-length heavy chain of the clotting factor.

IV. Methods of Administering Polypeptides of the Invention

The invention also relates to a method of treating, ameliorating, or preventing a hemostatic disorder to a subject comprising administering a therapeutically effective amount of a chimeric protein of the Invention. The treatment, amelioration, and prevention by the chimeric protein can be a bypass therapy. The subject in the bypass therapy may have already developed an inhibitor to a clotting factor, e.g., Factor VIII, or is subject to developing a clotting factor inhibitor.

Compositions for administration to a subject include nucleic acid molecules which comprise a nucleotide sequence encoding a chimeric clotting factor of the invention (for gene therapy applications) as well as polypeptide molecules.

In one embodiment, a chimeric protein composition of the invention is administered in combination with at least one other agent that promotes hemostasis. Said other agent that promotes hemostasis in a therapeutic with demonstrated clotting activity. As an example, but not as a limitation, hemostatic agent can include Factor V, Factor VII, Factor VIII, Factor IX, Factor X, Factor XI, Factor XII, Factor XIII, prothrombin, or fibrinogen or activated forms of any of the preceding. The clotting factor of hemostatic agent can also include anti-fibrinolytic drugs, e.g., epsilon-amino-caproic acid, tranexamic acid.

In one embodiment of the invention, the composition (e.g., the polypeptide or nucleic acid molecule encoding the polypeptide) is one in which the clotting factor is present in activatable form when administered to a subject. Such an activatable molecule can be activated in vivo at the site of clotting after administration to a subject.

The chimeric protein of the invention can be administered intravenously, subcutaneously, intramuscularly, or via any mucosal surface, e.g., orally, sublingually, buccally, sublingually, nasally, rectally, vaginally or via pulmonary route. The chimeric protein can be implanted within or linked to a biopolymer solid support that allows for the slow release of the chimeric protein to the desired site.

For oral administration, the pharmaceutical composition can take the form of tablets or capsules prepared by conventional means. The composition can also be prepared as a liquid for example a syrup or a suspension. The liquid can include suspending agents (e.g. sorbitol syrup, cellulose derivatives or hydrogenated edible fats), emulsifying agents (lecithin or acacia), non-aqueous vehicles (e.g. almond oil, oily esters, ethyl alcohol, or fractionated vegetable oils), and preservatives (e.g. methyl or propyl-p-hydroxybenzoates or sorbic acid). The preparations can also include flavoring, coloring and sweetening agents. Alternatively, the composition can be presented as a dry product for constitution with water or another suitable vehicle.

For buccal and sublingual administration the composition may take the form of tablets, lozenges or fast dissolving films according to conventional protocols.

For administration by inhalation, the chimeric proteins for use according to the present invention are conveniently delivered in the form of an aerosol spray from a pressurized pack or nebulizer (e.g. in PBS), with a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

In one embodiment, the route of administration of the polypeptides of the invention is parenteral. The term parenteral as used herein includes intravenous, intraarterial, intraperitoneal, intramuscular, subcutaneous, rectal or vaginal administration. The intravenous form of parenteral administration is preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will preferably have labels or package inserts indicating that the associated compositions are useful for treating a subject suffering from, or predisposed to clotting disorders.

The pharmaceutical composition can also be formulated for rectal administration as a suppository or retention enema, e.g., containing conventional suppository bases such as cocoa butter or other glycerides.

Effective doses of the compositions of the present invention, for the treatment of conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy.

In one embodiment, the dose of a biologically active moiety (e.g., comprising FVII), can range from about 90 to 270 ug/kg or 0.090 to 0.270 mg/kg. In another embodiment, the dose of a biologically active moiety (e.g., comprising FX), can range from about 1 μg/kg to 400 mg/kg.

Dosages can range from 1000 ug/kg to 0.1 ng/kg body weight. In one embodiment, the dosing range is 1 ug/kg to 100 ug/kg. The protein can be administered continuously or at specific timed intervals. In vitro assays may be employed to determine optimal dose ranges and/or schedules for administration. In vitro assays that measure clotting factor activity are known in the art, e.g., STA-CLOT VIIa-rTF clotting assay. Additionally, effective doses may be extrapolated from dose-response curves obtained from animal models, e. g., a hemophiliac dog (Mount et al. 2002, Blood 99 (8): 2670).

Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. In some methods, two or more polypeptides may be administered simultaneously, in which case the dosage of each polypeptide administered falls within the ranges indicated.

Polypeptides of the invention can be administered on multiple occasions. Intervals between single dosages can be daily, weekly, monthly or yearly. Intervals can also be irregular as indicated by measuring blood levels of modified polypeptide or antigen in the patient. Alternatively, polypeptides can be administered as a sustained release formulation, in which case less frequent administration is required. Dosage and frequency vary depending on the half-life of the polypeptide in the patient.

The dosage and frequency of administration can vary depending on whether the treatment is prophylactic or therapeutic. In prophylactic applications, compositions containing the polypeptides of the invention or a cocktail thereof are administered to a patient not already in the disease state to enhance the patient's resistance or minimize effects of disease. Such an amount is defined to be a "prophylactic effective dose." A relatively low dosage is administered at relatively infrequent intervals over a long period of time. Some patients continue to receive treatment for the rest of their lives.

Polypeptides of the invention can optionally be administered in combination with other agents that are effective in treating the disorder or condition in need of treatment (e.g., prophylactic or therapeutic).

As used herein, the administration of polypeptides of the invention in conjunction or combination with an adjunct therapy means the sequential, simultaneous, coextensive, concurrent, concomitant or contemporaneous administration or application of the therapy and the disclosed polypeptides. Those skilled in the art will appreciate that the administration or application of the various components of the combined therapeutic regimen may be timed to enhance the overall effectiveness of the treatment. A skilled artisan (e.g. a physician) would be readily be able to discern effective combined therapeutic regimens without undue experimentation based on the selected adjunct therapy and the teachings of the instant specification.

It will further be appreciated that the polypeptides of the instant invention may be used in conjunction or combination with an agent or agents (e.g. to provide a combined therapeutic regimen). Exemplary agents with which a polypeptide of the invention may be combined include agents that represent the current standard of care for a particular disorder being treated. Such agents may be chemical or biologic in nature. The term "biologic" or "biologic agent" refers to any pharmaceutically active agent made from living organisms and/or their products which is intended for use as a therapeutic.

The amount of agent to be used in combination with the polypeptides of the instant invention may vary by subject or may be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., $9^{th}$ ed. 1996). In another embodiment, an amount of such an agent consistent with the standard of care is administered.

As previously discussed, the polypeptides of the present invention, may be administered in a pharmaceutically effective amount for the in vivo treatment of clotting disorders. In this regard, it will be appreciated that the polypeptides of the invention can be formulated to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. Of course, the pharmaceutical compositions of the present invention may be administered in single or multiple doses to provide for a pharmaceutically effective amount of the polypeptide.

In one embodiment, a chimeric clotting factor of the invention can be administered as a nucleic acid molecule. Nucleic acid molecules can be administered using techniques known in the art, including via vector, plasmid, liposome, DNA injection, electroporation, gene gun, intravenously injection or hepatic artery infusion. Vectors for use in gene therapy embodiments are known in the art.

In keeping with the scope of the present disclosure, the chimeric clotting factors of the invention may be administered to a human or other animal in accordance with the aforementioned methods of treatment in an amount sufficient to produce a therapeutic or prophylactic effect.

The chimeric proteins of the invention have many uses as will be recognized by one skilled in the art, including, but not limited to methods of treating a subject with a disease or condition. The disease or condition can include, but is not limited to, hemostatic disorders.

In one embodiment, the invention relates to a method of treating a subject having a hemostatic disorder comprising administering a therapeutically effective amount of at least one chimeric protein of the invention.

The chimeric proteins of the invention treat or prevent a hemostatic disorder by promoting the formation of a fibrin clot. The chimeric protein of the invention can activate any member of a coagulation cascade. The clotting factor can be a participant in the extrinsic pathway, the intrinsic pathway or both.

A chimeric protein of the invention can be used to treat hemostatic disorders, e.g., those known to be treatable with the particular clotting factor present in the chimeric protein. The hemostatic disorders that may be treated by administration of the chimeric protein of the invention include, but are not limited to, hemophilia A, hemophilia B, von Willebrand's disease, Factor XI deficiency (PTA deficiency), Factor XII deficiency, as well as deficiencies or structural abnormalities in fibrinogen, prothrombin, Factor V, Factor VII, Factor X, or Factor XIII In one embodiment, the hemostatic disorder is an inherited disorder. In one embodiment, the subject has hemophilia A, and the chimeric protein comprises protease-activatable Factor VII linked to or associated with an enhancer moiety. In another embodiment, the subject has hemophilia A and the chimeric clotting factor comprises protease-activatable Factor VII linked to or associated with an enhancer moiety. In another embodiment, the subject has hemophilia B and the chimeric protein comprises protease-activatable Factor VII or Factor X linked to or associated with an enhancer moiety. In another embodiment, the subject has inhibitory antibodies to Factor VIII or Factor VIIIa and the chimeric clotting factor comprises protease-activatable Factor VII linked to or associated with an enhancer moiety. In yet another embodiment, the subject has inhibitory antibodies against Factor IX or Factor IXa and the chimeric protein comprises protease-activatable Factor VII linked to or associated with an enhancer moiety. In other embodiments, the subject has inhibitory antibodies to Factor VIII or Factor VIIIa and the chimeric clotting factor comprises protease-activatable Factor X linked to or associated with an enhancer moiety. In yet another embodiment, the subject has inhibitory antibodies against Factor IX or Factor IXa and the chimeric protein comprises protease-activatable Factor X linked to or associated with an enhancer moiety.

The chimeric clotting factor of the invention can be used to prophylactically treat a subject with a hemostatic disorder. The chimeric clotting factor of the invention can be used to treat an acute bleeding episode in a subject with a hemostatic disorder.

In one embodiment, the hemostatic disorder is the result of a deficiency in a clotting factor, e.g., Factor VII, Factor IX, or Factor VIII. In another embodiment, the hemostatic disorder can be the result of a defective clotting factor.

In another embodiment, the hemostatic disorder can be an acquired disorder. The acquired disorder can result from an underlying secondary disease or condition. The unrelated condition can be, as an example, but not as a limitation, cancer, an autoimmune disease, or pregnancy. The acquired disorder can result from old age or from medication to treat an underlying secondary disorder (e.g. cancer chemotherapy).

The invention also relates to methods of treating a subject that does not have a hemostatic disorder or a secondary disease or condition resulting in acquisition of a hemostatic disorder. The invention thus relates to a method of treating a subject in need of a general hemostatic agent comprising administering a therapeutically effective amount of at least one chimeric protein of the invention. For example, in one embodiment, the subject in need of a general hemostatic agent is undergoing, or is about to undergo, surgery. The chimeric protein of the invention can be administered prior to or after surgery as a prophylactic. The chimeric protein of the invention can be administered during or after surgery to control an acute bleeding episode. The surgery can include, but is not limited to, liver transplantation, liver resection, or stem cell transplantation.

In another embodiment, the chimeric protein of the invention can be used to treat a subject having an acute bleeding episode who does not have a hemostatic disorder. The acute bleeding episode can result from severe trauma, e.g., surgery, an automobile accident, wound, laceration gun shot, or any other traumatic event resulting in uncontrolled bleeding.

This invention is further illustrated by the following examples which should not be construed as limiting. The contents of all references, patents and published patent applications cited throughout this application are incorporated herein by reference.

EXAMPLES

Throughout the examples, the following materials and methods were used unless otherwise stated.

Example 1. Cloning of FVII-133

Figure 4:
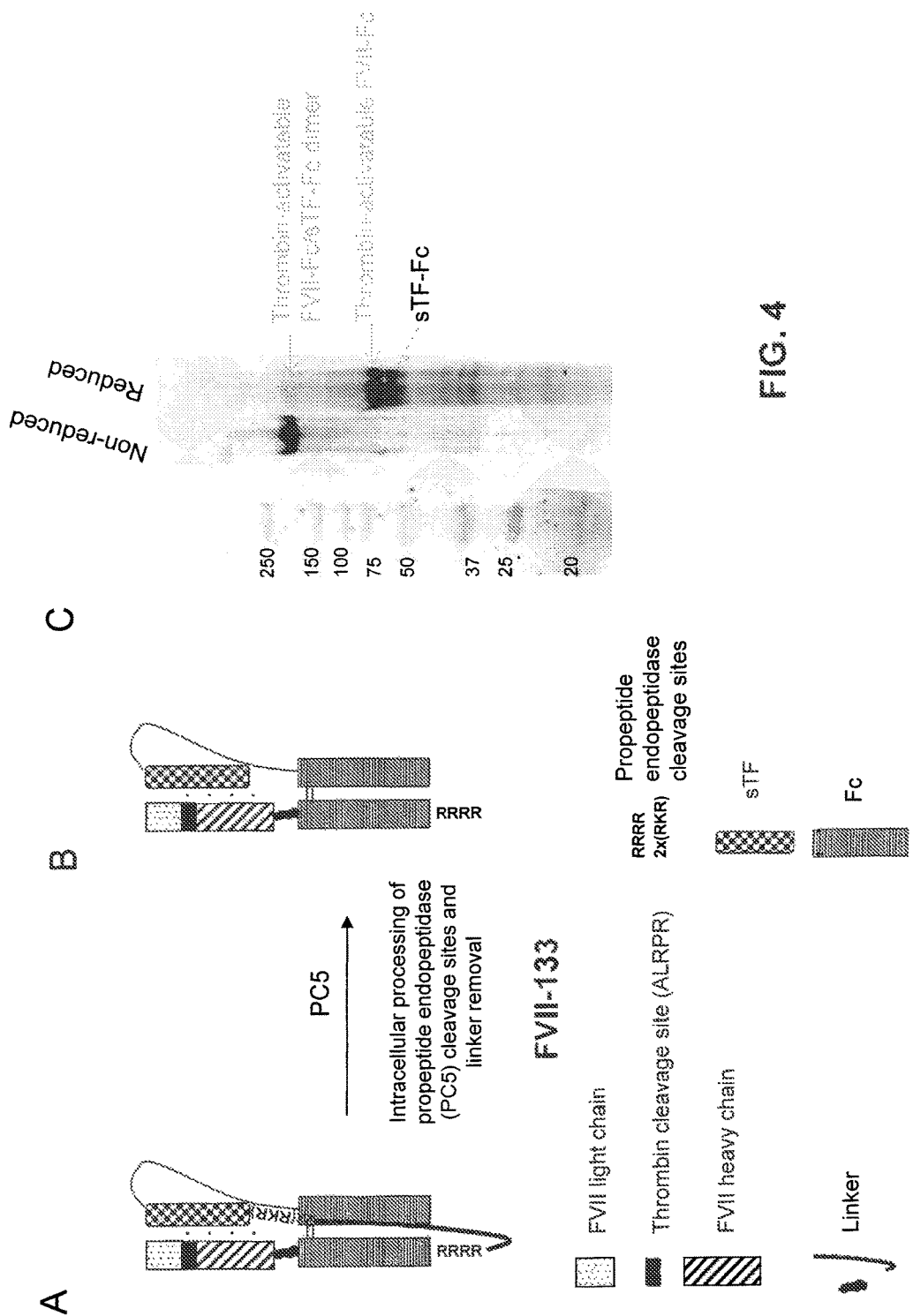
FIG. 4 shows a schematic diagram of generation of the construct in FIG. 4B (similar to FIG. 3A).

The DNA sequence comprising nucleotides from the HindIII site to the first EcoRI site of FVII-133 was synthesized and subcloned into the HindIII/EcoRI sites of pBUD-CE4.1 (Invitrogen), generating an intermediate construct. Next, the DNA region comprising nucleotides from the first EcoRI site to the second EcoRI site of FVII-133 was synthesized and subcloned into the EcoRI sites of the intermediate construct to generate FVII-133 (FIG. 4A).

Example 2. Transient Expression of FVII-133

For expression of FVII-133, HEK-293-F cells were grown in Freestyle media (Invitrogen) supplemented with vitamin K3 (Sigma Aldrich, St. Louis, Mo.) to 2 µg/liter (growth media) as suspension cells at 37° C./10% CO2. Cells were subcultured every three to four days by seeding at cell density of $5 \times 10^5$ cells/ml.

Twenty-four hours prior to transfection, cells were seeded at a density of $7 \times 10^5$ cells/ml in growth media. On the day of transfection, a transfection solution was made with a volume equal to 5% of the total volume of the cell culture to be transfected. In the transfection solution DNA was added (final concentration 20 mg/L) to a freshly made solution of PEI (60 mg/L) in growth media. The solution was swirled for 30 seconds and incubated for five minutes at room temperature before adding directly to the cell culture. Four hours later a volume equal to the cell culture volume of OptiCHO (Invitrogen) supplemented with vitamin K3 and 200 mM L-glutamine was added to the cells. The cell culture was allowed to grow as shown above and daily media samples were taken to assess protein expression. On the day of harvest, the cells were spun down and the media filtered in preparation for protein purification or protein analysis by protein A pulldown. For expression of FVII-133, a plasmid encoding FVII-133 was contransfected with a plasmid encoding the propeptide endopeptidase PC5 to ensure cleavage of the propeptide endopeptidase sites in the linker connecting the Fc to sTF (FIG. 4A).

Example 3. Analysis of Protein Generated from Transient Transfections

For analysis of protein from transient transfections, the conditioned media from cotransfections of FVII-133 with PC5 was subjected to protein A immunoprecipitation. Briefly, cell culture supernatant was mixed with approximately 50 µl of protein A-Sepharose 50% slurry and incubated at 4° C. with rocking for 1 hour, then centrifuged to pellet the protein A beads. Beads were washed twice by resuspending in 1 ml of PBS, spinning and aspirating. The beads were resuspended with sodium dodecylsulfate-polyacrylamide gel electrophoresis (SDS-PAGE) buffer under reducing or nonreducing conditions, heated for 5 minutes at 100° C., spun down and loaded on SDS-PAGE gels and run according to standard protocols. Under nonreducing conditions, 1 band with the expected molecular weight for the thrombin-activatable FVII-Fc/sTF-Fc dimer was observed (FIG. 4C). Under reducing conditions 2 bands were observed representing the thrombin-activatable FVII-Fc subunit and the sTF-Fc subunit.

Example 4. Small Scale Purification of FVII-133

FcRn Load Adjustment Buffer (0.5 ml) were added to 5 ml of filtered conditioned media from cells transiently transfected with FVII-133. The pH-adjusted media (~5.5 ml) was concentrated using a 30,000 MWCO, 15 ml centrifugal filter units (catalog # UFC 903008). The media was centrifuged for 10' at 4000 rpm to ~200 ul volume, transferred to a tube and the volume adjusted to 400 ul with equilibration buffer. 10 ul of FcRn resin were added and the mixture was rotated overnight at 4° C. The conditioned media with resin was loaded into mini-column and centrifuged for 30" at 2000 rpm. The column was washed extensively with equilibration buffer. The protein was eluted with 30 ul of elution buffer. Elution Buffer contains 50 mM Tris, 250 mM NaCl, and 0.02% Tween-80 @ pH 7.5. FcRn Load Adjustment Buffer contains 0.5M MES and 0.2% Tween-80 @ pH 6.0. FcRn resin contains soluble FcRn conjugated to Sepharose 4 Fast Flow. Equilibration buffer contains 10 mM MES, 250 mM NaCl, 0.02% Tween-80 @ pH 6.2

Figure 5:
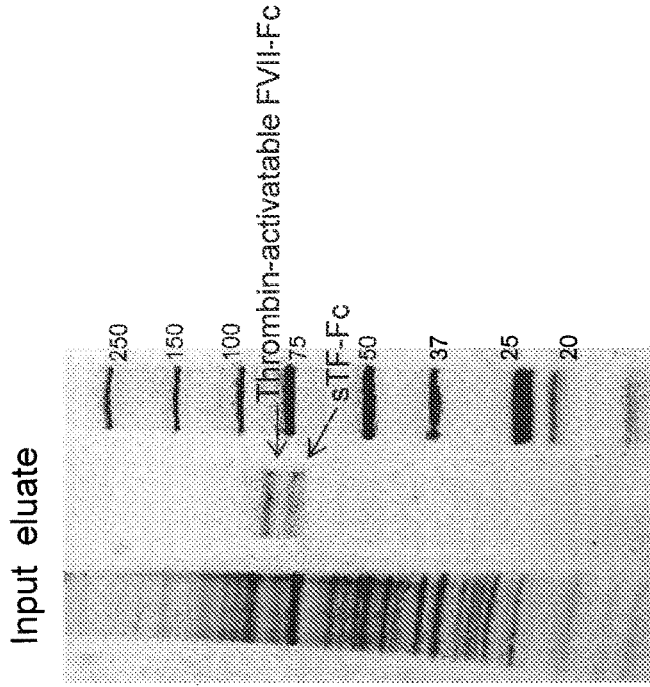
FIG. 5 shows an SDS-PAGE analysis of the thrombin-activatable FVII-Fc/sTF-Fc dimer (FVII-133) under reducing condition. The second lane (i.e., eluate) shows the purified thrombin-activatable FVII-Fc/sTF-Fc dimer.

The eluted material was analyzed by SDS PAGE under reducing conditions. Two bands with the expected molecular weight for the thrombin-activatable FVII-Fc and sTF-Fc subunits were observed (FIG. 5).

Example 5. Activity of FVII-133 by Prothrombin Time Assay

The activity of the FVIIaFc and purified FVII-133 was determined by the prothrombin time using Dade Innovin reagents (Siemens catalog number 539196), which measure the activity of total FVII, including FVIIa. Manufacturer recommendations were followed. We observed an activity of approximately 10, 000 IU/mg for FVIIaFc but the activity of FVII-133 was below the level of quantitation. Therefore, in the absence of thrombin, FVII-133 remained as a zymogen and inactive form.

Example 6. Activity of FVII-133 and FVIIaFc in Thrombin Generation Assays

Figure 6:
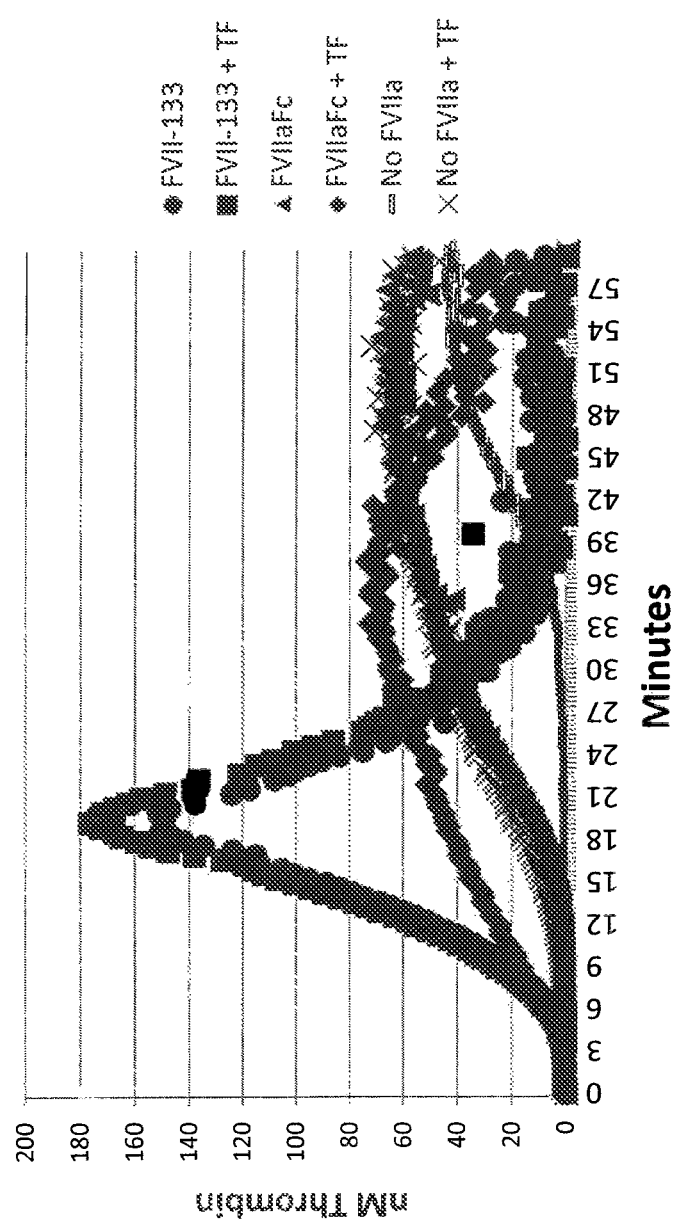
FIG. 6 shows data generated by thrombin generation assays to test the activity of FVII-133 and FVIIaFc. The activities of FVII-133 without or with Tissue Factor (TF) are shown as circle (•) and square (■), respectively. The activities of FVIIaFc without or with TF are shown as triangle (▲) or diamond (♦), respectively. The y-axis shows nanomoles (nM) of thrombin, and the x-axis shows time. The construct FVIIaFc consists of two polypeptide chains, a first chain consisting of an activated FVII (FVIIa) linked to a first Fc region, and a second chain consisting of an Fc region.

Thrombin generation assays were performed in a Fluoroskan Ascent fluorometer (Thermo Scientific) and reagents and analysis software from Thrombinoscope, according to manufacturer's recommendations. Briefly, human platelets were washed in 5.4 mM trisodium citrate, 146 mM NaCl, pH 6.8 and resuspended in FVIII-deficient human plasma (Siemens) to generate platelet-rich plasma (PRP) at a platelet concentration of $2 \times 10^8$ platelets/ml. Each reaction contained FVIII-deficient PRP, calibrator (Thrombinoscope) or Tyrode's buffer (15 mM Hepes pH 7.4, 138 mM NaCl, 2.7 mM KCl, 1 mM $MgCl_2$, 5.5 mM dextrose, 1 mg/ml BSA), FVII-133 or FVIIaFc (50 nM final concentration), and lipidated tissue factor (PRP reagent at a 1/8 dilution, Thrombinoscope) where indicated. Tissue factor, as a complex with endogenous FVIIa, is expected to activate the reaction by inducing the generation of small amounts of thrombin. As shown in FIG. 6, FVII-133 displayed much greater activity than FVIIaFc in the presence or in the absence of tissue factor (TF). Interestingly FVII-133 showed similar activity in the presence or in the absence of TF, but prothrombin time assays show that FVII-133 has no activity in the absence of thrombin. This suggests that trace amounts of thrombin or TF (that can in turn generate thrombin with endogenous FVIIa) in the PRP are sufficient to activate FVII-133. Furthermore, these data show that FVII-133 has the potential for high activity once activated.

Figure 7:
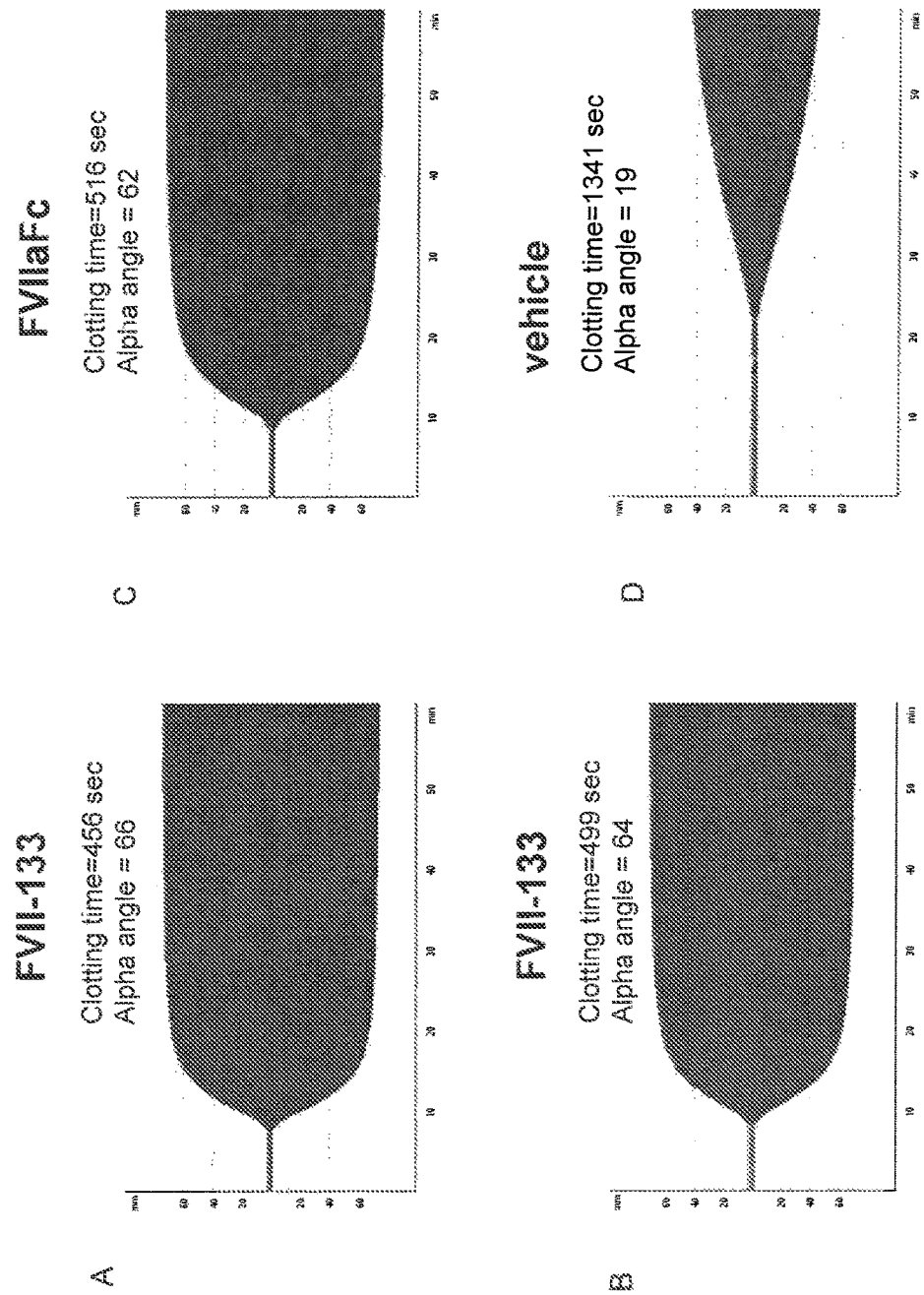
FIG. 7 shows data generated by ROTEM assays with mouse hemophilia B blood to test the activity of FVII-133 and FVIIaFc.

Example 7. Activity of FVII-133 and FVIIaFc in Rotational Thromboelastometry Assays Citrated blood from FIX-deficient mice was used for these experiments. Thromboelastography was carried out in a ROTEM analyzer (Pentapharm) according to the manufacturer's recommendations. Briefly, 280 ul of blood were transferred to a prewarmed ROTEM plastic cup and spiked with FVIIaFc or FVII-133 to a final concentration of 50 nM. EXTEM reagent (TF and Calcium) was added to initiate the reaction. Clotting time (CT) and alpha angle were measured. As shown in FIG. 7, both FVII-133 and FVIIaFc displayed clotting times and alpha angles that were significantly lower or higher, respectively, than vehicle. Lower clotting times and higher alpha angles indicate increased hemostatic activity. These data show that FVII-133 can display high activity when activated by thrombin.

Figure 2:
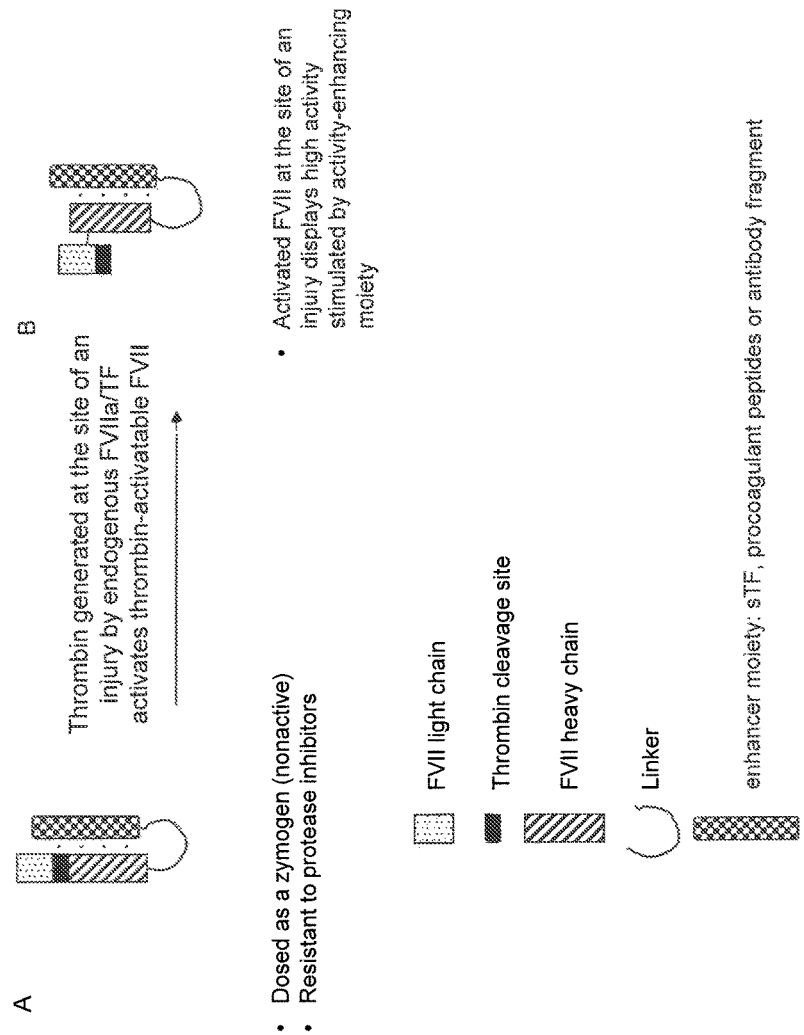
FIG. 2 illustrates a schematic diagram of a chimeric FVII protein comprising a thrombin-activatable molecule and an enhancer moiety.
Figure 3:
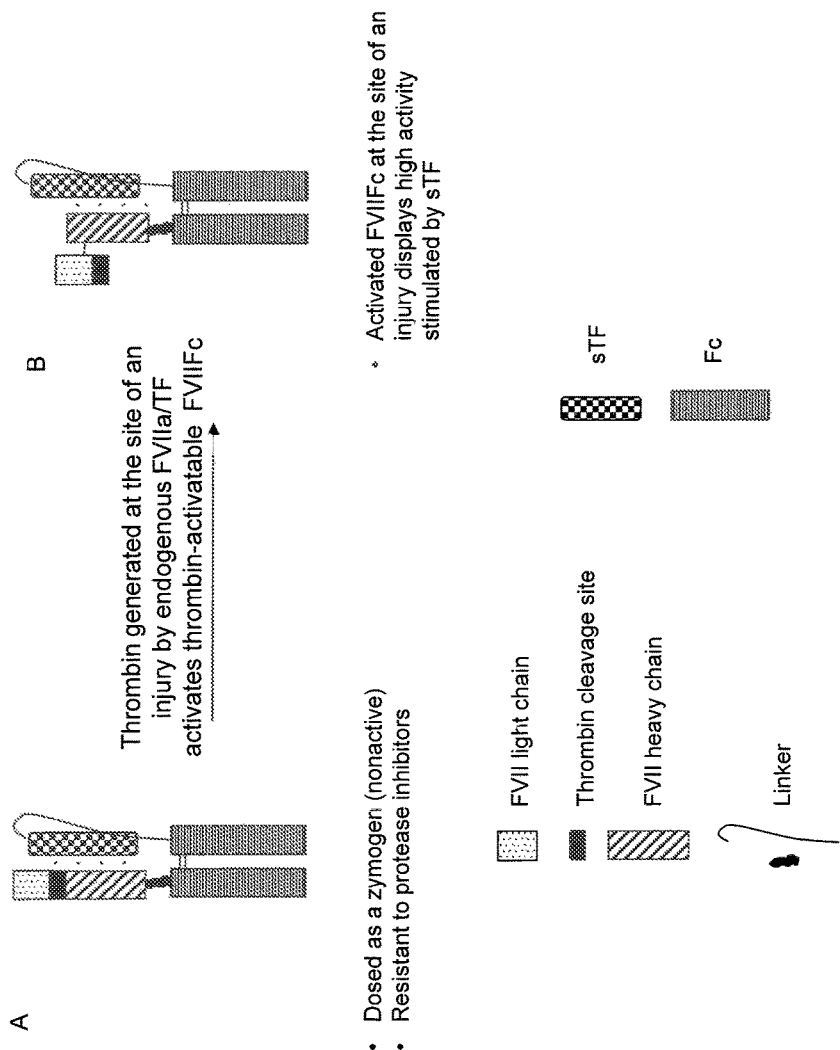
FIG. 3 illustrates a schematic diagram of a molecule comprising a thrombin activatable FVII molecule, a sTF molecule as an enhancer moiety and a heterologous moiety (Het), shown as an Fc moiety for half-life extension. The construct in FIG. 3A comprises a first polypeptide chain and a second polypeptide chain, wherein the first polypeptide chain comprises a FVII light chain, a thrombin cleavage site, a FVII heavy chain, a first linker, and a first Fc moiety (Het1) in the N terminus to C terminus order and the second polypeptide chain comprises sTF, a second linker, and a second Fc moiety (Het2) in the N-terminus to C terminus direction. The first linker and the second linker can be the same or different. The first Fc moiety and the second Fc moiety can be the same or different. When the construct in FIG. 3A (i.e., a zymogen (non-active form)) is dosed, the construct is resistant to protease inhibitors upon administration (prior to activation). When the clotting factors are activated by thrombin at the site of an injury, as shown in FIG. 3B, the clotting factors can display high activity stimulated by the enhancer moiety.

Example 8. Generation of Alternative Chimeric Clotting Factors Comprising an Activatable FVII and an Enhancer Moiety Constructs will be generated for the expression of thrombin-activatable FVII followed by a linker and an enhancer moiety (also referred to as "an enhancer moiety") as illustrated in FIG. 2. In one embodiment, the enhancer moiety will be soluble tissue factor (residues 1-219 from mature sequence). In another embodiment, the enhancer moiety will be procoagulant peptides SYN3731 or SYN3524 (see Int'l Appl. No. PCT/US2012/041777, filed Jun. 9, 2012 and published as WO 2012/170969, which is incorporated herein by reference in its entirety). In another embodiment the enhancer moiety will be an antibody fragment derived from antibodies that increase the activity of FVIIa. For example, antibodies that enhance the activity of FVIIa were described in Andersen L M et al. J Biol Chem. 287: 8994-9001 (Jan. 24, 2012). These constructs will be transiently expressed in mammalian cells, purified and tested for activity (prothrombin time, thrombin generation and ROTEM assays) as previously described.

Figure 8:
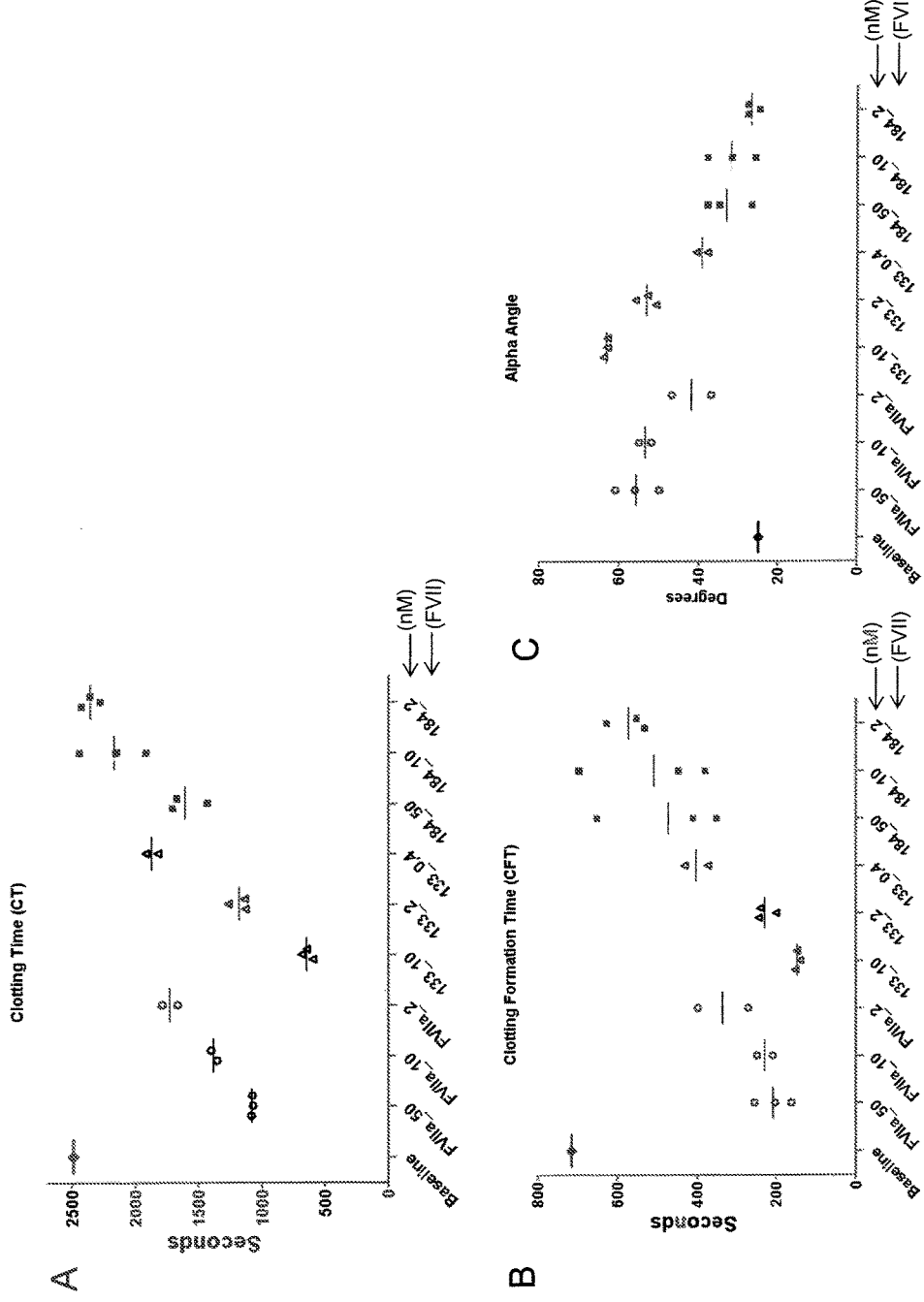
FIG. 8A-C shows FVII activity measured by ROTEM assay in human hemophilia A blood. FVII-133, FVII-184, and FVIIa were spiked into citrated human blood from hemophilia A donors. Structure of FVII-133 is shown in FIG. 4. FVII-184 is a mutant form of FVII-133 and is insensitive to thrombin activation due to mutation of the Arg residue, which is essential for thrombin cleavage, to Ala. FVIII-184 is otherwise identical to FVII-133. Clotting Time (CT), Clotting Formation Time (CFT), and Alpha Angle for FVII-133 (triangle), FVII-184 (square), and FVIIa (circle) were measured. The baseline clotting time in the hemophilia A donor is shown as diamond (◇).

Example 9. In Vitro Activity of FVII-133 in Human Hemophilia a Blood by Rotational Thromboelastometry Assays To determine the clotting activity, FVII-133 protein was spiked into citrated human whole blood from hemophilia A donors. Clot was initiated by adding $CaCl_2$; the clotting time, clotting formation time, and α-angle were measured on the ROTEM analyzer (Pentapharm) following the manufacturer's recommendations. FVIIa and FVII-184 were tested in parallel; whereas FVIIa was used as a comparator for activity, FVII-184 was employed as a control for determining the contribution of endogenous FVIIa that could be activated by the fusion protein itself, because FVII-184 was designed to be insensitive to thrombin activation by mutating the Arg essential for the thrombin cleavage site to Ala, but otherwise the same as FVII-133. As shown in FIG. 8, the clotting time in this hemophilia A donor recorded to be 2500 sec. Spiking FVII-133 in the whole blood resulted in a much shorter clotting time in a dose dependent manner. The clotting time recorded on 10 and 2 nM of FVII-133 was shorter than that of 50, 10 nM of rFVIIa respectively. Based on its clotting time profile, the activity of FVII-133 was estimated to be at least 10-fold higher than that of FVIIa. The faster clotting time of FVII-133 correlated with its shorter clotting formation time and higher α-angle, which agree with the higher hemostatic activity of FVII-133. Inactivating the thrombin cleavage site of FVII133 considerably reduced the activity; as the activity of FVII-184, which only became detectable at 50 nM, was much lower than that of FVIIa, indicating the activity of FVII-133 was indeed contributed by its own thrombin activated FVIIa, but not by the endogenous FVII/FVIIa.

Example 10. Ex Vivo Efficacy of FVII-133 in hemB Mice by ROTEM Analysis

Figure 9:
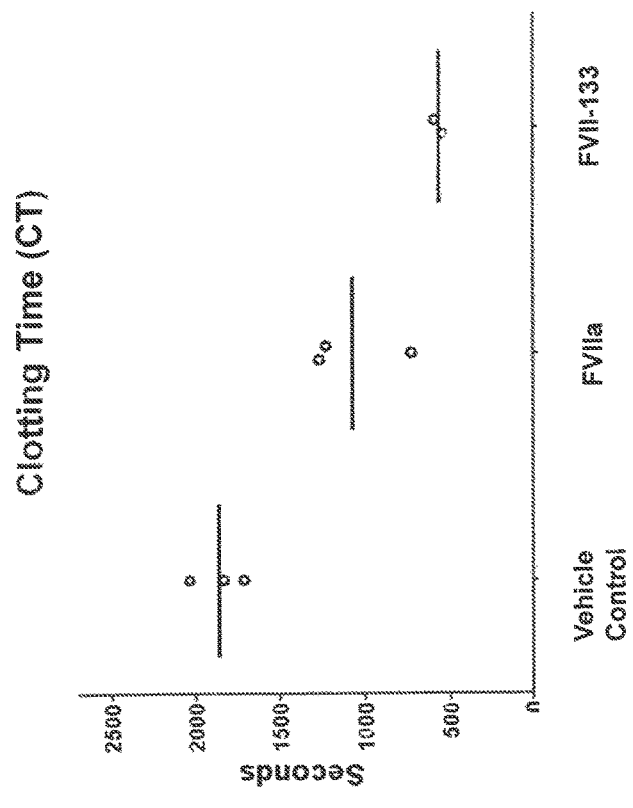
FIG. 9 shows FVII-133 ex vivo efficacy in hemB mice by ex vivo ROTEM assays. Clotting Time (CT) was measured on blood collected from mice that were dosed via tail vein injection by vehicle, FVIIa, and FVII-133, respectively.

To assess the ex vivo efficacy, hemophilia B (hemB) mice were dosed at 20 nmol/kg of FVII-133 or control protein rFVIIa via tail vein injection. At 2.5 hour after dosing, blood was collected in CTI at 9:1 ratio from mice via vena cava bleeding. Blood was re-calcified, and immediately measured on the ROTEM analyzer. As shown in FIG. 9, whereas the average clotting time in hemB blood measured was about 1800 sec, the clotting time of whole blood from mice injected with FVII-133 was much shorter, approaching 500 sec, indicating that FVII-133 was active in vivo.

Example 11. Improved PK Profile of FVII-133 Over rFVIIaFc

Figure 10A:
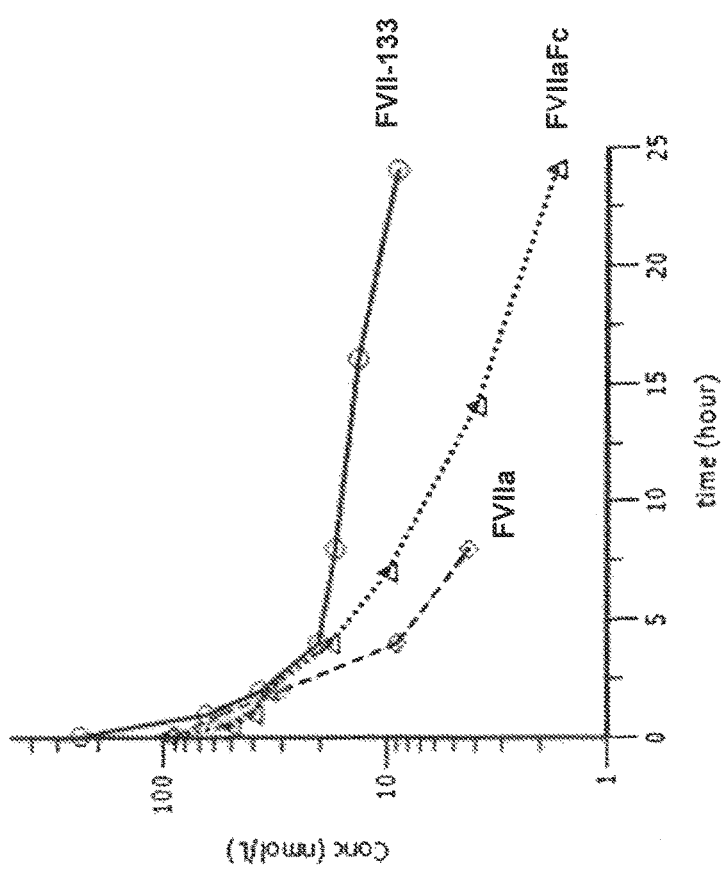
FIG. 10A-B shows the plasma level of FVII and FVII/ATIII complex as a function of time following administration of the proteins. HemB mice were administered i.v. with FVII-133, rFVIIaFc, or rFVIIa. The plasma samples at various time points were collected, and the FVII antigen level (FIG. 10A) and the FVII-133/ATIII or rFVIIFc-ATIII complex (FIG. 10B) were measured by ELISA. The PK properties, including the Mean Residence Time (MRT), of the FVII-133 (dotted line, circle) and FVIIaFc (solid line, triangle) were generated by 2 compartmental analysis using Phoenix 6 program.
Figure 10B:
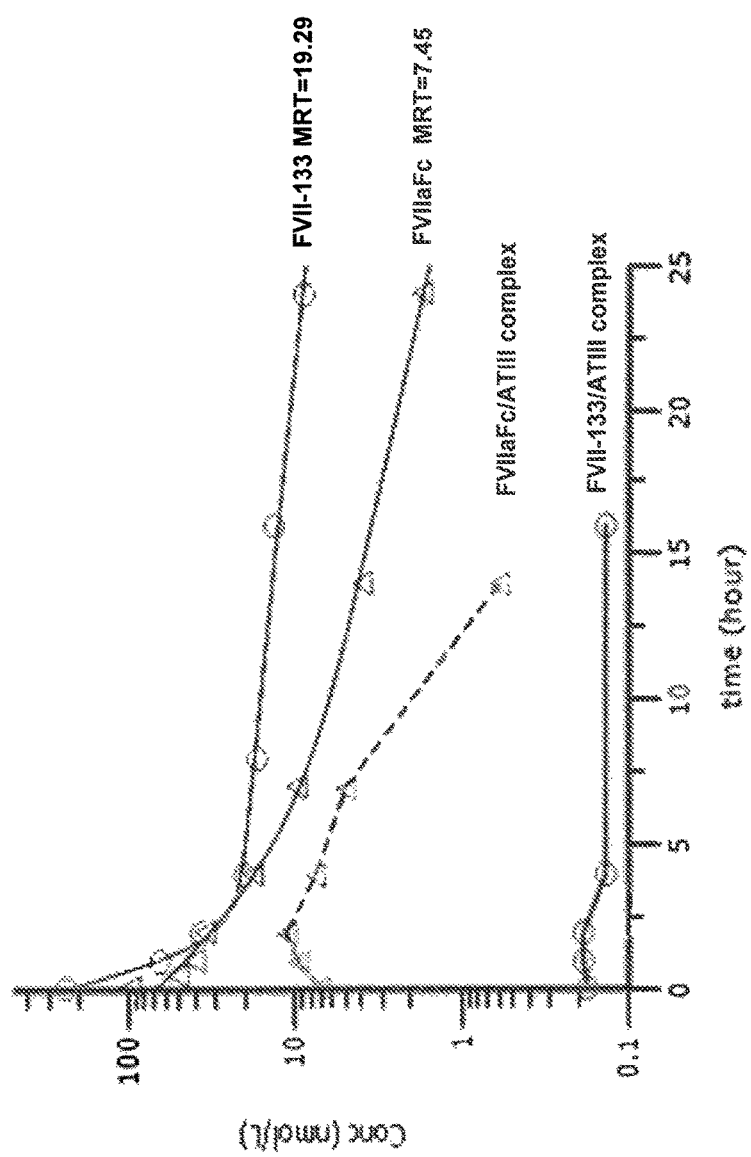

FVII-133 was designed to circulate as FVII zymogen, thus it is predicted to be less susceptible to antithrombin III (ATIII) mediated clearance. To evaluate the pharmacokinetic properties of FVII-133, the purified FVII-133, rFVIIaFc and rFVIIa were administered intravenously into hemB mice (n=4) at 10 nmol/kg, and plasma samples were collected via vena cava bleeding at various times and analyzed for FVII antigen, and FVII-ATIII complex by ELISA assays. Pharmacokinetic parameters were assessed by PK modeling using Phoenix program (Pharsight). Since rFVIIa was cleared much more rapidly than either FVII-133 or rFVIIaFc (FIG. 10A), we used rFVIIaFc as a comparator for the pharmacokinetic analysis of FVII-133 (FIG. 10B). Plasma concentration of the protein versus time curve was found to best fit in a two compartmental model; all the PK parameters indicated a marked improvement of FVII-133 over rFVIIaFc, with longer terminal half-life (Beta half life of 16.56 hour vs 7.78 hour, respectively) and longer mean residence time (MRT 19.29 hour vs 7.45 hour) as shown in Table 4.

TABLE 4

| | PK Parameters: FVII-133 vs FVIIaFc | | | | | |
|---|---|---|---|---|---|---|
| Treatment | Alpha $t_{1/2}$ (hour) | Beta $t_{1/2}$ (hour) | MRT (hour) | CL (mL/ hour/kg) | Vss (mL/kg) | AUC (hour * pmol/mL) |
| FVII-133 | 0.43 | 16.56 | 19.29 | 17.59 | 339.31 | 738.96 |
| FVIIaFc | 1.41 | 7.78 | 7.45 | 73.15 | 544.79 | 273.42 |

In addition, whereas a significant amount of rFVIIaFc/ATIII complex was detected, the FVII-133/ATIII complex in plasma was almost undetectable. Together, these results indicated that FVII-133 successfully escaped the ATIII-mediated clearance, leading to a marked improvement in PK profile over rFVIIaFc.

Example 12. Prolonged Ex Vivo Efficacy of FVII-212 Over rFVIIa in HemA Mice

Figure 11:
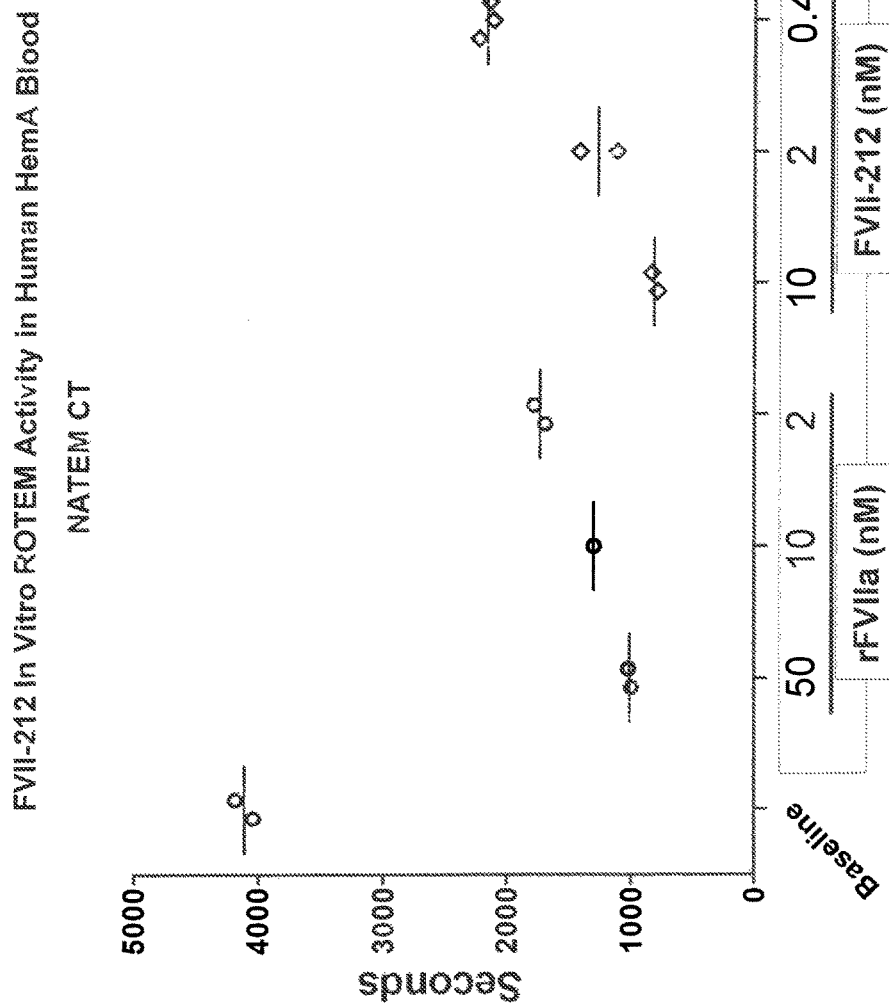
FIG. 11 shows in vitro clotting time measured by ROTEM assays in human HemA blood. The clotting activity of FVII-212, which has the identical structure as FVII-133, was measured. The proteins were spiked in citrated human HemA blood. The clotting was initiated by Calcium and the clotting time was recorded by ROTEM machine under the NATEM program. X axis shows concentrations of either rFVIIa or FVII-212 in nM, and y axis shows the clotting time.
Figure 12:
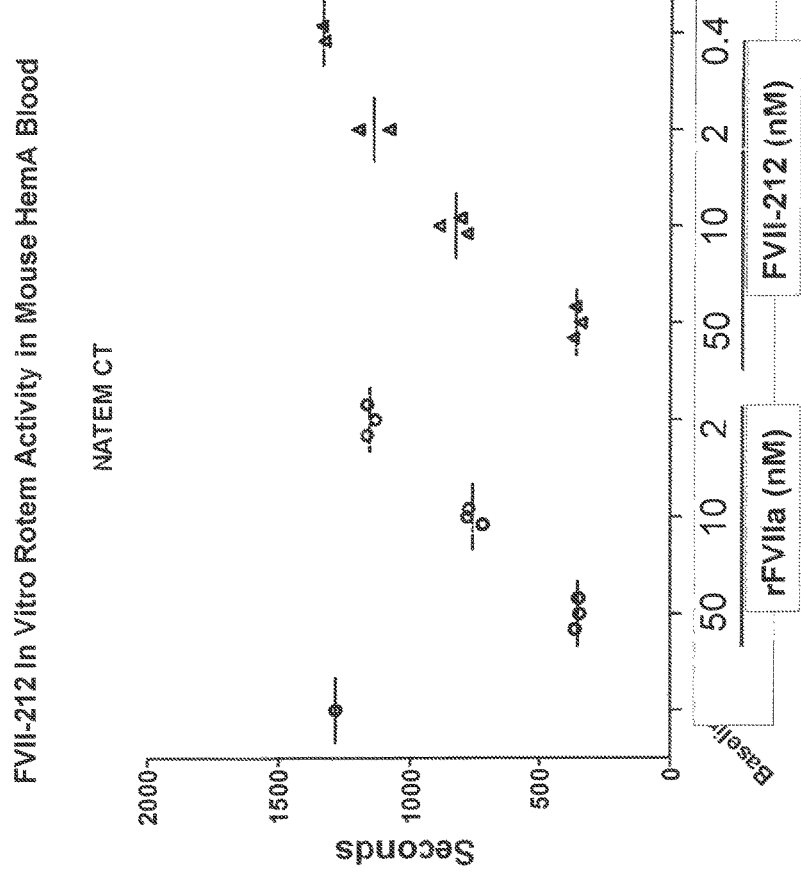
FIG. 12 shows in vitro clotting time measured by ROTEM assays in mouse HemA blood, which were collected by vena cava bleeding. The proteins were spiked into citrated mouse HemA blood. The clotting was initiated by Calcium and the clotting time was recorded in ROTEM machine under NATEM program. X axis shows the concentrations of spiked rFVIIa and FVII-212 in nM, and y axis shows the clotting time.

FVII-212 is identical to FVII-133, but encoded by an improved expression vector. Similar to FVII-133, FVII-212 displayed higher in vitro clotting activity than rFVIIa in human HemA blood per ROTEM assays (FIG. 11). In mouse HemA blood, however, the activity of FVII-212 was found to be similar to rFVIIa (FIG. 12), indicating FVII-212 is less active in mouse than human.

Figure 13:
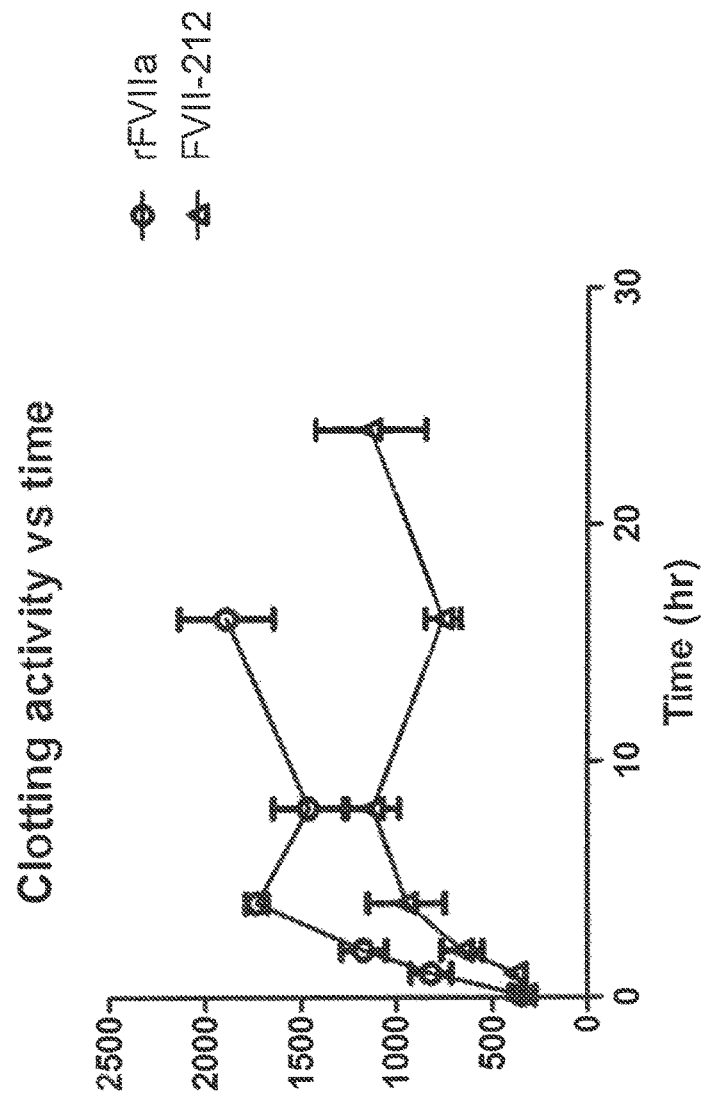
FIG. 13 shows ex vivo efficacy in HemA mice. FVII-212 (triangle) was administered in HemA mice at 10 nmol/kg. Blood was collected via vena cava with citrate and corn trypsin inhibitor (CTI) as an anti-coagulant at various times after dosing, and the clotting activity was measured by ROTEM analyzer under NATEM program. rFVIIa (circle) was used as a control. X axis shows the time (hr) following protein administration, and y axis shows the clotting time.

To assess the ex vivo efficacy of FVII-212 and corroborate the finding by example 10 (ex vivo efficacy of FVII-133 in HemB mice), FVII-212 was administered in HemA mice at 10 nmol/kg; blood was sampled at various times, and the clotting activity was measured by ROTEM analyzer under NATEM program. rFVIIa was included in parallel as a comparator. As shown in FIG. 13, although the clotting time from the blood collected at 5 min following dosing was similar between rFVII-212 and rFVIIa treated groups, the blood collected from the later time points of FVII-212 group clotted faster than that from the corresponding time point of rFVIIa group. The results indicate the prolonged ex-vivo efficacy of FVII-212 compared to rFVIIa.

Figure 14:
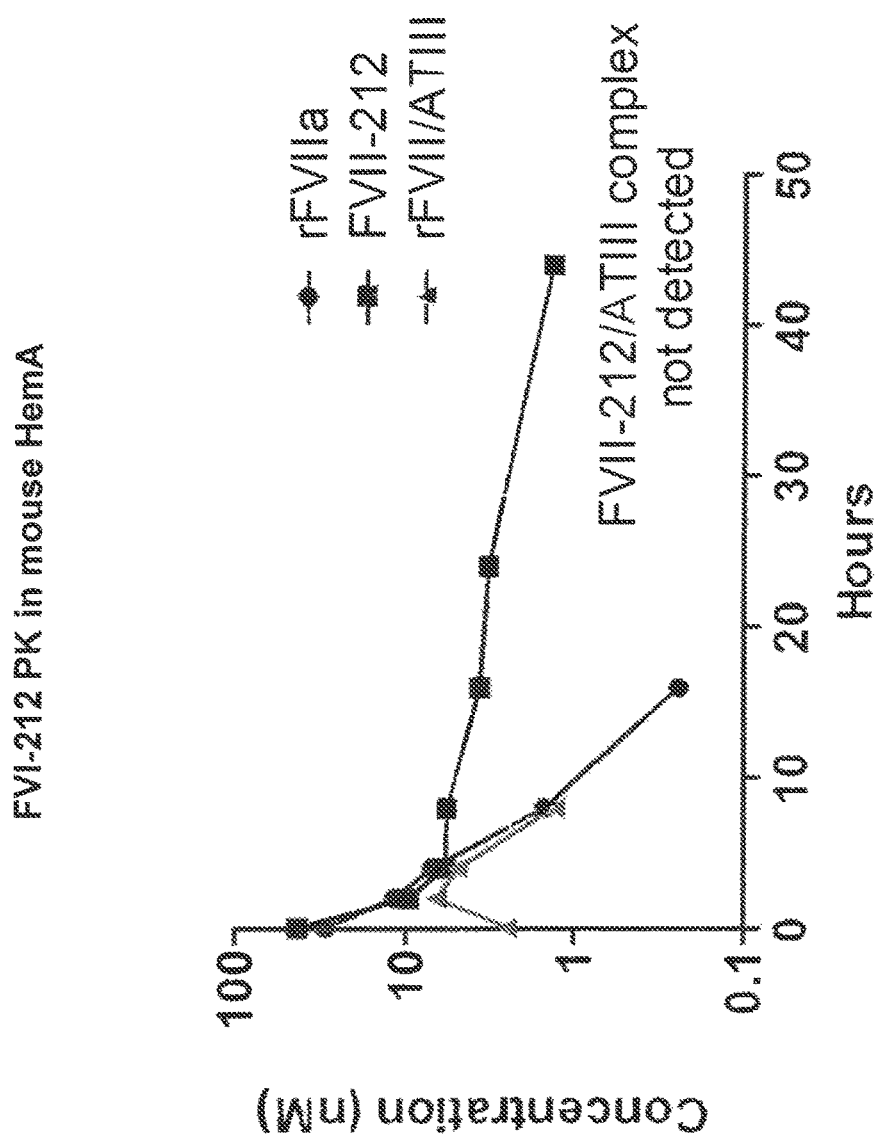
FIG. 14 shows pharmacokinetics of rFVIIa (circle), FVII-212 (square), and rFVII/ATIII (triangle) in HemA mice. The concentration of the proteins (y axis) is plotted against time (x axis).

As indicated in Example 11, FVII-133 displayed improved PK properties over rFVIIaFc in HemB mice, which were thought to contribute to the prolonged efficacy of this protein. Similar to FVII-133 in HemB mice, the clearance of FVII-212 in HemA mice was considerably slower than that of rFVIIa (FIG. 14), represented by a longer terminal half-life of about 18 hours (compared to the half-life about 1 hour in HemA plasma of rFVIIa when measured by rFVIIa's activity) as well as the absence of rFVII-212-ATIII complex in treated HemA mice.

Taken together, this example extended the previous finding and demonstrated that 1) FVII-212 displays prolonged ex vivo efficacy over rFVIIa in HemA mice; 2) the prolonged efficacy of FVII-212 is resulted from its improved PK properties; and 3) resistance to ATIII inhibition contributes, at least partly, to the PK improvement in FVII-212.

Example 13. Amidolytic Activity of FVII-212

Amidolytic activity of FVII-212 was measured before and after thrombin activation using a chromozyme t-PA substrate. For thrombin activation, FVII-212 (100 nM) was treated with thrombin (50 nM) for 20 minutes at 37° C. Thrombin was subsequently inhibited with hirudin (250 nM).

Figure 15:
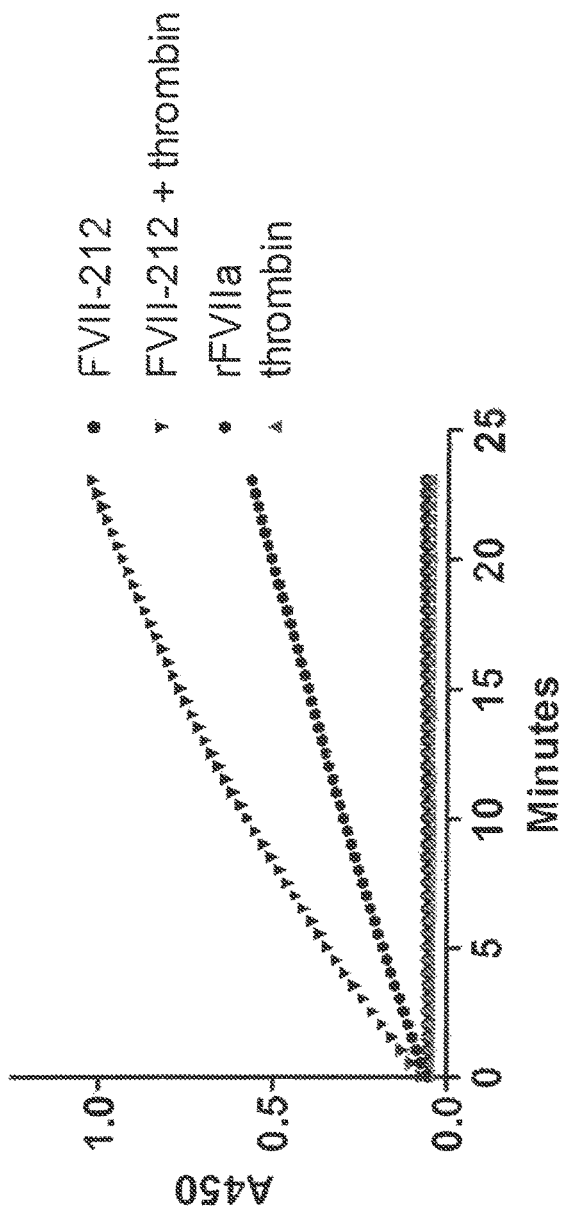
FIG. 15. shows amildolytic activity of FVII-212 measured before and after thrombin activation using a chromozyme t-PA substrate. FVII-212 with thrombin is represented as inverted triangle (the first line from top to bottom). rFVIIa is represented as circle (the second line from top to bottom). FVII-212 and thrombin are shown as the third and fourth lines (the bottom lines).
Figure 16:
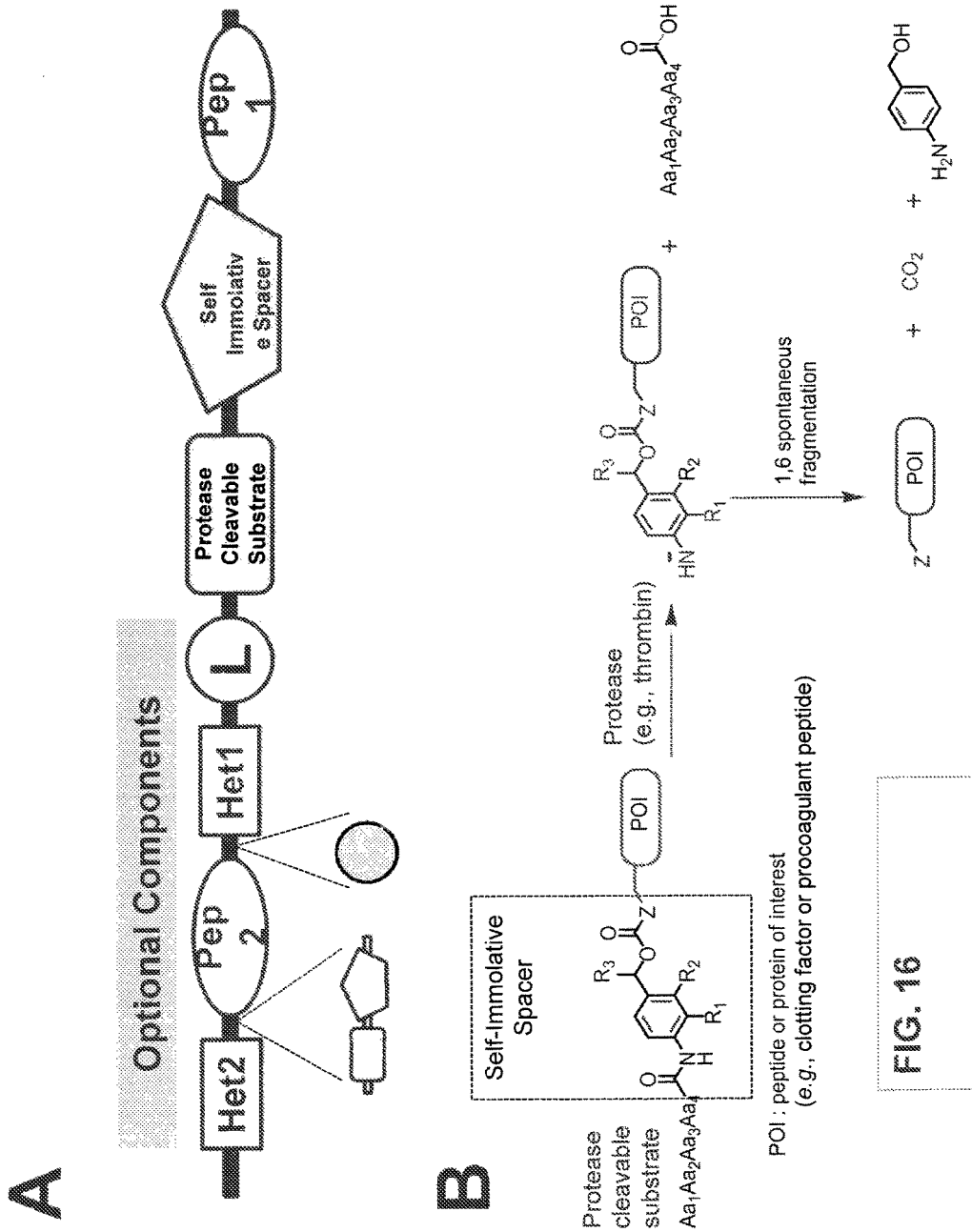
FIG. 16A shows the general organization of a protease-activatable procoagulant compound of the invention. Het2, Pep2, Het1 and L are independently optional components. Pep1 and Pep2 are polypeptides, at least one of which is a clotting factor or a procoagulant peptide. Het1 and Het are heterologous moieties. L is a linker. Additional linkers can connect the different moieties; for example, a linker could be located between Pep2 and Het1 (as shown in the diagram). Additional protease cleavable substrate and self-immolative spacer groups can be inserted at the N-terminus of other moieties such as polypeptides or heterologous moieties. The diagram shows the optional insertion of such a group at the N-terminus of Pep2.
FIG. 16B is a representation of an exemplary procoagulant compound of the invention comprising a protease cleavable substrate (Aa1Aa2Aa3Aa4), a self-immolative spacer and a protein of interest (POI; e.g., a clotting factor or procoagulant peptide); illustrating the fragmentation of the compound and the release of the peptide or protein of interest after proteolytic cleavage of the cleavable substrate and 1,6 spontaneous fragmentation.
Figure 17:
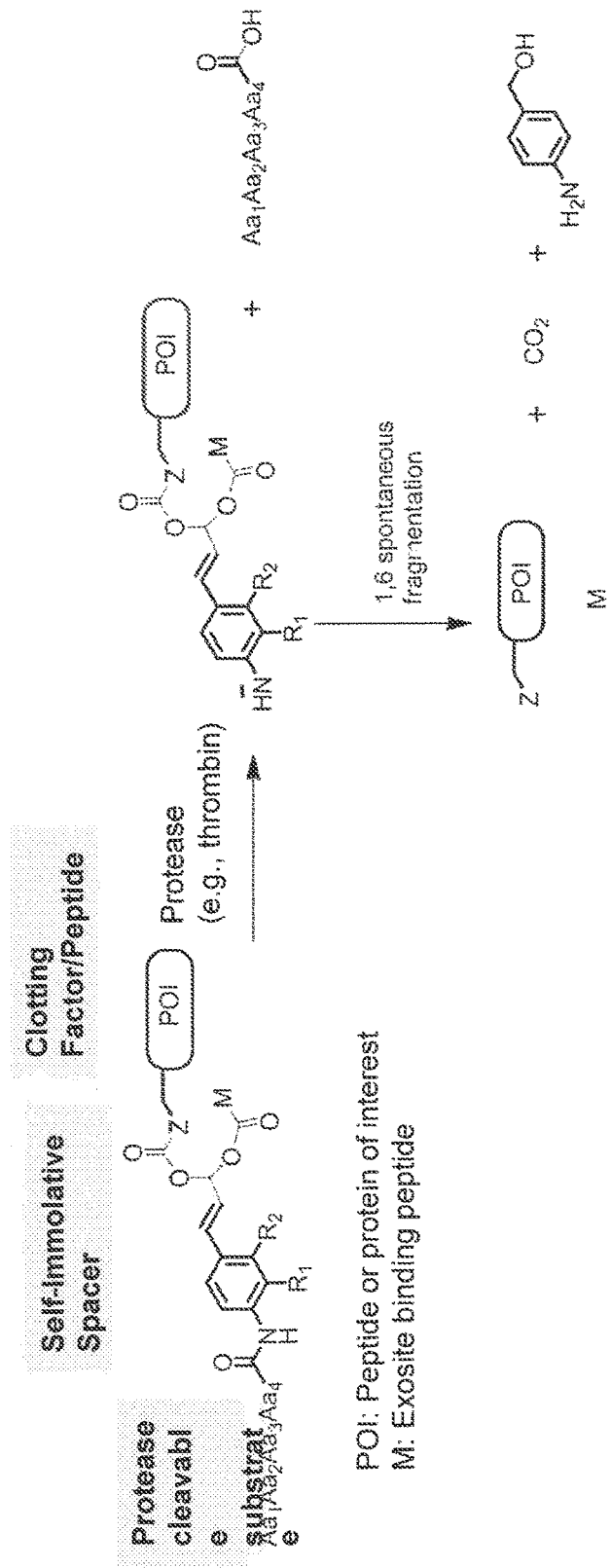
FIG. 17 is a representation of an alternative exemplary protease-activatable procoagulant compound of the invention which comprises an exosite binding peptide (M). The diagram illustrates the release of the peptide or protein of interest (POI; e.g., a clotting factor or procoagulant peptide) and the exosite binding peptide after proteolytic cleavage of a cleavable substrate (Aa1Aa2Aa3Aa4) and 1,6 spontaneous fragmentation.

As FIG. 15 shows, FVII-212 displayed no activity prior to thrombin activation. Following thrombin activation, the amidolytic activity associated with FVII-212 was greater than that observed for equal molar levels of rFVIIa. These data demonstrate that the activity of FVII-212 is dependent on thrombin activation.

Example 14. Thrombin-Activatable Procoagulant Compounds with PABC Self-Immolative Linker Six different peptides, designated Compound 1 to 6, were used in the experiments disclosed herein (TABLE 5). The sequence in Compounds 1 to 6 reproduces the coupling of a thrombin cleavable substrate and a self-immolative spacer to the N-terminus of a clotting factor or a fragment thereof, in this specific example, FX. These compounds comprise the six N-terminal amino acid residues of the heavy chain of the FXa clotting factor, Ile-Val-Gly-Gly-Gln-Glu (SEQ ID NO: 61), and serve as a model to show the applicability of the procoagulant compound design disclosed herein to clotting factors.

TABLE 5

| Compound | Structure |
| --- | --- |
| 1 | (D-Phe)-Pip-Arg-|PABC|-Ile-Val-Gly-Gly-Gln-Glu-NH$_2$ |
| 2 | (D-Phe)-Pip-Arg-Ile-Val-Gly-Gly-Gln-Glu-NH$_2$ |
| 3 | Ala-Leu-Arg-Pro-Arg-Ile-Val-Gly-Gly-Gln-Glu-NH$_2$ |
| 4 | (D-Phe)-Pro-Arg-|PABC|-Ile-Val-Gly-Gly-Gln-Glu-NH$_2$ |
| 5 | Ala-Leu-Val-Pro-Arg-|PABC|-Ile-Val-Gly-Gly-Gln-Glu-NH$_2$ |
| 6 | Ala-Leu-Val-Pro-Arg-Ile-Val-Gly-Gly-Gln-Glu-NH$_2$ |

Pip is pipecolic acid.
(D-Phe) is a-Phenyl alanine.
The sequences of the thrombin substrate are underlined.
The location PABC self-immolative linker is indicated by a box.

Figure 18:
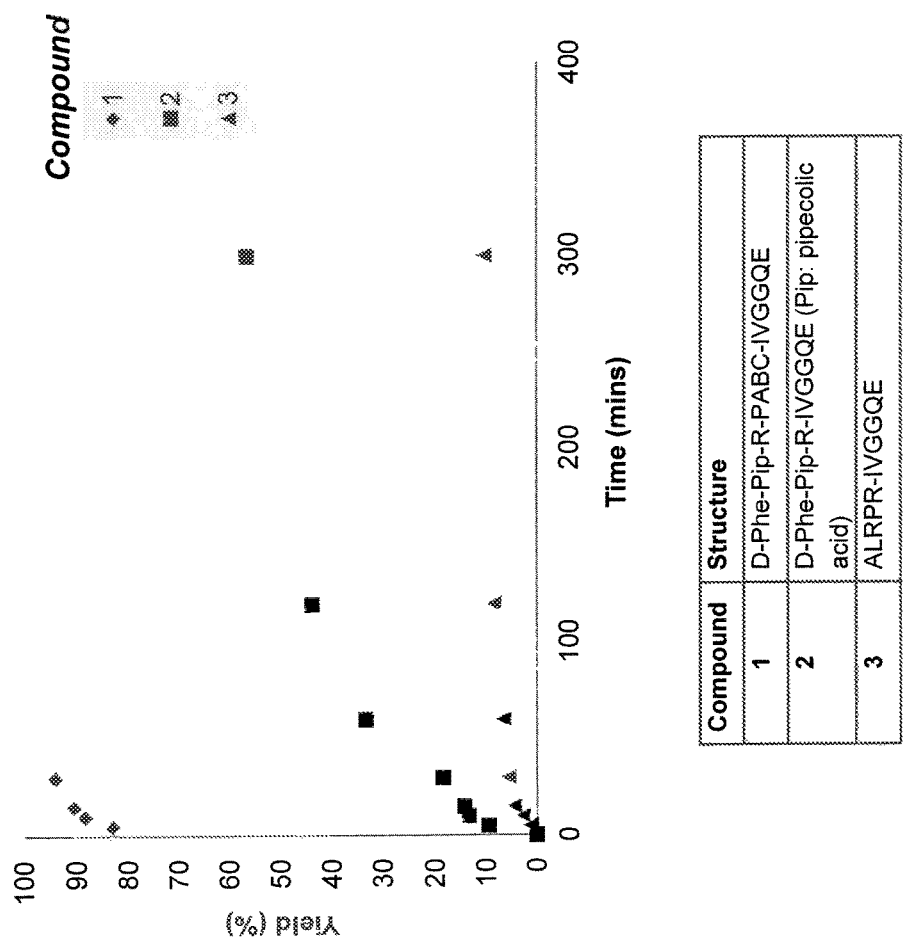
FIG. 18 shows the release kinetics of the peptide IVGGQE (SEQ ID NO: 61), which corresponds to the six N-terminal amino acid residues of the heavy chain of the FXa clotting factor, from different procoagulant compounds (Compounds 1, 2, and 3) following treatment with 14 nM thrombin.

FIG. 18 depicts the cleavage of Compounds 1, 2 and 3 by 14 nM thrombin. In this specific example, 50 μL of peptide (1 mM) in water was added to 900 μL PBS, followed by 50 μL of thrombin (278 nM, 10 μg/mL), giving the following approximate initial concentrations: thrombin=14 nM, peptide=50 μM. The mixture was incubated at room temperature. Aliquots (95 μL) at various time points were quenched with 5 μL of hirudin (2 μM) and injected into the HPLC (C-18 column, CH$_3$CN/H$_2$O, 0 to 70% over 12 minutes, 60° C. 0.5 mL/min, λ=280 nm). The decreases of peptide peak areas were used to calculate yield.

Compared to Compounds 2 and 3, the construct incorporating the thrombin-cleavable synthetic substrate D-Phe-Pip-Arg and the self-immolative spacer PABC (Compound 1) was a better substrate for thrombin. The incorporation of PABC to Compound 1 led to at least 10-fold increase in cleavage rate compared to that of Compound 2.

Figure 19:
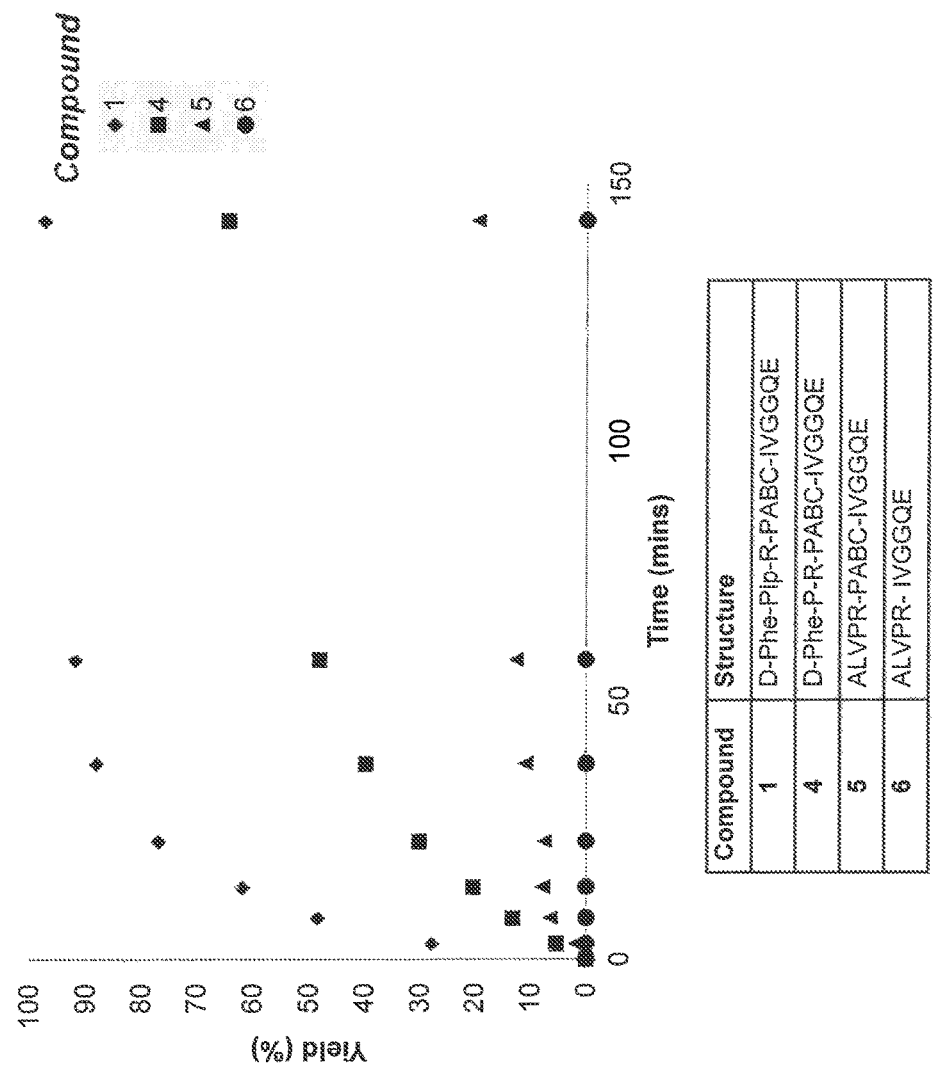
FIG. 19 shows the release kinetics of the peptide IVGGQE (SEQ ID NO: 61), which corresponds to the six N-terminal amino acid residues of the heavy chain of the FXa clotting factor, from different procoagulant compounds (Compounds 1, 4, 5 and 6) following treatment with 1.4 nM thrombin.
Figure 20:
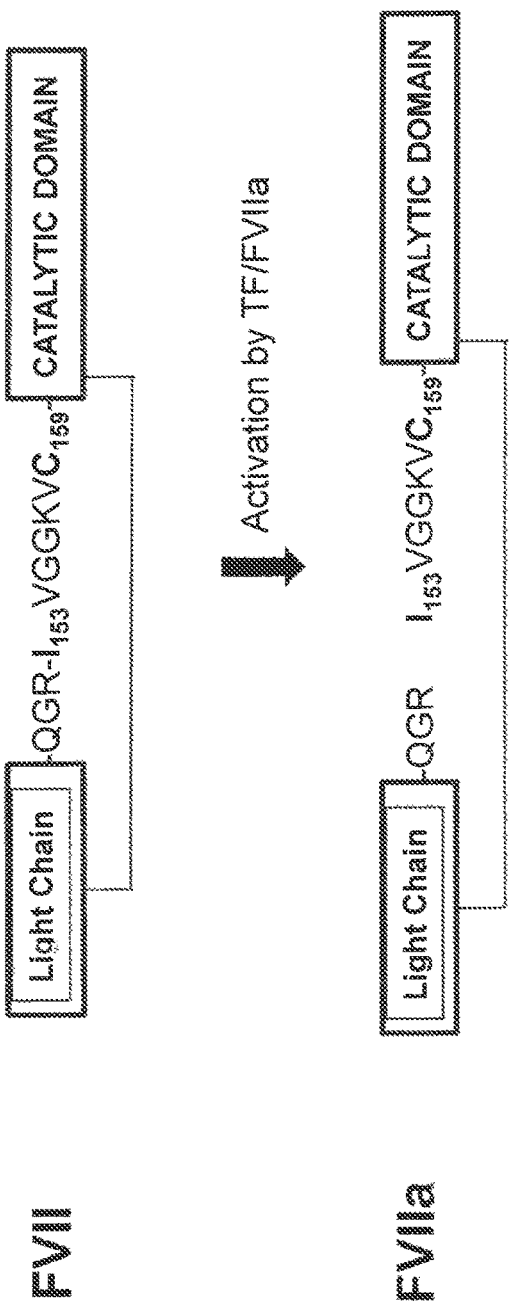
FIG. 20 shows the natural processing of factor VII to yield activated factor (FVIIa).
Figure 21:
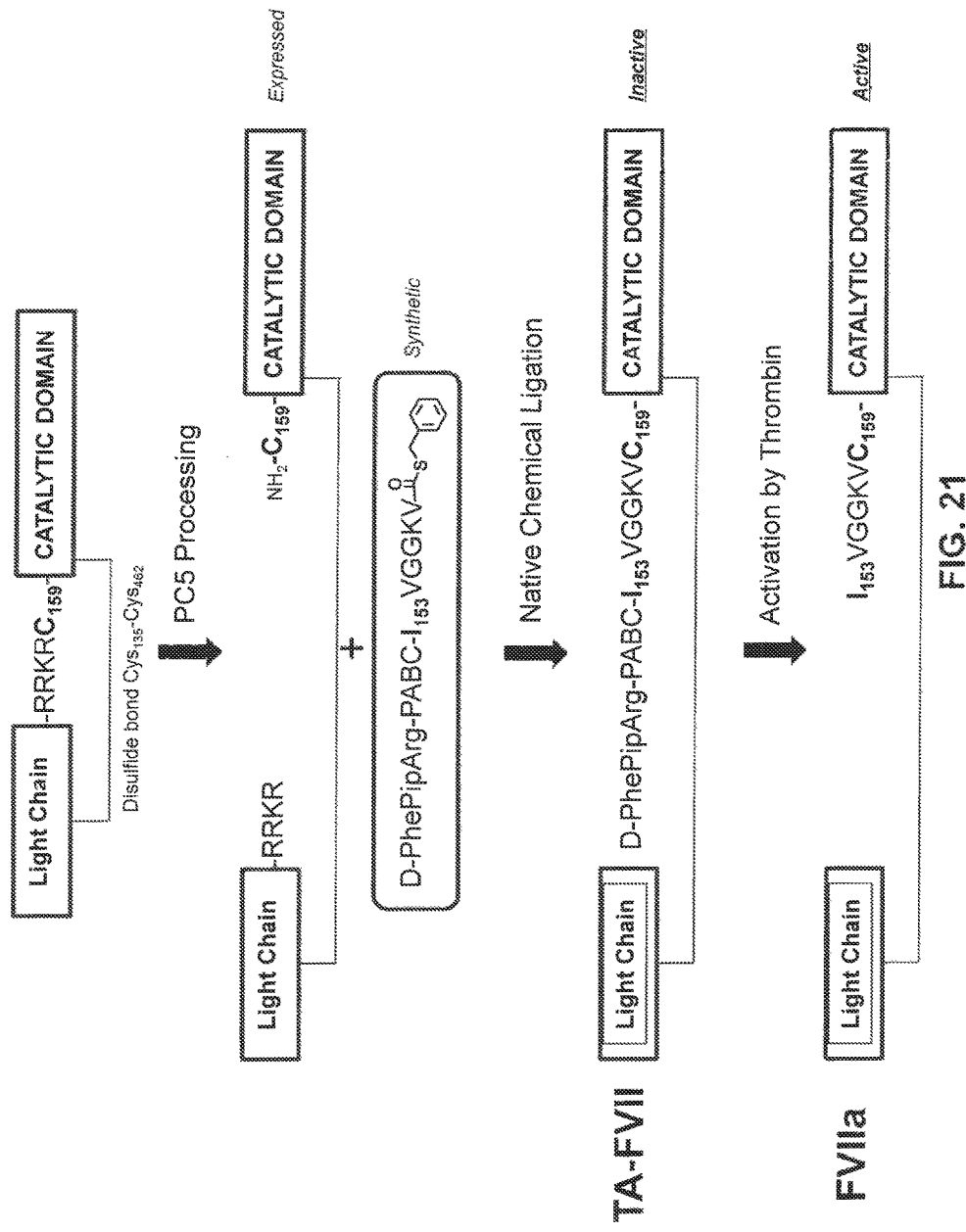
FIG. 21 is a representation of exemplary procoagulant compounds of the invention comprising FVIIa clotting factor.

FIG. 19 depicts the cleavage of Compounds 1, 4, 5 and 6 by 1.4 nM thrombin. Compounds 1, 4 and 5 incorporate PABC and different thrombin-cleavable substrates. 50 of peptide (1 mM) in water was added to 900 μL PBS. The mixture was incubated at 37° C. for 30 min, followed by 50 μL of thrombin (27.8 nM, 1 μg/mL), giving the following approximate initial concentrations: thrombin=1.4 nM, peptide=50 μM. The mixture was incubated at 37° C. Aliquots (95 μL) at various time points were quenched with 5 μL of hirudin (2 μM) and injected into the HPLC (C-18 column, CH$_3$CN/H$_2$O, 0 to 70% over 12 minutes, 60° C. 0.5 mL/min, λ=280 nm). The decreases of peptide peak areas were used to calculate yield.

Compound 1 was a better substrate for thrombin than Compounds 4 and 5. At 1.4 nM, a physiological relevant concentration of thrombin, 30% of Compound 1 was quickly cleaved and released. In contrast, thrombin-mediated release of peptide IVGGQE (SEQ ID NO: 61) from Compound 6 without PABC linker was not observed.

Example 15. Thrombin Activatable FVII-186 with SUMO Cleavage Site

For cloning of FVII-186, the DNA sequence comprising nucleotides from the HindIII site to the EcoRI site of FVII-186 (Table #) was synthesized. The DNA was subcloned into the HindIII/EcoRI sites of pcDNA.

Figure 22:
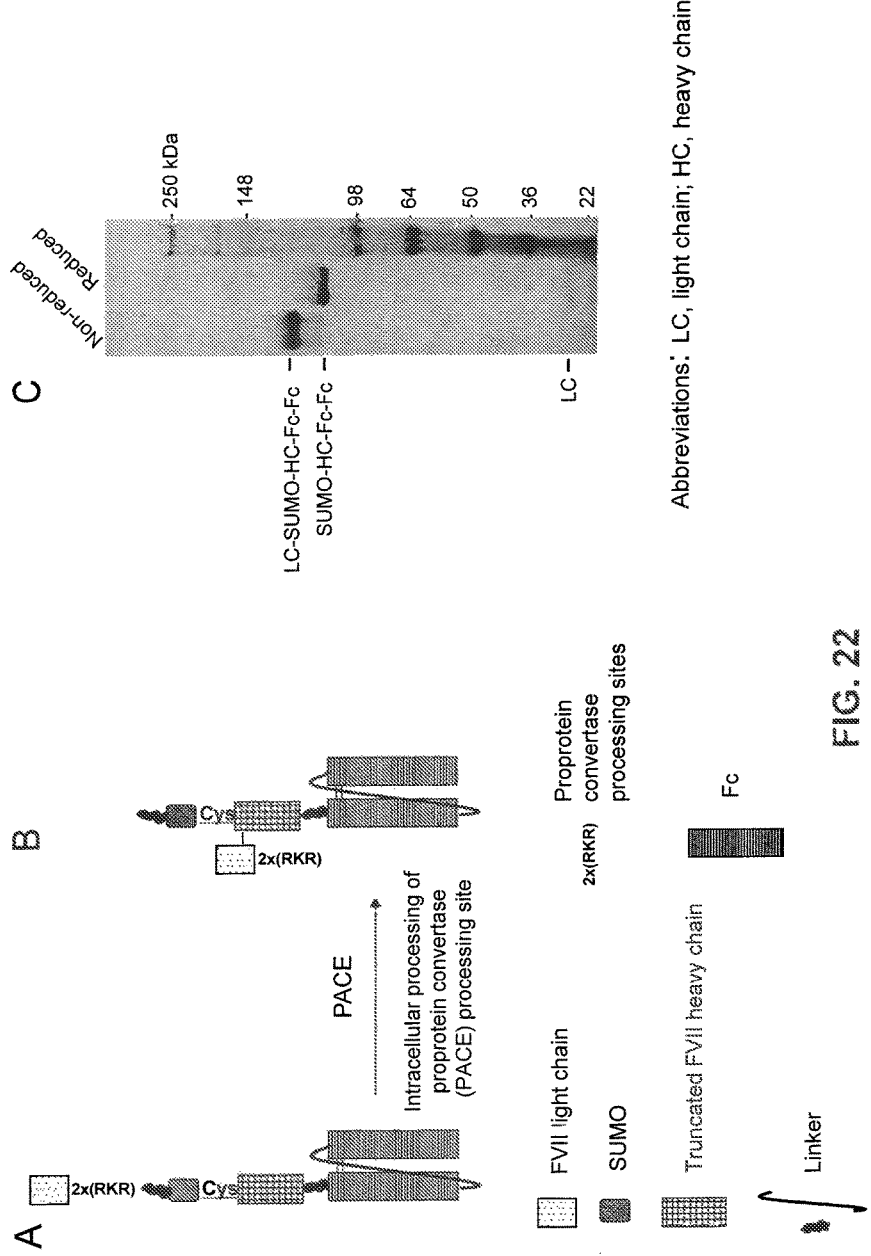
FIG. 22A-B shows a flow diagram of a cleavable polypeptide, FVII-186 (FIG. 22A) that can be processed by a proprotein convertase (e.g., PACE) to a processed cleavable polypeptide (FIG. 22B).
FIG. 22C demonstrates non-reduced (lane 1) or reduced (lane 2) SDS-PAGE, showing the above constructs and chains. (—) indicates a peptide bond.

To transiently express FVII-186, HEK-293-F cells were grown in suspension in FREESTYLE® media (Invitrogen) supplemented with vitamin K3 (Sigma Aldrich, St. Louis, Mo.) to 2 μg/liter (growth media) as suspension cells at 37° C./10% CO$_2$. Cells were subcultured every three to four days by seeding at cell density of 5×10$^5$ cells/ml. Twenty-four hours prior to transfection, cells were seeded at a density of 7×10$^5$ cells/ml in growth media. On the day of transfection, a transfection solution was made with a volume equal to 5% of the total volume of the cell culture to be transfected. In the transfection solution, DNA was added (final concentration 20 mg/L) to a freshly made solution of PEI (60 mg/L) in growth media. The solution was swirled for 30 seconds and incubated for five minutes at room temperature before adding directly to the cell culture. Four hours later a volume equal to the cell culture volume of OPTICHO™ (Invitrogen) supplemented with vitamin K3 and 200 mM L-glutamine was added to the cells. The cell culture was allowed to grow as shown above and daily media samples were taken to assess protein expression. On the day of harvest, the cells were spun down, and the media filtered in preparation for protein purification or protein analysis by protein A pulldown. For expression of FVII-186, a plasmid encoding FVII-186 was contransfected with a plasmid encoding the proprotein convertase PACE to ensure intracellular processing and cleavage of the proprotein convertase cleavage sites (2×(RKR) SEQ ID NO: 3) in the linker connecting the FVII light chain to SUMO (FIG. 22).

To purify FVII-186, conditioned medium was loaded onto a 25-mL column of Q SEPHAROSE® Fast Flow (GE HealthCare Life Sciences) after adjustment of pH to 7.4 with 2.0 M Tris, pH 8.0. Column was washed with 10 mM IVIES, 50 mM NaCl, pH 6.5. The protein was eluted with 10 mM IVIES, 100 mM NaCl, 20 mM CaCl$_2$, pH 6.5. The fractions containing FVII-186 were pooled and loaded onto a 25-mL column of rhFcRn– sepharose after adjustment of pH to 6.2 with 0.5 M IVIES, pH 5.5. After washing with 50 mM MES, 100 mM NaCl, pH 6.2, the bound material was eluted with 10 mM Tris, 250 mM NaCl, pH 8.0 and analyzed with SDS-PAGE.

FVII-186 was cleaved by a SUMO protease as follows. FVII-186 (0.83 mg/mL, 10 μL) was incubated with 10 μL of 100 mM HEPES, 20 mM CaCl$_2$, 0.004% Tween 80 containing 0.4 mM oxidized Glutathione (GSSG), 20 mM Glutathione (GSH), 0.2 U/μL SUMO protease (Invitrogen Cat. No. 12588-018) for 48 hours at room temperature. Reducing SDS-PAGE (FIG. 23, lane 3) showed almost complete conversion of FVII-186 to the desired FVIIHC.

For SUMO protease cleavage of FVII-186 and native chemical ligation with a thioester peptide, FVII-186 (0.83 mg/mL, 10 μL) was incubated with 10 μL of 100 mM HEPES, 20 mM CaCl$_2$, 0.004% Tween 80 containing 0.4 mM SYN470 as a positive control peptide, 0.4 mM GSSG, 20 mM GSH, 0.2 U/μL SUMO protease (Invitrogen Cat. No. 12588-018) for 48 hours at room temperature. Reducing SDS-PAGE (Figure #, lane 4) showed complete disappearance of the FVIIHC band and a single new band as the conjugate of the positive peptide control and the FVIIHC.

Figure 23:
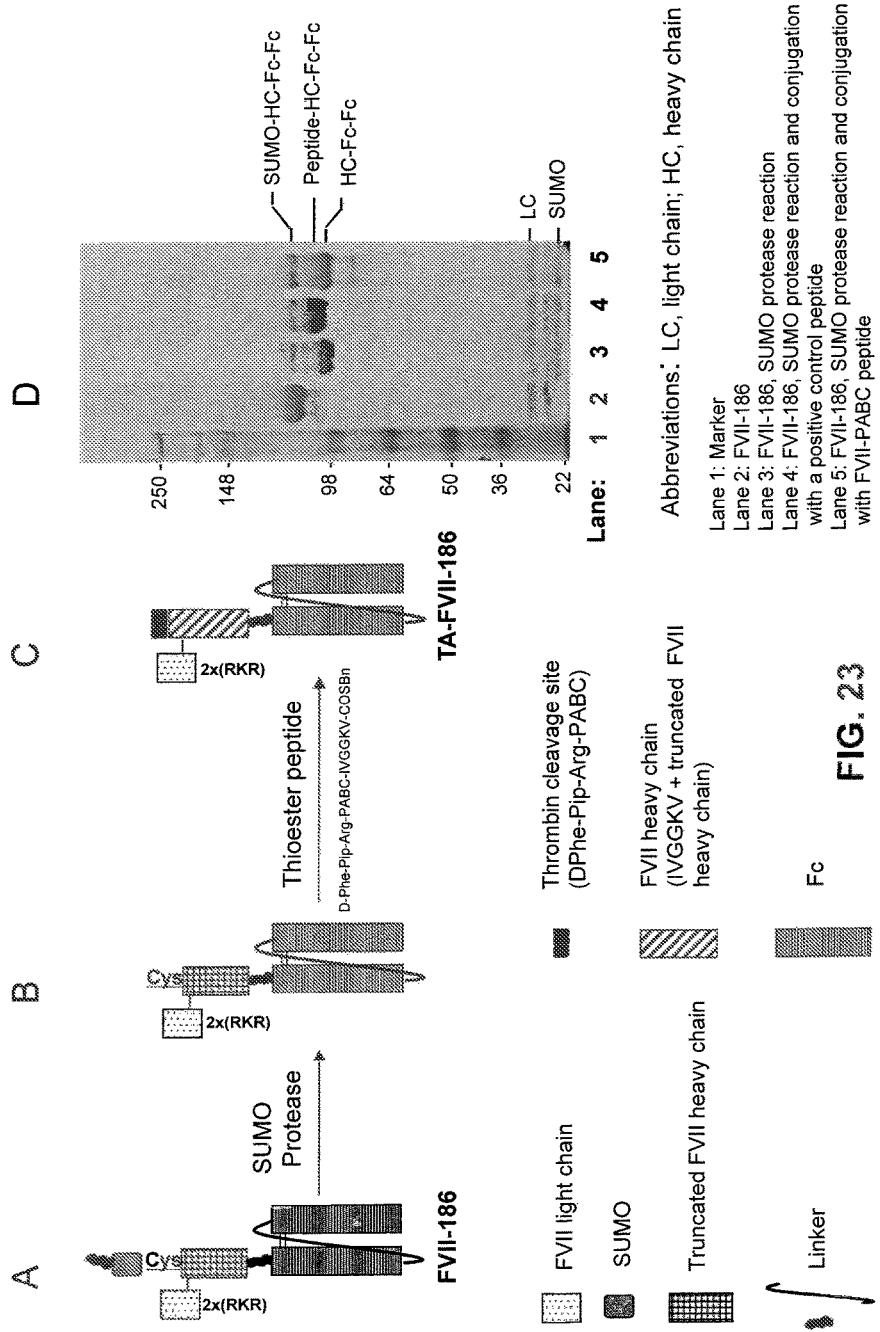
FIG. 23A-C shows a flow diagram of (i) FVII-186 cleavage by a SUMO protease (FIG. 23B) and (ii) its fusion to a thioester peptide (FIG. 23C).
FIG. 23D shows reducing SDS-PAGE indicating the constructs and chains: lane 1 shows marker; lane 2 shows FVII-186; lane 3 shows FVII-186 with SUMO protease reaction; lane 3 shows FVII-186 with SUMO protease reaction and conjugation with a positive control peptide; and lane 5 shows FVII-186 with SUMO protease reaction and conjugation with PABC peptide. (—) indicates a peptide bond.

In order to synthesize Thrombin Activatable FVII-186 (TA-FVII-186), FVII-186 (0.83 mg/mL, 200 μL) was incubated with 200 μL of 100 mM HEPES, 20 mM CaCl$_2$, 0.004% Tween 80 containing 0.4 mM FVII-PABC peptide (i.e., D-Phe-Pip-Arg-PABC-IVGGKV-COSBn) (SEQ ID NO: 66), 0.4 mM GSSG, 20 mM GSH, 0.2 U/μL SUMO protease (Invitrogen Cat. No. 12588-018) for 48 hours at room temperature and analyzed by reducing SDS-PAGE (FIG. 23, lane 5). Reaction mixture was placed in a 0.5 mL dialysis cassette with 10 k MWCO and dialyzed against 1 L of 10 mM Tris, 250 mM NaCl, pH 8.0 containing 0.4 mM GSSG, 2 mM GSH for 24 hours at 4° C. The conjugate was further purified by rhFcRn-sepharose column as described.

Figure 24:
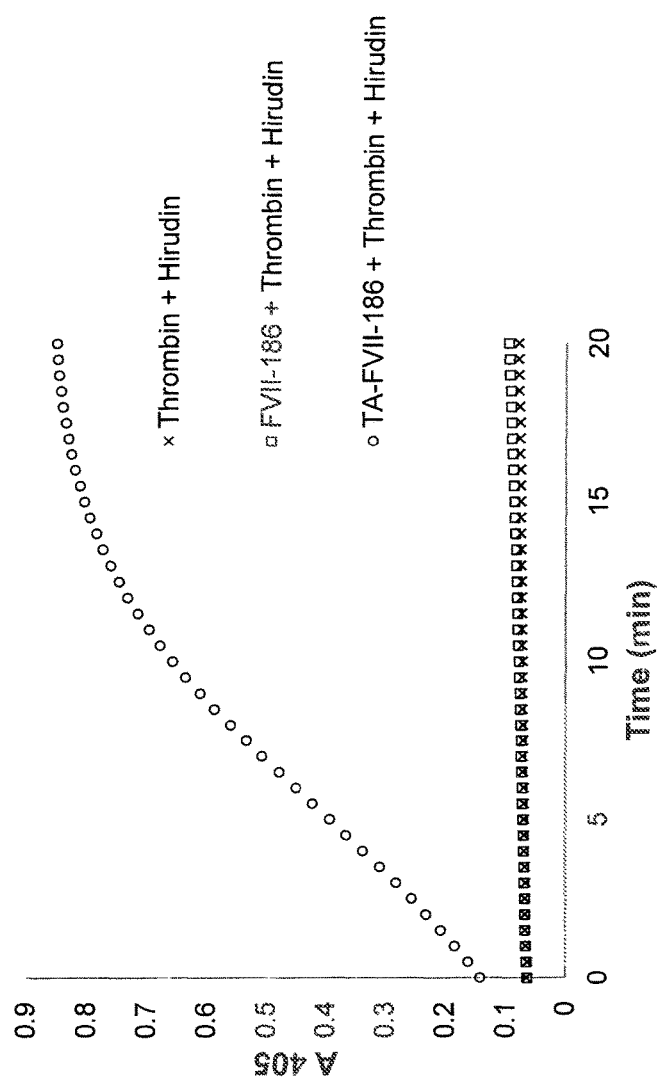
FIG. 24 shows FVIIa chromogenic assay after thrombin activation of TA-FVII-186. X axis indicates time (min), and Y axis indicates Absorbance (A405) measurement for FVIIa activity. (x) shows FVIIa activity of a mixture of thrombin and hirudin. (□) indicates FVIIa activity of a mixture of FVII-186, thrombin, and hirudin. (○) indicates FVIIa activity of a mixture of TA-FVII-186, thrombin, and hirudin.

FVIIa Chromogenic assay was performed after Thrombin cleavage and activation of TA-FVII-186 (FIG. 24). This assay measures the FX activation activity by measuring the ability of FVIIa to activate FX, as determined by measuring levels of a chromogenic substrate that is cleaved by activated FX (FXa). TA-FVII-186 (200 nM) was activated with Thrombin (140 nM) for 20 minutes at 37° C. Hirudin was added to quench Thrombin. sTF-PL mixture (A STACLOT® FVII-rTF kit), FX, and PEFACHROME® FXa substrate were added and reaction was monitored by measuring absorbance at 405 nm. FVII-186 missing the six N-terminal amino acids was not active in the presence of thrombin. Only TA-FVII-186 with a thrombin cleavage site connected to the complete heavy chain FVII showed activity after thrombin cleavage. The resulted activity demonstrated that the FVII PABC peptide was successfully conjugated to the N-terminal cysteine of the truncated heavy chain of FVII, the crucial N-terminal isoleucine residue was generated upon cleavage by thrombin, and the formed protein had the essential structure for activity.

The present invention has been described above with the aid of functional building blocks illustrating the implementation of specified functions and relationships thereof. The boundaries of these functional building blocks have been arbitrarily defined herein for the convenience of the description. Alternative boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents. Other embodiments of the invention will be apparent to those skilled in the art from consideration of the specification and practice of the invention disclosed herein.

All patents and publications cited herein are incorporated by reference herein in their entirety.

SEQUENCES

```
SEQ ID NO: 44 DNA sequence of FVII-133
  1 AAGCTTGCCG CCACCATGGT CTCCCAGGCC CTCAGGCTCC TCTGCCTTCT GCTTGGGCTT
    TTCGAACGGC GGTGGTACCA GAGGGTCCGG GAGTCCGAGG AGACGGAAGA CGAACCCGAA
 61 CAGGGCTGCC TGGCTGCAGT CTTCGTAACC CAGGAGGAAG CCCACGGCGT CCTGCACCGG
    GTCCCGACGG ACCGACGTCA GAAGCATTGG GTCCTCCTTC GGGTGCCGCA GGACGTGGCC
121 CGCCGGCGCG CCAACGCGTT CCTGGAGGAG CTGCGGCCGG GCTCCCTGGA GAGGGAGTGC
    GCGGCCGCGC GGTTGCGCAA GGACCTCCTC GACGCCGGCC CGAGGGACCT CTCCCTCACG
181 AAGGAGGAGC AGTGCTCTT CGAGGAGGCC CGGGAGATCT TCAAGGACGC GGAGAGGACG
    TTCCTCCTCG TCACGAGGAA GCTCCTCCGG GCCCTCTAGA AGTTCCTGCG CCTCTCCTGC
241 AAGCTGTTCT GGATTTCTTA CAGTGATGGG GACCAGTGTG CCTCAAGTCC ATGCCAGAAT
    TTCGACAAGA CCTAAAGAAT GTCACTACCC CTGGTCACAC GGAGTTCAGG TACGGTCTTA
301 GGGGGCTCCT GCAAGGACCA GCTCCAGTCC TATATCTGCT TCTGCCTCCC TGCCTTCGAG
    CCCCCGAGGA CGTTCCTGGT CGAGGTCAGG ATATAGACGA AGACGGAGGG ACGGAAGCTC
361 GGCCGGAACT GTGAGACGCA CAAGGATGAC CAGCTGATCT GTGTGAACGA GAACGGCGGC
    CCGGCCTTGA CACTCTGCGT GTTCCTACTG GTCGACTAGA CACACTTGCT CTTGCCGCCG
421 TGTGAGCAGT ACTGCAGTGA CCACACGGGC ACCAAGCGCT CCTGTCGGTG CCACGAGGGG
    ACACTCGTCA TGACGTCACT GGTGTGCCCG TGGTTCGCGA GGACAGCCAC GGTGCTCCCC
481 TACTCTCTGC TGGCAGACGG GGTGTCCTGC ACACCCACAG TTGAATATCC ATGTGGAAAA
    ATGAGAGACG ACCGTCTGCC CCACAGGACG TGTGGGTGTC AACTTATAGG TACACCTTTT
541 ATACCTATTC TAGAAAAAAG AAATGCCAGC AAACCCCAAG GCGCCCTGCG GCCCCGGATT
    TATGGATAAG ATCTTTTTTC TTTACGGTCG TTTGGGGTTC CGCGGGACGC CGGGGCCTAA
601 GTGGGGGGCA AGGTGTGCCC CAAAGGGGAG TGTCCATGGC AGGTCCTGTT GTTGGTGAAT
    CACCCCCCGT TCCACACGGG GTTTCCCCTC ACAGGTACCG TCCAGGACAA CAACCACTTA
661 GGAGCTCAGT TGTGTGGGGG GACCCTGATC AACACCATCT GGGTGGTCTC CGCGGCCCAC
    CCTCGAGTCA ACACACCCCC CTGGGACTAG TTGTGGTAGA CCCACCAGAG GCGCCGGGTG
721 TGTTTCGACA AAATCAAGAA CTGGAGGAAC CTGATCGCGG TGCTGGGCGA GCACGACCTC
    ACAAAGCTGT TTTAGTTCTT GACCTCCTTG GACTAGCGCC ACGACCCGCT CGTGCTGGAG
781 AGCGAGCACG ACGGGGATGA GCAGAGCCGG CGGGTGGCGC AGGTCATCAT CCCCAGCACG
    TCGCTCGTGC TGCCCCTACT CGTCTCGGCC GCCCACCGCG TCCAGTAGTA GGGGTCGTGC
841 TACGTCCCGG GCACCACCAA CCACGACATC GCGCTGCTCC GCCTGCACCA GCCCGTGGTC
    ATGCAGGGCC CGTGGTGGTT GGTGCTGTAG CGCGACGAGG CGGACGTGGT CGGGCACCAG
```

| SEQUENCES |
|---|
| 901 CTCACTGACC ATGTGGTGCC CCTCTGCCTG CCCGAACGGA CGTTCTCTGA GAGGACGCTG
      GAGTGACTGG TACACCACGG GGAGACGGAC GGGCTTGCCT GCAAGAGACT CTCCTGCGAC
 961 GCCTTCGTGC GCTTCTCATT GGTCAGCGGC TGGGGCCAGC TGCTGGACCG TGGCGCCACG
      CGGAAGCACG CGAAGAGTAA CCAGTCGCCG ACCCCGGTCG ACGACCTGGC ACCGCGGTGC
1021 GCCCTGGAGC TCATGGTCCT CAACGTGCCC CGGCTGATGA CCCAGGACTG CCTGCAGCAG
      CGGGACCTCG AGTACCAGGA GTTGCACGGG GCCGACTACT GGGTCCTGAC GGACGTCGTC
1081 TCACGGAAGG TGGGAGACTC CCCAAATATC ACGGAGTACA TGTTCTGTGC CGGCTACTCG
      AGTGCCTTCC ACCCTCTGAG GGGTTTATAG TGCCTCATGT ACAAGACACG GCCGATGAGC
1141 GATGGCAGCA AGGACTCCTG CAAGGGGGAC AGTGGAGGCC ACATGCCAC CCACTACCGG
      CTACCGTCGT TCCTGAGGAC GTTCCCCCTG TCACCTCCGG GTGTACGGTG GGTGATGGCC
1201 GGCACGTGGT ACCTGACGGG CATCGTCAGC TGGGGCCAGG GCTGCGCAAC CGTGGGCCAC
      CCGTGCACCA TGGACTGCCC GTAGCAGTCG ACCCCGGTCC CGACGCGTTG GCACCCGGTG
1261 TTTGGGGTGT ACACCAGGGT CTCCCAGTAC ATCGAGTGGC TGCAAAAGCT CATGCGCTCA
      AAACCCCACA TGTGGTCCCA GAGGGTCATG TAGCTCACCG ACGTTTTCGA GTACGCGAGT
1321 GAGCCACGCC CAGGAGTCCT CCTGCGAGCC CCATTTCCCG GTGGCGGTGG CTCCGGCGGA
      CTCGGTGCGG GTCCTCAGGA GGACGCTCGG GGTAAAGGGC CACCGCCACC GAGGCCGCCT
1381 GGTGGGTCCG GTGGCGGCGG ATCAGGTGGG GGTGGATCAG GCGGTGGAGG TTCCGGTGGC
      CCACCCAGGC CACCGCCGCC TAGTCCACCC CCACCTAGTC CGCCACCTCC AAGGCCACCG
1441 GGGGGATCCG ACAAAACTCA CACATGCCCA CCGTGCCCAG CTCCGGAACT CCTGGGAGGA
      CCCCCTAGGC TGTTTTGAGT GTGTACGGGT GGCACGGGTC GAGGCCTTGA GGACCCTCCT
1501 CCGTCAGTCT TCCTCTTCCC CCCAAAACCC AAGGACACCC TCATGATCTC CCGGACCCCT
      GGCAGTCAGA AGGAGAAGGG GGGTTTTGGG TTCCTGTGGG AGTACTAGAG GGCCTGGGGA
1561 GAGGTCACAT GCGTGGTGGT GGACGTGAGC CACGAAGACC CTGAGGTCAA GTTCAACTGG
      CTCCAGTGTA CGCACCACCA CCTGCACTCG GTGCTTCTGG GACTCCAGTT CAAGTTGACC
1621 TACGTGGACG GCGTGGAGGT GCATAATGCC AAGACAAAGC CGCGGGAGGA GCAGTACAAC
      ATGCACCTGC CGCACCTCCA CGTATTACGG TTCTGTTTCG GCGCCCTCCT CGTCATGTTG
1681 AGCACGTACC GTGTGGTCAG CGTCCTCACC GTCCTGCACC AGGACTGGCT GAATGGCAAG
      TCGTGCATGG CACACCAGTC GCAGGAGTGG CAGGACGTGG TCCTGACCGA CTTACCGTTC
1741 GAGTACAAGT GCAAGGTCTC CAACAAAGCC CTCCCAGCCC CCATCGAGAA AACCATCTCC
      CTCATGTTCA CGTTCCAGAG GTTGTTTCGG GAGGGTCGGG GGTAGCTCTT TTGGTAGAGG
1801 AAAGCCAAAG GCCAGCCCG AGAACCACAG GTGTACACCC TGCCCCCATC CCGGGATGAG
      TTTCGGTTTC CCGTCGGGGC TCTTGGTGTC CACATGTGGG ACGGGGGTAG GGCCCTACTC
1861 CTGACCAAGA ACCAGGTCAG CCTGACCTGC CTGGTCAAAG GCTTCTATCC CAGCGACATC
      GACTGGTTCT TGGTCCAGTC GGACTGGACG GACCAGTTTC CGAAGATAGG GTCGCTGTAG
1921 GCCGTGGAGT GGGAGAGCAA TGGGCAGCCG GAGAACAACT ACAAGACCAC GCCTCCCGTG
      CGGCACCTCA CCCTCTCGTT ACCCGTCGGC CTCTTGTTGA TGTTCTGGTG CGGAGGGCAC
1981 TTGGACTCCG ACGGCTCCTT CTTCCTCTAC AGCAAGCTCA CCGTCGACAA GAGCAGGTGG
      AACCTGAGGC TGCCGAGGAA GAAGGAGATG TCGTTCGAGT GGCAGCTGTT CTCGTCCACC
2041 CAGCAGGGGA ACGTCTTCTC ATGCTCCGTG ATGCATGAGG CTCTGCACAA CCACTACACG
      GTCGTCCCCT TGCAGAAGAG TACGAGGCAC TACGTACTCC GAGACGTGTT GGTGATGTGC
2101 CAGAAGAGCC TCTCCCTGTC TCCGGGTAAA CGGCGCCGCC GGAGCGGCGG TGGAGGTTCC
      GTCTTCTCGG AGAGGGACAG AGGCCCATTT GCCGCGGCGG CCTCGCCGCC ACCTCCAAGG
2161 GGTGGCGGCG GATCAGGTGG CGGCGGATCA GGTGGGGGTG GATCAGGTGG CGGGGGATCC
      CCACCGCCGC CTAGTCCACC GCCGCCTAGT CCACCCCCAC CTAGTCCACC GCCCCCTAGG
2221 AGGAAGAGGA GGAAGAGGTC AGGCACTACA AATACTGTGG CAGCATATAA TTTAACTTGG
      TCCTTCTCCT CCTTCTCCAG TCCGTGATGT TTATGACACC GTCGTATATT AAATTGAACC
2281 AAATCAACTA ATTTCAAGAC AATTTTGGPG TGGGAACCCA AACCCGTCAA TCAAGTCTAC
      TTTAGTTGAT TAAAGTTCTG TTAAAACCTC ACCCTTGGGT TTGGGCAGTT AGTTCAGATG
2341 ACTGTTCAAA TAAGCACTAA GTCAGGAGAT TGGAAAAGCA AATGCTTTTA CACAACAGAC
      TGACAAGTTT ATTCGTGATT CAGTCCTCTA ACCTTTTCGT TTACGAAAAT GTGTTGTCTG
2401 ACAGAGTGTG ACCTCACCGA CGAGATTGTG AAGGATGTGA AGCAGACGTA CTTGGCACGG
      TGTCTCACAC TGGAGTGGCT GCTCTAACAC TTCCTACACT TCGTCTGCAT GAACCGTGCC
2461 GTCTTCTCCT ACCCGGCAGG GAATGTGGAG AGCACCGGTT CTGCTGGGGA GCCTCTGTAT
      CAGAAGAGGA TGGGCCGTCC CTTACACCTC TCGTGGCCAA GACGACCCCT CGGAGACATA
2521 GAGAACTCCC CAGAGTTCAC ACCTTACCTG GAGACAAACC TCGGACAGCC AACAATTCAG
      CTCTTGAGGG GTCTCAAGTG TGGAATGGAC CTCGTTTGG AGCCTGTCGG TTGTTAAGTC
2581 AGTTTTGAAC AGGTGGGAAC AAAAGTGAAT GTGACCGTAG AAGATGAACG GACTTTAGTC
      TCAAAACTTG TCCACCCTTG TTTTCACTTA CACTGGCATC TTCTACTTGC CTGAAATCAG
2641 AGAAGGAACA ACACTTTCCT AAGCCTCCGG GATGTTTTTG GCAAGGACTT AATTTATACA
      TCTTCCTTGT TGTGAAAGGA TTCGGAGGCC CTACAAAAAC CGTTCCTGAA TTAAATATGT
2701 CTTTATTATT GGAAATCTTC AAGTTCAGGA AAGAAAACAG CCAAAACAAA CACTAATGAG
      GAAATAATAA CCTTTAGAAG TTCAAGTCCT TTCTTTTGTC GGTTTTGTTT GTGATTACTC
2761 TTTTTGATTG ATGTGGATAA AGGAGAAAAC TACTGTTTCA GTGTTCAAGC AGTGATTCCC
      AAAAACTAAC TACACCTATT TCCTCTTTTG ATGACAAAGT CACAAGTTCG TCACTAAGGG
2821 TCCCGAACAG TTAACCGGAA GAGTACAGAC AGCCCGGTAG AGTGTATGGG CCAGGAGAAA
      AGGGCTTGTC AATTGGCCTT CTCATGTCTG TCGGGCCATC TCACATACCC GGTCCTCTTT
2881 GGGGAATTCA GAGAAGGTGG CGGCGGATCA GGTGGGGGTG GATCAGGCGG TGGAGGTTCC
      CCCCTTAAGT CTCTTCCACC GCCGCCTAGT CCACCCCCAC CTAGTCCGCC ACCTCCAAGG
2941 GGTGGCGGCG GATCAGGTGG CGGCGGATCA GGTGGGGGTG GATCAGGTGG CGGCGGATCA
      CCACCGCCGC CTAGTCCACC GCCGCCTAGT CCACCCCCAC CTAGTCCACC GCCGCCTAGT
3001 GGTGGCGGGG GATCAGACAA AACTCACACA TGCCCACCGT GCCCAGCACC GGAACTCCTG
      CCACCGCCCC CTAGTCTGTT TTGAGTGTGT ACGGGTGGCA CGGGTCGTGG CCTTGAGGAC
3061 GGCGGACCGT CAGTCTTCCT CTTCCCCCCA AAACCCAAGG ACACCCTCAT GATCTCCCGG
      CCGCCTGGCA GTCAGAAGGA GAAGGGGGGT TTTGGGTTCC TGTGGGAGTA CTAGAGGGCC
3121 ACCCCTGAGG TCACATGCGT GGTGGTGGAC GTGAGCCACG AAGACCCTGA GGTCAAGTTC
      TGGGGACTCC AGTGTACGCA CCACCACCTG CACTCGGTGC TTCTGGGACT CCAGTTCAAG |

```
3181 AACTGGTACG TGGACGGCGT GGAGGTGCAT AATGCCAAGA CAAAGCCGCG GGAGGAGCAG
     TTGACCATGC ACCTGCCGCA CCTCCACGTA TTACGGTTCT GTTTCGGCGC CCTCCTCGTC
3241 TACAACAGCA CGTACCGTGT GGTCAGCGTC CTCACCGTCC TGCACCAGGA CTGGCTGAAT
     ATGTTGTCGT GCATGGCACA CCAGTCGCAG GAGTGGCAGG ACGTGGTCCT GACCGACTTA
3301 GGCAAGGAGT ACAAGTGCAA GGTCTCCAAC AAAGCCCTCC CAGCCCCCAT CGAGAAAACC
     CCGTTCCTCA TGTTCACGTT CCAGAGGTTG TTTCGGGAGG GTCGGGGGTA GCTCTTTTGG
3361 ATCTCCAAAG CCAAAGGGCA GCCCCGAGAA CCACAGGTGT ACACCCTGCC CCCATCCCGG
     TAGAGGTTTC GGTTTCCCGT CGGGGCTCTT GGTGTCCACA TGTGGGACGG GGGTAGGGCC
3421 GATGAGCTGA CCAAGAACCA GGTCAGCCTG ACCTGCCTGG TCAAAGGCTT CTATCCCAGC
     CTACTCGACT GGTTCTTGGT CCAGTCGGAC TGGACGGACC AGTTTCCGAA GATAGGGTCG
3481 GACATCGCCG TGGAGTGGGA GAGCAATGGG CAGCCGGAGA ACAACTACAA GACCACGCCT
     CTGTAGCGGC ACCTCACCCT CTCGTTACCC GTCGGCCTCT TGTTGATGTT CTGGTGCGGA
3541 CCCGTGTTGG ACTCCGACGG CTCCTTCTTC CTCTACAGCA AGCTCACCGT GGACAAGAGC
     GGGCACAACC TGAGGCTGCC GAGGAAGAAG GAGATGTCGT TCGAGTGGCA CCTGTTCTCG
3601 AGGTGGCAGC AGGGGAACGT CTTCTCATGC TCCGTGATGC ATGAGGCTCT GCACAACCAC
     TCCACCGTCG TCCCCTTGCA GAAGAGTACG AGGCACTACG TACTCCGAGA CGTGTTGGTG
3661 TACACGCAGA AGAGCCTCTC CCTGTCTCCG GGTAAATGAG AATTC
     ATGTGCGTCT TCTCGGAGAG GGACAGAGGC CCATTTACTC TTAAG

SEQ ID NO: 45: FVII-133 amino acid sequence. Signal sequence
is shown in dotted underline, propeptide is wave underlined,
thrombin cleavage site inserted between the light and heavy
chains is double underlined, linker region connecting FVII
to Fc region is underlined, linker with proprotein
convertase processing sites connecting the Fc and sTF is
shown in bold, and linker region connecting sTF to Fc is in
dashed underline. The light chain expands from residues
39 to 189, the heavy chain from residues 195 to 448 and sTF
from residues 742 to 960.

1 MVSQALRLLC LLLGLQGCLA AVFVTQEEAH GVLHRRRRAN AFLEELRPGS LERECKEEQC

61 SFEEAREIFK DAERTKLFWI SYSDGDQCAS SPCQNGGSCK DQLQSYICFC LPAFEGRNCE
 121 THKDDQLICV NENGGCEQYC SDHTGTKRSC RCHEGYSLLA DGVSCTPTVE YPCGKIPILE

181 KRNASKPQGA LRPRIVGGKV CPKGECPWQV LLLVNGAQLC GGTLINTIWV VSAAHCFDKI

241 KNWRNLIAVL GEHDLSEHDG DEQSRRVAQV IIPSTYVPGT TNHDIALLRL HQPVVLTDHV
 301 VPLCLPERTF SERTLAFVRF SLVSGWGQLL DRGATALELM VLNVPRLMTQ DCLQQSRKVG
 361 DSPNITEYMF CAGYSDGSKD SCKGDSGGPH ATHYRGTWYL TGIVSWGQGC ATVGHFGVYT
 421 RVSQYIEWLQ KLMRSEPRPG VLLRAPFPGG GGSGGGGSGG GGSGGGGSGG GGSGGGGSDK
 481 THTCPPCPAP ELLGGPSVFL FPPKPKDTEM ISRTPEVTCV VVDVSHi15PE VKFNWYVDGV
 541 EVHNAKTKPR EEQYNSTYRV VSVLTVLHQD WLNGKEYKCK VSNKALPAPI EKTISKAKGQ
 601 PREPQVYTLP PSRDELTKNQ VSLTCLVKGF YPSDIAVEWE SNGQPENNYK TTPPVLDSDG
 661 SFFLYSKLTV DKSRWQQGNV FSCSVMHEAL HNHYTQKSLS LSPGKRRRRS GGGGSGGGGS
 721 GGGGSGGGGS GGGGSRKRRK RSGTTNTVAA YNLTWKSTNF KTILEWEPKP VNQVYTVQIS
 781 TKSGDWKSKC FYTTDTECDL TDEIVKDVKQ TYLARVFSYP AGNVESTGSA GEPLYENSPE
 841 FTPYLETNLG QPTIQSFEQV GTKVNVTVED ERTLVRRNNT FLSRDVPGK DLIYTLYYWK
 901 SSSSGKKTAK TNTNEFLIDV DKGENYCFSV QAVIPSRTVN RKSTDSPVEC MGQEKGEFRE

961 GGGGSGGGGS GGGGSGGGGS GGGGSGGGGS GGGGSGGGGS DKTHTCPPCP APELLGGPSV

1021 FLFPPKPKDT EMTSRTPEVT CVIADVSHED PEVKFNWYVD GVEVHNAKTK PREEQYNSTY
1081 RVVSVLTVLH QDWLNGKEYK CKVSNKALPA PIEKTISKAK GQPREPQVYT LPPSRDELTK
1141 NQVSLTCLVK GFYPSDIAVE WESNGQPENN YKTTPPVLDS DGSFFLYSKL TVDKSRWQQG
1201 NVFSCSVMHE ALHNHYTQKS LSLSPGK*

SEQ ID NO: 46 DNA sequence of FVII-184.
   1 AAGCTTGCCG CCACCATGGT CTCCCAGGCC CTCAGGCTCC TCTGCCTTCT GCTTGGGCTT
     TTCGAACGGC GGTGGTACCA GAGGGTCCGG GAGTCCGAGG AGACGGAAGA CGAACCCGAA
  61 CAGGGCTGCC TGGCTGCAGT CTTCGTAACC CAGGAGGAAG CCCACGGCGT CCTGCACCGG
     GTCCCGACGG ACCGACGTCA GAAGCATTGG GTCCTCCTTC GGGTGCCGCA GGACGTGGCC
 121 CGCCGGCCGC CCAACGCGTT CCTGGAGGAG CTGCGGCCGG GCTCCCTGGA GAGGGAGTGC
     GCGGCCGGCG GGTTGCGCAA GGACCTCCTC GACGCCGGCC CGAGGGACCT CTCCCTCACG
 181 AAGGAGGAGC AGTGCTCCTT CGAGGAGGCC CGGGAGATCT TCAAGGACGC GGAGAGGACG
     TTCCTCCTCG TCACGAGGAA GCTCCTCCGG GCCCTCTAGA AGTTCCTGCG CCTCTCCTGC
 241 AAGCTGTTCT GGATTTCTTA CAGTGATGGG GACCAGTGTG CCTCAAGTCC ATGCCAGAAT
     TTCGACAAGA CCTAAAGAAT GTCACTACCC CTGGTCACAC GGAGTTCAGG TACGGTCTTA
 301 GGGGGCTCCT GCAAGGACCA GCTCCAGTCC TATATCTGCT TCTGCCTCCC TGCCTTCGAG
     CCCCCGAGGA CGTTCCTGGT CGAGGTCAGG ATATAGACGA AGACGGAGGG ACGGAAGCTC
 361 GGCCGGAACT GTGAGACGCA CAAGGATGAC CAGCTGATCT GTGTGAACGA GAACGGCGGC
     CCGGCCTTGA CACTCTGCGT GTTCCTACTG GTCGACTAGA CACACTTGCT CTTGCCGCCG
 421 TGTGAGCAGT ACTGCAGTGA CCACACGGGC ACCAAGCGCT CCTGTCGGTG CCACGAGGGG
     ACACTCGTCA TGACGTCACT GGTGTGCCCG TGGTTCGCGA GGACAGCCAC GGTGCTCCCC
```

-continued

| | SEQUENCES | | | | |
|---|---|---|---|---|---|
| 481 | TACTCTCTGC | TGGCAGACGG | GGTGTCCTGC | ACACCCACAG | TTGAATATCC ATGTGGAAAA |
| | ATGAGAGACG | ACCGTCTGCC | CCACAGGACG | TGTGGGTGTC | AACTTATAGG TACACCTTTT |
| 541 | ATACCTATTC | TAGAAAAAAG | AAATGCCAGC | AAACCCCAAG | GCGCCCTGCG GCCCGCCATT |
| | TATGGATAAG | ATCTTTTTTC | TTTACGGTCG | TTTGGGGTTC | CGCGGGACGC CGGGCGGTAA |
| 601 | GTGGGGGGCA | AGGTGTGCCC | CAAAGGGGAG | TGTCCATGGC | AGGTCCTGTT GTTGGTGAAT |
| | CACCCCCCGT | TCCACACGGG | GTTTCCCCTC | ACAGGTACCG | TCCAGGACAA CAACCACTTA |
| 661 | GGAGCTCAGT | TGTGTGGGGG | GACCCTGATC | AACACCATCT | GGGTGGTCTC CGCGGCCCAC |
| | CCTCGAGTCA | ACACACCCCC | CTGGGACTAG | TTGTGGTAGA | CCCACCGAG GCGCCGGGTG |
| 721 | TGTTTCGACA | AAATCAAGAA | CTGGAGGAAC | CTGATCGCGG | TGCTGGGCGA GCACGACCTC |
| | ACAAAGCTGT | TTTAGTTCTT | GACCTCCTTG | GACTAGCGCC | ACGACCCGCT CGTGCTGGAG |
| 781 | AGCGAGCACG | ACGGGGATGA | GCAGAGCCGG | CGGGTGGCGC | AGGTCATCAT CCCCAGCACG |
| | TCGCTCGTGC | TGCCCCTACT | CGTCTCGGCC | GCCCACCGCG | TCCAGTAGTA GGGGTCGTGC |
| 841 | TACGTCCCGG | GCACCACCAA | CCACGACATC | GCGCTGCTCC | GCCTGCACCA GCCCGTGGTC |
| | ATGCAGGGCC | CGTGGTGGTT | GGTGCTGTAG | CGCGACGAGG | CGGACGTGGT CGGGCACCAG |
| 901 | CTCACTGACC | ATGTGGTGCC | CCTCTGCCTG | CCCGAACGGA | CGTTCTCTGA GAGGACGCTG |
| | GAGTGACTGG | TACACCACGG | GGAGACGGAC | GGGCTTGCCT | GCAAGAGACT CTCCTGCGAC |
| 961 | GCCTTCGTGC | GCTTCTCATT | GGTCAGCGGC | TGGGGCCAGC | TGCTGGACCG TGGCGCCACG |
| | CGGAAGCACG | CGAAGAGTAA | CCAGTCGCCG | ACCCCGGTCG | ACGACCTGGC ACCGCGGTGC |
| 1021 | GCCCTGGAGC | TCATGGTCCT | CAACGTGCCC | CGGCTGATGA | CCCAGGACTG CCTGCAGCAG |
| | CGGGACCTCG | AGTACCAGGA | GTTGCACGGG | GCCGACTACT | GGGTCCTGAC GGACGTCGTC |
| 1081 | TCACGGAAGG | TGGGAGACTC | CCCAAATATC | ACGGAGTACA | TGTTCTGTGC CGGCTACTCG |
| | AGTGCCTTCC | ACCCTCTGAG | GGGTTTATAG | TGCCTCATGT | ACAAGACACG GCCGATGAGC |
| 1141 | GATGGCAGCA | AGGACTCCTG | CAAGGGGGAC | AGTGGAGGCC | CACATGCCAC CCACTACCGG |
| | CTACCGTCGT | TCCTGAGGAC | GTTCCCCCTG | TCACCTCCGG | GTGTACGGTG GGTGATGGCC |
| 1201 | GGCACGTGGT | ACCTGACGGG | CATCGTCAGC | TGGGGCCAGG | GCTGCGCAAC CGTGGGCCAC |
| | CCGTGCACCA | TGGACTGCCC | GTAGCAGTCG | ACCCCGGTCC | CGACGCGTTG GCACCCGGTG |
| 1261 | TTTGGGGTGT | ACACCAGGGT | CTCCCAGTAC | ATCGAGTGGC | TGCAAAAGCT CATGCGCTCA |
| | AAACCCCACA | TGTGGTCCCA | GAGGGTCATG | TAGCTCACCG | ACGTTTTCGA GTACGCGAGT |
| 1321 | GAGCCACGCC | CAGGAGTCCT | CCTGCGAGCC | CCATTTCCCG | GTGGCGGTGG CTCCGGCGGA |
| | CTCGGTGCGG | GTCCTCAGGA | GGACGCTCGG | GGTAAAGGGC | CACCGCCACC GAGGCCGCCT |
| 1381 | GGTGGGTCCG | GTGGCGGCGG | ATCAGGTGGG | GGTGGATCAG | GCGGTGGAGG TTCCGGTGGC |
| | CCACCCAGGC | CACCGCCGCC | TAGTCCACCC | CCACCTAGTC | CGCCACCTCC AAGGCCACCG |
| 1441 | GGGGGATCCG | ACAAAACTCA | CACATGCCCA | CCGTGCCCAG | CTCCGGAACT CCTGGGAGGA |
| | CCCCCTAGGC | TGTTTTGAGT | GTGTACGGGT | GGCACGGGTC | GAGGCCTTGA GGACCCTCCT |
| 1501 | CCGTCAGTCT | TCCTCTTCCC | CCCAAAACCC | AAGGACACCC | TCATGATCTC CCGGACCCCT |
| | GGCAGTCAGA | AGGAGAAGGG | GGGTTTTGGG | TTCCTGTGGG | AGTACTAGAG GGCCTGGGGA |
| 1561 | GAGGTCACAT | GCGTGGTGGT | GGACGTGAGC | CACGAAGACC | CTGAGGTCAA GTTCAACTGG |
| | CTCCAGTGTA | CGCACCACCA | CCTGCACTCG | GTGCTTCTGG | GACTCCAGTT CAAGTTGACC |
| 1621 | TACGTGGACG | GCGTGGAGGT | GCATAATGCC | AAGACAAAGC | CGCGGGAGGA GCAGTACAAC |
| | ATGCACCTGC | CGCACCTCCA | CGTATTACGG | TTCTGTTTCG | GCGCCCTCCT CGTCATGTTG |
| 1681 | AGCACGTACC | GTGTGGTCAG | CGTCCTCACC | GTCCTGCACC | AGGACTGGCT GAATGGCAAG |
| | TCGTGCATGG | CACACCAGTC | GCAGGAGTGG | CAGGACGTGG | TCCTGACCGA CTTACCGTTC |
| 1741 | GAGTACAAGT | GCAAGGTCTC | CAACAAAGCC | CTCCCAGCCC | CCATCGAGAA AACCATCTCC |
| | CTCATGTTCA | CGTTCCAGAG | GTTGTTTCGG | GAGGGTCGGG | GGTAGCTCTT TTGGTAGAGG |
| 1801 | AAAGCCAAAG | GGCAGCCCCG | AGAACCACAG | GTGTACACCC | TGCCCCCATC CCGGGATGAG |
| | TTTCGGTTTC | CCGTCGGGGC | TCTTGGTGTC | CACATGTGGG | ACGGGGGTAG GGCCCTACTC |
| 1861 | CTGACCAAGA | ACCAGGTCAG | CCTGACCTGC | CTGGTCAAAG | GCTTCTATCC CAGCGACATC |
| | GACTGGTTCT | TGGTCCAGTC | GGACTGGACG | GACCAGTTTC | CGAAGATAGG GTCGCTGTAG |
| 1921 | GCCGTGGAGT | GGGAGAGCAA | TGGGCAGCCG | GAGAACAACT | ACAAGACCAC GCCTCCCGTG |
| | CGGCACCTCA | CCCTCTCGTT | ACCCGTCGGC | CTCTTGTTGA | TGTTCTGGTG CGGAGGGCAC |
| 1981 | TTGGACTCCG | ACGGCTCCTT | CTTCCTCTAC | AGCAAGCTCA | CCGTCGACAA GAGCAGGTGG |
| | AACCTGAGGC | TGCCGAGGAA | GAAGGAGATG | TCGTTCGAGT | GGCAGCTGTT CTCGTCCACC |
| 2041 | CAGCAGGGGA | ACGTCTTCTC | ATGCTCCGTG | ATGCATGAGG | CTCTGCACAA CCACTACACG |
| | GTCGTCCCCT | TGCAGAAGAG | TACGAGGCAC | TACGTACTCC | GAGACGTGTT GGTGATGTGC |
| 2101 | CAGAAGAGCC | TCTCCCTGTC | TCCGGGTAAA | CGGCGCCGCC | GGAGCGGCGG TGGAGGTTCC |
| | GTCTTCTCGG | AGAGGGACAG | AGGCCCATTT | GCCGCGGCGG | CCTCGCCGCC ACCTCCAAGG |
| 2161 | GGTGGCGGCG | GATCAGGTGG | CGGCGGATCA | GGTGGGGGTG | GATCAGGTGG CGGGGGATCC |
| | CCACCGCCGC | CTAGTCCACC | GCCGCCTAGT | CCACCCCCAC | CTAGTCCACC GCCCCCTAGG |
| 2221 | AGGAAGAGGA | GGAAGAGGTC | AGGCACTACA | AATACTGTGG | CAGCATATAA TTTAACTTGG |
| | TCCTTCTCCT | CCTTCTCCAG | TCCGTGATGT | TTATGACACC | GTCGTATATT AAATTGAACC |
| 2281 | AAATCAACTA | ATTTCAAGAC | AATTTTGGAG | TGGGAACCCA | AACCCGTCAA TCAAGTCTAC |
| | TTTAGTTGAT | TAAAGTTCTG | TTAAAACCTC | ACCCTTGGGT | TTGGGCAGTT AGTTCAGATG |
| 2341 | ACTGTTCAAA | TAAGCACTAA | GTCAGGAGAT | TGGAAAAGCA | AATGCTTTTA CACAACAGAC |
| | TGACAAGTTT | ATTCGTGATT | CAGTCCTCTA | ACCTTTTCGT | TTACGAAAAT GTGTTGTCTG |
| 2401 | ACAGAGTGTG | ACCTCACCGA | CGAGATTGTG | AAGGATGTGA | AGCAGACGTA CTTGGCAGGG |
| | TGTCTCACAC | TGGAGTGGCT | GCTCTAACAC | TTCCTACACT | TCGTCTGCAT GAACCGTGCC |
| 2461 | GTCTTCTCCT | ACCCGGCAGG | GAATGTGGAG | AGCACCGGTT | CTGCTGGGGA GCCTCTGTAT |
| | CAGAAGAGGA | TGGGCCGTCC | CTTACACCTC | TCGTGGCCAA | GACGACCCCT CGGAGACATA |
| 2521 | GAGAACTCCC | CAGAGTTCAC | ACCTTACCTG | GAGACAAACC | TCGACAGCC AACAATTCAG |
| | CTCTTGAGGG | GTCTCAAGTG | TGGAATGGAC | CTCTGTTTGG | AGCCTGTCGG TTGTTAAGTC |
| 2581 | AGTTTTGAAC | AGGTGGGAAC | AAAAGTGAAT | GTGACCGTAG | AAGATGAACG GACTTTAGTC |
| | TCAAAACTTG | TCCACCCTTG | TTTTCACTTA | CACTGGCATC | TTCTACTTGC CTGAAATCAG |
| 2641 | AGAAGGAACA | ACACTTTCCT | AAGCCTCCGG | GATGTTTTTG | GCAAGGACTT AATTTATACA |
| | TCTTCCTTGT | TGTGAAAGGA | TTCGGAGGCC | CTACAAAAAC | CGTTCCTGAA TTAAATATGT |
| 2701 | CTTTATTATT | GGAAATCTTC | AAGTTCAGGA | AAGAAAACAG | CCAAAACAAA CACTAATGAG |
| | GAAATAATAA | CCTTTAGAAG | TTCAAGTCCT | TTCTTTTGTC | GGTTTTGTTT GTGATTACTC |

```
                              SEQUENCES
2761 TTTTTGATTG ATGTGGATAA AGGAGAAAAC TACTGTTTCA GTGTTCAAGC AGTGATTCCC
     AAAAACTAAC TACACCTATT TCCTCTTTTG ATGACAAAGT CACAAGTTCG TCACTAAGGG
2821 TCCCGAACAG TTAACCGGAA GAGTACAGAC AGCCCGGTAG AGTGTATGGG CCAGGAGAAA
     AGGGCTTGTC AATTGGCCTT CTCATGTCTG TCGGGCCATC TCACATACCC GGTCCTCTTT
2881 GGGGAATTCA GAGAAGGTGG CGGCGGATCA GGTGGGGGTG GATCAGGCGG TGGAGGTTCC
     CCCCTTAAGT CTCTTCCACC GCCGCCTAGT CCACCCCCAC CTAGTCCGCC AAACCCAAGG
2941 GGTGGCGGCG GATCAGGTGG CGGCGGATCA GGTGGGGGTG GATCAGGTGG CGGCGGATCA
     CCACCGCCGC CTAGTCCACC GCCGCCTAGT CCACCCCCAC CTAGTCCACC GCCGCCTAGT
3001 GGTGGCGGGG GATCAGACAA AACTCACACA TGCCCACCGT GCCCAGCACC GGAACTCCTG
     CCACCGCCCC CTAGTCTGTT TTGAGTGTGT ACGGGTGGCA CGGGTCGTGG CCTTGAGGAC
3061 GGCGGACCGT CAGTCTTCCT CTTCCCCCCA AAACCCAAGG ACACCCTCAT GATCTCCCGG
     CCGCCTGGCA GTCAGAAGGA GAAGGGGGGT TTTGGGTTCC TGTGGGAGTA CTAGAGGGCC
3121 ACCCCTGAGG TCACATGCGT GGTGGTGGAC GTGAGCCACG AAGACCCTGA GGTCAAGTTC
     TGGGGACTCC AGTGTACGCA CCACCACCTG CACTCGGTGC TTCTGGGACT CCAGTTCAAG
3181 AACTGGTACG TGGACGGCGT GGAGGTGCAT AATGCCAAGA CAAAGCCGCG GGAGGAGCGA
     TTGACCATGC ACCTGCCGCA CCTCCACGTA TTACGGTTCT GTTTCGGCGC CCTCCTCGTC
3241 TACAACAGCA CGTACCGTGT GGTCAGCGTC CTCACCGTCC TGCACCAGGA CTGGCTGAAT
     ATGTTGTCGT GCATGGCACA CCAGTCGCAG GAGTGGCAGG ACGTGGTCCT GACCGACTTA
3301 GGCAAGGAGT ACAAGTGCAA GGTCTCCAAC AAAGCCCTCC CAGCCCCCAT CGAGAAAACC
     CCGTTCCTCA TGTTCACGTT CCAGAGGTTG TTTCGGGAGG GTCGGGGGTA GCTCTTTTGG
3361 ATCTCCAAAG CCAAAGGGCA GCCCCGAGAA CCACAGGTGT ACACCCTGCC CCCATCCCGG
     TAGAGGTTTC GGTTTCCCGT CGGGGCTCTT GGTGTCCACA TGTGGGACGG GGGTAGGGCC
3421 GATGAGCTGA CCAAGAACCA GGTCAGCCTG ACCTGCCTGG TCAAAGGCTT CTATCCCAGC
     CTACTCGACT GGTTCTTGGT CCAGTCGGAC TGGACGGACC AGTTTCCGAA GATAGGGTCG
3481 GACATCGCCG TGGAGTGGGA GAGCAATGGG CAGCCGGAGA ACAACTACAA GACCACGCCT
     CTGTAGCGGC ACCTCACCCT CTCGTTACCC GTCGGCCTCT TGTTGATGTT CTGGTGCGGA
3541 CCCGTGTTGG ACTCCGACGG CTCCTTCTTC CTCTACAGCA AGCTCACCGT GGACAAGAGC
     GGGCACAACC TGAGGCTGCC GAGGAAGAAG GAGATGTCGT TCGAGTGGCA CCTGTTCTCG
3601 AGGTGGCAGC AGGGGAACGT CTTCTCATGC TCCGTGATGC ATGAGGCTCT GCACAACCAC
     TCCACCGTCG TCCCCTTGCA GAAGAGTACG AGGCACTACG TACTCCGAGA CGTGTTGGTG
3661 TACACGCAGA AGAGCCTCTC CCTGTCTCCG GGTAAATGA
     ATGTGCGTCT TCTCGGAGAG GGACAGAGGC CCATTTACT
```

SEQ ID NO 47 FVII-184 amino acid sequence. Signal sequence is shown in dotted underline, propeptide is wave underlined, the mutated thrombin cleavage site inserted between the light and heavy chains is double underlined with the Arg to Ala mutation (residue 194) in bold, linker region connecting FVII to Fc region is underlined, linker with proprotein convertase processing sites connecting, the Fc and sTF is shown in bold, and linker region connecting sTF to Fc is in dashed underline. The light chain expands from residues 39 to 189, the heavy chain from residues 195 to 448 and sTF from residues 742 to 960.

```
   1 MVSQALRLLC LLLGLQGCLA AVFVTQEEAH GVLHRRRRAN AFLEELRPGS LERECKEEQC
  61 SFEEAREIFK DAERTKLFWI SYSDGDQCAS SPCQNGGSCK DQLQSYICFC LPAFEGRNCE
 121 THKDDQLICV NENGGCEQYC SDHTGTKRSC RCHEGYSLLA DGVSCTPTVE YPCGKIPILE
 181 KRNASKPQGA LRPAIVGGKV CPKGECPWQV LLLVNGAQLC GGTLINTIWV VSAAHCFDKI
 241 KNWRNLIAVL GEHDLSEHDG DEQSRRVAQV IIPSTYVPGT TNHDIALLRL HQPVVLTDHV
 301 VPLCLPERTF SERTLAFVRF SLVSGWGQLL DRGATALELM VLNVPRLMTQ DCLQQSRKVG
 361 DSPNITEYMF CAGYSDGSKD SCKGDSGGPH ATHYRGTWYL TGIVSWGQGC ATVGHFGVYT
 421 RVSQYIEWLQ KLMRSEPRPG VLLRAPFPGG GGSGGGGSGG GGSGGGGSGG GGSGGGGSDK
 481 THTCPPCPAP ELLGGPSVFL FPPKPKDTLM ISRTPEVTCV VVDVSHEDPE VKFNWYVDGV
 541 EVHNAKTKPR EEQYNSTYRV VSVLTVLHQD WLNGKEYKCK VSNKALPAPI EKTISKAKGQ
 601 PREPQVYTLP PSRDELTKNQ VSLTCLVKGF YPSDIAVEWE SNGQPENNYK TTPPVLDSDG
 661 SFFLYSKLTV DKSRWQQGNV FSCSVMHEAL HNHYTQKSLS LSPGKRRRRS GGGGSGGGGS
 721 GGGGSGGGGS GGGGSRKRRK RSGTTNTVAA YNLTWKSTNF KTILEWEPKP VNQVYTVQIS
 781 TKSGDWKSKC FYTTDTECDL TDEIVKDVKQ TYLARVFSYP AGNVESTGSA GEPLYENSPE
 841 FTPYLETNLG QPTIQSFEQV GTKVNVTVED ERTLVRRNNT FLSRDVFGK DLIYTLYYWK
 901 SSSSGKKTAK TNTNEFLIDV DKGENYCFSV QAVIPSRTVN RKSTDSPVEC MGQEKGEFRE
 961 -GGGGSGGGGS GGGGSGGGGS GGGGSGGGGS GGGGSGGGGS DKTHTCPPCP APELLGGPSV
1021 FLFPPKPKDT LMISRTPEVT CVVVDVSHED PEVKFNWYVD GVEVHNAKTK PREEQYNSTY
1081 RVVSVLTVLH QDWLNGKEYK CKVSNKALPA PIEKTISKAK GQPREPQVYT LPPSRDELTK
1141 NQVSLTCLVK GFYPSDIAVE WESNGQPENN YKTTPPVLDS DGSFFLYSKL TVDKSRWQQG
1201 NVFSCSVMHE ALHNHYTQKS LSLSPGK*
```

SEQ ID NO: 32
>CTP peptide 1
DPRFQDSSSSKAPPPSLPSPSRLPGPSDTPIL

SEQUENCES

SEQ ID NO: 33
>CTP peptide 2
SSSSKAPPPSLPSPSRLPGPSDTPILPQ

SEQ ID NO: 36
>PAS peptide 1
ASPAAPAPASPAAPAPSAPA

SEQ ID NO: 37
>PAS peptide 2
AAPASPAPAAPSAPAPAAPS

SEQ ID NO: 38
>PAS PePtide 3
APSSPSPSAPPSPASPSS

SEQ ID NO: 39
>PAS Peptide 4
APSSPSPSAPSSPSPASPS

SEQ ID NO: 40
>PAS peptide 5
SSPSAPSPSSPASPSPSSPA

SEQ ID NO: 41
>PAS peptide 6
AASPAAPSAPPAAASPAAPSAPPA

SEQ ID NO: 42
>PAS peptide 7
ASAAAPAAASAAASAPSAAA

SEQ ID NO: 35
>Albumin Binding Peptide Core Sequence
DICLPRWGCLW

SEQ ID NO: 48
>GFP protein sequence (Genbank ID AAG34521.1)
MSKGEELFTGVVPILVELDGDVNGHKFSVSGEGEGDATYGKLTLKFICTTGKLPVPWPTL
VTTFGYGVQCFARYPDHMKQHDFFKSAMPEGYVQERTIFFKDDGNYKTRAEVKFEGDTLV
NRIELKGIDFKEDGNILGHKLEYNYNSHNVYIMADKQKNGIKVNFKIRHNIEDGSVQLAD
HYQQNTPIGDGPVLLPDNHYLSTQSALSKDPNEKRDHMVLLFFVTAAGITHGMDELYKSR
TSGSPGLQEFDIKLIDTVDLESCN SEQ ID NO: 49
>Example: Single-chain Human IgG1 Fc. (Fc sequences with Gly/Ser
linker underlined.)
DKTHTCPPCPAPELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTISKAK
GQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK<u>GGGGSGGGGSGGG
GSGGGGS</u>DKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGK SEQ ID NO: 50
>Mature human albumin protein sequence (derived from NCBI Ref.
Sequence NP_000468):
RGVFRRDAHKSEVAHRFKDLGEENFKALVLIAFAQYLQQCPFEDHVKLVNEVTEFAKTCV
ADESAENCDKSLHTLFGDKLCTVATLRETYGEMADCCAKQEPERNECFLQHKDDNPNLPR
LVRPEVDVMCTAFHDNEETFLKKYLYEIAKRHPYFYAPELLFFAKRYKAAFTECCQAADK
AACLLPKLDELRDEGKASSAKQRLKCASLQKFGERAFKAWAVARLSQRFPKAEFAEVSKL
VTDLTKVHTECCHGDLLECADDRADLAKYICENQDSISSKLKECCEKPLLEKSHCIAEVE
NDEMPADLPSLAADFVESKDVCKNYAEAKDVFLGMFLYEYARRHPDYSVVLLLRLAKTYE
TTLEKCCAAADPHECYAKVFDEFKPLVEEPQNLIKQNCELFEQLGEYKFQNALLVRYTKK
VPQVSTPTLVEVSRNLGKVGSKCCKHPEAKRMPCAEDYLSVVLNQLCVLHEKTPVSDRVT
KCCTESLVNRRPCFSALEVDETYVPKEFNAETFTFHADICTLSEKERQIKKQTALVELVK
HPKATKEQLKAVMDDFAAFVEKCCKADDKETCFAEEGKKLVAASQAALGL SEQ ID NO: 51
>Albumin binding peptide 1
RLIEDICLPRWGCLWEDD SEQ ID NO: 52
Albumin binding peptide 2
QRLMEDICLPRWGCLWEDDF -continued

| SEQUENCES |
|---|

SEQ ID NO: 53
>Albumin binding peptide 3
QGLIGDICLPRWGCLWGDSVK

SEQ ID NO: 54
>Albumin binding pe3Dtit.ie 4
GEWWEDICLPRWGCLWEEED

SEQ ID NO: 55
>Cysteine-containing )e3:)tide
GGGSGCGGGS

SEQ ID NO: 56
>Human LRP1 sequence (signal peptide and transmembrane
segment underlined; NCBI Reference Sequence: CAA32112)
MLTPPLLLLLPLLSALVAAAIDAPKTCSPKWACRDQITCTSYGWRCDGERDQPDGSDEA
PEICPQSKAQRCQPNEHNCLGTELCVPMSRLCNGVQDCMDGSDEGPHCRELQGNCSHLGC
QHHCVPTLDGPTCYCNSSFQLQADGKTCKDFDECSVYGTCSQLCTNTDGSFICGCVEGYL
LQPDNRSCKAKNEPVDRPPVLLIANSQNILATYLSGAQVSTITPTSTRQTTAMDFSYANE
TVCWVHVGDSAAQTQLKCARMPGLKGFVDEHTINISLSLHHVEQMAIDWLTGNFYFVDDI
DDRIFVCNRNGDTCVTLLDLELYNPKGIALDPAMGKVFFTDYGQIPKVERCDMDGQNRTK
LVDSKIVFPHGITLDLVSRLVYWADAYLDYIEVVDYEGKGRQTIIQGILIEHLYGLTVFE
NYLYATNSDNANAQQKTSVIRVNRFNSTEYQVVTRVDKGGALHIYHQRRQPRVRSHACEN
DQYGKPGGCSDICLLANSHKARTCRCRSGFSLGSDGKSCKKPEHELFLVYGKGRPGIIRG
MDMGAKVPDEHMIPIENLMNPRALDFHAETGFIYFADTTSYLIGRQKIDGTERETILKDG
IHNVEGVAVDWMGDNLYWTDDGPKKTISVARLEKAAQTRKTLIEGKMTHPRAIVVDPLNG
WMYWTDWEEDPKDSRRGRLERAWMDGSHRDIFVTSKTVLWPNGLSLDIPAGRLYWVDAFY
DRIETILLNGTDRKIVYEGPELNHAFGLCHHGNYLFWTEYRSGSVYRLERGVGGAPPTVT
LLRSERPPIFEIRMYDAQQQQVGTNKCRVNNGGCSSLCLATPGSRQCACAEDQVLDADGV
TCLANPSYVPPPQCQPGEFACANSRCIQERWKCDGDNDCLDNSDEAPALCHQHTCPSDRF
KCENNRCIPNRWLCDGDNDCGNSEDESNATCSARTCPPNQFSCASGRCIPISWTODLDDD
CGDRSDESASCAYPTCFPLTQFTCNNGRCININWRCDNDNDCGDNSDEAGCSHSCSSTQF
KCNSGRCIPEHWTCDGDNDCGDYSDETHANCTNQATRPPGGCHTDEFQCRLDGLCIPLRW
RCDGDTDCMDSSDEKSCEGVTHVCDPSVKFGCKDSARCISKAWVCDGDNDCEDNSDEENC
ESLACRPPSHPCANNTSVCLPPDKLCDGNDDCGDGSDEGELCDQCSLNNGGCSHNCSVAP
GEGIVCSCPLGMELGPDNHTCQIQSYCAKHLKCSQKCDQNKFSVKCSCYEGWVLEPDGES
CRSLDPFKPFIIFSNRHEIRRIDLHKGDYSVLVPGLRNTIALDFHLSQSALYWTDVVEDK
IYRGKLLDNGALTSFEVVIQYGLATPEGLAVDWIAGNIYWVESNLDQIEVAKLDGTLRTT
LLAGDIEHPRAIALDPRDGILFWTDWDASLPRIEAASMSGAGRRTVHRETGSGGWPNGLT
DVTLEKRILWIDARSDAIYSARYDGSGHMEVLRGHEFLSHPFAVTLYGGEVYWTDWRTNT
LAKANKWTGHNVTVVQRTNTQPFDLQVYHPSRQPMAPNPCEANGGQGPCSHLCLINYNRT
VSCACPHLMKLHKDNTTCYEFKKFLLYARQMEIRGVDLDAPYYNYIISFTVPDIDNVTVL
DYDAREQRVYWSDVRTQAIKRAFINGTGVETVVSADLPNAHGLAVDWVSRNLFWTSYDTN
KKQINVARLDGSFKNAVVQGLEQPHGLVVHPLRGKLYWTDGDNISMANMDGSNRTLLFSG
QKGPVGLAIDFPESKLYWISSGNHTINRCNLDGSGLEVIDAMRSQLGKATALAIMGDKLW
WADQVSEKMGTCSKADGSGSVVLRNSTTLVMHMKVYDESIQLDHKGTNPCSVNNGDCSQL
CLPTSETTRSCMCTAGYSLRSGQQACEGVGSFLLYSVHEGIRGIPLDPNDKSDALVPVSG
TSLAVGIDFHAENDTIYWVDMGLSTISRAKRDQTWREDVVTNGIGRVEGIAVDWIAGNIY
WTDQGFDVIEVARLNGSFRYVVISQGLDKPRAITVHPEKGYLFWTEWGQYPRIERSRLDG
TERVVLVNVSISWPNGISVDYQDGKLYWCDARTDKIEPIDLETGENREVVLSSNNMDMFS
VSVFEDPIYWSDRTHANGSIKRGSKDNATDSVPLRTGIGVQLKDIKVFNRDRQKGTNVCA
VANGGCQQLCLYRGRGQRACACAHGMLAEDGASCREYAGYLLYSERTILKSIHLSDERNL
NAPVQPFEDPEHMKNVIALAFDYRAGTSPGTPNRIFFSDIHFGNIQQINDDGSRRITIVE
NVGSVEGLAYHRGWDTLYWTSYTTSTITRHTVDQTRPGAFERETVITMSGDDHPRAFVLD
ECQNLMFWTNWNEQHPSIMRAALSGANVLTLIEKDIRTPNGLAIDHRAEKLYFSDATLDK
IERCEYDGSHRYVILKSEPVHPFGLAVYGEHIFWTDWVRRAVQRANKHVGSNMKLLRVDI
PQQPMGIIAVANDTNSCELSPCRINNGGCQDLCLLTHQGHVNCSCRGGRILQDDLTCRAV
NSSCRAQDEFECANGECINFSLTCDGVPHCKDKSDEKPSYCNSRRCKKTFRQCSNGRCVS
NMLWCNGADDCGDGSDEIPCNKTACGVGEFRCRDGTCIGNSSRCNQFVDCEDASDEMNCS
ATDCSSYFRLGVKGVLFQPCERTSLCYAPSWVCDGANDCGDYSDERDCPGVKRPRCPLNY
FACPSGRCIPMSWTCDKEDDCEHGEDETHCNKFCSEAQFECQNHRCISKQWLCDGSDDCG
DGSDEAAHCEGKTCGPSSFSCPGTHVCVPERWLCDGDKDCADGADESIAAGCLYNSTCDD
REFMCQNRQCIPKHFVCDHDRDCADGSDESPECEYPTCGPSEFRCANGRCLSSRQWECDG
ENDCHDQSDEAPKNPHCTSPEHKCNASSQFLCSSGRCVAEALLCNGQDDCGDSSDERGCH
INECLSRKLSGCSQDCEDLKIGFKCRCRPGFRLKDDGRTCADVDECSTTFPCSQRCINTH
GSYKCLCVEGYAPRGGDPHSCKAVTDEEPFLIFANRYYLRKLNLDGSNYTLLKQGLNNAV
ALDFDYREQMIYWTDVTTQGSMIRRMHLNGSNVQVLHRTGLSNPDGLAVDWVGGNLYWCD
KGRDTIEVSKLNGAYRTVLVSSGLREPRALVVDVQNGYLYWTDWGDHSLIGRIGMDGSSR
SVIVDTKITWPNGLTLDYVTERIYWADAREDYIEFASLDGSNRhVVLSQDIPHIFALTLF
EDYVYWTDWETKSINRAHKTTGTNKTLLISTLHRPMDLHVFHALRQPDVPNHPCKVNNGG
CSNLCLLSPGGGHKCACPTNFYLGSDGRTCVSNCTASQFVCKNDKCIPFWWKCDTEDDCG
DHSDEPPDCPEFKCRPGQFQCSTGICTNPAFICDGDNDCQDNSDEANCDIHVCLPSQFKC
TNTNRCIPGIFRCNGQDNCGDEDERDCPEVTCAPNQFQCSITKRCIPRVVWCDRDNDCV
DGSDEPANCTQMTCGVDEFRCKDSGRCIPARWKCDGEDDCGDGSDEPKEECDERTCEPYQ
FRCKNNRCVPGRWQCDYDNDCGDNSDEESCTPRPCSESEFSCANGRCIAGRWKCDGDHDC
ADGSDEKDCTPRCDMDQFQCKSGHCIPLRWRCDADADCMDGSDEEACGTGVRTCPLDEFQ
CNNTLCKPLAWKCDGEDDCGDNSDENPEECARFVCPPNRPFRCKNDRVCLWIGRQCDGTD

SEQUENCES

NCGDGTDEEDCEPPTAHTTHCKDKKEFLCRNQRCLSSSLRCNMFDDCGDGSDEEDCSIDP
KLTSCATNASICGDEARCVRTEKAAYCACRSGFHTVPGQPGCQDINECLRFGTCSQLCNN
TKGGHLCSCAPNFMKTHNTCKAEGSEYQVLYIADDNEIRSLFPGHPHSAYEQAFQGDESV
RIDAMDVHVKAGRVYWTNWHTGTISYRSLPPAAPPTTSNRHRRQIDRGVTHLNISGLKMP
RGIAIDWVAGNVYWTDSGRDVIEVAQMKGENRKTLISGMIDEPHAIVVDPLRGTMYWSDW
GNHPKIETAAMDGTLRETLVQDNIQWPTGLAVDYHNERLYWADAKLSVIGSIRLNGTDPI
VAADSKRGLSHPFSIDVFEDYIYGVTYINNRVFKIHKFGHSPLVNLTGGLSHASDVVLYH
QHKQPEVTNPCDRKKCEWLCLLSPSGPVCTCPNGKRLDNGTCVPVPSPTPPPDAPRPGTC
NLQCFNGGSCFLNARRQPKCRCQPRYTGDKCELDQCWEHCRNGGTCAASPSGMPTCRCPT
GFTGPKCTQQVCAGYCANNSTCTVNQGNQPQCRCLPGFLGDRCQYRQCSGYCENEGTCQM
AADGSRQCRCTAYFEGSRCEVNKCSRCLEGACVVNKQSGDVTCNCTDGRVAPSCLTCVGH
CSNGGSCTMNSKNMPECQCPPHMTGPRCEEHVESQQQPGHIAS<u>ILIPLLLLLLVLVAGV
VFWY</u>KRRVQGAKGFQHQRMTNGAMNVEIGNPTYKMYEGGEPDDVGGLLDADFALDPDKPT
NFTNPVYATLYMGGHGSRHSLASTDEKRELLGRGPEDEIGDPLA

SEQ ID NO: 57
>Biotin Acceptor Peptide (BAP)
LNDIFEAQKIEWH

SEQ ID NO: 58
>Lipoate Acceptor Peptide 2 (LAP2)
GFEIDKVWYDLDA

SEQ ID NO: 4
>HAPylation motif, n = 1 to 400
(Gly4Ser)n

SEQ ID NO: 59
>CTP
DSSSSKAPPPSLPSPSRLPGPSDTPILPQ

SEQ ID NO: 70
>SUMO
SLQDSEVNQEAKPEVKPEVKPETHINLKVSDGSSEIFFKIKRTTPLERLMEAFAKR
QGKEMDSLRFLYDGIRIQADQAPEDLDMEDNDIIEAHREQIGG

What is claimed is:

1. A chimeric protein comprising two polypeptides, wherein (A) the first polypeptide comprises (i) an activatable Factor VII (Ac) and (ii) a first Fc domain (Het1), wherein the activatable Factor VII comprises a Factor VII (FVII) zymogen comprising a heavy chain (HC), a light chain (LC), and a protease-cleavage site that is not naturally occurring in the FVII zymogen inserted between the HC and the LC; wherein (B) the second polypeptide comprises (i) a soluble Tissue Factor (Em) and (ii) a second Fc domain (Het2); and wherein the chimeric protein has a higher thrombin activity compared to a reference FVII protein comprising an activated FVII (FVIIa) alone or an FVIIaFc fusion protein, as measured by a thrombin generation assay.

2. The chimeric protein according to claim 1, wherein the first polypeptide comprises a structure represented by formula Ac-L1-Het1, and wherein Ac comprises the activatable FVII, L1 comprises a first linker, and Het1 comprises the first Fc domain; wherein the second polypeptide comprises a structure represented by formula Em-L2-Het2, wherein Em comprises the soluble Tissue Factor, L2 comprises a second linker, and Het2 comprises the second Fc domain.

3. The chimeric protein according to claim 1, further a self-immolative moiety inserted between the protease-cleavage site and the HC.

4. The chimeric protein according to claim 1, wherein the protease-cleavage site is cleaved by a protease selected from the group consisting of thrombin (factor IIa), factor XIIa, kallikrein, factor VIIa, factor IXa, and factor Xa.

5. The chimeric protein according to claim 3, wherein the self-immolative moiety comprises p-amino benzyl carbamate (PABC), a p-amino benzyl ether (PABE), or a p-amino benzyl carbonate.

6. The chimeric protein according to claim 2, wherein the L2 is identical to the L1.

7. The chimeric protein according to claim 2, wherein the L1 and/or L2 comprises a gly/ser peptide.

8. The chimeric protein according to claim 1, wherein the protease-cleavage site is a thrombin cleavage site.

9. The chimeric protein according to claim 1, wherein an intracellular processing site is inserted between the LC of the FVII zymogen and the protease-cleavage site.

10. A pharmaceutical composition comprising the chimeric protein of claim 1 and a pharmaceutically acceptable carrier.

11. The chimeric protein according to claim 1, wherein the Het1 and the Het2 are the same.

12. The chimeric protein according to claim 1, wherein the Het1 and the Het2 are different.

13. The chimeric protein according to claim 2, wherein the L2 is different from the L1.

14. The chimeric protein according to claim 3, wherein the self-immolative moiety is PABC.

* * * * *

UNITED STATES PATENT AND TRADEMARK OFFICE
CERTIFICATE OF CORRECTION

PATENT NO. : 10,202,595 B2
APPLICATION NO. : 14/406160
DATED : February 12, 2019
INVENTOR(S) : Salas et al.

It is certified that error appears in the above-identified patent and that said Letters Patent is hereby corrected as shown below:

On the Title Page

Item [72], 4th inventor, delete "Adam R. Meso" and insert --Adam R. Mezo--.

Signed and Sealed this
Thirteenth Day of August, 2019

Andrei Iancu
*Director of the United States Patent and Trademark Office*

SEQUENCE LISTING

<160> NUMBER OF SEQ ID NOS: 70

<210> SEQ ID NO 1
<211> LENGTH: 5
<212> TYPE: PRT
<213> ORGANISM: Artificial Sequence
<220> FEATURE:
<223> OTHER INFORMATION: cleavage site

<400> SEQUENCE: 1

Ala Leu Arg Pro Arg
1               5

<210> SEQ ID NO 2
<211> LENGTH: 4
<212> TYPE: PRT
<213> ORGANISM: Artificial Sequence
<220> FEATURE:
<223> OTHER INFORMATION: intracellular processing site

<400> SEQUENCE: 2

Arg Arg Arg Arg
1

<210> SEQ ID NO 3
<211> LENGTH: 6
<212> TYPE: PRT
<213> ORGANISM: Artificial Sequence
<220> FEATURE:
<223> OTHER INFORMATION: intracellular processing site

```
<400> SEQUENCE: 3

Arg Lys Arg Arg Lys Arg
1               5

<210> SEQ ID NO 4
<211> LENGTH: 5
<212> TYPE: PRT
<213> ORGANISM: Artificial Sequence
<220> FEATURE:
<223> OTHER INFORMATION: peptide linker
<220> FEATURE:
<221> NAME/KEY: REPEAT
<222> LOCATION: (1)..(5)
<223> OTHER INFORMATION: may be repeated 1-400 times

<400> SEQUENCE: 4

Gly Gly Gly Gly Ser
1               5

<210> SEQ ID NO 5
<211> LENGTH: 6
<212> TYPE: PRT
<213> ORGANISM: Artificial Sequence
<220> FEATURE:
<223> OTHER INFORMATION: peptide linker
<220> FEATURE:
<221> NAME/KEY: REPEAT
<222> LOCATION: (2)..(6)
<223> OTHER INFORMATION: n is 1, 2, 3, 4, 5, 6, 7, 8, 9, 10, 15, 20, 25,
      30, 35, 40, 46, 50, 55, 60, 70, 80, 90, or 100

<400> SEQUENCE: 5

Ser Gly Gly Gly Gly Ser
1               5

<210> SEQ ID NO 6
<211> LENGTH: 9
<212> TYPE: PRT
<213> ORGANISM: Artificial Sequence
<220> FEATURE:
<223> OTHER INFORMATION: cleavage site

<400> SEQUENCE: 6

Thr Gln Ser Phe Asn Asp Phe Thr Arg
1               5

<210> SEQ ID NO 7
<211> LENGTH: 10
<212> TYPE: PRT
<213> ORGANISM: Artificial Sequence
<220> FEATURE:
<223> OTHER INFORMATION: cleavage site

<400> SEQUENCE: 7

Ser Val Ser Gln Thr Ser Lys Leu Thr Arg
1               5                   10

<210> SEQ ID NO 8
<211> LENGTH: 10
<212> TYPE: PRT
<213> ORGANISM: Artificial Sequence
<220> FEATURE:
<223> OTHER INFORMATION: cleavage site

<400> SEQUENCE: 8

Asp Phe Leu Ala Glu Gly Gly Gly Val Arg
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: cleavage site

<400> SEQUENCE: 9

```
Thr Thr Lys Ile Lys Pro Arg
1               5
```

<210> SEQ ID NO 10
<211> LENGTH: 5
<212> TYPE: PRT
<213> ORGANISM: Artificial Sequence
<220> FEATURE:
<223> OTHER INFORMATION: cleavage site

<400> SEQUENCE: 10

```
Leu Val Pro Arg Gly
1               5
```

<210> SEQ ID NO 11
<211> LENGTH: 488
<212> TYPE: PRT
<213> ORGANISM: Homo sapiens

<400> SEQUENCE: 11

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240
```

Cys Lys Asp Gly Glu Cys Pro Trp Gln Ala Leu Leu Ile Asn Glu Glu
             245                 250                 255

Asn Glu Gly Phe Cys Gly Gly Thr Ile Leu Ser Glu Phe Tyr Ile Leu
         260                 265                 270

Thr Ala Ala His Cys Leu Tyr Gln Ala Lys Arg Phe Lys Val Arg Val
     275                 280                 285

Gly Asp Arg Asn Thr Glu Gln Glu Glu Gly Gly Glu Ala Val His Glu
 290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
             325                 330                 335

Asn Val Ala Pro Ala Cys Leu Pro Glu Arg Asp Trp Ala Glu Ser Thr
         340                 345                 350

Leu Met Thr Gln Lys Thr Gly Ile Val Ser Gly Phe Gly Arg Thr His
     355                 360                 365

Glu Lys Gly Arg Gln Ser Thr Arg Leu Lys Met Leu Glu Val Pro Tyr
 370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
             405                 410                 415

Gly Asp Ser Gly Gly Pro His Val Thr Arg Phe Lys Asp Thr Tyr Phe
         420                 425                 430

Val Thr Gly Ile Val Ser Trp Gly Glu Gly Cys Ala Arg Lys Gly Lys
     435                 440                 445

Tyr Gly Ile Tyr Thr Lys Val Thr Ala Phe Leu Lys Trp Ile Asp Arg
 450                 455                 460

Ser Met Lys Thr Arg Gly Leu Pro Lys Ala Lys Ser His Ala Pro Glu
465                 470                 475                 480

Val Ile Thr Ser Ser Pro Leu Lys
             485

<210> SEQ ID NO 12
<211> LENGTH: 1467
<212> TYPE: DNA
<213> ORGANISM: Homo sapiens

<400> SEQUENCE: 12
atggggcgcc cactgcacct cgtcctgctc agtgcctccc tggctggcct cctgctgctc    60
ggggaaagtc tgttcatccg cagggagcag gccaacaaca tcctggcgag ggtcacgagg   120
gccaattcct ttcttgaaga gatgaagaaa ggacacctcg aaagagagtg catggaagag   180
acctgctcat acgaagaggc ccgcgaggtc tttgaggaca cgacaagac gaatgaattc   240 tggaataaat acaaagatgg cgaccagtgt gagaccagtc cttgccagaa ccagggcaaa   300
tgtaaagacg gcctcgggga atacacctgc acctgtttag aaggattcga aggcaaaaac   360
tgtgaattat tcacacggaa gctctgcagc ctggacaacg ggactgtga ccagttctgc   420 cacgaggaac agaactctgt ggtgtgctcc tgcgcccgcg gtacaccct ggctgacaac   480 ggcaaggcct gcattcccac agggccctac ccctgtggga acagaccct ggaacgcagg   540 aagaggtcag tggcccaggc caccagcagc agcggggagg ccctgacag catcacatgg   600 aagccatatg atgcagccga cctggacccc accgagaacc ccttcgacct gcttgacttc   660
aaccagacgc agcctgagag gggcgacaac aacctcacca ggatcgtggg aggccaggaa   720

```
tgcaaggacg gggagtgtcc ctggcaggcc ctgctcatca atgaggaaaa cgagggtttc    780
tgtggtggaa ccattctgag cgagttctac atcctaacgg cagcccactg tctctaccaa    840
gccaagagat tcaaggtgag ggtaggggac cggaacacgg agcaggagga gggcggtgag    900
gcggtgcacg aggtggaggt ggtcatcaag cacaaccggt tcacaaagga gacctatgac    960
ttcgacatcg ccgtgctccg gctcaagacc cccatcacct tccgcatgaa cgtggcgcct   1020
gcctgcctcc ccgagcgtga ctgggccgag tccacgctga tgacgcagaa gacggggatt   1080
gtgagcggct cgggcgcac ccacgagaag ggccggcagt ccaccaggct caagatgctg   1140
gaggtgccct acgtggaccg caacagctgc aagctgtcca gcagcttcat catcacccag   1200
aacatgttct gtgccggcta cgacaccaag caggaggatg cctgccaggg ggacagcggg   1260
ggcccgcacg tcacccgctt caaggacacc tacttcgtga caggcatcgt cagctgggga   1320
gagggctgtg cccgtaaggg gaagtacggg atctacacca aggtcaccgc cttcctcaag   1380
tggatcgaca ggtccatgaa aaccagggc ttgcccaagg ccaagagcca tgccccggag   1440
gtcataacgt cctctccatt aaagtga                                        1467
```

<210> SEQ ID NO 13
<211> LENGTH: 4
<212> TYPE: PRT
<213> ORGANISM: Artificial Sequence
<220> FEATURE:
<223> OTHER INFORMATION: cleavage site

<400> SEQUENCE: 13

Lys Leu Thr Arg
1

<210> SEQ ID NO 14
<211> LENGTH: 4
<212> TYPE: PRT
<213> ORGANISM: Artificial Sequence
<220> FEATURE:
<223> OTHER INFORMATION: cleavage site

<400> SEQUENCE: 14

Asp Phe Thr Arg
1

<210> SEQ ID NO 15
<211> LENGTH: 295
<212> TYPE: PRT
<213> ORGANISM: Homo sapiens

<400> SEQUENCE: 15

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

| | | | | | | | | | | | |
|---|---|---|---|---|---|---|---|---|---|---|---|
|Lys|Asp|Val|Lys|Gln|Thr|Tyr|Leu|Ala|Arg|Val|Phe|Ser|Tyr|Pro|Ala|
| | | |100| | | |105| | | |110| | | | |

Lys Asp Val Lys Gln Thr Tyr Leu Ala Arg Val Phe Ser Tyr Pro Ala
              100                 105                 110

Gly Asn Val Glu Ser Thr Gly Ser Ala Gly Glu Pro Leu Tyr Glu Asn
              115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
            195                 200                 205

Ile Asp Val Asp Lys Gly Glu Asn Tyr Cys Phe Ser Val Gln Ala Val
210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
            260                 265                 270

Ser Leu His Lys Cys Arg Lys Ala Gly Val Gly Gln Ser Trp Lys Glu
            275                 280                 285

Asn Ser Pro Leu Asn Val Ser
    290                 295

<210> SEQ ID NO 16
<211> LENGTH: 888
<212> TYPE: DNA
<213> ORGANISM: Homo sapiens

<400> SEQUENCE: 16
atggagaccc tgcctggcc ccgggtcccg cgccccgaga ccgccgtcgc tcggacgctc      60
ctgctcggct gggtcttcgc ccaggtggcc ggcgcttcag gcactacaaa tactgtggca     120
gcatataatt taacttggaa atcaactaat ttcaagacaa ttttggagtg ggaacccaaa     180
cccgtcaatc aagtctacac tgttcaaata agcactaagt caggagattg gaaaagcaaa     240
tgcttttaca acagacacac agagtgtgac ctcaccgacg agattgtgaa ggatgtgaag     300
cagacgtact tggcacgggt cttctcctac ccggcaggga tgtggagag caccggttct      360
gctggggagc tctgtatga gaactcccca gagttcacac cttacctgga gacaaacctc      420
ggacagccaa caattcagag ttttgaacag gtgggaacaa agtgaatgt gaccgtagaa      480
gatgaacgga ctttagtcag aaggaacaac actttcctaa gcctccggga tgtttttggc     540
aaggacttaa tttatacact ttattattgg aaatcttcaa gttcaggaaa gaaaacagcc     600
aaaacaaaca ctaatgagtt tttgattgat gtggataaag gagaaaacta ctgtttcagt     660
gttcaagcag tgattccctc ccgaacagtt aaccggaaga gtacagacag cccggtagag     720
tgtatgggcc aggagaaagg ggaattcaga gaaatattct acatcattgg agctgtggta     780
tttgtggtca tcatccttgt catcatcctg ctatatctc tacacaagtg tagaaaggca     840
ggagtggggc agagctggaa ggagaactcc ccactgaatg tttcataa                 888

<210> SEQ ID NO 17

```
<211> LENGTH: 2224
<212> TYPE: PRT
<213> ORGANISM: Homo sapiens

<400> SEQUENCE: 17
```

| | | | | | | | | | | | | | | |
|---|---|---|---|---|---|---|---|---|---|---|---|---|---|---|
| Met | Phe | Pro | Gly | Cys | Pro | Arg | Leu | Trp | Val | Leu | Val | Leu | Gly | Thr |
| 1 | | | | 5 | | | | | 10 | | | | | 15 |
| Ser | Trp | Val | Gly | Trp | Gly | Ser | Gln | Gly | Thr | Glu | Ala | Ala | Gln | Leu | Arg |
| | | | 20 | | | | | 25 | | | | | 30 | | |
| Gln | Phe | Tyr | Val | Ala | Ala | Gln | Gly | Ile | Ser | Trp | Ser | Tyr | Arg | Pro | Glu |
| | | | 35 | | | | | 40 | | | | | 45 | | |
| Pro | Thr | Asn | Ser | Ser | Leu | Asn | Leu | Ser | Val | Thr | Ser | Phe | Lys | Lys | Ile |
| | 50 | | | | | 55 | | | | | 60 | | | | |
| Val | Tyr | Arg | Glu | Tyr | Glu | Pro | Tyr | Phe | Lys | Lys | Glu | Lys | Pro | Gln | Ser |
| 65 | | | | | 70 | | | | | 75 | | | | | 80 |
| Thr | Ile | Ser | Gly | Leu | Leu | Gly | Pro | Thr | Leu | Tyr | Ala | Glu | Val | Gly | Asp |
| | | | | 85 | | | | | 90 | | | | | 95 | |
| Ile | Ile | Lys | Val | His | Phe | Lys | Asn | Lys | Ala | Asp | Lys | Pro | Leu | Ser | Ile |
| | | | 100 | | | | | 105 | | | | | 110 | | |
| His | Pro | Gln | Gly | Ile | Arg | Tyr | Ser | Lys | Leu | Ser | Glu | Gly | Ala | Ser | Tyr |
| | | | 115 | | | | | 120 | | | | | 125 | | |
| Leu | Asp | His | Thr | Phe | Pro | Ala | Glu | Lys | Met | Asp | Asp | Ala | Val | Ala | Pro |
| | 130 | | | | | 135 | | | | | 140 | | | | |
| Gly | Arg | Glu | Tyr | Thr | Tyr | Glu | Trp | Ser | Ile | Ser | Glu | Asp | Ser | Gly | Pro |
| 145 | | | | | 150 | | | | | 155 | | | | | 160 |
| Thr | His | Asp | Asp | Pro | Pro | Cys | Leu | Thr | His | Ile | Tyr | Tyr | Ser | His | Glu |
| | | | | 165 | | | | | 170 | | | | | 175 | |
| Asn | Leu | Ile | Glu | Asp | Phe | Asn | Ser | Gly | Leu | Ile | Gly | Pro | Leu | Leu | Ile |
| | | | 180 | | | | | 185 | | | | | 190 | | |
| Cys | Lys | Lys | Gly | Thr | Leu | Thr | Glu | Gly | Gly | Thr | Gln | Lys | Thr | Phe | Asp |
| | | | 195 | | | | | 200 | | | | | 205 | | |
| Lys | Gln | Ile | Val | Leu | Leu | Phe | Ala | Val | Phe | Asp | Glu | Ser | Lys | Ser | Trp |
| | 210 | | | | | 215 | | | | | 220 | | | | |
| Ser | Gln | Ser | Ser | Ser | Leu | Met | Tyr | Thr | Val | Asn | Gly | Tyr | Val | Asn | Gly |
| 225 | | | | | 230 | | | | | 235 | | | | | 240 |
| Thr | Met | Pro | Asp | Ile | Thr | Val | Cys | Ala | His | Asp | His | Ile | Ser | Trp | His |
| | | | | 245 | | | | | 250 | | | | | 255 | |
| Leu | Leu | Gly | Met | Ser | Ser | Gly | Pro | Glu | Leu | Phe | Ser | Ile | His | Phe | Asn |
| | | | 260 | | | | | 265 | | | | | 270 | | |
| Gly | Gln | Val | Leu | Glu | Gln | Asn | His | His | Lys | Val | Ser | Ala | Ile | Thr | Leu |
| | | | 275 | | | | | 280 | | | | | 285 | | |
| Val | Ser | Ala | Thr | Ser | Thr | Thr | Ala | Asn | Met | Thr | Val | Gly | Pro | Glu | Gly |
| | 290 | | | | | 295 | | | | | 300 | | | | |
| Lys | Trp | Ile | Ile | Ser | Ser | Leu | Thr | Pro | Lys | His | Leu | Gln | Ala | Gly | Met |
| 305 | | | | | 310 | | | | | 315 | | | | | 320 |
| Gln | Ala | Tyr | Ile | Asp | Ile | Lys | Asn | Cys | Pro | Lys | Lys | Thr | Arg | Asn | Leu |
| | | | | 325 | | | | | 330 | | | | | 335 | |
| Lys | Lys | Ile | Thr | Arg | Glu | Gln | Arg | Arg | His | Met | Lys | Arg | Trp | Glu | Tyr |
| | | | 340 | | | | | 345 | | | | | 350 | | |
| Phe | Ile | Ala | Ala | Glu | Glu | Val | Ile | Trp | Asp | Tyr | Ala | Pro | Val | Ile | Pro |
| | | | 355 | | | | | 360 | | | | | 365 | | |
| Ala | Asn | Met | Asp | Lys | Lys | Tyr | Arg | Ser | Gln | His | Leu | Asp | Asn | Phe | Ser |
| | 370 | | | | | 375 | | | | | 380 | | | | |
| Asn | Gln | Ile | Gly | Lys | His | Tyr | Lys | Lys | Val | Met | Tyr | Thr | Gln | Tyr | Glu |

```
            385                 390                 395                 400
Asp Glu Ser Phe Thr Lys His Thr Val Asn Pro Asn Met Lys Glu Asp
                    405                 410                 415

Gly Ile Leu Gly Pro Ile Ile Arg Ala Gln Val Arg Asp Thr Leu Lys
                420                 425                 430

Ile Val Phe Lys Asn Met Ala Ser Arg Pro Tyr Ser Ile Tyr Pro His
            435                 440                 445

Gly Val Thr Phe Ser Pro Tyr Glu Asp Glu Val Asn Ser Ser Phe Thr
        450                 455                 460

Ser Gly Arg Asn Asn Thr Met Ile Arg Ala Val Gln Pro Gly Glu Thr
465                 470                 475                 480

Tyr Thr Tyr Lys Trp Asn Ile Leu Glu Phe Asp Pro Thr Glu Asn
                485                 490                 495

Asp Ala Gln Cys Leu Thr Arg Pro Tyr Tyr Ser Asp Val Asp Ile Met
                500                 505                 510

Arg Asp Ile Ala Ser Gly Leu Ile Gly Leu Leu Leu Ile Cys Lys Ser
            515                 520                 525

Arg Ser Leu Asp Arg Arg Gly Ile Gln Arg Ala Ala Asp Ile Glu Gln
        530                 535                 540

Gln Ala Val Phe Ala Val Phe Asp Glu Asn Lys Ser Trp Tyr Leu Glu
545                 550                 555                 560

Asp Asn Ile Asn Lys Phe Cys Glu Asn Pro Asp Glu Val Lys Arg Asp
                565                 570                 575

Asp Pro Lys Phe Tyr Glu Ser Asn Ile Met Ser Thr Ile Asn Gly Tyr
            580                 585                 590

Val Pro Glu Ser Ile Thr Thr Leu Gly Phe Cys Phe Asp Asp Thr Val
        595                 600                 605

Gln Trp His Phe Cys Ser Val Gly Thr Gln Asn Glu Ile Leu Thr Ile
610                 615                 620

His Phe Thr Gly His Ser Phe Ile Tyr Gly Lys Arg His Glu Asp Thr
625                 630                 635                 640

Leu Thr Leu Phe Pro Met Arg Gly Glu Ser Val Thr Val Thr Met Asp
                645                 650                 655

Asn Val Gly Thr Trp Met Leu Thr Ser Met Asn Ser Ser Pro Arg Ser
            660                 665                 670

Lys Lys Leu Arg Leu Lys Phe Arg Asp Val Lys Cys Ile Pro Asp Asp
        675                 680                 685

Asp Glu Asp Ser Tyr Glu Ile Phe Glu Pro Pro Glu Ser Thr Val Met
        690                 695                 700

Ala Thr Arg Lys Met His Asp Arg Leu Glu Pro Glu Asp Glu Glu Ser
705                 710                 715                 720

Asp Ala Asp Tyr Asp Tyr Gln Asn Arg Leu Ala Ala Ala Leu Gly Ile
                725                 730                 735

Arg Ser Phe Arg Asn Ser Ser Leu Asn Gln Glu Glu Glu Phe Asn
            740                 745                 750

Leu Thr Ala Leu Ala Leu Glu Asn Gly Thr Glu Phe Val Ser Ser Asn
        755                 760                 765

Thr Asp Ile Ile Val Gly Ser Asn Tyr Ser Ser Pro Ser Asn Ile Ser
    770                 775                 780

Lys Phe Thr Val Asn Asn Leu Ala Glu Pro Gln Lys Ala Pro Ser His
785                 790                 795                 800

Gln Gln Ala Thr Thr Ala Gly Ser Pro Leu Arg His Leu Ile Gly Lys
                805                 810                 815
```

```
Asn Ser Val Leu Asn Ser Ser Thr Ala Glu His Ser Ser Pro Tyr Ser
            820                 825                 830

Glu Asp Pro Ile Glu Asp Pro Leu Gln Pro Asp Val Thr Gly Ile Arg
            835                 840                 845

Leu Leu Ser Leu Gly Ala Gly Glu Phe Lys Ser Gln Glu His Ala Lys
        850                 855                 860

His Lys Gly Pro Lys Val Glu Arg Asp Gln Ala Ala Lys His Arg Phe
865                 870                 875                 880

Ser Trp Met Lys Leu Leu Ala His Lys Val Gly Arg His Leu Ser Gln
                885                 890                 895

Asp Thr Gly Ser Pro Ser Gly Met Arg Pro Trp Glu Asp Leu Pro Ser
            900                 905                 910

Gln Asp Thr Gly Ser Pro Ser Arg Met Arg Pro Trp Lys Asp Pro Pro
        915                 920                 925

Ser Asp Leu Leu Leu Leu Lys Gln Ser Asn Ser Ser Lys Ile Leu Val
    930                 935                 940

Gly Arg Trp His Leu Ala Ser Glu Lys Gly Ser Tyr Glu Ile Ile Gln
945                 950                 955                 960

Asp Thr Asp Glu Asp Thr Ala Val Asn Asn Trp Leu Ile Ser Pro Gln
                965                 970                 975

Asn Ala Ser Arg Ala Trp Gly Glu Ser Thr Pro Leu Ala Asn Lys Pro
            980                 985                 990

Gly Lys Gln Ser Gly His Pro Lys Phe Pro Arg Val Arg His Lys Ser
        995                 1000                1005

Leu Gln Val Arg Gln Asp Gly Gly Lys Ser Arg Leu Lys Lys Ser
    1010                1015                1020

Gln Phe Leu Ile Lys Thr Arg Lys Lys Lys Glu Lys His Thr
    1025                1030                1035

His His Ala Pro Leu Ser Pro Arg Thr Phe His Pro Leu Arg Ser
    1040                1045                1050

Glu Ala Tyr Asn Thr Phe Ser Glu Arg Arg Leu Lys His Ser Leu
    1055                1060                1065

Val Leu His Lys Ser Asn Glu Thr Ser Leu Pro Thr Asp Leu Asn
    1070                1075                1080

Gln Thr Leu Pro Ser Met Asp Phe Gly Trp Ile Ala Ser Leu Pro
    1085                1090                1095

Asp His Asn Gln Asn Ser Ser Asn Asp Thr Gly Gln Ala Ser Cys
    1100                1105                1110

Pro Pro Gly Leu Tyr Gln Thr Val Pro Pro Glu Glu His Tyr Gln
    1115                1120                1125

Thr Phe Pro Ile Gln Asp Pro Asp Gln Met His Ser Thr Ser Asp
    1130                1135                1140

Pro Ser His Arg Ser Ser Pro Glu Leu Ser Glu Met Leu Glu
    1145                1150                1155

Tyr Asp Arg Ser His Lys Ser Phe Pro Thr Asp Ile Ser Gln Met
    1160                1165                1170

Ser Pro Ser Ser Glu His Glu Val Trp Gln Thr Val Ile Ser Pro
    1175                1180                1185

Asp Leu Ser Gln Val Thr Leu Ser Pro Glu Leu Ser Gln Thr Asn
    1190                1195                1200

Leu Ser Pro Asp Leu Ser His Thr Thr Leu Ser Pro Glu Leu Ile
    1205                1210                1215
```

```
Gln Arg Asn Leu Ser Pro Ala Leu Gly Gln Met Pro Ile Ser Pro
    1220                1225                1230

Asp Leu Ser His Thr Thr Leu Ser Pro Asp Leu Ser His Thr Thr
    1235                1240                1245

Leu Ser Leu Asp Leu Ser Gln Thr Asn Leu Ser Pro Glu Leu Ser
    1250                1255                1260

Gln Thr Asn Leu Ser Pro Ala Leu Gly Gln Met Pro Leu Ser Pro
    1265                1270                1275

Asp Leu Ser His Thr Thr Leu Ser Leu Asp Phe Ser Gln Thr Asn
    1280                1285                1290

Leu Ser Pro Glu Leu Ser His Met Thr Leu Ser Pro Glu Leu Ser
    1295                1300                1305

Gln Thr Asn Leu Ser Pro Ala Leu Gly Gln Met Pro Ile Ser Pro
    1310                1315                1320

Asp Leu Ser His Thr Thr Leu Ser Leu Asp Phe Ser Gln Thr Asn
    1325                1330                1335

Leu Ser Pro Glu Leu Ser Gln Thr Asn Leu Ser Pro Ala Leu Gly
    1340                1345                1350

Gln Met Pro Leu Ser Pro Asp Pro Ser His Thr Thr Leu Ser Leu
    1355                1360                1365

Asp Leu Ser Gln Thr Asn Leu Ser Pro Glu Leu Ser Gln Thr Asn
    1370                1375                1380

Leu Ser Pro Asp Leu Ser Glu Met Pro Leu Phe Ala Asp Leu Ser
    1385                1390                1395

Gln Ile Pro Leu Thr Pro Asp Leu Asp Gln Met Thr Leu Ser Pro
    1400                1405                1410

Asp Leu Gly Glu Thr Asp Leu Ser Pro Asn Phe Gly Gln Met Ser
    1415                1420                1425

Leu Ser Pro Asp Leu Ser Gln Val Thr Leu Ser Pro Asp Ile Ser
    1430                1435                1440

Asp Thr Thr Leu Leu Pro Asp Leu Ser Gln Ile Ser Pro Pro Pro
    1445                1450                1455

Asp Leu Asp Gln Ile Phe Tyr Pro Ser Glu Ser Ser Gln Ser Leu
    1460                1465                1470

Leu Leu Gln Glu Phe Asn Glu Ser Phe Pro Tyr Pro Asp Leu Gly
    1475                1480                1485

Gln Met Pro Ser Pro Ser Ser Pro Thr Leu Asn Asp Thr Phe Leu
    1490                1495                1500

Ser Lys Glu Phe Asn Pro Leu Val Ile Val Gly Leu Ser Lys Asp
    1505                1510                1515

Gly Thr Asp Tyr Ile Glu Ile Ile Pro Lys Glu Val Gln Ser
    1520                1525                1530

Ser Glu Asp Asp Tyr Ala Glu Ile Asp Tyr Val Pro Tyr Asp Asp
    1535                1540                1545

Pro Tyr Lys Thr Asp Val Arg Thr Asn Ile Asn Ser Ser Arg Asp
    1550                1555                1560

Pro Asp Asn Ile Ala Ala Trp Tyr Leu Arg Ser Asn Asn Gly Asn
    1565                1570                1575

Arg Arg Asn Tyr Tyr Ile Ala Ala Glu Glu Ile Ser Trp Asp Tyr
    1580                1585                1590

Ser Glu Phe Val Gln Arg Glu Thr Asp Ile Glu Asp Ser Asp Asp
    1595                1600                1605

Ile Pro Glu Asp Thr Thr Tyr Lys Lys Val Val Phe Arg Lys Tyr
```

```
              1610                1615                1620

Leu Asp Ser Thr Phe Thr Lys Arg Asp Pro Arg Gly Glu Tyr Glu
              1625                1630                1635

Glu His Leu Gly Ile Leu Gly Pro Ile Ile Arg Ala Glu Val Asp
              1640                1645                1650

Asp Val Ile Gln Val Arg Phe Lys Asn Leu Ala Ser Arg Pro Tyr
              1655                1660                1665

Ser Leu His Ala His Gly Leu Ser Tyr Glu Lys Ser Ser Glu Gly
              1670                1675                1680

Lys Thr Tyr Glu Asp Asp Ser Pro Glu Trp Phe Lys Glu Asp Asn
              1685                1690                1695

Ala Val Gln Pro Asn Ser Ser Tyr Thr Tyr Val Trp His Ala Thr
              1700                1705                1710

Glu Arg Ser Gly Pro Glu Ser Pro Gly Ser Ala Cys Arg Ala Trp
              1715                1720                1725

Ala Tyr Tyr Ser Ala Val Asn Pro Glu Lys Asp Ile His Ser Gly
              1730                1735                1740

Leu Ile Gly Pro Leu Leu Ile Cys Gln Lys Gly Ile Leu His Lys
              1745                1750                1755

Asp Ser Asn Met Pro Met Asp Met Arg Glu Phe Val Leu Leu Phe
              1760                1765                1770

Met Thr Phe Asp Glu Lys Lys Ser Trp Tyr Tyr Glu Lys Lys Ser
              1775                1780                1785

Arg Ser Ser Trp Arg Leu Thr Ser Ser Glu Met Lys Lys Ser His
              1790                1795                1800

Glu Phe His Ala Ile Asn Gly Met Ile Tyr Ser Leu Pro Gly Leu
              1805                1810                1815

Lys Met Tyr Glu Gln Glu Trp Val Arg Leu His Leu Leu Asn Ile
              1820                1825                1830

Gly Gly Ser Gln Asp Ile His Val Val His Phe His Gly Gln Thr
              1835                1840                1845

Leu Leu Glu Asn Gly Asn Lys Gln His Gln Leu Gly Val Trp Pro
              1850                1855                1860

Leu Leu Pro Gly Ser Phe Lys Thr Leu Glu Met Lys Ala Ser Lys
              1865                1870                1875

Pro Gly Trp Trp Leu Leu Asn Thr Glu Val Gly Glu Asn Gln Arg
              1880                1885                1890

Ala Gly Met Gln Thr Pro Phe Leu Ile Met Asp Arg Asp Cys Arg
              1895                1900                1905

Met Pro Met Gly Leu Ser Thr Gly Ile Ile Ser Asp Ser Gln Ile
              1910                1915                1920

Lys Ala Ser Glu Phe Leu Gly Tyr Trp Glu Pro Arg Leu Ala Arg
              1925                1930                1935

Leu Asn Asn Gly Gly Ser Tyr Asn Ala Trp Ser Val Glu Lys Leu
              1940                1945                1950

Ala Ala Glu Phe Ala Ser Lys Pro Trp Ile Gln Val Asp Met Gln
              1955                1960                1965

Lys Glu Val Ile Ile Thr Gly Ile Gln Thr Gln Gly Ala Lys His
              1970                1975                1980

Tyr Leu Lys Ser Cys Tyr Thr Thr Glu Phe Tyr Val Ala Tyr Ser
              1985                1990                1995

Ser Asn Gln Ile Asn Trp Gln Ile Phe Lys Gly Asn Ser Thr Arg
              2000                2005                2010
```

| | | | | | | | | | | |
|---|---|---|---|---|---|---|---|---|---|---|
| Asn | Val | Met | Tyr | Phe | Asn | Gly | Asn | Ser | Asp | Ala | Ser | Thr | Ile | Lys |
| | 2015 | | | | 2020 | | | | 2025 | |

Glu Asn Gln Phe Asp Pro Pro Ile Val Ala Arg Tyr Ile Arg Ile
   2030                2035              2040

Ser Pro Thr Arg Ala Tyr Asn Arg Pro Thr Leu Arg Leu Glu Leu
   2045                2050              2055

Gln Gly Cys Glu Val Asn Gly Cys Ser Thr Pro Leu Gly Met Glu
   2060                2065              2070

Asn Gly Lys Ile Glu Asn Lys Gln Ile Thr Ala Ser Ser Phe Lys
   2075                2080              2085

Lys Ser Trp Trp Gly Asp Tyr Trp Glu Pro Phe Arg Ala Arg Leu
   2090                2095              2100

Asn Ala Gln Gly Arg Val Asn Ala Trp Gln Ala Lys Ala Asn Asn
   2105                2110              2115

Asn Lys Gln Trp Leu Glu Ile Asp Leu Leu Lys Ile Lys Lys Ile
   2120                2125              2130

Thr Ala Ile Ile Thr Gln Gly Cys Lys Ser Leu Ser Ser Glu Met
   2135                2140              2145

Tyr Val Lys Ser Tyr Thr Ile His Tyr Ser Glu Gln Gly Val Glu
   2150                2155              2160

Trp Lys Pro Tyr Arg Leu Lys Ser Ser Met Val Asp Lys Ile Phe
   2165                2170              2175

Glu Gly Asn Thr Asn Thr Lys Gly His Val Lys Asn Phe Phe Asn
   2180                2185              2190

Pro Pro Ile Ile Ser Arg Phe Ile Arg Val Ile Pro Lys Thr Trp
   2195                2200              2205

Asn Gln Ser Ile Ala Leu Arg Leu Glu Leu Phe Gly Cys Asp Ile
   2210                2215              2220

Tyr

<210> SEQ ID NO 18
<211> LENGTH: 6675
<212> TYPE: DNA
<213> ORGANISM: Homo sapiens

<400> SEQUENCE: 18

```
atgttcccag gctgcccacg cctctgggtc ctggtggtct tgggcaccag ctgggtaggc    60
tgggggagcc aagggacaga agcggcacag ctaaggcagt tctacgtggc tgctcagggc   120
atcagttgga gctaccgacc tgagcccaca aactcaagtt tgaatctttc tgtaacttcc   180
tttaagaaaa ttgtctacag agagtatgaa ccatatttta agaaagaaaa accacaatct   240
accatttcag gacttcttgg gcctacttta tatgctgaag tcggagacat cataaaagtt   300
cactttaaaa ataaggcaga taagcccttg agcatccatc ctcaaggaat taggtacagt   360
aaattatcag aaggtgcttc ttaccttgac cacacattcc ctgcggagaa gatggacgac   420
gctgtggctc caggccgaga atacacctat gaatggagta tcagtgagga cagtggaccc   480
acccatgatg accctccatg cctcacacac atctattact cccatgaaaa tctgatcgag   540
gatttcaact cggggctgat tgggcccctg cttatctgta aaaaagggac cctaactgag   600
ggtgggacac agaagacgtt tgacaagcaa atcgtgctac tatttgctgt gtttgatgaa   660
agcaagagct ggagccagtc atcatcccta atgtacacag tcaatggata tgtgaatggg   720
acaatgccag atataacagt tgtgcccat gaccacatca gctggcatct gctgggaatg   780
```

```
agctcggggc cagaattatt ctccattcat ttcaacggcc aggtcctgga gcagaaccat    840
cataaggtct cagccatcac ccttgtcagt gctacatcca ctaccgcaaa tatgactgtg    900
ggcccagagg gaaagtggat catatcttct ctcaccccaa acatttgca agctgggatg    960
caggcttaca ttgacattaa aaactgccca agaaaaccca ggaatcttaa gaaaataact   1020
cgtgagcaga ggcggcacat gaagaggtgg gaatacttca ttgctgcaga ggaagtcatt   1080
tgggactatg cacctgtaat accagcgaat atggacaaaa aatacaggtc tcagcatttg   1140
gataatttct caaaccaaat tggaaaacat tataagaaag ttatgtacac acagtacgaa   1200
gatgagtcct tcaccaaaca tacagtgaat cccaatatga agaagatgg gattttgggt    1260
cctattatca gagcccaggt cagagacaca ctcaaaatcg tgttcaaaaa tatggccagc   1320
cgccccctata gcatttaccc tcatggagtg accttctcgc ttatgaaga tgaagtcaac    1380
tcttctttca cctcaggcag gaacaacacc atgatcagag cagttcaacc aggggaaacc   1440
tatacttata agtggaacat cttagagttt gatgaaccca cagaaaatga tgcccagtgc   1500
ttaacaagac catactacag tgacgtggac atcatgagag acatcgcctc tgggctaata   1560
ggactacttc taatctgtaa gagcagatcc ctggacaggc gaggaataca gagggcagca   1620
gacatcgaac agcaggctgt gtttgctgtg tttgatgaga caaaagctg gtaccttgag    1680
gacaacatca caagttttg tgaaaatcct gatgaggtga acgtgatga ccccaagttt     1740
tatgaatcaa acatcatgag cactatcaat ggctatgtgc ctgagagcat aactactctt   1800
ggattctgct ttgatgacac tgtccagtgg cacttctgta gtgtgggac ccagaatgaa    1860
attttgacca tccacttcac tgggcactca ttcatctatg aaagaggca tgaggacacc    1920
ttgaccctct tccccatgcg tggagaatct gtgacggtca caatggataa tgttggaact   1980
tggatgttaa cttccatgaa ttctagtcca agaagcaaaa agctgaggct gaaattcagg   2040
gatgttaaat gtatcccaga tgatgatgaa gactcatatg agattttga acctccagaa    2100
tctacagtca tggctacacg gaaaatgcat gatcgtttag aacctgaaga tgaagagagt   2160
gatgctgact atgattacca gaacagactg gctgcagcat taggaatcag gtcattccga   2220
aactcatcat tgaatcagga agaagaagag ttcaatctta ctgccctagc tctggagaat   2280
ggcactgaat tcgtttcttc aaacacagat ataattgttg gttcaaatta ttcttcccca   2340
agtaatatta gtaagttcac tgtcaataac cttgcagaac ctcagaaagc ccttctcac    2400
caacaagcca ccacagctgg ttccccactg agacacctca ttggcaagaa ctcagttctc   2460
aattcttcca cagcagagca ttccagccca tattctgaag accctataga ggatcctcta   2520
cagccagatg tcacagggat acgtctactt tcacttggtg ctggagaatt caaaagtcaa   2580
gaacatgcta agcataaggg acccaaggta gaaagagatc aagcagcaaa gcacaggttc   2640
tcctggatga aattactagc acataaagtt gggagacacc taagccaaga cactggttct   2700
ccttccggaa tgaggccctg ggaggacctt cctagccaag acactggttc tccttccaga   2760
atgaggccct ggaaggaccc tcctagtgat ctgttactct taaaacaaag taactcatct   2820
aagattttgg ttgggagatg gcatttggct tctgagaaag gtagctatga aataatccaa   2880
gatactgatg aagacacagc tgttaacaat tggctgatca gccccagaa tgcctcacgt    2940
gcttggggag aaagcacccc tcttgccaac aagcctggaa agcagagtgg ccacccaaag   3000
tttcctagag ttagacataa atctctacaa gtaagacagg atggaggaaa gagtagactg   3060
aagaaaagcc agtttctcat taagacacga aaaagaaaa aagagaagca cacacaccat    3120
gctccttatt ctccgaggac ctttcaccct ctaagaagtg aagcctacaa cacatttca    3180
```

```
gaaagaagac ttaagcattc gttggtgctt cataaatcca atgaaacatc tcttcccaca    3240
gacctcaatc agacattgcc ctctatggat tttggctgga tagcctcact tcctgaccat    3300
aatcagaatt cctcaaatga cactggtcag gcaagctgtc ctccaggtct ttatcagaca    3360
gtgcccccag aggaacacta tcaaacattc cccattcaag accctgatca aatgcactct    3420
acttcagacc ccagtcacag atcctcttct ccagagctca gtgaaatgct tgagtatgac    3480
cgaagtcaca agtccttccc cacagatata agtcaaatgt ccccttcctc agaacatgaa    3540
gtctggcaga cagtcatctc tccagacctc agccaggtga ccctctctcc agaactcagc    3600
cagacaaacc tctctccaga cctcagccac acgactctct ctccagaact cattcagaga    3660
aacctttccc cagccctcgg tcagatgccc atttctccag acctcagcca tacaacccct    3720
tctccagacc tcagccatac aacccttttct ttagacctca gccagacaaa cctctctcca    3780
gaactcagtc agacaaacct ttctccagcc ctcggtcaga tgcccctttc tccagacctc    3840
agccatacaa ccctttctct agacttcagc cagacaaacc tctctccaga actcagccat    3900
atgactctct ctccagaact cagtcagaca acctttccc cagccctcgg tcagatgccc    3960
atttctccag acctcagcca tacaacccctt tctctagact tcagccagac aaacctctct    4020
ccagaactca gtcaaacaaa cctttcccca gccctcggtc agatgcccct ttctccagac    4080
cccagccata caacccttt tctagacctc agccagacaa acctctctcc agaactcagt    4140
cagacaaacc tttccccaga cctcagtgag atgcccctct ttgcagatct cagtcaaatt    4200 cccccttaccc cagacctcga ccagatgaca ctttctccag accttggtga gacagatctt    4260
tccccaaact ttggtcagat gtccctttcc ccagacctca gccaggtgac tctctctcca    4320
gacatcagtg acaccaccct ctcccggat ctcagccaga tatcacctcc tccagacctt    4380
gatcagatat tctaccccttc tgaatctagt cagtcattgc ttcttcaaga atttaatgag    4440
tcttttcctt atccagacct tggtcagatg ccatctcctt catctcctac tctcaatgat    4500 actttctat caaaggaatt taatccactg gttatagtgg gcctcagtaa agatggtaca    4560
gattacattg agatcattcc aaaggaagag gtccagagca gtgaagatga ctatgctgaa    4620
attgattatg tgccctatga tgaccctac aaaactgatg ttaggacaaa catcaactcc    4680
tccagagatc ctgacaacat tgcagcatgg tacctccgca gcaacaatgg aaacagaaga    4740
aattattaca ttgctgctga agaaatatcc tgggattatt cagaatttgt acaaaggaa    4800 acagatattg aagactctga tgatattcca gaagatacca catataagaa agtagttttt    4860
cgaaagtacc tcgacagcac ttttaccaaa cgtgatcctc gaggggagta tgaagagcat    4920
ctcggaattc ttggtcctat tatcagagct gaagtggatg atgttatcca agttcgtttt    4980
aaaaatttag catccagacc gtattctcta catgcccatg actttcctta tgaaaaatca    5040
tcagagggaa agacttatga agatgactct cctgaatggt ttaaggaaga taatgctgtt    5100
cagccaaata gcagttatac ctacgtatgg catgccactg agcgatcagg ccagaaagt    5160 cctggctctg cctgtcgggc ttgggcctac tactcagctg tgaacccaga aaagatatt    5220 cactcaggct tgataggtcc cctcctaatc tgccaaaaag gaatactaca taaggacagc    5280
aacatgccta tggacatgag agaatttgtc ttactattta tgacctttga tgaaaagaag    5340
agctggtact atgaaaagaa gtcccgaagt tcttggagac tcacatcctc agaaatgaaa    5400
aaatcccatg agtttcacgc cattaatggg atgatctaca gcttgcctgg cctgaaaatg    5460
tatgagcaag agtgggtgag gttacacctg ctgaacatag gcggctccca agacattcac    5520
```

```
gtggttcact ttcacggcca gaccttgctg gaaaatggca ataaacagca ccagttaggg    5580
gtctggcccc ttctgcctgg ttcatttaaa actcttgaaa tgaaggcatc aaaacctggc    5640
tggtggctcc taaacacaga ggttggagaa accagagag cagggatgca aacgccattt     5700
cttatcatgg acagagactg taggatgcca atgggactaa gcactggtat catatctgat    5760
tcacagatca aggcttcaga gtttctgggt tactgggagc ccagattagc aagattaaac    5820
aatggtggat cttataatgc ttggagtgta gaaaaacttg cagcagaatt tgcctctaaa    5880
ccttggatcc aggtggacat gcaaaaggaa gtcataatca cagggatcca gacccaaggt    5940
gccaaacact acctgaagtc ctgctatacc acagagttct atgtagctta cagttccaac    6000
cagatcaact ggcagatctt caaagggaac agcacaagga atgtgatgta ttttaatggc    6060
aattcagatg cctctacaat aaaagagaat cagtttgacc cacctattgt ggctagatat    6120
attaggatct ctccaactcg agcctataac agacctaccc ttcgattgga actgcaaggt    6180
tgtgaggtaa atggatgttc cacacccctg ggtatggaaa atggaaagat agaaaacaag    6240
caaatcacag cttcttcgtt taagaaatct tggtggggag attactggga acccttccgt    6300
gcccgtctga atgcccaggg acgtgtgaat gcctggcaag ccaaggcaaa caacaataag    6360
cagtggctag aaattgatct actcaagatc aagaagataa cggcaattat aacacagggc    6420
tgcaagtctc tgtcctctga atgtatgta aagagctata ccatccacta cagtgagcag    6480
ggagtggaat ggaaaccata caggctgaaa tcctccatgg tggacaagat ttttgaagga    6540
aatactaata ccaaaggaca tgtgaagaac ttttcaacc ccccaatcat ttccaggttt    6600
atccgtgtca ttcctaaaac atggaatcaa agtattgcac ttcgcctgga actctttggc    6660
tgtgatattt actag                                                    6675
```

<210> SEQ ID NO 19
<211> LENGTH: 12
<212> TYPE: PRT
<213> ORGANISM: Artificial Sequence
<220> FEATURE:
<223> OTHER INFORMATION: procoagulant peptide

<400> SEQUENCE: 19

Lys Leu Thr Cys Leu Ala Ser Tyr Cys Trp Leu Phe
1               5                   10

<210> SEQ ID NO 20
<211> LENGTH: 22
<212> TYPE: PRT
<213> ORGANISM: Artificial Sequence
<220> FEATURE:
<223> OTHER INFORMATION: procoagulant peptide

<400> SEQUENCE: 20

Arg Arg Ala Pro Gly Lys Leu Thr Cys Leu Ala Ser Tyr Cys Trp Leu
1               5                   10                  15

Phe Trp Thr Gly Ile Ala
            20

<210> SEQ ID NO 21
<211> LENGTH: 22
<212> TYPE: PRT
<213> ORGANISM: Artificial Sequence
<220> FEATURE:
<223> OTHER INFORMATION: procoagulant peptide

<400> SEQUENCE: 21

Arg Arg Ala Pro Gly Lys Leu Gln Cys Leu Ala Ser Tyr Cys Trp Leu
1               5                   10                  15

Phe Trp Thr Gly Ile Ala
            20

<210> SEQ ID NO 22
<211> LENGTH: 32
<212> TYPE: PRT
<213> ORGANISM: Artificial Sequence
<220> FEATURE:
<223> OTHER INFORMATION: procoagulant peptide

<400> SEQUENCE: 22

Pro Arg Ile Arg Thr Val Gly Pro Gly Ser Arg Ser Ala Ser Gly Lys
1               5                   10                  15

Leu Thr Cys Leu Ala Ser Tyr Cys Trp Leu Phe Trp Thr Gly Ile Ala
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: procoagulant peptide

<400> SEQUENCE: 23

Ser Lys Gln Gly Arg Pro Ile Ser Pro Asp Arg Arg Ala Ala Gly Lys
1               5                   10                  15

Leu Thr Cys Leu Ala Ser Tyr Cys Trp Leu Phe Trp Thr Gly Ile Ala
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: procoagulant peptide

<400> SEQUENCE: 24

Pro Arg Ile Arg Thr Val Gly Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30

<210> SEQ ID NO 25
<211> LENGTH: 32
<212> TYPE: PRT
<213> ORGANISM: Artificial Sequence
<220> FEATURE:
<223> OTHER INFORMATION: procoagulant peptide

<400> SEQUENCE: 25

Ser Arg Ile Arg Thr Val Ser Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30

<210> SEQ ID NO 26
<211> LENGTH: 32
<212> TYPE: PRT
<213> ORGANISM: Artificial Sequence
<220> FEATURE:
<223> OTHER INFORMATION: procoagulant peptide

<400> SEQUENCE: 26

```
Pro Arg Ser Arg Thr Val Gly Pro Gly Ser Arg Ser Ala Ser Gly Lys
1               5                   10                  15

Ser Thr Cys Leu Ala Ser Tyr Cys Trp Leu Phe Trp Thr Gly Ile Ala
            20                  25                  30
```

<210> SEQ ID NO 27
<211> LENGTH: 11
<212> TYPE: PRT
<213> ORGANISM: Artificial Sequence
<220> FEATURE:
<223> OTHER INFORMATION: immunoglobulin constant region

<400> SEQUENCE: 27

```
Pro Lys Asn Ser Ser Met Ile Ser Asn Thr Pro
1               5                   10
```

<210> SEQ ID NO 28
<211> LENGTH: 7
<212> TYPE: PRT
<213> ORGANISM: Artificial Sequence
<220> FEATURE:
<223> OTHER INFORMATION: immunoglobulin constant region

<400> SEQUENCE: 28

```
His Gln Ser Leu Gly Thr Gln
1               5
```

<210> SEQ ID NO 29
<211> LENGTH: 8
<212> TYPE: PRT
<213> ORGANISM: Artificial Sequence
<220> FEATURE:
<223> OTHER INFORMATION: immunoglobulin constant region

<400> SEQUENCE: 29

```
His Gln Asn Leu Ser Asp Gly Lys
1               5
```

<210> SEQ ID NO 30
<211> LENGTH: 8
<212> TYPE: PRT
<213> ORGANISM: Artificial Sequence
<220> FEATURE:
<223> OTHER INFORMATION: immunoglobulin constant region

<400> SEQUENCE: 30

```
His Gln Asn Ile Ser Asp Gly Lys
1               5
```

<210> SEQ ID NO 31
<211> LENGTH: 8
<212> TYPE: PRT
<213> ORGANISM: Artificial Sequence
<220> FEATURE:
<223> OTHER INFORMATION: immunoglobulin constant region

<400> SEQUENCE: 31

```
Val Ile Ser Ser His Leu Gly Gln
1               5
```

<210> SEQ ID NO 32
<211> LENGTH: 32
<212> TYPE: PRT
<213> ORGANISM: Artificial Sequence
<220> FEATURE:
<223> OTHER INFORMATION: CTP peptide

```
<400> SEQUENCE: 32

Asp Pro Arg Phe Gln Asp Ser Ser Ser Lys Ala Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 33
<211> LENGTH: 28
<212> TYPE: PRT
<213> ORGANISM: Artificial Sequence
<220> FEATURE:
<223> OTHER INFORMATION: CTP peptide

<400> SEQUENCE: 33

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 34
<211> LENGTH: 6
<212> TYPE: PRT
<213> ORGANISM: Artificial Sequence
<220> FEATURE:
<223> OTHER INFORMATION: albumin binging protein
<220> FEATURE:
<221> NAME/KEY: VARIANT
<222> LOCATION: (2)..(2)
<223> OTHER INFORMATION: Xaa is Asp, Asn, Ser, Thr, or Trp
<220> FEATURE:
<221> NAME/KEY: VARIANT
<222> LOCATION: (3)..(3)
<223> OTHER INFORMATION: Xaa is Asn, Gln, H is, Ile, Leu, or Lys
<220> FEATURE:
<221> NAME/KEY: VARIANT
<222> LOCATION: (4)..(4)
<223> OTHER INFORMATION: Xaa is Ala, Asp, Phe, Trp, or Tyr
<220> FEATURE:
<221> NAME/KEY: VARIANT
<222> LOCATION: (5)..(5)
<223> OTHER INFORMATION: Xaa is Asp, Gly, Leu, Phe, Ser, or Thr

<400> SEQUENCE: 34

Cys Xaa Xaa Xaa Xaa Cys
1               5

<210> SEQ ID NO 35
<211> LENGTH: 11
<212> TYPE: PRT
<213> ORGANISM: Artificial Sequence
<220> FEATURE:
<223> OTHER INFORMATION: albumin binding peptide

<400> SEQUENCE: 35

Asp Ile Cys Leu Pro Arg Trp Gly Cys Leu Trp
1               5                   10

<210> SEQ ID NO 36
<211> LENGTH: 20
<212> TYPE: PRT
<213> ORGANISM: Artificial Sequence
<220> FEATURE:
<223> OTHER INFORMATION: PAS sequence

<400> SEQUENCE: 36

Ala Ser Pro Ala Ala Pro Ala Pro Ala Ser Pro Ala Ala Pro Ala Pro
1               5                   10                  15
```

Ser Ala Pro Ala
            20

<210> SEQ ID NO 37
<211> LENGTH: 20
<212> TYPE: PRT
<213> ORGANISM: Artificial Sequence
<220> FEATURE:
<223> OTHER INFORMATION: PAS sequence

<400> SEQUENCE: 37

Ala Ala Pro Ala Ser Pro Ala Pro Ala Ala Pro Ser Ala Pro Ala Pro
1               5                   10                  15

Ala Ala Pro Ser
            20

<210> SEQ ID NO 38
<211> LENGTH: 20
<212> TYPE: PRT
<213> ORGANISM: Artificial Sequence
<220> FEATURE:
<223> OTHER INFORMATION: PAS sequence

<400> SEQUENCE: 38

Ala Pro Ser Ser Pro Ser Pro Ser Ala Pro Ser Ser Pro Ser Pro Ala
1               5                   10                  15

Ser Pro Ser Ser
            20

<210> SEQ ID NO 39
<211> LENGTH: 19
<212> TYPE: PRT
<213> ORGANISM: Artificial Sequence
<220> FEATURE:
<223> OTHER INFORMATION: PAS sequence

<400> SEQUENCE: 39

Ala Pro Ser Ser Pro Ser Pro Ser Ala Pro Ser Ser Pro Ser Pro Ala
1               5                   10                  15

Ser Pro Ser

<210> SEQ ID NO 40
<211> LENGTH: 20
<212> TYPE: PRT
<213> ORGANISM: Artificial Sequence
<220> FEATURE:
<223> OTHER INFORMATION: PAS sequence

<400> SEQUENCE: 40

Ser Ser Pro Ser Ala Pro Ser Pro Ser Ser Pro Ala Ser Pro Ser Pro
1               5                   10                  15

Ser Ser Pro Ala
            20

<210> SEQ ID NO 41
<211> LENGTH: 24
<212> TYPE: PRT
<213> ORGANISM: Artificial Sequence
<220> FEATURE:
<223> OTHER INFORMATION: PAS sequence

<400> SEQUENCE: 41

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 42
<211> LENGTH: 20
<212> TYPE: PRT
<213> ORGANISM: Artificial Sequence
<220> FEATURE:
<223> OTHER INFORMATION: PAS sequence

<400> SEQUENCE: 42

Ala Ser Ala Ala Ala Pro Ala Ala Ala Ser Ala Ala Ala Ser Ala Pro
1               5                   10                  15

Ser Ala Ala Ala
            20

<210> SEQ ID NO 43
<211> LENGTH: 10
<212> TYPE: PRT
<213> ORGANISM: Artificial Sequence
<220> FEATURE:
<223> OTHER INFORMATION: gly-ser linker

<400> SEQUENCE: 43

Gly Gly Gly Ser Ser Gly Gly Gly Ser Gly
1               5                   10

<210> SEQ ID NO 44
<211> LENGTH: 3660
<212> TYPE: DNA
<213> ORGANISM: Homo sapiens

<400> SEQUENCE: 44

```
aagcttgccg ccaccatggt ctcccaggcc ctcaggctcc tctgccttct gcttgggctt    60
cagggctgcc tggctgcagt cttcgtaacc caggaggaag cccacggcgt cctgcaccgg   120
cgccggcgcg ccaacgcgtt cctggaggag ctgcggccgg gctccctgga gagggagtgc   180
aaggaggagc agtgctcctt cgaggaggcc cgggagatct tcaaggacgc ggagaggacg   240
aagctgttct ggatttctta cagtgatggg gaccagtgtg cctcaagtcc atgccagaat   300
gggggctcct gcaaggacca gctccagtcc tatatctgct tctgcctccc tgccttcgag   360
ggccggaact gtgagacgca caaggatgac cagctgatct gtgtgaacga aaccggcggc   420
tgtgagcagt actgcagtga ccacacgggc accaagcgct cctgtcggtg ccacgagggg   480
tactctctgc tggcagacgg ggtgtcctgc acccacagtt gaatatcc atgtggaaaa   540 atacctattc tagaaaaaag aaatgccagc aaaccccaag gcgccctgcg gccccggatt   600 gtgggggca aggtgtgccc caaagggag tgtccatggc aggtcctgtt gttggtgaat   660
ggagctcagt tgtgtggggg gaccctgatc aacaccatct gggtggtctc cgcggcccac   720
tgtttcgaca aaatcaagaa ctggaggaac ctgatcgcgg tgctgggcga gcacgacctc   780
agcgagcacg acggggatga gcagagccgg cgggtggcgc aggtcatcat ccccagcacg   840
tacgtcccgg gcaccaccaa ccacgacatc gcgctgctcc gcctgcacca gcccgtggtc   900
ctcactgacc atgtggtgcc cctctgcctg cccgaacgga cgttctctga aggacgctgc   960
gccttcgtgc gcttctcatt ggtcagcggc tgggccagc tgctggaccg tgcgccacg  1020 gccctggagc tcatggtcct caacgtgccc cggctgatga cccaggactg cctgcagcag  1080
tcacggaagg tgggagactc cccaaatatc acggagtaca tgttctgtgc cggctactcg  1140
```

```
gatggcagca aggactcctg caaggqggac agtggaggcc acatgccac ccactaccgg    1200
ggcacgtggt acctgacggg catcgtcagc tggggccagg gctgcgcaac cgtgggccac    1260
tttggggtgt acaccagggt ctcccagtac atcgagtggc tgcaaaagct catgcgctca    1320
gagccacgcc caggagtcct cctgcgagcc ccatttcccg gtggcggtgg ctccggcgga    1380
ggtgggtccg gtggcggcgg atcaggtggg ggtggatcag gcggtggagg ttccggtggc    1440
gggggatccg acaaaactca cacatgccca ccgtgcccag ctccggaact cctgggagga    1500
ccgtcagtct tcctcttccc cccaaaaccc aaggacaccc tcatgatctc ccggacccct    1560
gaggtcacat gcgtggtggt ggacgtgagc cacgaagacc ctgaggtcaa gttcaactgg    1620
tacgtggacg gcgtggaggt gcataatgcc aagacaaagc cgcgggagga gcagtacaac    1680
agcacgtacc gtgtggtcag cgtcctcacc gtcctgcacc aggactggct gaatggcaag    1740
gagtacaagt gcaaggtctc caacaaagcc ctcccagccc ccatcgagaa aaccatctcc    1800
aaagccaaag gcagccccg agaaccacag gtgtacaccc tgcccccatc ccgggatgag    1860
ctgaccaaga accaggtcag cctgacctgc ctggtcaaag gcttctatcc cagcgacatc    1920
gccgtggagt gggagagcaa tgggcagccg gagaacaact acaagaccac gcctcccgtg    1980
ttggactccg acggctcctt cttcctctac agcaagctca ccgtcgacaa gagcaggtgg    2040
cagcagggga acgtcttctc atgctccgtg atgcatgagg ctctgcacaa ccactacacg    2100
cagaagagcc tctccctgtc tccgggtaaa cggcgccgcc ggagcggcgg tggaggttcc    2160
ggtggcggcg gatcaggtgg cggcggatca ggtggggtg gatcaggtgg cggggatcc    2220
aggaagagga ggaagaggtc aggcactaca aatactgtgg cagcatataa tttaacttgg    2280
aaatcaacta atttcaagac aattttggag tgggaaccca acccgtcaa tcaagtctac    2340
actgttcaaa taagcactaa gtcaggagat tggaaaagca aatgctttta cacaacagac    2400
acagagtgtg acctcaccga cgagattgtg aaggatgtga agcagacgta cttggcacgg    2460
gtcttctcct acccggcagg gaatgtggag agcaccggtt ctgctgggga gcctctgtat    2520
gagaactccc cagagttcac accttacctg agacaaaacc tcggacagcc aacaattcag    2580
agttttgaac aggtgggaac aaaagtgaat gtgaccgtag aagatgaacg gactttagtc    2640
agaaggaaca cactttcct aagcctccgg gatgtttttg gcaaggactt aatttataca    2700
ctttattatt ggaaatcttc aagttcagga agaaaacag ccaaaacaaa cactaatgag    2760
tttttgattg atgtggataa aggagaaaac tactgttca gtgttcaagc agtgattccc    2820
tcccgaacag ttaaccggaa gagtacagac agcccggtag agtgtatggg ccaggagaaa    2880
ggggaattca gagaaggtgg cggcggatca ggtggggtg gatcaggcgg tggaggttcc    2940
ggtggcggcg gatcaggtgg cggcggatca ggtggggtg gatcaggtgg cggcggatca    3000
ggtggcgggg atcagacaa aactcacaca tgcccaccgt gcccagcacc ggaactcctg    3060
ggcggaccgt cagtcttcct cttcccccca aaacccaagg acacctcat gatctcccgg    3120
accccctgagg tcacatgcgt ggtggtgac gtgagccacg aagaccctga ggtcaagttc    3180
aactggtacg tggacggcgt ggaggtgcat aatgccaaga caaagccgcg ggaggagcag    3240
tacaacagca cgtaccgtgt ggtcagcgtc ctcaccgtcc tgcaccagga ctggctgaat    3300
ggcaaggagt acaagtgcaa ggtctccaac aaagccctcc cagcccccat cgagaaaacc    3360
atctccaaag ccaaagggca gccccgagaa ccacaggtgt acaccctgcc cccatcccgg    3420
gatgagctga ccaagaacca ggtcagcctg acctgcctgg tcaaaggctt ctatcccagc    3480
gacatcgccg tggagtggga gagcaatggg cagccggaga acaactacaa gaccacgcct    3540
```

```
cccgtgttgg actccgacgg ctccttcttc ctctacagca agctcaccgt ggacaagagc    3600
aggtggcagc aggggaacgt cttctcatgc tccgtgatgc atgaggctct gcacaaccac    3660
```

<210> SEQ ID NO 45
<211> LENGTH: 1227
<212> TYPE: PRT
<213> ORGANISM: Homo sapiens

<400> SEQUENCE: 45

| Met | Val | Ser | Gln | Ala | Leu | Arg | Leu | Leu | Cys | Leu | Leu | Leu | Gly | Leu | Gln |
|---|---|---|---|---|---|---|---|---|---|---|---|---|---|---|---|
| 1 | | | | 5 | | | | | 10 | | | | | 15 | |

| Gly | Cys | Leu | Ala | Ala | Val | Phe | Val | Thr | Gln | Glu | Glu | Ala | His | Gly | Val |
|---|---|---|---|---|---|---|---|---|---|---|---|---|---|---|---|
| | | | 20 | | | | | 25 | | | | | 30 | | |

| Leu | His | Arg | Arg | Arg | Ala | Asn | Ala | Phe | Leu | Glu | Glu | Leu | Arg | Pro |
|---|---|---|---|---|---|---|---|---|---|---|---|---|---|---|
| | | 35 | | | | | 40 | | | | | 45 | | |

| Gly | Ser | Leu | Glu | Arg | Glu | Cys | Lys | Glu | Glu | Gln | Cys | Ser | Phe | Glu | Glu |
|---|---|---|---|---|---|---|---|---|---|---|---|---|---|---|---|
| | 50 | | | | | 55 | | | | | 60 | | | | |

| Ala | Arg | Glu | Ile | Phe | Lys | Asp | Ala | Glu | Arg | Thr | Lys | Leu | Phe | Trp | Ile |
|---|---|---|---|---|---|---|---|---|---|---|---|---|---|---|---|
| 65 | | | | | 70 | | | | | 75 | | | | | 80 |

| Ser | Tyr | Ser | Asp | Gly | Asp | Gln | Cys | Ala | Ser | Pro | Cys | Gln | Asn | Gly |
|---|---|---|---|---|---|---|---|---|---|---|---|---|---|---|
| | | | | 85 | | | | | 90 | | | | | 95 |

| Gly | Ser | Cys | Lys | Asp | Gln | Leu | Gln | Ser | Tyr | Ile | Cys | Phe | Cys | Leu | Pro |
|---|---|---|---|---|---|---|---|---|---|---|---|---|---|---|---|
| | | | 100 | | | | | 105 | | | | | 110 | | |

| Ala | Phe | Glu | Gly | Arg | Asn | Cys | Glu | Thr | His | Lys | Asp | Asp | Gln | Leu | Ile |
|---|---|---|---|---|---|---|---|---|---|---|---|---|---|---|---|
| | | 115 | | | | | 120 | | | | | 125 | | | |

| Cys | Val | Asn | Glu | Asn | Gly | Gly | Cys | Glu | Gln | Tyr | Cys | Ser | Asp | His | Thr |
|---|---|---|---|---|---|---|---|---|---|---|---|---|---|---|---|
| | 130 | | | | | 135 | | | | | 140 | | | | |

| Gly | Thr | Lys | Arg | Ser | Cys | Arg | Cys | His | Glu | Gly | Tyr | Ser | Leu | Leu | Ala |
|---|---|---|---|---|---|---|---|---|---|---|---|---|---|---|---|
| 145 | | | | | 150 | | | | | 155 | | | | | 160 |

| Asp | Gly | Val | Ser | Cys | Thr | Pro | Thr | Val | Glu | Tyr | Pro | Cys | Gly | Lys | Ile |
|---|---|---|---|---|---|---|---|---|---|---|---|---|---|---|---|
| | | | | 165 | | | | | 170 | | | | | 175 | |

| Pro | Ile | Leu | Glu | Lys | Arg | Asn | Ala | Ser | Lys | Pro | Gln | Gly | Ala | Leu | Arg |
|---|---|---|---|---|---|---|---|---|---|---|---|---|---|---|---|
| | | | | 180 | | | | | 185 | | | | | 190 | |

| Pro | Arg | Ile | Val | Gly | Gly | Lys | Val | Cys | Pro | Lys | Gly | Glu | Cys | Pro | Trp |
|---|---|---|---|---|---|---|---|---|---|---|---|---|---|---|---|
| | | 195 | | | | | 200 | | | | | 205 | | | |

| Gln | Val | Leu | Leu | Leu | Val | Asn | Gly | Ala | Gln | Leu | Cys | Gly | Gly | Thr | Leu |
|---|---|---|---|---|---|---|---|---|---|---|---|---|---|---|---|
| | 210 | | | | | 215 | | | | | 220 | | | | |

| Ile | Asn | Thr | Ile | Trp | Val | Val | Ser | Ala | Ala | His | Cys | Phe | Asp | Lys | Ile |
|---|---|---|---|---|---|---|---|---|---|---|---|---|---|---|---|
| 225 | | | | | 230 | | | | | 235 | | | | | 240 |

| Lys | Asn | Trp | Arg | Asn | Leu | Ile | Ala | Val | Leu | Gly | Glu | His | Asp | Leu | Ser |
|---|---|---|---|---|---|---|---|---|---|---|---|---|---|---|---|
| | | | | 245 | | | | | 250 | | | | | 255 | |

| Glu | His | Asp | Gly | Asp | Glu | Gln | Ser | Arg | Arg | Val | Ala | Gln | Val | Ile | Ile |
|---|---|---|---|---|---|---|---|---|---|---|---|---|---|---|---|
| | | | 260 | | | | | 265 | | | | | 270 | | |

| Pro | Ser | Thr | Tyr | Val | Pro | Gly | Thr | Thr | Asn | His | Asp | Ile | Ala | Leu | Leu |
|---|---|---|---|---|---|---|---|---|---|---|---|---|---|---|---|
| | | 275 | | | | | 280 | | | | | 285 | | | |

| Arg | Leu | His | Gln | Pro | Val | Val | Leu | Thr | Asp | His | Val | Val | Pro | Leu | Cys |
|---|---|---|---|---|---|---|---|---|---|---|---|---|---|---|---|
| | 290 | | | | | 295 | | | | | 300 | | | | |

| Leu | Pro | Glu | Arg | Thr | Phe | Ser | Glu | Arg | Thr | Leu | Ala | Phe | Val | Arg | Phe |
|---|---|---|---|---|---|---|---|---|---|---|---|---|---|---|---|
| 305 | | | | | 310 | | | | | 315 | | | | | 320 |

| Ser | Leu | Val | Ser | Gly | Trp | Gly | Gln | Leu | Leu | Asp | Arg | Gly | Ala | Thr | Ala |
|---|---|---|---|---|---|---|---|---|---|---|---|---|---|---|---|
| | | | | 325 | | | | | 330 | | | | | 335 | |

| Leu | Glu | Leu | Met | Val | Leu | Asn | Val | Pro | Arg | Leu | Met | Thr | Gln | Asp | Cys |
|---|---|---|---|---|---|---|---|---|---|---|---|---|---|---|---|
| | | | 340 | | | | | 345 | | | | | 350 | | |

```
Leu Gln Gln Ser Arg Lys Val Gly Asp Ser Pro Asn Ile Thr Glu Tyr
            355                 360                 365
Met Phe Cys Ala Gly Tyr Ser Asp Gly Ser Lys Asp Ser Cys Lys Gly
    370                 375                 380
Asp Ser Gly Gly Pro His Ala Thr His Tyr Arg Gly Thr Trp Tyr Leu
385                 390                 395                 400
Thr Gly Ile Val Ser Trp Gly Gln Gly Cys Ala Thr Val Gly His Phe
                405                 410                 415
Gly Val Tyr Thr Arg Val Ser Gln Tyr Ile Glu Trp Leu Gln Lys Leu
            420                 425                 430
Met Arg Ser Glu Pro Arg Pro Gly Val Leu Leu Arg Ala Pro Phe Pro
    435                 440                 445
Gly Gly Gly Gly Ser Gly Gly Gly Ser Gly Gly Gly Ser Gly
450                 455                 460
Gly Gly Gly Ser Gly Gly Gly Ser Gly Gly Gly Ser Asp Lys
465                 470                 475                 480
Thr His Thr Cys Pro Pro Cys Pro Ala Pro Glu Leu Leu Gly Gly Pro
                485                 490                 495
Ser Val Phe Leu Phe Pro Pro Lys Pro Lys Asp Thr Leu Met Ile Ser
            500                 505                 510
Arg Thr Pro Glu Val Thr Cys Val Val Val Asp Val Ser His Glu Asp
        515                 520                 525
Pro Glu Val Lys Phe Asn Trp Tyr Val Asp Gly Val Glu Val His Asn
    530                 535                 540
Ala Lys Thr Lys Pro Arg Glu Glu Gln Tyr Asn Ser Thr Tyr Arg Val
545                 550                 555                 560
Val Ser Val Leu Thr Val Leu His Gln Asp Trp Leu Asn Gly Lys Glu
                565                 570                 575
Tyr Lys Cys Lys Val Ser Asn Lys Ala Leu Pro Ala Pro Ile Glu Lys
            580                 585                 590
Thr Ile Ser Lys Ala Lys Gly Gln Pro Arg Glu Pro Gln Val Tyr Thr
        595                 600                 605
Leu Pro Pro Ser Arg Asp Glu Leu Thr Lys Asn Gln Val Ser Leu Thr
    610                 615                 620
Cys Leu Val Lys Gly Phe Tyr Pro Ser Asp Ile Ala Val Glu Trp Glu
625                 630                 635                 640
Ser Asn Gly Gln Pro Glu Asn Asn Tyr Lys Thr Thr Pro Pro Val Leu
                645                 650                 655
Asp Ser Asp Gly Ser Phe Phe Leu Tyr Ser Lys Leu Thr Val Asp Lys
            660                 665                 670
Ser Arg Trp Gln Gln Gly Asn Val Phe Ser Cys Ser Val Met His Glu
        675                 680                 685
Ala Leu His Asn His Tyr Thr Gln Lys Ser Leu Ser Leu Ser Pro Gly
    690                 695                 700
Lys Arg Arg Arg Ser Gly Gly Gly Ser Gly Gly Gly Gly Ser
705                 710                 715                 720
Gly Gly Gly Gly Ser Gly Gly Gly Gly Ser Gly Gly Gly Ser Arg
                725                 730                 735
Lys Arg Arg Lys Arg Ser Gly Thr Thr Asn Thr Val Ala Ala Tyr Asn
            740                 745                 750
Leu Thr Trp Lys Ser Thr Asn Phe Lys Thr Ile Leu Glu Trp Glu Pro
        755                 760                 765
Lys Pro Val Asn Gln Val Tyr Thr Val Gln Ile Ser Thr Lys Ser Gly
```

```
              770             775             780
Asp Trp Lys Ser Lys Cys Phe Tyr Thr Thr Asp Thr Glu Cys Asp Leu
785             790             795             800

Thr Asp Glu Ile Val Lys Asp Val Lys Gln Thr Tyr Leu Ala Arg Val
            805             810             815

Phe Ser Tyr Pro Ala Gly Asn Val Glu Ser Thr Gly Ser Ala Gly Glu
            820             825             830

Pro Leu Tyr Glu Asn Ser Pro Glu Phe Thr Pro Tyr Leu Glu Thr Asn
            835             840             845

Leu Gly Gln Pro Thr Ile Gln Ser Phe Glu Gln Val Gly Thr Lys Val
            850             855             860

Asn Val Thr Val Glu Asp Glu Arg Thr Leu Val Arg Arg Asn Asn Thr
865             870             875             880

Phe Leu Ser Leu Arg Asp Val Phe Gly Lys Asp Leu Ile Tyr Thr Leu
            885             890             895

Tyr Tyr Trp Lys Ser Ser Ser Gly Lys Lys Thr Ala Lys Thr Asn
            900             905             910

Thr Asn Glu Phe Leu Ile Asp Val Asp Lys Gly Glu Asn Tyr Cys Phe
            915             920             925

Ser Val Gln Ala Val Ile Pro Ser Arg Thr Val Asn Arg Lys Ser Thr
930             935             940

Asp Ser Pro Val Glu Cys Met Gly Gln Glu Lys Gly Glu Phe Arg Glu
945             950             955             960

Gly Gly Gly Gly Ser Gly Gly Gly Ser Gly Gly Gly Ser Gly
            965             970             975

Gly Gly Ser Gly Gly Gly Ser Gly Gly Gly Ser Gly Gly
            980             985             990

Gly Gly Ser Gly Gly Gly Ser Asp Lys Thr His Thr Cys Pro Pro
            995             1000            1005

Cys Pro Ala Pro Glu Leu Leu Gly Gly Pro Ser Val Phe Leu Phe
1010            1015            1020

Pro Pro Lys Pro Lys Asp Thr Leu Met Ile Ser Arg Thr Pro Glu
1025            1030            1035

Val Thr Cys Val Val Val Asp Val Ser His Glu Asp Pro Glu Val
1040            1045            1050

Lys Phe Asn Trp Tyr Val Asp Gly Val Glu Val His Asn Ala Lys
1055            1060            1065

Thr Lys Pro Arg Glu Glu Gln Tyr Asn Ser Thr Tyr Arg Val Val
1070            1075            1080

Ser Val Leu Thr Val Leu His Gln Asp Trp Leu Asn Gly Lys Glu
1085            1090            1095

Tyr Lys Cys Lys Val Ser Asn Lys Ala Leu Pro Ala Pro Ile Glu
1100            1105            1110

Lys Thr Ile Ser Lys Ala Lys Gly Gln Pro Arg Glu Pro Gln Val
1115            1120            1125

Tyr Thr Leu Pro Pro Ser Arg Asp Glu Leu Thr Lys Asn Gln Val
1130            1135            1140

Ser Leu Thr Cys Leu Val Lys Gly Phe Tyr Pro Ser Asp Ile Ala
1145            1150            1155

Val Glu Trp Glu Ser Asn Gly Gln Pro Glu Asn Asn Tyr Lys Thr
1160            1165            1170

Thr Pro Pro Val Leu Asp Ser Asp Gly Ser Phe Phe Leu Tyr Ser
1175            1180            1185
```

```
Lys Leu Thr Val Asp Lys Ser Arg Trp Gln Gln Gly Asn Val Phe
    1190            1195                1200

Ser Cys Ser Val Met His Glu Ala Leu His Asn His Tyr Thr Gln
    1205            1210                1215

Lys Ser Leu Ser Leu Ser Pro Gly Lys
    1220            1225

<210> SEQ ID NO 46
<211> LENGTH: 3699
<212> TYPE: DNA
<213> ORGANISM: Homo sapiens

<400> SEQUENCE: 46
aagcttgccg ccaccatggt ctcccaggcc ctcaggctcc tctgccttct gcttgggctt     60
cagggctgcc tggctgcagt cttcgtaacc caggaggaag cccacggcgt cctgcaccgg    120
cgccggcgcg ccaacgcgtt cctggaggag ctgcggccgg ctccctgga gagggagtgc     180 aaggaggagc agtgctcctt cgaggaggcc cgggagatct tcaaggacgc ggagaggacg    240
aagctgttct ggatttctta cagtgatggg gaccagtgtg cctcaagtcc atgccagaat    300
gggggctcct gcaaggacca gctccagtcc tatatctgct tctgcctccc tgccttcgag    360
ggccggaact gtgagacgca aaggatgac cagctgatct gtgtgaacga aacggcggc     420 tgtgagcagt actgcagtga ccacacgggg accaagcgct cctgtcggtg ccacgagggg    480
tactctctgc tggcagacgg ggtgtcctgc acacccacag ttgaatatcc atgtggaaaa    540
atacctattc tagaaaaaag aaatgccagc aaacccaag gcgccctgcg gcccgccatt    600 gtgggggca aggtgtgccc caaggggag tgtccatggc aggtcctgtt gttggtgaat     660
ggagctcagt tgtgtggggg gaccctgatc aacaccatct gggtggtctc cgcggcccac    720
tgtttcgaca aaatcaagaa ctggaggaac ctgatcgcgg tgctgggcga gcacgacctc    780
agcgagcacg acggggatga gcagagccgg cgggtggcgc aggtcatcat ccccagcacg    840
tacgtcccgg gcaccaccaa ccacgacatc gcgctgctcc gcctgcacca gcccgtggtc    900
ctcactgacc atgtggtgcc cctctgcctg cccgaacgga cgttctctga ggacgctg     960 gccttcgtgc gcttctcatt ggtcagcggc tggggccagc tgctggaccg tggcgccacg   1020
gccctggagc tcatggtcct caacgtgccc cggctgatga cccaggactg cctgcagcag   1080
tcacggaagg tgggagactc cccaaatatc acggagtaca tgttctgtgc cggctactcg   1140
gatggcagca aggactcctg caaggggac agtggaggcc acatgccac ccactaccgg    1200 ggcacgtggt acctgacggg catcgtcagc tggggccagg ctgcgcaac cgtgggccac    1260 tttgggtgt acaccagggt ctcccagtac atcgagtggc tgcaaaagct catgcgctca    1320
gagccacgcc caggagtcct cctgcgagcc ccatttcccg gtggcggtgg ctccggcgga   1380
ggtgggtccg gtggcggcgg atcaggtggg ggtggatcag gcggtggagg ttccggtggc   1440 ggggatccg acaaaactca cacatgccca ccgtgcccag ctccggaact cctgggagga   1500
ccgtcagtct tcctcttccc cccaaaaccc aaggacaccc tcatgatctc ccggacccct   1560
gaggtcacat gcgtggtggt ggacgtgagc cacgaagacc ctgaggtcaa gttcaactgg   1620
tacgtggacg gcgtggaggt gcataatgcc aagacaaagc cgcgggagga gcagtacaac   1680
agcacgtacc gtgtggtcag cgtcctcacc gtcctgcacc aggactggct gaatggcaag   1740
gagtacaagt gcaaggtctc caacaaagcc ctcccagccc ccatcgagaa aaccatctcc   1800
aaagccaaag ggcagccccg agaaccacag gtgtacaccc tgcccccatc ccgggatgag   1860
```

```
ctgaccaaga accaggtcag cctgacctgc ctggtcaaag gcttctatcc cagcgacatc      1920
gccgtggagt gggagagcaa tgggcagccg gagaacaact acaagaccac gcctcccgtg      1980
ttggactccg acggctcctt cttcctctac agcaagctca ccgtcgacaa gagcaggtgg      2040
cagcagggga acgtcttctc atgctccgtg atgcatgagg ctctgcacaa ccactacacg      2100
cagaagagcc tctccctgtc tccgggtaaa cggcgccgcc ggagcggcgg tggaggttcc      2160
ggtggcggcg gatcaggtgg cggcggatca ggtgggggtg gatcaggtgg cggggatcc       2220 aggaagagga ggaagaggtc aggcactaca atactgtgg cagcatataa tttaacttgg       2280
aaatcaacta atttcaagac aattttggag tgggaaccca aacccgtcaa tcaagtctac      2340
actgttcaaa taagcactaa gtcaggagat tggaaaagca atgcttttta cacaacagac      2400
acagagtgtg acctcaccga cgagattgtg aaggatgtga agcagacgta cttggcacgg      2460
gtcttctcct acccggcagg gaatgtggag agcaccggtt ctgctgggga gcctctgtat      2520
gagaactccc cagagttcac accttacctg gagacaaacc tcggacagcc aacaattcag      2580
agttttgaac aggtgggaac aaaagtgaat gtgaccgtag aagatgaacg gactttagtc      2640
agaaggaaca cactttcct aagcctccgg gatgtttttg caaggactt aatttataca       2700 ctttattatt ggaaatcttc aagttcagga agaaaacag ccaaaacaaa cactaatgag       2760
tttttgattg atgtggataa aggagaaaac tactgtttca gtgttcaagc agtgattccc      2820
tcccgaacag ttaaccggaa gagtacagac agcccggtag agtgtatggg ccaggagaaa      2880
ggggaattca gagaaggtgg cggcggatca ggtgggggtg gatcaggcgg tggaggttcc      2940
ggtggcggcg gatcaggtgg cggcggatca ggtgggggtg gatcaggtgg cggcggatca      3000
ggtggcgggg gatcagacaa aactcacaca tgcccaccgt gcccagcacc ggaactcctg      3060
ggcggaccgt cagtcttcct cttcccccca aaacccaagg acaccctcat gatctcccgg      3120
acccctgagg tcacatgcgt ggtggtggac gtgagccacg aagaccctga ggtcaagttc      3180
aactggtacg tggacggcgt ggaggtgcat aatgccaaga caaagccgcg ggaggagcag      3240
tacaacagca cgtaccgtgt ggtcagcgtc ctcaccgtcc tgcaccagga ctggctgaat      3300
ggcaaggagt acaagtgcaa ggtctccaac aaagccctcc cagcccccat cgagaaaacc      3360
atctccaaag ccaaagggca gccccgagaa ccacaggtgt acaccctgcc cccatcccgg      3420
gatgagctga ccaagaacca ggtcagcctg acctgcctgg tcaaaggctt ctatcccagc      3480
gacatcgccg tggagtggga gagcaatggg cagccggaga acaactacaa gaccacgcct      3540
cccgtgttgg actccgacgg ctccttcttc ctctacagca agctcaccgt ggacaagagc      3600
aggtggcagc aggggaacgt cttctcatgc tccgtgatgc atgaggctct gcacaaccac      3660
tacacgcaga gagcctctc cctgtctccg ggtaaatga                              3699
```

<210> SEQ ID NO 47
<211> LENGTH: 1227
<212> TYPE: PRT
<213> ORGANISM: Homo sapiens

<400> SEQUENCE: 47

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

```
Gly Ser Leu Glu Arg Glu Cys Lys Glu Glu Gln Cys Ser Phe Glu Glu
         50                  55                  60

Ala Arg Glu Ile Phe Lys Asp Ala Glu Arg Thr Lys Leu Phe Trp Ile
 65                  70                  75                  80

Ser Tyr Ser Asp Gly Asp Gln Cys Ala Ser Pro Cys Gln Asn Gly
                     85                  90                  95

Gly Ser Cys Lys Asp Gln Leu Gln Ser Tyr Ile Cys Phe Cys Leu Pro
                100                 105                 110

Ala Phe Glu Gly Arg Asn Cys Glu Thr His Lys Asp Gln Leu Ile
            115                 120                 125

Cys Val Asn Glu Asn Gly Gly Cys Glu Gln Tyr Cys Ser Asp His Thr
        130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Ala Leu Arg
                180                 185                 190

Pro Ala Ile Val Gly Gly Lys Val Cys Pro Lys Gly Glu Cys Pro Trp
            195                 200                 205

Gln Val Leu Leu Leu Val Asn Gly Ala Gln Leu Cys Gly Gly Thr Leu
    210                 215                 220

Ile Asn Thr Ile Trp Val Val Ser Ala Ala His Cys Phe Asp Lys Ile
225                 230                 235                 240

Lys Asn Trp Arg Asn Leu Ile Ala Val Leu Gly Glu His Asp Leu Ser
                245                 250                 255

Glu His Asp Gly Asp Glu Gln Ser Arg Arg Val Ala Gln Val Ile Ile
            260                 265                 270

Pro Ser Thr Tyr Val Pro Gly Thr Thr Asn His Asp Ile Ala Leu Leu
        275                 280                 285

Arg Leu His Gln Pro Val Val Leu Thr Asp His Val Val Pro Leu Cys
    290                 295                 300

Leu Pro Glu Arg Thr Phe Ser Glu Arg Thr Leu Ala Phe Val Arg Phe
305                 310                 315                 320

Ser Leu Val Ser Gly Trp Gly Gln Leu Leu Asp Arg Gly Ala Thr Ala
                325                 330                 335

Leu Glu Leu Met Val Leu Asn Val Pro Arg Leu Met Thr Gln Asp Cys
            340                 345                 350

Leu Gln Gln Ser Arg Lys Val Gly Asp Ser Pro Asn Ile Thr Glu Tyr
        355                 360                 365

Met Phe Cys Ala Gly Tyr Ser Asp Gly Ser Lys Asp Ser Cys Lys Gly
    370                 375                 380

Asp Ser Gly Gly Pro His Ala Thr His Tyr Arg Gly Thr Trp Tyr Leu
385                 390                 395                 400

Thr Gly Ile Val Ser Trp Gly Gln Gly Cys Ala Thr Val Gly His Phe
                405                 410                 415

Gly Val Tyr Thr Arg Val Ser Gln Tyr Ile Glu Trp Leu Gln Lys Leu
            420                 425                 430

Met Arg Ser Glu Pro Arg Pro Gly Val Leu Leu Arg Ala Pro Phe Pro
        435                 440                 445

Gly Gly Gly Gly Ser Gly Gly Gly Ser Gly Gly Gly Gly Ser Gly
    450                 455                 460
```

```
Gly Gly Gly Ser Gly Gly Gly Ser Gly Gly Gly Ser Asp Lys
465                 470                 475                 480

Thr His Thr Cys Pro Cys Pro Ala Pro Glu Leu Leu Gly Pro
            485                 490                 495

Ser Val Phe Leu Phe Pro Pro Lys Pro Lys Asp Thr Leu Met Ile Ser
                500                 505                 510

Arg Thr Pro Glu Val Thr Cys Val Val Val Asp Val Ser His Glu Asp
        515                 520                 525

Pro Glu Val Lys Phe Asn Trp Tyr Val Asp Gly Val Glu Val His Asn
    530                 535                 540

Ala Lys Thr Lys Pro Arg Glu Glu Gln Tyr Asn Ser Thr Tyr Arg Val
545                 550                 555                 560

Val Ser Val Leu Thr Val Leu His Gln Asp Trp Leu Asn Gly Lys Glu
                565                 570                 575

Tyr Lys Cys Lys Val Ser Asn Lys Ala Leu Pro Ala Pro Ile Glu Lys
            580                 585                 590

Thr Ile Ser Lys Ala Lys Gly Gln Pro Arg Glu Pro Gln Val Tyr Thr
        595                 600                 605

Leu Pro Pro Ser Arg Asp Glu Leu Thr Lys Asn Gln Val Ser Leu Thr
    610                 615                 620

Cys Leu Val Lys Gly Phe Tyr Pro Ser Asp Ile Ala Val Glu Trp Glu
625                 630                 635                 640

Ser Asn Gly Gln Pro Glu Asn Asn Tyr Lys Thr Thr Pro Pro Val Leu
                645                 650                 655

Asp Ser Asp Gly Ser Phe Phe Leu Tyr Ser Lys Leu Thr Val Asp Lys
            660                 665                 670

Ser Arg Trp Gln Gln Gly Asn Val Phe Ser Cys Ser Val Met His Glu
        675                 680                 685

Ala Leu His Asn His Tyr Thr Gln Lys Ser Leu Ser Leu Ser Pro Gly
    690                 695                 700

Lys Arg Arg Arg Ser Gly Gly Gly Ser Gly Gly Gly Ser
705                 710                 715                 720

Gly Gly Gly Gly Ser Gly Gly Gly Ser Gly Gly Gly Ser Arg
                725                 730                 735

Lys Arg Arg Lys Arg Ser Gly Thr Thr Asn Thr Val Ala Ala Tyr Asn
            740                 745                 750

Leu Thr Trp Lys Ser Thr Asn Phe Lys Thr Ile Leu Glu Trp Glu Pro
        755                 760                 765

Lys Pro Val Asn Gln Val Tyr Thr Val Gln Ile Ser Thr Lys Ser Gly
    770                 775                 780

Asp Trp Lys Ser Lys Cys Phe Tyr Thr Thr Asp Thr Glu Cys Asp Leu
785                 790                 795                 800

Thr Asp Glu Ile Val Lys Asp Val Lys Gln Thr Tyr Leu Ala Arg Val
                805                 810                 815

Phe Ser Tyr Pro Ala Gly Asn Val Glu Ser Thr Gly Ser Ala Gly Glu
            820                 825                 830

Pro Leu Tyr Glu Asn Ser Pro Glu Phe Thr Pro Tyr Leu Glu Thr Asn
        835                 840                 845

Leu Gly Gln Pro Thr Ile Gln Ser Phe Glu Gln Val Gly Thr Lys Val
    850                 855                 860

Asn Val Thr Val Glu Asp Glu Arg Thr Leu Val Arg Arg Asn Asn Thr
865                 870                 875                 880

Phe Leu Ser Leu Arg Asp Val Phe Gly Lys Asp Leu Ile Tyr Thr Leu
```

```
                    885             890              895
Tyr Tyr Trp Lys Ser Ser Ser Gly Lys Lys Thr Ala Lys Thr Asn
                900             905              910
Thr Asn Glu Phe Leu Ile Asp Val Asp Lys Gly Glu Asn Tyr Cys Phe
                915             920              925
Ser Val Gln Ala Val Ile Pro Ser Arg Thr Val Asn Arg Lys Ser Thr
        930             935              940
Asp Ser Pro Val Glu Cys Met Gly Gln Glu Lys Gly Glu Phe Arg Glu
945             950              955              960
Gly Gly Gly Gly Ser Gly Gly Gly Ser Gly Gly Gly Ser Gly
                965             970              975
Gly Gly Ser Gly Gly Gly Ser Gly Gly Gly Ser Gly Gly
            980             985              990
Gly Gly Ser Gly Gly Gly Ser  Asp Lys Thr His Thr Cys Pro Pro
            995            1000             1005
Cys Pro  Ala Pro Glu Leu Leu  Gly Gly Pro Ser Val  Phe Leu Phe
    1010             1015             1020
Pro Pro  Lys Pro Lys Asp Thr  Leu Met Ile Ser Arg  Thr Pro Glu
    1025             1030             1035
Val Thr  Cys Val Val Val Asp  Val Ser His Glu Asp  Pro Glu Val
    1040             1045             1050
Lys Phe  Asn Trp Tyr Val Asp  Gly Val Glu Val His  Asn Ala Lys
    1055             1060             1065
Thr Lys  Pro Arg Glu Glu Gln  Tyr Asn Ser Thr Tyr  Arg Val Val
    1070             1075             1080
Ser Val  Leu Thr Val Leu His  Gln Asp Trp Leu Asn  Gly Lys Glu
    1085             1090             1095
Tyr Lys  Cys Lys Val Ser Asn  Lys Ala Leu Pro Ala  Pro Ile Glu
    1100             1105             1110
Lys Thr  Ile Ser Lys Ala Lys  Gly Gln Pro Arg Glu  Pro Gln Val
    1115             1120             1125
Tyr Thr  Leu Pro Pro Ser Arg  Asp Glu Leu Thr Lys  Asn Gln Val
    1130             1135             1140
Ser Leu  Thr Cys Leu Val Lys  Gly Phe Tyr Pro Ser  Asp Ile Ala
    1145             1150             1155
Val Glu  Trp Glu Ser Asn Gly  Gln Pro Glu Asn Asn  Tyr Lys Thr
    1160             1165             1170
Thr Pro  Pro Val Leu Asp Ser  Asp Gly Ser Phe Phe  Leu Tyr Ser
    1175             1180             1185
Lys Leu  Thr Val Asp Lys Ser  Arg Trp Gln Gln Gly  Asn Val Phe
    1190             1195             1200
Ser Cys  Ser Val Met His Glu  Ala Leu His Asn His  Tyr Thr Gln
    1205             1210             1215
Lys Ser  Leu Ser Leu Ser Pro  Gly Lys
    1220             1225

<210> SEQ ID NO 48
<211> LENGTH: 264
<212> TYPE: PRT
<213> ORGANISM: Artificial Sequence
<220> FEATURE:
<223> OTHER INFORMATION: GFP protein

<400> SEQUENCE: 48

Met Ser Lys Gly Glu Glu Leu Phe Thr Gly Val Val Pro Ile Leu Val
```

-continued

```
               1               5                  10                 15
              Glu Leu Asp Gly Asp Val Asn Gly His Lys Phe Ser Val Ser Gly Glu
                              20                  25                 30
              Gly Glu Gly Asp Ala Thr Tyr Gly Lys Leu Thr Leu Lys Phe Ile Cys
                              35                  40                 45
              Thr Thr Gly Lys Leu Pro Val Pro Trp Pro Thr Leu Val Thr Thr Phe
                          50                  55                 60
              Gly Tyr Gly Val Gln Cys Phe Ala Arg Tyr Pro Asp His Met Lys Gln
              65                  70                  75                 80
              His Asp Phe Phe Lys Ser Ala Met Pro Glu Gly Tyr Val Gln Glu Arg
                              85                  90                 95
              Thr Ile Phe Phe Lys Asp Asp Gly Asn Tyr Lys Thr Arg Ala Glu Val
                              100                 105                110
              Lys Phe Glu Gly Asp Thr Leu Val Asn Arg Ile Glu Leu Lys Gly Ile
                              115                 120                125
              Asp Phe Lys Glu Asp Gly Asn Ile Leu Gly His Lys Leu Glu Tyr Asn
                              130                 135                140
              Tyr Asn Ser His Asn Val Tyr Ile Met Ala Asp Lys Gln Lys Asn Gly
              145                 150                 155                160
              Ile Lys Val Asn Phe Lys Ile Arg His Asn Ile Glu Asp Gly Ser Val
                                  165                 170                175
              Gln Leu Ala Asp His Tyr Gln Gln Asn Thr Pro Ile Gly Asp Gly Pro
                              180                 185                190
              Val Leu Leu Pro Asp Asn His Tyr Leu Ser Thr Gln Ser Ala Leu Ser
                              195                 200                205
              Lys Asp Pro Asn Glu Lys Arg Asp His Met Val Leu Leu Glu Phe Val
                              210                 215                220
              Thr Ala Ala Gly Ile Thr His Gly Met Asp Glu Leu Tyr Lys Ser Arg
              225                 230                 235                240
              Thr Ser Gly Ser Pro Gly Leu Gln Glu Phe Asp Ile Lys Leu Ile Asp
                              245                 250                255
              Thr Val Asp Leu Glu Ser Cys Asn
                              260

<210> SEQ ID NO 49
<211> LENGTH: 474
<212> TYPE: PRT
<213> ORGANISM: Homo sapiens

<400> SEQUENCE: 49

Asp Lys Thr His Thr Cys Pro Pro Cys Pro Ala Pro Glu Leu Leu Gly
              1               5                  10                 15
              Gly Pro Ser Val Phe Leu Phe Pro Pro Lys Pro Lys Asp Thr Leu Met
                              20                  25                 30
              Ile Ser Arg Thr Pro Glu Val Thr Cys Val Val Val Asp Val Ser His
                              35                  40                 45
              Glu Asp Pro Glu Val Lys Phe Asn Trp Tyr Val Asp Gly Val Glu Val
                          50                  55                 60
              His Asn Ala Lys Thr Lys Pro Arg Glu Glu Gln Tyr Asn Ser Thr Tyr
              65                  70                  75                 80
              Arg Val Val Ser Val Leu Thr Val Leu His Gln Asp Trp Leu Asn Gly
                              85                  90                 95
              Lys Glu Tyr Lys Cys Lys Val Ser Asn Lys Ala Leu Pro Ala Pro Ile
                              100                 105                110
```

```
Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
            210                 215                 220

Pro Gly Lys Gly Gly Gly Gly Ser Gly Gly Gly Gly Ser Gly Gly Gly
225                 230                 235                 240

Gly Ser Gly Gly Gly Gly Ser Asp Lys Thr His Thr Cys Pro Pro Cys
                245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Asp Glu
370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
                420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
            450                 455                 460

Gln Lys Ser Leu Ser Leu Ser Pro Gly Lys
465                 470

<210> SEQ ID NO 50
<211> LENGTH: 591
<212> TYPE: PRT
<213> ORGANISM: Homo sapiens

<400> SEQUENCE: 50

Arg Gly Val Phe Arg Arg Asp Ala His Lys Ser Glu Val Ala His Arg
1               5                   10                  15
```

-continued

Phe Lys Asp Leu Gly Glu Glu Asn Phe Lys Ala Leu Val Leu Ile Ala
              20                  25                  30
Phe Ala Gln Tyr Leu Gln Gln Cys Pro Phe Glu Asp His Val Lys Leu
          35                  40                  45
Val Asn Glu Val Thr Glu Phe Ala Lys Thr Cys Val Ala Asp Glu Ser
    50                  55                  60
Ala Glu Asn Cys Asp Lys Ser Leu His Thr Leu Phe Gly Asp Lys Leu
65                  70                  75                  80
Cys Thr Val Ala Thr Leu Arg Glu Thr Tyr Gly Glu Met Ala Asp Cys
                85                  90                  95
Cys Ala Lys Gln Glu Pro Glu Arg Asn Glu Cys Phe Leu Gln His Lys
            100                 105                 110
Asp Asp Asn Pro Asn Leu Pro Arg Leu Val Arg Pro Glu Val Asp Val
        115                 120                 125
Met Cys Thr Ala Phe His Asp Asn Glu Glu Thr Phe Leu Lys Lys Tyr
130                 135                 140
Leu Tyr Glu Ile Ala Arg Arg His Pro Tyr Phe Tyr Ala Pro Glu Leu
145                 150                 155                 160
Leu Phe Phe Ala Lys Arg Tyr Lys Ala Ala Phe Thr Glu Cys Cys Gln
                165                 170                 175
Ala Ala Asp Lys Ala Ala Cys Leu Leu Pro Lys Leu Asp Glu Leu Arg
            180                 185                 190
Asp Glu Gly Lys Ala Ser Ser Ala Lys Gln Arg Leu Lys Cys Ala Ser
        195                 200                 205
Leu Gln Lys Phe Gly Glu Arg Ala Phe Lys Ala Trp Ala Val Ala Arg
210                 215                 220
Leu Ser Gln Arg Phe Pro Lys Ala Glu Phe Ala Glu Val Ser Lys Leu
225                 230                 235                 240
Val Thr Asp Leu Thr Lys Val His Thr Glu Cys Cys His Gly Asp Leu
                245                 250                 255
Leu Glu Cys Ala Asp Asp Arg Ala Asp Leu Ala Lys Tyr Ile Cys Glu
            260                 265                 270
Asn Gln Asp Ser Ile Ser Ser Lys Leu Lys Glu Cys Cys Glu Lys Pro
        275                 280                 285
Leu Leu Glu Lys Ser His Cys Ile Ala Glu Val Glu Asn Asp Glu Met
290                 295                 300
Pro Ala Asp Leu Pro Ser Leu Ala Ala Asp Phe Val Glu Ser Lys Asp
305                 310                 315                 320
Val Cys Lys Asn Tyr Ala Glu Ala Lys Asp Val Phe Leu Gly Met Phe
                325                 330                 335
Leu Tyr Glu Tyr Ala Arg Arg His Pro Asp Tyr Ser Val Val Leu Leu
            340                 345                 350
Leu Arg Leu Ala Lys Thr Tyr Glu Thr Thr Leu Glu Lys Cys Cys Ala
        355                 360                 365
Ala Ala Asp Pro His Glu Cys Tyr Ala Lys Val Phe Asp Glu Phe Lys
370                 375                 380
Pro Leu Val Glu Glu Pro Gln Asn Leu Ile Lys Gln Asn Cys Glu Leu
385                 390                 395                 400
Phe Glu Gln Leu Gly Glu Tyr Lys Phe Gln Asn Ala Leu Leu Val Arg
                405                 410                 415
Tyr Thr Lys Lys Val Pro Gln Val Ser Thr Pro Thr Leu Val Glu Val
            420                 425                 430

Ser Arg Asn Leu Gly Lys Val Gly Ser Lys Cys Cys Lys His Pro Glu
         435                 440                 445

Ala Lys Arg Met Pro Cys Ala Glu Asp Tyr Leu Ser Val Val Leu Asn
450                 455                 460

Gln Leu Cys Val Leu His Glu Lys Thr Pro Val Ser Asp Arg Val Thr
465                 470                 475                 480

Lys Cys Cys Thr Glu Ser Leu Val Asn Arg Arg Pro Cys Phe Ser Ala
             485                 490                 495

Leu Glu Val Asp Glu Thr Tyr Val Pro Lys Glu Phe Asn Ala Glu Thr
             500                 505                 510

Phe Thr Phe His Ala Asp Ile Cys Thr Leu Ser Glu Lys Glu Arg Gln
         515                 520                 525

Ile Lys Lys Gln Thr Ala Leu Val Glu Leu Val Lys His Lys Pro Lys
530                 535                 540

Ala Thr Lys Glu Gln Leu Lys Ala Val Met Asp Asp Phe Ala Ala Phe
545                 550                 555                 560

Val Glu Lys Cys Cys Lys Ala Asp Asp Lys Glu Thr Cys Phe Ala Glu
             565                 570                 575

Glu Gly Lys Lys Leu Val Ala Ala Ser Gln Ala Ala Leu Gly Leu
             580                 585                 590

<210> SEQ ID NO 51
<211> LENGTH: 18
<212> TYPE: PRT
<213> ORGANISM: Artificial Sequence
<220> FEATURE:
<223> OTHER INFORMATION: Albumin binding peptide

<400> SEQUENCE: 51

Arg Leu Ile Glu Asp Ile Cys Leu Pro Arg Trp Gly Cys Leu Trp Glu
1               5                   10                  15

Asp Asp

<210> SEQ ID NO 52
<211> LENGTH: 20
<212> TYPE: PRT
<213> ORGANISM: Artificial Sequence
<220> FEATURE:
<223> OTHER INFORMATION: Albumin binding peptide

<400> SEQUENCE: 52

Gln Arg Leu Met Glu Asp Ile Cys Leu Pro Arg Trp Gly Cys Leu Trp
1               5                   10                  15

Glu Asp Asp Phe
             20

<210> SEQ ID NO 53
<211> LENGTH: 21
<212> TYPE: PRT
<213> ORGANISM: Artificial Sequence
<220> FEATURE:
<223> OTHER INFORMATION: Albumin binding peptide

<400> SEQUENCE: 53

Gln Gly Leu Ile Gly Asp Ile Cys Leu Pro Arg Trp Gly Cys Leu Trp
1               5                   10                  15

Gly Asp Ser Val Lys
             20

<210> SEQ ID NO 54

```
<211> LENGTH: 20
<212> TYPE: PRT
<213> ORGANISM: Artificial Sequence
<220> FEATURE:
<223> OTHER INFORMATION: Albumin binding peptide

<400> SEQUENCE: 54

Gly Glu Trp Trp Glu Asp Ile Cys Leu Pro Arg Trp Gly Cys Leu Trp
1               5                   10                  15

Glu Glu Glu Asp
            20

<210> SEQ ID NO 55
<211> LENGTH: 10
<212> TYPE: PRT
<213> ORGANISM: Artificial Sequence
<220> FEATURE:
<223> OTHER INFORMATION: cysteine-containing peptide

<400> SEQUENCE: 55

Gly Gly Gly Ser Gly Cys Gly Gly Gly Ser
1               5                   10

<210> SEQ ID NO 56
<211> LENGTH: 4544
<212> TYPE: PRT
<213> ORGANISM: Homo sapiens

<400> SEQUENCE: 56

Met Leu Thr Pro Pro Leu Leu Leu Leu Leu Pro Leu Leu Ser Ala Leu
1               5                   10                  15

Val Ala Ala Ala Ile Asp Ala Pro Lys Thr Cys Ser Pro Lys Gln Phe
                20                  25                  30

Ala Cys Arg Asp Gln Ile Thr Cys Ile Ser Lys Gly Trp Arg Cys Asp
            35                  40                  45

Gly Glu Arg Asp Cys Pro Asp Gly Ser Asp Glu Ala Pro Glu Ile Cys
        50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
                100                 105                 110

Gly Asn Cys Ser Arg Leu Gly Cys Gln His His Cys Val Pro Thr Leu
            115                 120                 125

Asp Gly Pro Thr Cys Tyr Cys Asn Ser Ser Phe Gln Leu Gln Ala Asp
        130                 135                 140

Gly Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
                180                 185                 190

Glu Pro Val Asp Arg Pro Pro Val Leu Leu Ile Ala Asn Ser Gln Asn
            195                 200                 205

Ile Leu Ala Thr Tyr Leu Ser Gly Ala Gln Val Ser Thr Ile Thr Pro
        210                 215                 220

Thr Ser Thr Arg Gln Thr Thr Ala Met Asp Phe Ser Tyr Ala Asn Glu
225                 230                 235                 240
```

-continued

Thr Val Cys Trp Val His Val Gly Asp Ser Ala Ala Gln Thr Gln Leu
            245                 250                 255

Lys Cys Ala Arg Met Pro Gly Leu Lys Gly Phe Val Asp Glu His Thr
            260                 265                 270

Ile Asn Ile Ser Leu Ser Leu His His Val Glu Gln Met Ala Ile Asp
            275                 280                 285

Trp Leu Thr Gly Asn Phe Tyr Phe Val Asp Asp Ile Asp Asp Arg Ile
            290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
            325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
            355                 360                 365

Pro His Gly Ile Thr Leu Asp Leu Val Ser Arg Leu Val Tyr Trp Ala
            370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
            405                 410                 415

Thr Val Phe Glu Asn Tyr Leu Tyr Ala Thr Asn Ser Asp Asn Ala Asn
            420                 425                 430

Ala Gln Lys Thr Ser Val Ile Arg Val Asn Arg Phe Asn Ser Thr
            435                 440                 445

Glu Tyr Gln Val Val Thr Arg Val Asp Lys Gly Gly Ala Leu His Ile
            450                 455                 460

Tyr His Gln Arg Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
            485                 490                 495

Asn Ser His Lys Ala Arg Thr Cys Arg Cys Arg Ser Gly Phe Ser Leu
            500                 505                 510

Gly Ser Asp Gly Lys Ser Cys Lys Lys Pro Glu His Glu Leu Phe Leu
            515                 520                 525

Val Tyr Gly Lys Gly Arg Pro Gly Ile Ile Arg Gly Met Asp Met Gly
            530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
            565                 570                 575

Asp Thr Thr Ser Tyr Leu Ile Gly Arg Gln Lys Ile Asp Gly Thr Glu
            580                 585                 590

Arg Glu Thr Ile Leu Lys Asp Gly Ile His Asn Val Glu Gly Val Ala
            595                 600                 605

Val Asp Trp Met Gly Asp Asn Leu Tyr Trp Thr Asp Asp Gly Pro Lys
            610                 615                 620

Lys Thr Ile Ser Val Ala Arg Leu Glu Lys Ala Ala Gln Thr Arg Lys
625                 630                 635                 640

Thr Leu Ile Glu Gly Lys Met Thr His Pro Arg Ala Ile Val Val Asp
            645                 650                 655

```
Pro Leu Asn Gly Trp Met Tyr Trp Thr Asp Trp Glu Glu Asp Pro Lys
            660                 665                 670

Asp Ser Arg Arg Gly Arg Leu Glu Arg Ala Trp Met Asp Gly Ser His
        675                 680                 685

Arg Asp Ile Phe Val Thr Ser Lys Thr Val Leu Trp Pro Asn Gly Leu
    690                 695                 700

Ser Leu Asp Ile Pro Ala Gly Arg Leu Tyr Trp Val Asp Ala Phe Tyr
705                 710                 715                 720

Asp Arg Ile Glu Thr Ile Leu Leu Asn Gly Thr Asp Arg Lys Ile Val
            725                 730                 735

Tyr Glu Gly Pro Glu Leu Asn His Ala Phe Gly Leu Cys His His Gly
        740                 745                 750

Asn Tyr Leu Phe Trp Thr Glu Tyr Arg Ser Gly Ser Val Tyr Arg Leu
    755                 760                 765

Glu Arg Gly Val Gly Gly Ala Pro Pro Thr Val Thr Leu Leu Arg Ser
770                 775                 780

Glu Arg Pro Pro Ile Phe Glu Ile Arg Met Tyr Asp Ala Gln Gln Gln
785                 790                 795                 800

Gln Val Gly Thr Asn Lys Cys Arg Val Asn Asn Gly Gly Cys Ser Ser
        805                 810                 815

Leu Cys Leu Ala Thr Pro Gly Ser Arg Gln Cys Ala Cys Ala Glu Asp
            820                 825                 830

Gln Val Leu Asp Ala Asp Gly Val Thr Cys Leu Ala Asn Pro Ser Tyr
        835                 840                 845

Val Pro Pro Pro Gln Cys Gln Pro Gly Glu Phe Ala Cys Ala Asn Ser
850                 855                 860

Arg Cys Ile Gln Glu Arg Trp Lys Cys Asp Gly Asp Asn Asp Cys Leu
865                 870                 875                 880

Asp Asn Ser Asp Glu Ala Pro Ala Leu Cys His Gln His Thr Cys Pro
        885                 890                 895

Ser Asp Arg Phe Lys Cys Glu Asn Asn Arg Cys Ile Pro Asn Arg Trp
            900                 905                 910

Leu Cys Asp Gly Asp Asn Asp Cys Gly Asn Ser Glu Asp Glu Ser Asn
        915                 920                 925

Ala Thr Cys Ser Ala Arg Thr Cys Pro Pro Asn Gln Phe Ser Cys Ala
930                 935                 940

Ser Gly Arg Cys Ile Pro Ile Ser Trp Thr Cys Asp Leu Asp Asp Asp
945                 950                 955                 960

Cys Gly Asp Arg Ser Asp Glu Ser Ala Ser Cys Ala Tyr Pro Thr Cys
        965                 970                 975

Phe Pro Leu Thr Gln Phe Thr Cys Asn Asn Gly Arg Cys Ile Asn Ile
            980                 985                 990

Asn Trp Arg Cys Asp Asn Asp Asn Asp Cys Gly Asp Asn Ser Asp Glu
        995                 1000                1005

Ala Gly Cys Ser His Ser Cys Ser Ser Thr Gln Phe Lys Cys Asn
    1010                1015                1020

Ser Gly Arg Cys Ile Pro Glu His Trp Thr Cys Asp Gly Asp Asn
    1025                1030                1035

Asp Cys Gly Asp Tyr Ser Asp Glu Thr His Ala Asn Cys Thr Asn
    1040                1045                1050

Gln Ala Thr Arg Pro Pro Gly Gly Cys His Thr Asp Glu Phe Gln
    1055                1060                1065

Cys Arg Leu Asp Gly Leu Cys Ile Pro Leu Arg Trp Arg Cys Asp
```

```
                1070                1075                1080
Gly Asp Thr Asp Cys Met Asp Ser Ser Asp Glu Lys Ser Cys Glu
    1085                1090                1095
Gly Val Thr His Val Cys Asp Pro Ser Val Lys Phe Gly Cys Lys
    1100                1105                1110
Asp Ser Ala Arg Cys Ile Ser Lys Ala Trp Val Cys Asp Gly Asp
    1115                1120                1125
Asn Asp Cys Glu Asp Asn Ser Asp Glu Glu Asn Cys Glu Ser Leu
    1130                1135                1140
Ala Cys Arg Pro Pro Ser His Pro Cys Ala Asn Asn Thr Ser Val
    1145                1150                1155
Cys Leu Pro Pro Asp Lys Leu Cys Asp Gly Asn Asp Asp Cys Gly
    1160                1165                1170
Asp Gly Ser Asp Glu Gly Glu Leu Cys Asp Gln Cys Ser Leu Asn
    1175                1180                1185
Asn Gly Gly Cys Ser His Asn Cys Ser Val Ala Pro Gly Glu Gly
    1190                1195                1200
Ile Val Cys Ser Cys Pro Leu Gly Met Glu Leu Gly Pro Asp Asn
    1205                1210                1215
His Thr Cys Gln Ile Gln Ser Tyr Cys Ala Lys His Leu Lys Cys
    1220                1225                1230
Ser Gln Lys Cys Asp Gln Asn Lys Phe Ser Val Lys Cys Ser Cys
    1235                1240                1245
Tyr Glu Gly Trp Val Leu Glu Pro Asp Gly Glu Ser Cys Arg Ser
    1250                1255                1260
Leu Asp Pro Phe Lys Pro Phe Ile Ile Phe Ser Asn Arg His Glu
    1265                1270                1275
Ile Arg Arg Ile Asp Leu His Lys Gly Asp Tyr Ser Val Leu Val
    1280                1285                1290
Pro Gly Leu Arg Asn Thr Ile Ala Leu Asp Phe His Leu Ser Gln
    1295                1300                1305
Ser Ala Leu Tyr Trp Thr Asp Val Val Glu Asp Lys Ile Tyr Arg
    1310                1315                1320
Gly Lys Leu Leu Asp Asn Gly Ala Leu Thr Ser Phe Glu Val Val
    1325                1330                1335
Ile Gln Tyr Gly Leu Ala Thr Pro Glu Gly Leu Ala Val Asp Trp
    1340                1345                1350
Ile Ala Gly Asn Ile Tyr Trp Val Glu Ser Asn Leu Asp Gln Ile
    1355                1360                1365
Glu Val Ala Lys Leu Asp Gly Thr Leu Arg Thr Thr Leu Leu Ala
    1370                1375                1380
Gly Asp Ile Glu His Pro Arg Ala Ile Ala Leu Asp Pro Arg Asp
    1385                1390                1395
Gly Ile Leu Phe Trp Thr Asp Trp Asp Ala Ser Leu Pro Arg Ile
    1400                1405                1410
Glu Ala Ala Ser Met Ser Gly Ala Gly Arg Arg Thr Val His Arg
    1415                1420                1425
Glu Thr Gly Ser Gly Gly Trp Pro Asn Gly Leu Thr Val Asp Tyr
    1430                1435                1440
Leu Glu Lys Arg Ile Leu Trp Ile Asp Ala Arg Ser Asp Ala Ile
    1445                1450                1455
Tyr Ser Ala Arg Tyr Asp Gly Ser Gly His Met Glu Val Leu Arg
    1460                1465                1470
```

```
Gly His Glu Phe Leu Ser His Pro Phe Ala Val Thr Leu Tyr Gly
1475                1480                1485

Gly Glu Val Tyr Trp Thr Asp Trp Arg Thr Asn Thr Leu Ala Lys
1490                1495                1500

Ala Asn Lys Trp Thr Gly His Asn Val Thr Val Gln Arg Thr
1505                1510                1515

Asn Thr Gln Pro Phe Asp Leu Gln Val Tyr His Pro Ser Arg Gln
1520                1525                1530

Pro Met Ala Pro Asn Pro Cys Glu Ala Asn Gly Gly Gln Gly Pro
1535                1540                1545

Cys Ser His Leu Cys Leu Ile Asn Tyr Asn Arg Thr Val Ser Cys
1550                1555                1560

Ala Cys Pro His Leu Met Lys Leu His Lys Asp Asn Thr Thr Cys
1565                1570                1575

Tyr Glu Phe Lys Lys Phe Leu Leu Tyr Ala Arg Gln Met Glu Ile
1580                1585                1590

Arg Gly Val Asp Leu Asp Ala Pro Tyr Tyr Asn Tyr Ile Ile Ser
1595                1600                1605

Phe Thr Val Pro Asp Ile Asp Asn Val Thr Val Leu Asp Tyr Asp
1610                1615                1620

Ala Arg Glu Gln Arg Val Tyr Trp Ser Asp Val Arg Thr Gln Ala
1625                1630                1635

Ile Lys Arg Ala Phe Ile Asn Gly Thr Gly Val Glu Thr Val Val
1640                1645                1650

Ser Ala Asp Leu Pro Asn Ala His Gly Leu Ala Val Asp Trp Val
1655                1660                1665

Ser Arg Asn Leu Phe Trp Thr Ser Tyr Asp Thr Asn Lys Lys Gln
1670                1675                1680

Ile Asn Val Ala Arg Leu Asp Gly Ser Phe Lys Asn Ala Val Val
1685                1690                1695

Gln Gly Leu Glu Gln Pro His Gly Leu Val Val His Pro Leu Arg
1700                1705                1710

Gly Lys Leu Tyr Trp Thr Asp Gly Asp Asn Ile Ser Met Ala Asn
1715                1720                1725

Met Asp Gly Ser Asn Arg Thr Leu Leu Phe Ser Gly Gln Lys Gly
1730                1735                1740

Pro Val Gly Leu Ala Ile Asp Phe Pro Glu Ser Lys Leu Tyr Trp
1745                1750                1755

Ile Ser Ser Gly Asn His Thr Ile Asn Arg Cys Asn Leu Asp Gly
1760                1765                1770

Ser Gly Leu Glu Val Ile Asp Ala Met Arg Ser Gln Leu Gly Lys
1775                1780                1785

Ala Thr Ala Leu Ala Ile Met Gly Asp Lys Leu Trp Trp Ala Asp
1790                1795                1800

Gln Val Ser Glu Lys Met Gly Thr Cys Ser Lys Ala Asp Gly Ser
1805                1810                1815

Gly Ser Val Val Leu Arg Asn Ser Thr Thr Leu Val Met His Met
1820                1825                1830

Lys Val Tyr Asp Glu Ser Ile Gln Leu Asp His Lys Gly Thr Asn
1835                1840                1845

Pro Cys Ser Val Asn Asn Gly Asp Cys Ser Gln Leu Cys Leu Pro
1850                1855                1860
```

```
Thr Ser Glu Thr Thr Arg Ser Cys Met Cys Thr Ala Gly Tyr Ser
    1865                1870                1875

Leu Arg Ser Gly Gln Gln Ala Cys Glu Gly Val Gly Ser Phe Leu
    1880                1885                1890

Leu Tyr Ser Val His Glu Gly Ile Arg Gly Ile Pro Leu Asp Pro
    1895                1900                1905

Asn Asp Lys Ser Asp Ala Leu Val Pro Val Ser Gly Thr Ser Leu
    1910                1915                1920

Ala Val Gly Ile Asp Phe His Ala Glu Asn Asp Thr Ile Tyr Trp
    1925                1930                1935

Val Asp Met Gly Leu Ser Thr Ile Ser Arg Ala Lys Arg Asp Gln
    1940                1945                1950

Thr Trp Arg Glu Asp Val Val Thr Asn Gly Ile Gly Arg Val Glu
    1955                1960                1965

Gly Ile Ala Val Asp Trp Ile Ala Gly Asn Ile Tyr Trp Thr Asp
    1970                1975                1980

Gln Gly Phe Asp Val Ile Glu Val Ala Arg Leu Asn Gly Ser Phe
    1985                1990                1995

Arg Tyr Val Val Ile Ser Gln Gly Leu Asp Lys Pro Arg Ala Ile
    2000                2005                2010

Thr Val His Pro Glu Lys Gly Tyr Leu Phe Trp Thr Glu Trp Gly
    2015                2020                2025

Gln Tyr Pro Arg Ile Glu Arg Ser Arg Leu Asp Gly Thr Glu Arg
    2030                2035                2040

Val Val Leu Val Asn Val Ser Ile Ser Trp Pro Asn Gly Ile Ser
    2045                2050                2055

Val Asp Tyr Gln Asp Gly Lys Leu Tyr Trp Cys Asp Ala Arg Thr
    2060                2065                2070

Asp Lys Ile Glu Arg Ile Asp Leu Glu Thr Gly Glu Asn Arg Glu
    2075                2080                2085

Val Val Leu Ser Ser Asn Asn Met Asp Met Phe Ser Val Ser Val
    2090                2095                2100

Phe Glu Asp Phe Ile Tyr Trp Ser Asp Arg Thr His Ala Asn Gly
    2105                2110                2115

Ser Ile Lys Arg Gly Ser Lys Asp Asn Ala Thr Asp Ser Val Pro
    2120                2125                2130

Leu Arg Thr Gly Ile Gly Val Gln Leu Lys Asp Ile Lys Val Phe
    2135                2140                2145

Asn Arg Asp Arg Gln Lys Gly Thr Asn Val Cys Ala Val Ala Asn
    2150                2155                2160

Gly Gly Cys Gln Gln Leu Cys Leu Tyr Arg Gly Arg Gly Gln Arg
    2165                2170                2175

Ala Cys Ala Cys Ala His Gly Met Leu Ala Glu Asp Gly Ala Ser
    2180                2185                2190

Cys Arg Glu Tyr Ala Gly Tyr Leu Leu Tyr Ser Glu Arg Thr Ile
    2195                2200                2205

Leu Lys Ser Ile His Leu Ser Asp Glu Arg Asn Leu Asn Ala Pro
    2210                2215                2220

Val Gln Pro Phe Glu Asp Pro Glu His Met Lys Asn Val Ile Ala
    2225                2230                2235

Leu Ala Phe Asp Tyr Arg Ala Gly Thr Ser Pro Gly Thr Pro Asn
    2240                2245                2250

Arg Ile Phe Phe Ser Asp Ile His Phe Gly Asn Ile Gln Gln Ile
```

```
                  2255                2260                2265
Asn Asp Asp Gly Ser Arg Arg Ile Thr Ile Val Glu Asn Val Gly
    2270                2275                2280

Ser Val Glu Gly Leu Ala Tyr His Arg Gly Trp Asp Thr Leu Tyr
    2285                2290                2295

Trp Thr Ser Tyr Thr Thr Ser Thr Ile Thr Arg His Thr Val Asp
    2300                2305                2310

Gln Thr Arg Pro Gly Ala Phe Glu Arg Glu Thr Val Ile Thr Met
    2315                2320                2325

Ser Gly Asp Asp His Pro Arg Ala Phe Val Leu Asp Glu Cys Gln
    2330                2335                2340

Asn Leu Met Phe Trp Thr Asn Trp Asn Glu Gln His Pro Ser Ile
    2345                2350                2355

Met Arg Ala Ala Leu Ser Gly Ala Asn Val Leu Thr Leu Ile Glu
    2360                2365                2370

Lys Asp Ile Arg Thr Pro Asn Gly Leu Ala Ile Asp His Arg Ala
    2375                2380                2385

Glu Lys Leu Tyr Phe Ser Asp Ala Thr Leu Asp Lys Ile Glu Arg
    2390                2395                2400

Cys Glu Tyr Asp Gly Ser His Arg Tyr Val Ile Leu Lys Ser Glu
    2405                2410                2415

Pro Val His Pro Phe Gly Leu Ala Val Tyr Gly Glu His Ile Phe
    2420                2425                2430

Trp Thr Asp Trp Val Arg Arg Ala Val Gln Arg Ala Asn Lys His
    2435                2440                2445

Val Gly Ser Asn Met Lys Leu Leu Arg Val Asp Ile Pro Gln Gln
    2450                2455                2460

Pro Met Gly Ile Ile Ala Val Ala Asn Asp Thr Asn Ser Cys Glu
    2465                2470                2475

Leu Ser Pro Cys Arg Ile Asn Asn Gly Gly Cys Gln Asp Leu Cys
    2480                2485                2490

Leu Leu Thr His Gln Gly His Val Asn Cys Ser Cys Arg Gly Gly
    2495                2500                2505

Arg Ile Leu Gln Asp Asp Leu Thr Cys Arg Ala Val Asn Ser Ser
    2510                2515                2520

Cys Arg Ala Gln Asp Glu Phe Glu Cys Ala Asn Gly Glu Cys Ile
    2525                2530                2535

Asn Phe Ser Leu Thr Cys Asp Gly Val Pro His Cys Lys Asp Lys
    2540                2545                2550

Ser Asp Glu Lys Pro Ser Tyr Cys Asn Ser Arg Arg Cys Lys Lys
    2555                2560                2565

Thr Phe Arg Gln Cys Ser Asn Gly Arg Cys Val Ser Asn Met Leu
    2570                2575                2580

Trp Cys Asn Gly Ala Asp Asp Cys Gly Asp Gly Ser Asp Glu Ile
    2585                2590                2595

Pro Cys Asn Lys Thr Ala Cys Gly Val Gly Glu Phe Arg Cys Arg
    2600                2605                2610

Asp Gly Thr Cys Ile Gly Asn Ser Ser Arg Cys Asn Gln Phe Val
    2615                2620                2625

Asp Cys Glu Asp Ala Ser Asp Glu Met Asn Cys Ser Ala Thr Asp
    2630                2635                2640

Cys Ser Ser Tyr Phe Arg Leu Gly Val Lys Gly Val Leu Phe Gln
    2645                2650                2655
```

-continued

Pro Cys Glu Arg Thr Ser Leu Cys Tyr Ala Pro Ser Trp Val Cys
2660                    2665                2670

Asp Gly Ala Asn Asp Cys Gly Asp Tyr Ser Asp Glu Arg Asp Cys
2675                    2680                2685

Pro Gly Val Lys Arg Pro Arg Cys Pro Leu Asn Tyr Phe Ala Cys
2690                    2695                2700

Pro Ser Gly Arg Cys Ile Pro Met Ser Trp Thr Cys Asp Lys Glu
2705                    2710                2715

Asp Asp Cys Glu His Gly Glu Asp Glu Thr His Cys Asn Lys Phe
2720                    2725                2730

Cys Ser Glu Ala Gln Phe Glu Cys Gln Asn His Arg Cys Ile Ser
2735                    2740                2745

Lys Gln Trp Leu Cys Asp Gly Ser Asp Asp Cys Gly Asp Gly Ser
2750                    2755                2760

Asp Glu Ala Ala His Cys Glu Gly Lys Thr Cys Gly Pro Ser Ser
2765                    2770                2775

Phe Ser Cys Pro Gly Thr His Val Cys Val Pro Glu Arg Trp Leu
2780                    2785                2790

Cys Asp Gly Asp Lys Asp Cys Ala Asp Gly Ala Asp Glu Ser Ile
2795                    2800                2805

Ala Ala Gly Cys Leu Tyr Asn Ser Thr Cys Asp Asp Arg Glu Phe
2810                    2815                2820

Met Cys Gln Asn Arg Gln Cys Ile Pro Lys His Phe Val Cys Asp
2825                    2830                2835

His Asp Arg Asp Cys Ala Asp Gly Ser Asp Glu Ser Pro Glu Cys
2840                    2845                2850

Glu Tyr Pro Thr Cys Gly Pro Ser Glu Phe Arg Cys Ala Asn Gly
2855                    2860                2865

Arg Cys Leu Ser Ser Arg Gln Trp Glu Cys Asp Gly Glu Asn Asp
2870                    2875                2880

Cys His Asp Gln Ser Asp Glu Ala Pro Lys Asn Pro His Cys Thr
2885                    2890                2895

Ser Pro Glu His Lys Cys Asn Ala Ser Ser Gln Phe Leu Cys Ser
2900                    2905                2910

Ser Gly Arg Cys Val Ala Glu Ala Leu Leu Cys Asn Gly Gln Asp
2915                    2920                2925

Asp Cys Gly Asp Ser Ser Asp Glu Arg Gly Cys His Ile Asn Glu
2930                    2935                2940

Cys Leu Ser Arg Lys Leu Ser Gly Cys Ser Gln Asp Cys Glu Asp
2945                    2950                2955

Leu Lys Ile Gly Phe Lys Cys Arg Cys Arg Pro Gly Phe Arg Leu
2960                    2965                2970

Lys Asp Asp Gly Arg Thr Cys Ala Asp Val Asp Glu Cys Ser Thr
2975                    2980                2985

Thr Phe Pro Cys Ser Gln Arg Cys Ile Asn Thr His Gly Ser Tyr
2990                    2995                3000

Lys Cys Leu Cys Val Glu Gly Tyr Ala Pro Arg Gly Gly Asp Pro
3005                    3010                3015

His Ser Cys Lys Ala Val Thr Asp Glu Glu Pro Phe Leu Ile Phe
3020                    3025                3030

Ala Asn Arg Tyr Tyr Leu Arg Lys Leu Asn Leu Asp Gly Ser Asn
3035                    3040                3045

```
Tyr Thr Leu Leu Lys Gln Gly Leu Asn Asn Ala Val Ala Leu Asp
    3050            3055            3060

Phe Asp Tyr Arg Glu Gln Met Ile Tyr Trp Thr Asp Val Thr Thr
    3065            3070            3075

Gln Gly Ser Met Ile Arg Arg Met His Leu Asn Gly Ser Asn Val
    3080            3085            3090

Gln Val Leu His Arg Thr Gly Leu Ser Asn Pro Asp Gly Leu Ala
    3095            3100            3105

Val Asp Trp Val Gly Gly Asn Leu Tyr Trp Cys Asp Lys Gly Arg
    3110            3115            3120

Asp Thr Ile Glu Val Ser Lys Leu Asn Gly Ala Tyr Arg Thr Val
    3125            3130            3135

Leu Val Ser Ser Gly Leu Arg Glu Pro Arg Ala Leu Val Val Asp
    3140            3145            3150

Val Gln Asn Gly Tyr Leu Tyr Trp Thr Asp Trp Gly Asp His Ser
    3155            3160            3165

Leu Ile Gly Arg Ile Gly Met Asp Gly Ser Ser Arg Ser Val Ile
    3170            3175            3180

Val Asp Thr Lys Ile Thr Trp Pro Asn Gly Leu Thr Leu Asp Tyr
    3185            3190            3195

Val Thr Glu Arg Ile Tyr Trp Ala Asp Ala Arg Glu Asp Tyr Ile
    3200            3205            3210

Glu Phe Ala Ser Leu Asp Gly Ser Asn Arg His Val Val Leu Ser
    3215            3220            3225

Gln Asp Ile Pro His Ile Phe Ala Leu Thr Leu Phe Glu Asp Tyr
    3230            3235            3240

Val Tyr Trp Thr Asp Trp Glu Thr Lys Ser Ile Asn Arg Ala His
    3245            3250            3255

Lys Thr Thr Gly Thr Asn Lys Thr Leu Leu Ile Ser Thr Leu His
    3260            3265            3270

Arg Pro Met Asp Leu His Val Phe His Ala Leu Arg Gln Pro Asp
    3275            3280            3285

Val Pro Asn His Pro Cys Lys Val Asn Asn Gly Gly Cys Ser Asn
    3290            3295            3300

Leu Cys Leu Leu Ser Pro Gly Gly Gly His Lys Cys Ala Cys Pro
    3305            3310            3315

Thr Asn Phe Tyr Leu Gly Ser Asp Gly Arg Thr Cys Val Ser Asn
    3320            3325            3330

Cys Thr Ala Ser Gln Phe Val Cys Lys Asn Asp Lys Cys Ile Pro
    3335            3340            3345

Phe Trp Trp Lys Cys Asp Thr Glu Asp Asp Cys Gly Asp His Ser
    3350            3355            3360

Asp Glu Pro Pro Asp Cys Pro Glu Phe Lys Cys Arg Pro Gly Gln
    3365            3370            3375

Phe Gln Cys Ser Thr Gly Ile Cys Thr Asn Pro Ala Phe Ile Cys
    3380            3385            3390

Asp Gly Asp Asn Asp Cys Gln Asp Asn Ser Asp Glu Ala Asn Cys
    3395            3400            3405

Asp Ile His Val Cys Leu Pro Ser Gln Phe Lys Cys Thr Asn Thr
    3410            3415            3420

Asn Arg Cys Ile Pro Gly Ile Phe Arg Cys Asn Gly Gln Asp Asn
    3425            3430            3435

Cys Gly Asp Gly Glu Asp Glu Arg Asp Cys Pro Glu Val Thr Cys
```

```
            3440            3445            3450
Ala Pro Asn Gln Phe Gln Cys Ser Ile Thr Lys Arg Cys Ile Pro
    3455            3460            3465
Arg Val Trp Val Cys Asp Arg Asp Asn Asp Cys Val Asp Gly Ser
    3470            3475            3480
Asp Glu Pro Ala Asn Cys Thr Gln Met Thr Cys Gly Val Asp Glu
    3485            3490            3495
Phe Arg Cys Lys Asp Ser Gly Arg Cys Ile Pro Ala Arg Trp Lys
    3500            3505            3510
Cys Asp Gly Glu Asp Cys Gly Asp Gly Ser Asp Glu Pro Lys
    3515            3520            3525
Glu Glu Cys Asp Glu Arg Thr Cys Glu Pro Tyr Gln Phe Arg Cys
    3530            3535            3540
Lys Asn Asn Arg Cys Val Pro Gly Arg Trp Gln Cys Asp Tyr Asp
    3545            3550            3555
Asn Asp Cys Gly Asp Asn Ser Asp Glu Glu Ser Cys Thr Pro Arg
    3560            3565            3570
Pro Cys Ser Glu Ser Glu Phe Ser Cys Ala Asn Gly Arg Cys Ile
    3575            3580            3585
Ala Gly Arg Trp Lys Cys Asp Gly Asp His Asp Cys Ala Asp Gly
    3590            3595            3600
Ser Asp Glu Lys Asp Cys Thr Pro Arg Cys Asp Met Asp Gln Phe
    3605            3610            3615
Gln Cys Lys Ser Gly His Cys Ile Pro Leu Arg Trp Arg Cys Asp
    3620            3625            3630
Ala Asp Ala Asp Cys Met Asp Gly Ser Asp Glu Glu Ala Cys Gly
    3635            3640            3645
Thr Gly Val Arg Thr Cys Pro Leu Asp Glu Phe Gln Cys Asn Asn
    3650            3655            3660
Thr Leu Cys Lys Pro Leu Ala Trp Lys Cys Asp Gly Glu Asp Asp
    3665            3670            3675
Cys Gly Asp Asn Ser Asp Glu Asn Pro Glu Glu Cys Ala Arg Phe
    3680            3685            3690
Val Cys Pro Pro Asn Arg Pro Phe Arg Cys Lys Asn Asp Arg Val
    3695            3700            3705
Cys Leu Trp Ile Gly Arg Gln Cys Asp Gly Thr Asp Asn Cys Gly
    3710            3715            3720
Asp Gly Thr Asp Glu Glu Asp Cys Glu Pro Pro Thr Ala His Thr
    3725            3730            3735
Thr His Cys Lys Asp Lys Lys Glu Phe Leu Cys Arg Asn Gln Arg
    3740            3745            3750
Cys Leu Ser Ser Ser Leu Arg Cys Asn Met Phe Asp Asp Cys Gly
    3755            3760            3765
Asp Gly Ser Asp Glu Glu Asp Cys Ser Ile Asp Pro Lys Leu Thr
    3770            3775            3780
Ser Cys Ala Thr Asn Ala Ser Ile Cys Gly Asp Glu Ala Arg Cys
    3785            3790            3795
Val Arg Thr Glu Lys Ala Ala Tyr Cys Ala Cys Arg Ser Gly Phe
    3800            3805            3810
His Thr Val Pro Gly Gln Pro Gly Cys Gln Asp Ile Asn Glu Cys
    3815            3820            3825
Leu Arg Phe Gly Thr Cys Ser Gln Leu Cys Asn Asn Thr Lys Gly
    3830            3835            3840
```

Gly His Leu Cys Ser Cys Ala Arg Asn Phe Met Lys Thr His Asn
3845                3850                3855

Thr Cys Lys Ala Glu Gly Ser Glu Tyr Gln Val Leu Tyr Ile Ala
3860                3865                3870

Asp Asp Asn Glu Ile Arg Ser Leu Phe Pro Gly His Pro His Ser
3875                3880                3885

Ala Tyr Glu Gln Ala Phe Gln Gly Asp Glu Ser Val Arg Ile Asp
3890                3895                3900

Ala Met Asp Val His Val Lys Ala Gly Arg Val Tyr Trp Thr Asn
3905                3910                3915

Trp His Thr Gly Thr Ile Ser Tyr Arg Ser Leu Pro Pro Ala Ala
3920                3925                3930

Pro Pro Thr Thr Ser Asn Arg His Arg Arg Gln Ile Asp Arg Gly
3935                3940                3945

Val Thr His Leu Asn Ile Ser Gly Leu Lys Met Pro Arg Gly Ile
3950                3955                3960

Ala Ile Asp Trp Val Ala Gly Asn Val Tyr Trp Thr Asp Ser Gly
3965                3970                3975

Arg Asp Val Ile Glu Val Ala Gln Met Lys Gly Glu Asn Arg Lys
3980                3985                3990

Thr Leu Ile Ser Gly Met Ile Asp Glu Pro His Ala Ile Val Val
3995                4000                4005

Asp Pro Leu Arg Gly Thr Met Tyr Trp Ser Asp Trp Gly Asn His
4010                4015                4020

Pro Lys Ile Glu Thr Ala Ala Met Asp Gly Thr Leu Arg Glu Thr
4025                4030                4035

Leu Val Gln Asp Asn Ile Gln Trp Pro Thr Gly Leu Ala Val Asp
4040                4045                4050

Tyr His Asn Glu Arg Leu Tyr Trp Ala Asp Ala Lys Leu Ser Val
4055                4060                4065

Ile Gly Ser Ile Arg Leu Asn Gly Thr Asp Pro Ile Val Ala Ala
4070                4075                4080

Asp Ser Lys Arg Gly Leu Ser His Pro Phe Ser Ile Asp Val Phe
4085                4090                4095

Glu Asp Tyr Ile Tyr Gly Val Thr Tyr Ile Asn Asn Arg Val Phe
4100                4105                4110

Lys Ile His Lys Phe Gly His Ser Pro Leu Val Asn Leu Thr Gly
4115                4120                4125

Gly Leu Ser His Ala Ser Asp Val Val Leu Tyr His Gln His Lys
4130                4135                4140

Gln Pro Glu Val Thr Asn Pro Cys Asp Arg Lys Lys Cys Glu Trp
4145                4150                4155

Leu Cys Leu Leu Ser Pro Ser Gly Pro Val Cys Thr Cys Pro Asn
4160                4165                4170

Gly Lys Arg Leu Asp Asn Gly Thr Cys Val Pro Val Pro Ser Pro
4175                4180                4185

Thr Pro Pro Pro Asp Ala Pro Arg Pro Gly Thr Cys Asn Leu Gln
4190                4195                4200

Cys Phe Asn Gly Gly Ser Cys Phe Leu Asn Ala Arg Arg Gln Pro
4205                4210                4215

Lys Cys Arg Cys Gln Pro Arg Tyr Thr Gly Asp Lys Cys Glu Leu
4220                4225                4230

```
Asp Gln Cys Trp Glu His Cys Arg Asn Gly Gly Thr Cys Ala Ala
    4235                4240                4245

Ser Pro Ser Gly Met Pro Thr Cys Arg Cys Pro Thr Gly Phe Thr
    4250                4255                4260

Gly Pro Lys Cys Thr Gln Gln Val Cys Ala Gly Tyr Cys Ala Asn
    4265                4270                4275

Asn Ser Thr Cys Thr Val Asn Gln Gly Asn Gln Pro Gln Cys Arg
    4280                4285                4290

Cys Leu Pro Gly Phe Leu Gly Asp Arg Cys Gln Tyr Arg Gln Cys
    4295                4300                4305

Ser Gly Tyr Cys Glu Asn Phe Gly Thr Cys Gln Met Ala Ala Asp
    4310                4315                4320

Gly Ser Arg Gln Cys Arg Cys Thr Ala Tyr Phe Glu Gly Ser Arg
    4325                4330                4335

Cys Glu Val Asn Lys Cys Ser Arg Cys Leu Glu Gly Ala Cys Val
    4340                4345                4350

Val Asn Lys Gln Ser Gly Asp Val Thr Cys Asn Cys Thr Asp Gly
    4355                4360                4365

Arg Val Ala Pro Ser Cys Leu Thr Cys Val Gly His Cys Ser Asn
    4370                4375                4380

Gly Gly Ser Cys Thr Met Asn Ser Lys Met Met Pro Glu Cys Gln
    4385                4390                4395

Cys Pro Pro His Met Thr Gly Pro Arg Cys Glu Glu His Val Phe
    4400                4405                4410

Ser Gln Gln Gln Pro Gly His Ile Ala Ser Ile Leu Ile Pro Leu
    4415                4420                4425

Leu Leu Leu Leu Leu Leu Val Leu Val Ala Gly Val Val Phe Trp
    4430                4435                4440

Tyr Lys Arg Arg Val Gln Gly Ala Lys Gly Phe Gln His Gln Arg
    4445                4450                4455

Met Thr Asn Gly Ala Met Asn Val Glu Ile Gly Asn Pro Thr Tyr
    4460                4465                4470

Lys Met Tyr Glu Gly Gly Glu Pro Asp Asp Val Gly Gly Leu Leu
    4475                4480                4485

Asp Ala Asp Phe Ala Leu Asp Pro Asp Lys Pro Thr Asn Phe Thr
    4490                4495                4500

Asn Pro Val Tyr Ala Thr Leu Tyr Met Gly Gly His Gly Ser Arg
    4505                4510                4515

His Ser Leu Ala Ser Thr Asp Glu Lys Arg Glu Leu Leu Gly Arg
    4520                4525                4530

Gly Pro Glu Asp Glu Ile Gly Asp Pro Leu Ala
    4535                4540

<210> SEQ ID NO 57
<211> LENGTH: 13
<212> TYPE: PRT
<213> ORGANISM: Artificial Sequence
<220> FEATURE:
<223> OTHER INFORMATION: Biotin Acceptor Peptide

<400> SEQUENCE: 57

Leu Asn Asp Ile Phe Glu Ala Gln Lys Ile Glu Trp His
1               5                   10

<210> SEQ ID NO 58
<211> LENGTH: 13
```

```
<212> TYPE: PRT
<213> ORGANISM: Artificial Sequence
<220> FEATURE:
<223> OTHER INFORMATION: Lipoate Acceptor Peptide

<400> SEQUENCE: 58

Gly Phe Glu Ile Asp Lys Val Trp Tyr Asp Leu Asp Ala
1               5                   10

<210> SEQ ID NO 59
<211> LENGTH: 29
<212> TYPE: PRT
<213> ORGANISM: Artificial Sequence
<220> FEATURE:
<223> OTHER INFORMATION: CTP

<400> SEQUENCE: 59

Asp Ser Ser Ser Ser Lys Ala Pro Pro Ser Leu Pro Ser Pro Ser
1               5                   10                  15

Arg Leu Pro Gly Pro Ser Asp Thr Pro Ile Leu Pro Gln
            20                  25

<210> SEQ ID NO 60
<211> LENGTH: 6
<212> TYPE: PRT
<213> ORGANISM: Artificial Sequence
<220> FEATURE:
<223> OTHER INFORMATION: FVII

<400> SEQUENCE: 60

Ile Val Gly Gly Lys Val
1               5

<210> SEQ ID NO 61
<211> LENGTH: 6
<212> TYPE: PRT
<213> ORGANISM: Artificial Sequence
<220> FEATURE:
<223> OTHER INFORMATION: Factor X

<400> SEQUENCE: 61

Ile Val Gly Gly Gln Glu
1               5

<210> SEQ ID NO 62
<211> LENGTH: 11
<212> TYPE: PRT
<213> ORGANISM: Artificial Sequence
<220> FEATURE:
<223> OTHER INFORMATION: FVII

<400> SEQUENCE: 62

Ile Val Gly Gly Lys Val Cys Pro Lys Gly Glu
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Factor X

<400> SEQUENCE: 63

Ile Val Gly Gly Gln Glu Cys Lys Asp Gly Glu
1               5                   10
```

```
<210> SEQ ID NO 64
<211> LENGTH: 12
<212> TYPE: PRT
<213> ORGANISM: Artificial Sequence
<220> FEATURE:
<223> OTHER INFORMATION: FX-PABC peptide
<220> FEATURE:
<221> NAME/KEY: MOD_RES
<222> LOCATION: (3)..(3)
<223> OTHER INFORMATION: Xaa is DPhe
<220> FEATURE:
<221> NAME/KEY: MOD_RES
<222> LOCATION: (4)..(4)
<223> OTHER INFORMATION: Xaa is Pip
<220> FEATURE:
<221> NAME/KEY: MOD_RES
<222> LOCATION: (6)..(6)
<223> OTHER INFORMATION: Xaa is P-amino benzyl carbamate

<400> SEQUENCE: 64

Gly Gly Xaa Xaa Arg Xaa Ile Val Gly Gly Lys Val
1               5                   10

<210> SEQ ID NO 65
<211> LENGTH: 12
<212> TYPE: PRT
<213> ORGANISM: Artificial Sequence
<220> FEATURE:
<223> OTHER INFORMATION: mature FVII sequence

<400> SEQUENCE: 65

Leu Gln Gln Ser Arg Lys Val Gly Asp Ser Pro Asn
1               5                   10

<210> SEQ ID NO 66
<211> LENGTH: 7
<212> TYPE: PRT
<213> ORGANISM: Artificial Sequence
<220> FEATURE:
<223> OTHER INFORMATION: mature FVII sequence

<400> SEQUENCE: 66

Glu Ala Ser Tyr Pro Gly Lys
1               5

<210> SEQ ID NO 67
<211> LENGTH: 11
<212> TYPE: PRT
<213> ORGANISM: Artificial Sequence
<220> FEATURE:
<223> OTHER INFORMATION: Thrombine Activatable Procoagulant Compounds

<400> SEQUENCE: 67

Ala Leu Arg Pro Arg Ile Val Gly Gly Gln Glu
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Thrombin-Activatable Procoagulant Compounds
      with PABC self Immolative Linker
<220> FEATURE:
<221> NAME/KEY: MISC_FEATURE
<222> LOCATION: (6)..(6)
<223> OTHER INFORMATION: PABC self Immolative linker
```

```
<400> SEQUENCE: 68

Ala Leu Val Pro Arg Xaa Ile Val Gly Gly Gln Glu
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Thrombin-Activatable Procoagulant compounds
      with PABC Self-Immolative Linker

<400> SEQUENCE: 69

Ala Leu Val Pro Arg Ile Val Gly Gly Gln Glu
1               5                   10

<210> SEQ ID NO 70
<211> LENGTH: 99
<212> TYPE: PRT
<213> ORGANISM: Artificial Sequence
<220> FEATURE:
<223> OTHER INFORMATION: SUMO Protease

<400> SEQUENCE: 70

Ser Leu Gln Asp Ser Glu Val Asn Gln Glu Ala Lys Pro Glu Val Lys
1               5                   10                  15

Pro Glu Val Lys Pro Glu Thr His Ile Asn Leu Lys Val Ser Asp Gly
                20                  25                  30

Ser Ser Glu Ile Phe Phe Lys Ile Lys Lys Thr Thr Pro Leu Arg Arg
            35                  40                  45

Leu Met Glu Ala Phe Ala Lys Arg Gln Gly Lys Glu Met Asp Ser Leu
        50                  55                  60

Arg Phe Leu Tyr Asp Gly Ile Arg Ile Gln Ala Asp Gln Ala Pro Glu
65                  70                  75                  80

Asp Leu Asp Met Glu Asp Asn Asp Ile Ile Glu Ala His Arg Glu Gln
                85                  90                  95

Ile Gly Gly
```